United States Patent
Plantier

(10) Patent No.: US 10,364,424 B2
(45) Date of Patent: Jul. 30, 2019

(54) FACTOR X MUTANTS

(71) Applicant: LABORATOIRE FRANCAIS DU FRACTIONNEMENT ET DES BIOTECHNOLOGIES, Les Ulis (FR)

(72) Inventor: Jean-Luc Plantier, Croix (FR)

(73) Assignee: LABORATOIRE FRANCAIS DU FRACTIONNEMENT ET DES BIOTECHNOLOGIES, Les Ulis (FR)

( * ) Notice: Subject to any disclaimer, the term of this patent is extended or adjusted under 35 U.S.C. 154(b) by 484 days.

(21) Appl. No.: 14/765,073

(22) PCT Filed: Feb. 3, 2014

(86) PCT No.: PCT/FR2014/050191
§ 371 (c)(1),
(2) Date: Nov. 12, 2015

(87) PCT Pub. No.: WO2014/118481
PCT Pub. Date: Aug. 7, 2014

(65) Prior Publication Data
US 2016/0145598 A1 May 26, 2016

(30) Foreign Application Priority Data

Feb. 4, 2013 (FR) ...................................... 13 50930

(51) Int. Cl.
*C12N 9/64* (2006.01)
*A61K 38/48* (2006.01)

(52) U.S. Cl.
CPC ........ *C12N 9/6432* (2013.01); *A61K 38/4846* (2013.01); *C12Y 304/21006* (2013.01)

(58) Field of Classification Search
None
See application file for complete search history.

(56) References Cited

FOREIGN PATENT DOCUMENTS

| WO | WO 01/10896 A2 | 2/2001 |
| WO | WO2001-10896 | * 2/2001 |
| WO | WO 2006/018204 A1 | 2/2006 |
| WO | WO 2006/128668 A2 | 12/2006 |

OTHER PUBLICATIONS (National Hemophilia Foundation, accessed Jan. 22, 2017: https://www.hemophilia.org/Bleeding-Disorders/Types-of-Bleeding-Disorders/Other-Factor-Deficiencies/Factor-X).*

The Merck Manual (accessed Jan. 22, 2018; https://www.merckmanuals.com/professional/hematology-and-oncology/thrombocytopenia-and-platelet-dysfunction/von-willebrand-diseasediscloses).*
The National Hemophilia Foundation (accessed Jan. 22, 2018; <https://www.hemophilia.org/Bleeding-Disorders/Types-of-Bleeding-Disorders/Other-Factor-Deficiencies/Factor-I>).*
NCBI Reference Sequence: XP_001682755.1 (https://www.ncbi.nlm.nih.gov/protein/XP_001682755?report=genbank&log$=protalign&blast_rank=11&RID=90VD727N014, Genome Res. 21(12) 2011).*
International Search Report issued in application No. PCT/FR2014/050191 dated Apr. 30, 2014.

* cited by examiner

*Primary Examiner* — Jennifer Pitrak McDonald
*Assistant Examiner* — Tara L Martinez
(74) *Attorney, Agent, or Firm* — Potomac Law Group, PLLC

(57) ABSTRACT

The present invention concerns a protein comprising a mutated sequence of SEQ ID No. 1, said mutated sequence of SEQ ID No. 1 comprising at least one mutation A, A', B, C or C', in which: mutation A consists of substituting amino acids 43 to 52 of sequence SEQ ID No. 1 with a sequence chosen from DFLAEGLTPR (SEQ ID NO: 159), KATN*ATLSPR (SEQ ID NO: 160) and KATXATLSPR (SEQ ID NO: 161), mutation A' consists of substituting amino acids 47 to 52 of sequence SEQ ID No. 1 with a sequence chosen from TSKLTR (SEQ ID NO: 162), FNDFTR (SEQ ID NO: 163), LSSMTR (SEQ ID NO: 164), PPSLTR (SEQ ID NO: 165) and LSCGQR (SEQ ID NO: 166), mutation B consists of inserting a sequence chosen from DFLAEGLTPR (SEQ ID NO: 159), KATN*ATLSPR (SEQ ID NO: 160), KATXATLSPR (SEQ ID NO: 161), TSKLTR (SEQ ID NO: 162), FNDFTR (SEQ ID NO: 163), LSSMTR (SEQ ID NO: 164), PPSLTR (SEQ ID NO: 165) and LSCGQR (SEQ ID NO: 166), between amino acids 52 and 53 of sequence SEQ ID No. 1, mutation C consists of inserting a sequence chosen from DFLAEGLTPR (SEQ ID NO: 159), KATN*ATLSPR (SEQ ID NO: 160) and KATXATLSPR (SEQ ID NO: 161), between amino acids 52 and 53 of sequence SEQ ID No. 1, and of deleting amino acids 4 to 13 from sequence SEQ ID No. 1, mutation C' consists of inserting a sequence chosen from TSKLTR (SEQ ID NO: 162), FNDFTR (SEQ ID NO: 163), LSSMTR (SEQ ID NO: 164), PPSLTR (SEQ ID NO: 165) and LSCGQR (SEQ ID NO: 166), between amino acids 52 and 53 of sequence SEQ ID No. 1, and of deleting amino acids 4 to 9 from sequence SEQ ID No. 1.

7 Claims, 14 Drawing Sheets
Specification includes a Sequence Listing.

```
                        SEQUENCE LISTING

<160> NUMBER OF SEQ ID NOS: 169

<210> SEQ ID NO 1
<211> LENGTH: 306
<212> TYPE: PRT
<213> ORGANISM: Homo sapiens

<400> SEQUENCE: 1

Ser Val Ala Gln Ala Thr Ser Ser Gly Glu Ala Pro Asp Ser Ile
1               5                   10                  15

Thr Trp Lys Pro Tyr Asp Ala Ala Asp Leu Asp Pro Thr Glu Asn Pro
                20                  25                  30

Phe Asp Leu Leu Asp Phe Asn Gln Thr Gln Pro Glu Arg Gly Asp Asn
            35                  40                  45

Asn Leu Thr Arg Ile Val Gly Gly Gln Glu Cys Lys Asp Gly Glu Cys
        50                  55                  60

Pro Trp Gln Ala Leu Leu Ile Asn Glu Glu Asn Glu Gly Phe Cys Gly
65                  70                  75                  80

Gly Thr Ile Leu Ser Glu Phe Tyr Ile Leu Thr Ala Ala His Cys Leu
                85                  90                  95

Tyr Gln Ala Lys Arg Phe Lys Val Arg Val Gly Asp Arg Asn Thr Glu
            100                 105                 110

Gln Glu Glu Gly Gly Glu Ala Val His Glu Val Glu Val Val Ile Lys
        115                 120                 125

His Asn Arg Phe Thr Lys Glu Thr Tyr Asp Phe Asp Ile Ala Val Leu
    130                 135                 140

Arg Leu Lys Thr Pro Ile Thr Phe Arg Met Asn Val Ala Pro Ala Cys
145                 150                 155                 160

Leu Pro Glu Arg Asp Trp Ala Glu Ser Thr Leu Met Thr Gln Lys Thr
                165                 170                 175

Gly Ile Val Ser Gly Phe Gly Arg Thr His Glu Lys Gly Arg Gln Ser
            180                 185                 190
```

```
Thr Arg Leu Lys Met Leu Glu Val Pro Tyr Val Asp Arg Asn Ser Cys
            195                 200                 205
Lys Leu Ser Ser Ser Phe Ile Ile Thr Gln Asn Met Phe Cys Ala Gly
            210                 215                 220
Tyr Asp Thr Lys Gln Glu Asp Ala Cys Gln Gly Asp Ser Gly Gly Pro
225                 230                 235                 240
His Val Thr Arg Phe Lys Asp Thr Tyr Phe Val Thr Gly Ile Val Ser
            245                 250                 255
Trp Gly Glu Gly Cys Ala Arg Lys Gly Lys Tyr Gly Ile Tyr Thr Lys
            260                 265                 270
Val Thr Ala Phe Leu Lys Trp Ile Asp Arg Ser Met Lys Thr Arg Gly
            275                 280                 285
Leu Pro Lys Ala Lys Ser His Ala Pro Glu Val Ile Thr Ser Ser Pro
            290                 295                 300
Leu Lys
305

<210> SEQ ID NO 2
<211> LENGTH: 182
<212> TYPE: PRT
<213> ORGANISM: Homo sapiens

<400> SEQUENCE: 2

Met Gly Arg Pro Leu His Leu Val Leu Leu Ser Ala Ser Leu Ala Gly
1               5                   10                  15
Leu Leu Leu Leu Gly Glu Ser Leu Phe Ile Arg Arg Glu Gln Ala Asn
            20                  25                  30
Asn Ile Leu Ala Arg Val Thr Arg Ala Asn Ser Phe Leu Glu Glu Met
            35                  40                  45
Lys Lys Gly His Leu Glu Arg Glu Cys Met Glu Glu Thr Cys Ser Tyr
        50                  55                  60
Glu Glu Ala Arg Glu Val Phe Glu Asp Ser Asp Lys Thr Asn Glu Phe
65                  70                  75                  80
Trp Asn Lys Tyr Lys Asp Gly Asp Gln Cys Glu Thr Ser Pro Cys Gln
                85                  90                  95
Asn Gln Gly Lys Cys Lys Asp Gly Leu Gly Glu Tyr Thr Cys Thr Cys
            100                 105                 110
Leu Glu Gly Phe Glu Gly Lys Asn Cys Glu Leu Phe Thr Arg Lys Leu
            115                 120                 125
Cys Ser Leu Asp Asn Gly Asp Cys Asp Gln Phe Cys His Glu Glu Gln
        130                 135                 140
Asn Ser Val Val Cys Ser Cys Ala Arg Gly Tyr Thr Leu Ala Asp Asn
145                 150                 155                 160
Gly Lys Ala Cys Ile Pro Thr Gly Pro Tyr Pro Cys Gly Lys Gln Thr
                165                 170                 175
Leu Glu Arg Arg Lys Arg
            180

<210> SEQ ID NO 3
<211> LENGTH: 52
<212> TYPE: PRT
<213> ORGANISM: Homo sapiens

<400> SEQUENCE: 3

Ser Val Ala Gln Ala Thr Ser Ser Ser Gly Glu Ala Pro Asp Ser Ile
1               5                   10                  15
```

```
Thr Trp Lys Pro Tyr Asp Ala Ala Asp Leu Asp Pro Thr Glu Asn Pro
            20                  25                  30

Phe Asp Leu Leu Asp Phe Asn Gln Thr Gln Pro Glu Arg Gly Asp Asn
        35                  40                  45

Asn Leu Thr Arg
        50

<210> SEQ ID NO 4
<211> LENGTH: 488
<212> TYPE: PRT
<213> ORGANISM: Homo sapiens

<400> SEQUENCE: 4

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Glu Gly Gly Glu Ala Val His Glu
    290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
```

```
                        325                 330                 335
Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
    370                 375                 380

Val Asp Arg Asn Ser Cys Lys Leu Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys
                485

<210> SEQ ID NO 5
<211> LENGTH: 142
<212> TYPE: PRT
<213> ORGANISM: Homo sapiens

<400> SEQUENCE: 5

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
                100                 105                 110

Arg Gly Tyr Thr Leu Ala Asp Asn Gly Lys Ala Cys Ile Pro Thr Gly
            115                 120                 125

Pro Tyr Pro Cys Gly Lys Gln Thr Leu Glu Arg Arg Lys Arg
    130                 135                 140

<210> SEQ ID NO 6
<211> LENGTH: 254
<212> TYPE: PRT
<213> ORGANISM: Homo sapiens

<400> SEQUENCE: 6

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
```

```
                 20                  25                  30
Ser Glu Phe Tyr Ile Leu Thr Ala Ala His Cys Leu Tyr Gln Ala Lys
             35                  40                  45

Arg Phe Lys Val Arg Val Gly Asp Arg Asn Thr Glu Gln Glu Glu Gly
         50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                 85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Arg Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ser Gly Gly Pro His Val Thr Arg
            180                 185                 190

Phe Lys Asp Thr Tyr Phe Val Thr Gly Ile Val Ser Trp Gly Glu Gly
        195                 200                 205

Cys Ala Arg Lys Gly Lys Tyr Gly Ile Tyr Thr Lys Val Thr Ala Phe
    210                 215                 220

Leu Lys Trp Ile Asp Arg Ser Met Lys Thr Arg Gly Leu Pro Lys Ala
225                 230                 235                 240

Lys Ser His Ala Pro Glu Val Ile Thr Ser Ser Pro Leu Lys
                245                 250

<210> SEQ ID NO 7
<211> LENGTH: 500
<212> TYPE: PRT
<213> ORGANISM: Homo sapiens

<400> SEQUENCE: 7

Met Gly Arg Pro Leu His Leu Val Leu Leu Ser Ala Ser Leu Ala Gly
1               5                  10                  15

Leu Leu Leu Leu Gly Glu Ser Leu Phe Ile Arg Arg Glu Gln Ala Asn
                 20                  25                  30

Asn Ile Leu Ala Arg Val Arg Arg Ala Asn Ser Phe Leu Glu Glu Met
             35                  40                  45

Lys Lys Gly His Leu Glu Arg Glu Cys Met Glu Glu Thr Cys Ser Tyr
         50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                 85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140
```

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
    210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
                260                 265                 270

Thr Ala Ala His Cys Leu Tyr Gln Ala Lys Arg Phe Lys Val Arg Val
            275                 280                 285

Gly Asp Arg Asn Thr Glu Gln Glu Glu Gly Gly Glu Ala Val His Glu
290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
                340                 345                 350

Leu Met Thr Gln Lys Thr Gly Ile Val Ser Gly Phe Gly Arg Thr His
            355                 360                 365

Glu Lys Gly Arg Gln Ser Thr Arg Leu Lys Met Leu Glu Val Pro Tyr
        370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys Glu Asp Gln Val Asp Pro Arg Leu
                485                 490                 495

Ile Asp Gly Lys
            500

<210> SEQ ID NO 8
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
210                 215                 220

Asp Phe Leu Ala Glu Gly Gly Val Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Gly Gly Glu Ala Val His Glu
290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415
```

```
Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
            435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys Glu Asp Gln Val Asp Pro Arg Leu
                485                 490                 495

Ile Asp Gly Lys
            500

<210> SEQ ID NO 9
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
    210                 215                 220

Asp Phe Leu Ala Glu Gly Leu Thr Pro Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270
```

```
Thr Ala Ala His Cys Leu Tyr Gln Ala Lys Arg Phe Lys Val Arg Val
        275                 280                 285

Gly Asp Arg Asn Thr Glu Gln Glu Glu Gly Gly Glu Ala Val His Glu
290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
370                 375                 380

Val Asp Arg Asn Ser Cys Lys Leu Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys Glu Asp Gln Val Asp Pro Arg Leu
                485                 490                 495

Ile Asp Gly Lys
            500

<210> SEQ ID NO 10
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
                20                  25                  30

Asn Ile Leu Ala Arg Val Arg Arg Ala Asn Ser Phe Leu Glu Glu Met
            35                  40                  45

Lys Lys Gly His Leu Glu Arg Glu Cys Met Glu Glu Thr Cys Ser Tyr
        50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
```

```
            115                 120                 125
Cys Ser Leu Asp Asn Gly Asp Cys Asp Gln Phe Cys His Glu Glu Gln
130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
    210                 215                 220

Lys Ala Thr Asn Ala Thr Leu Ser Pro Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Glu Gly Gly Glu Ala Val His Glu
    290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
    370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys Glu Asp Gln Val Asp Pro Arg Leu
                485                 490                 495

Ile Asp Gly Lys
            500

<210> SEQ ID NO 11
<211> LENGTH: 500
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 11

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Arg Ala Asn Ser Phe Leu Glu Glu Met
        35                  40                  45

Lys Lys Gly His Leu Glu Arg Glu Cys Met Glu Glu Thr Cys Ser Tyr
50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
210                 215                 220

Lys Ala Thr Gln Ala Thr Leu Ser Pro Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Glu Gly Gly Glu Ala Val His Glu
290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
370                 375                 380

Val Asp Arg Asn Ser Cys Lys Leu Ser Ser Ser Phe Ile Ile Thr Gln
```

```
                385                 390                 395                 400
        Asn Met Phe Cys Ala Gly Tyr Asp Thr Lys Gln Glu Asp Ala Cys Gln
                        405                 410                 415

Gly Asp Ser Gly Gly Pro His Val Thr Arg Phe Lys Asp Thr Tyr Phe
                        420                 425                 430

Val Thr Gly Ile Val Ser Trp Gly Glu Gly Cys Ala Arg Lys Gly Lys
                        435                 440                 445

Tyr Gly Ile Tyr Thr Lys Val Thr Ala Phe Leu Lys Trp Ile Asp Arg
                        450                 455                 460

Ser Met Lys Thr Arg Gly Leu Pro Lys Ala Lys Ser His Ala Pro Glu
        465                 470                 475                 480

Val Ile Thr Ser Ser Pro Leu Lys Glu Asp Gln Val Asp Pro Arg Leu
                        485                 490                 495

Ile Asp Gly Lys
                    500

<210> SEQ ID NO 12
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
                20                  25                  30

Asn Ile Leu Ala Arg Val Arg Arg Ala Asn Ser Phe Leu Glu Glu Met
                35                  40                  45

Lys Lys Gly His Leu Glu Arg Glu Cys Met Glu Glu Thr Cys Ser Tyr
            50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
                100                 105                 110

Leu Glu Gly Phe Glu Gly Lys Asn Cys Glu Leu Phe Thr Arg Lys Leu
            115                 120                 125

Cys Ser Leu Asp Asn Gly Asp Cys Asp Gln Phe Cys His Glu Glu Gln
130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
                180                 185                 190

Glu Ala Pro Asp Ser Ile Thr Trp Lys Pro Tyr Asp Ala Ala Asp Leu
            195                 200                 205

Asp Pro Thr Glu Asn Pro Phe Asp Leu Leu Asp Phe Asn Gln Thr Gln
            210                 215                 220

Pro Glu Arg Gly Thr Ser Lys Leu Thr Arg Ile Val Gly Gly Gln Glu
225                 230                 235                 240
```

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Glu Gly Gly Glu Ala Val His Glu
    290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
    370                 375                 380

Val Asp Arg Asn Ser Cys Lys Leu Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys Glu Asp Gln Val Asp Pro Arg Leu
                485                 490                 495

Ile Asp Gly Lys
            500

<210> SEQ ID NO 13
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

-continued

```
Asn Gln Gly Lys Cys Lys Asp Gly Leu Gly Glu Tyr Thr Cys Thr Cys
            100                 105                 110
Leu Glu Gly Phe Glu Gly Lys Asn Cys Glu Leu Phe Thr Arg Lys Leu
            115                 120                 125
Cys Ser Leu Asp Asn Gly Asp Cys Asp Gln Phe Cys His Glu Glu Gln
            130                 135                 140
Asn Ser Val Val Cys Ser Cys Ala Arg Gly Tyr Thr Leu Ala Asp Asn
145                 150                 155                 160
Gly Lys Ala Cys Ile Pro Thr Gly Pro Tyr Pro Cys Gly Lys Gln Thr
                165                 170                 175
Leu Glu Arg Arg Lys Arg Ser Val Ala Gln Ala Thr Ser Ser Ser Gly
            180                 185                 190
Glu Ala Pro Asp Ser Ile Thr Trp Lys Pro Tyr Asp Ala Ala Asp Leu
            195                 200                 205
Asp Pro Thr Glu Asn Pro Phe Asp Leu Leu Asp Phe Asn Gln Thr Gln
            210                 215                 220
Pro Glu Arg Gly Phe Asn Asp Phe Thr Arg Ile Val Gly Gly Gln Glu
225                 230                 235                 240
Cys Lys Asp Gly Glu Cys Pro Trp Gln Ala Leu Leu Ile Asn Glu Glu
                245                 250                 255
Asn Glu Gly Phe Cys Gly Gly Thr Ile Leu Ser Glu Phe Tyr Ile Leu
            260                 265                 270
Thr Ala Ala His Cys Leu Tyr Gln Ala Lys Arg Phe Lys Val Arg Val
            275                 280                 285
Gly Asp Arg Asn Thr Glu Gln Glu Glu Gly Gly Glu Ala Val His Glu
            290                 295                 300
Val Glu Val Val Ile Lys His Asn Arg Phe Thr Lys Glu Thr Tyr Asp
305                 310                 315                 320
Phe Asp Ile Ala Val Leu Arg Leu Lys Thr Pro Ile Thr Phe Arg Met
                325                 330                 335
Asn Val Ala Pro Ala Cys Leu Pro Glu Arg Asp Trp Ala Glu Ser Thr
            340                 345                 350
Leu Met Thr Gln Lys Thr Gly Ile Val Ser Gly Phe Gly Arg Thr His
            355                 360                 365
Glu Lys Gly Arg Gln Ser Thr Arg Leu Lys Met Leu Glu Val Pro Tyr
            370                 375                 380
Val Asp Arg Asn Ser Cys Lys Leu Ser Ser Ser Phe Ile Ile Thr Gln
385                 390                 395                 400
Asn Met Phe Cys Ala Gly Tyr Asp Thr Lys Gln Glu Asp Ala Cys Gln
                405                 410                 415
Gly Asp Ser Gly Gly Pro His Val Thr Arg Phe Lys Asp Thr Tyr Phe
            420                 425                 430
Val Thr Gly Ile Val Ser Trp Gly Glu Gly Cys Ala Arg Lys Gly Lys
            435                 440                 445
Tyr Gly Ile Tyr Thr Lys Val Thr Ala Phe Leu Lys Trp Ile Asp Arg
            450                 455                 460
Ser Met Lys Thr Arg Gly Leu Pro Lys Ala Lys Ser His Ala Pro Glu
465                 470                 475                 480
Val Ile Thr Ser Ser Pro Leu Lys Glu Asp Gln Val Asp Pro Arg Leu
                485                 490                 495
Ile Asp Gly Lys
            500
```

<210> SEQ ID NO 14
<211> LENGTH: 500
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

Met Gly Arg Pro Leu His Leu Val Leu Ser Ala Ser Leu Ala Gly
1               5                   10                  15

Leu Leu Leu Leu Gly Glu Ser Leu Phe Ile Arg Arg Glu Gln Ala Asn
                20                  25                  30

Asn Ile Leu Ala Arg Val Arg Arg Ala Asn Ser Phe Leu Glu Glu Met
            35                  40                  45

Lys Lys Gly His Leu Glu Arg Glu Cys Met Glu Glu Thr Cys Ser Tyr
50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
    210                 215                 220

Pro Glu Arg Gly Leu Ser Ser Met Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Glu Gly Gly Glu Ala Val His Glu
    290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

```
Glu Lys Gly Arg Gln Ser Thr Arg Leu Lys Met Leu Glu Val Pro Tyr
        370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
                420                 425                 430

Val Thr Gly Ile Val Ser Trp Gly Glu Gly Cys Ala Arg Lys Gly Lys
            435                 440                 445

Tyr Gly Ile Tyr Thr Lys Val Thr Ala Phe Leu Lys Trp Ile Asp Arg
        450                 455                 460

Ser Met Lys Thr Arg Gly Leu Pro Lys Ala Lys Ser His Ala Pro Glu
465                 470                 475                 480

Val Ile Thr Ser Ser Pro Leu Lys Glu Asp Gln Val Asp Pro Arg Leu
                485                 490                 495

Ile Asp Gly Lys
            500

<210> SEQ ID NO 15
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
```

```
                210                 215                 220
Pro Glu Arg Gly Pro Pro Ser Leu Thr Arg Ile Val Gly Gly Gln Glu
225                 230                 235                 240

Cys Lys Asp Gly Glu Cys Pro Trp Gln Ala Leu Leu Ile Asn Glu Glu
            245                 250                 255

Asn Glu Gly Phe Cys Gly Gly Thr Ile Leu Ser Glu Phe Tyr Ile Leu
        260                 265                 270

Thr Ala Ala His Cys Leu Tyr Gln Ala Lys Arg Phe Lys Val Arg Val
    275                 280                 285

Gly Asp Arg Asn Thr Glu Gln Glu Glu Gly Gly Glu Ala Val His Glu
290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
            325                 330                 335

Asn Val Ala Pro Ala Cys Leu Pro Glu Arg Asp Trp Ala Glu Ser Thr
        340                 345                 350

Leu Met Thr Gln Lys Thr Gly Ile Val Ser Gly Phe Gly Arg Thr His
    355                 360                 365

Glu Lys Gly Arg Gln Ser Thr Arg Leu Lys Met Leu Glu Val Pro Tyr
370                 375                 380

Val Asp Arg Asn Ser Cys Lys Leu Ser Ser Phe Ile Ile Thr Gln
385                 390                 395                 400

Asn Met Phe Cys Ala Gly Tyr Asp Thr Lys Gln Glu Asp Ala Cys Gln
            405                 410                 415

Gly Asp Ser Gly Gly Pro His Val Thr Arg Phe Lys Asp Thr Tyr Phe
        420                 425                 430

Val Thr Gly Ile Val Ser Trp Gly Glu Gly Cys Ala Arg Lys Gly Lys
    435                 440                 445

Tyr Gly Ile Tyr Thr Lys Val Thr Ala Phe Leu Lys Trp Ile Asp Arg
450                 455                 460

Ser Met Lys Thr Arg Gly Leu Pro Lys Ala Lys Ser His Ala Pro Glu
465                 470                 475                 480

Val Ile Thr Ser Ser Pro Leu Lys Glu Asp Gln Val Asp Pro Arg Leu
            485                 490                 495

Ile Asp Gly Lys
        500

<210> SEQ ID NO 16
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60
```

Glu Glu Ala Arg Glu Val Phe Glu Asp Ser Asp Lys Thr Asn Glu Phe
 65                  70                  75                  80

Trp Asn Lys Tyr Lys Asp Gly Asp Gln Cys Glu Thr Ser Pro Cys Gln
                 85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
210                 215                 220

Pro Glu Arg Gly Leu Ser Cys Gly Gln Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Glu Gly Gly Glu Ala Val His Glu
    290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
    370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys Glu Asp Gln Val Asp Pro Arg Leu

```
                    485                 490                 495

Ile Asp Gly Lys
        500

<210> SEQ ID NO 17
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
        35                  40                  45

Lys Lys Gly His Leu Glu Arg Glu Cys Met Glu Glu Thr Cys Ser Tyr
50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
210                 215                 220

Pro Glu Arg Gly Asp Asn Asn Leu Thr Arg Asp Phe Leu Ala Glu Gly
225                 230                 235                 240

Gly Gly Val Arg Ile Val Gly Gly Gln Glu Cys Lys Asp Gly Glu Cys
                245                 250                 255

Pro Trp Gln Ala Leu Leu Ile Asn Glu Glu Asn Glu Gly Phe Cys Gly
            260                 265                 270

Gly Thr Ile Leu Ser Glu Phe Tyr Ile Leu Thr Ala Ala His Cys Leu
        275                 280                 285

Tyr Gln Ala Lys Arg Phe Lys Val Arg Val Gly Asp Arg Asn Thr Glu
290                 295                 300

Gln Glu Glu Gly Gly Glu Ala Val His Glu Val Glu Val Val Ile Lys
305                 310                 315                 320

His Asn Arg Phe Thr Lys Glu Thr Tyr Asp Phe Asp Ile Ala Val Leu
                325                 330                 335
```

-continued

```
Arg Leu Lys Thr Pro Ile Thr Phe Arg Met Asn Val Ala Pro Ala Cys
                340                 345                 350

Leu Pro Glu Arg Asp Trp Ala Glu Ser Thr Leu Met Thr Gln Lys Thr
            355                 360                 365

Gly Ile Val Ser Gly Phe Gly Arg Thr His Glu Lys Gly Arg Gln Ser
        370                 375                 380

Thr Arg Leu Lys Met Leu Glu Val Pro Tyr Val Asp Arg Asn Ser Cys
385                 390                 395                 400

Lys Leu Ser Ser Ser Phe Ile Ile Thr Gln Asn Met Phe Cys Ala Gly
                405                 410                 415

Tyr Asp Thr Lys Gln Glu Asp Ala Cys Gln Gly Asp Ser Gly Gly Pro
            420                 425                 430

His Val Thr Arg Phe Lys Asp Thr Tyr Phe Val Thr Gly Ile Val Ser
        435                 440                 445

Trp Gly Glu Gly Cys Ala Arg Lys Gly Lys Tyr Gly Ile Tyr Thr Lys
        450                 455                 460

Val Thr Ala Phe Leu Lys Trp Ile Asp Arg Ser Met Lys Thr Arg Gly
465                 470                 475                 480

Leu Pro Lys Ala Lys Ser His Ala Pro Glu Val Ile Thr Ser Ser Pro
                485                 490                 495

Leu Lys Glu Asp Gln Val Asp Pro Arg Leu Ile Asp Gly Lys
            500                 505                 510

<210> SEQ ID NO 18
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
                20                  25                  30

Asn Ile Leu Ala Arg Val Arg Arg Ala Asn Ser Phe Leu Glu Glu Met
            35                  40                  45

Lys Lys Gly His Leu Glu Arg Glu Cys Met Glu Glu Thr Cys Ser Tyr
        50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190
```

```
Glu Ala Pro Asp Ser Ile Thr Trp Lys Pro Tyr Asp Ala Asp Leu
        195                 200                 205

Asp Pro Thr Glu Asn Pro Phe Asp Leu Leu Asp Phe Asn Gln Thr Gln
    210                 215                 220

Pro Glu Arg Gly Asp Asn Asn Leu Thr Arg Asp Phe Leu Ala Glu Gly
225                 230                 235                 240

Leu Thr Pro Arg Ile Val Gly Gly Gln Glu Cys Lys Asp Gly Glu Cys
                245                 250                 255

Pro Trp Gln Ala Leu Leu Ile Asn Glu Glu Asn Glu Gly Phe Cys Gly
            260                 265                 270

Gly Thr Ile Leu Ser Glu Phe Tyr Ile Leu Thr Ala Ala His Cys Leu
        275                 280                 285

Tyr Gln Ala Lys Arg Phe Lys Val Arg Val Gly Asp Arg Asn Thr Glu
    290                 295                 300

Gln Glu Glu Gly Gly Glu Ala Val His Glu Val Glu Val Val Ile Lys
305                 310                 315                 320

His Asn Arg Phe Thr Lys Glu Thr Tyr Asp Phe Asp Ile Ala Val Leu
                325                 330                 335

Arg Leu Lys Thr Pro Ile Thr Phe Arg Met Asn Val Ala Pro Ala Cys
            340                 345                 350

Leu Pro Glu Arg Asp Trp Ala Glu Ser Thr Leu Met Thr Gln Lys Thr
        355                 360                 365

Gly Ile Val Ser Gly Phe Gly Arg Thr His Glu Lys Gly Arg Gln Ser
    370                 375                 380

Thr Arg Leu Lys Met Leu Glu Val Pro Tyr Val Asp Arg Asn Ser Cys
385                 390                 395                 400

Lys Leu Ser Ser Ser Phe Ile Ile Thr Gln Asn Met Phe Cys Ala Gly
                405                 410                 415

Tyr Asp Thr Lys Gln Glu Asp Ala Cys Gln Gly Asp Ser Gly Gly Pro
            420                 425                 430

His Val Thr Arg Phe Lys Asp Thr Tyr Phe Val Thr Gly Ile Val Ser
        435                 440                 445

Trp Gly Glu Gly Cys Ala Arg Lys Gly Lys Tyr Gly Ile Tyr Thr Lys
    450                 455                 460

Val Thr Ala Phe Leu Lys Trp Ile Asp Arg Ser Met Lys Thr Arg Gly
465                 470                 475                 480

Leu Pro Lys Ala Lys Ser His Ala Pro Glu Val Ile Thr Ser Ser Pro
                485                 490                 495

Leu Lys Glu Asp Gln Val Asp Pro Arg Leu Ile Asp Gly Lys
            500                 505                 510

<210> SEQ ID NO 19
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
```

```
                35                  40                  45
Lys Lys Gly His Leu Glu Arg Glu Cys Met Glu Thr Cys Ser Tyr
 50                  55                  60
Glu Glu Ala Arg Glu Val Phe Glu Asp Ser Asp Lys Thr Asn Glu Phe
 65                      70                  75                  80
Trp Asn Lys Tyr Lys Asp Gly Asp Gln Cys Glu Thr Ser Pro Cys Gln
                     85                  90                  95
Asn Gln Gly Lys Cys Lys Asp Gly Leu Gly Glu Tyr Thr Cys Thr Cys
                100                 105                 110
Leu Glu Gly Phe Glu Gly Lys Asn Cys Glu Leu Phe Thr Arg Lys Leu
                115                 120                 125
Cys Ser Leu Asp Asn Gly Asp Cys Asp Gln Phe Cys His Glu Glu Gln
                130                 135                 140
Asn Ser Val Val Cys Ser Cys Ala Arg Gly Tyr Thr Leu Ala Asp Asn
145                 150                 155                 160
Gly Lys Ala Cys Ile Pro Thr Gly Pro Tyr Pro Cys Gly Lys Gln Thr
                165                 170                 175
Leu Glu Arg Arg Lys Arg Ser Val Ala Gln Ala Thr Ser Ser Ser Gly
                180                 185                 190
Glu Ala Pro Asp Ser Ile Thr Trp Lys Pro Tyr Asp Ala Ala Asp Leu
                195                 200                 205
Asp Pro Thr Glu Asn Pro Phe Asp Leu Leu Asp Phe Asn Gln Thr Gln
                210                 215                 220
Pro Glu Arg Gly Asp Asn Asn Leu Thr Arg Lys Ala Thr Asn Ala Thr
225                 230                 235                 240
Leu Ser Pro Arg Ile Val Gly Gly Gln Glu Cys Lys Asp Gly Glu Cys
                245                 250                 255
Pro Trp Gln Ala Leu Leu Ile Asn Glu Glu Asn Glu Gly Phe Cys Gly
                260                 265                 270
Gly Thr Ile Leu Ser Glu Phe Tyr Ile Leu Thr Ala Ala His Cys Leu
                275                 280                 285
Tyr Gln Ala Lys Arg Phe Lys Val Arg Val Gly Asp Arg Asn Thr Glu
                290                 295                 300
Gln Glu Glu Gly Gly Glu Ala Val His Glu Val Glu Val Val Ile Lys
305                 310                 315                 320
His Asn Arg Phe Thr Lys Glu Thr Tyr Asp Phe Asp Ile Ala Val Leu
                325                 330                 335
Arg Leu Lys Thr Pro Ile Thr Phe Arg Met Asn Val Ala Pro Ala Cys
                340                 345                 350
Leu Pro Glu Arg Asp Trp Ala Glu Ser Thr Leu Met Thr Gln Lys Thr
                355                 360                 365
Gly Ile Val Ser Gly Phe Gly Arg Thr His Glu Lys Gly Arg Gln Ser
                370                 375                 380
Thr Arg Leu Lys Met Leu Glu Val Pro Tyr Val Asp Arg Asn Ser Cys
385                 390                 395                 400
Lys Leu Ser Ser Ser Phe Ile Ile Thr Gln Asn Met Phe Cys Ala Gly
                405                 410                 415
Tyr Asp Thr Lys Gln Glu Asp Ala Cys Gln Gly Asp Ser Gly Gly Pro
                420                 425                 430
His Val Thr Arg Phe Lys Asp Thr Tyr Phe Val Thr Gly Ile Val Ser
                435                 440                 445
Trp Gly Glu Gly Cys Ala Arg Lys Gly Lys Tyr Gly Ile Tyr Thr Lys
450                 455                 460
```

```
Val Thr Ala Phe Leu Lys Trp Ile Asp Arg Ser Met Lys Thr Arg Gly
465                 470                 475                 480

Leu Pro Lys Ala Lys Ser His Ala Pro Glu Val Ile Thr Ser Ser Pro
            485                 490                 495

Leu Lys Glu Asp Gln Val Asp Pro Arg Leu Ile Asp Gly Lys
        500                 505                 510

<210> SEQ ID NO 20
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
    210                 215                 220

Pro Glu Arg Gly Asp Asn Asn Leu Thr Arg Lys Ala Thr Gln Ala Thr
225                 230                 235                 240

Leu Ser Pro Arg Ile Val Gly Gly Gln Glu Cys Lys Asp Gly Glu Cys
                245                 250                 255

Pro Trp Gln Ala Leu Leu Ile Asn Glu Glu Asn Glu Gly Phe Cys Gly
            260                 265                 270

Gly Thr Ile Leu Ser Glu Phe Tyr Ile Leu Thr Ala Ala His Cys Leu
        275                 280                 285

Tyr Gln Ala Lys Arg Phe Lys Val Arg Val Gly Asp Arg Asn Thr Glu
    290                 295                 300

Gln Glu Glu Gly Gly Glu Ala Val His Glu Val Glu Val Val Ile Lys
```

```
            305                 310                 315                 320
His Asn Arg Phe Thr Lys Glu Thr Tyr Asp Phe Asp Ile Ala Val Leu
                325                 330                 335

Arg Leu Lys Thr Pro Ile Thr Phe Arg Met Asn Val Ala Pro Ala Cys
                340                 345                 350

Leu Pro Glu Arg Asp Trp Ala Glu Ser Thr Leu Met Thr Gln Lys Thr
                355                 360                 365

Gly Ile Val Ser Gly Phe Gly Arg Thr His Glu Lys Gly Arg Gln Ser
                370                 375                 380

Thr Arg Leu Lys Met Leu Glu Val Pro Tyr Val Asp Arg Asn Ser Cys
385                 390                 395                 400

Lys Leu Ser Ser Ser Phe Ile Ile Thr Gln Asn Met Phe Cys Ala Gly
                405                 410                 415

Tyr Asp Thr Lys Gln Glu Asp Ala Cys Gln Gly Asp Ser Gly Gly Pro
                420                 425                 430

His Val Thr Arg Phe Lys Asp Thr Tyr Phe Val Thr Gly Ile Val Ser
                435                 440                 445

Trp Gly Glu Gly Cys Ala Arg Lys Gly Lys Tyr Gly Ile Tyr Thr Lys
                450                 455                 460

Val Thr Ala Phe Leu Lys Trp Ile Asp Arg Ser Met Lys Thr Arg Gly
465                 470                 475                 480

Leu Pro Lys Ala Lys Ser His Ala Pro Glu Val Ile Thr Ser Ser Pro
                485                 490                 495

Leu Lys Glu Asp Gln Val Asp Pro Arg Leu Ile Asp Gly Lys
                500                 505                 510

<210> SEQ ID NO 21
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
                20                  25                  30

Asn Ile Leu Ala Arg Val Arg Arg Ala Asn Ser Phe Leu Glu Glu Met
                35                  40                  45

Lys Lys Gly His Leu Glu Arg Glu Cys Met Glu Glu Thr Cys Ser Tyr
                50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
                100                 105                 110

Leu Glu Gly Phe Glu Gly Lys Asn Cys Glu Leu Phe Thr Arg Lys Leu
                115                 120                 125

Cys Ser Leu Asp Asn Gly Asp Cys Asp Gln Phe Cys His Glu Glu Gln
                130                 135                 140

Asn Ser Val Val Cys Ser Cys Ala Arg Gly Tyr Thr Leu Ala Asp Asn
145                 150                 155                 160
```

```
Gly Lys Ala Cys Ile Pro Thr Gly Pro Tyr Pro Cys Gly Lys Gln Thr
            165                 170                 175

Leu Glu Arg Arg Lys Arg Ser Val Ala Gln Ala Thr Ser Ser Ser Gly
        180                 185                 190

Glu Ala Pro Asp Ser Ile Thr Trp Lys Pro Tyr Asp Ala Ala Asp Leu
    195                 200                 205

Asp Pro Thr Glu Asn Pro Phe Asp Leu Leu Asp Phe Asn Gln Thr Gln
210                 215                 220

Pro Glu Arg Gly Asp Asn Asn Leu Thr Arg Thr Ser Lys Leu Thr Arg
225                 230                 235                 240

Ile Val Gly Gly Gln Glu Cys Lys Asp Gly Glu Cys Pro Trp Gln Ala
                245                 250                 255

Leu Leu Ile Asn Glu Glu Asn Glu Gly Phe Cys Gly Gly Thr Ile Leu
            260                 265                 270

Ser Glu Phe Tyr Ile Leu Thr Ala Ala His Cys Leu Tyr Gln Ala Lys
        275                 280                 285

Arg Phe Lys Val Arg Val Gly Asp Arg Asn Thr Glu Gln Glu Glu Gly
    290                 295                 300

Gly Glu Ala Val His Glu Val Glu Val Val Ile Lys His Asn Arg Phe
305                 310                 315                 320

Thr Lys Glu Thr Tyr Asp Phe Asp Ile Ala Val Leu Arg Leu Lys Thr
                325                 330                 335

Pro Ile Thr Phe Arg Met Asn Val Ala Pro Ala Cys Leu Pro Glu Arg
            340                 345                 350

Asp Trp Ala Glu Ser Thr Leu Met Thr Gln Lys Thr Gly Ile Val Ser
        355                 360                 365

Gly Phe Gly Arg Thr His Glu Lys Gly Arg Gln Ser Thr Arg Leu Lys
    370                 375                 380

Met Leu Glu Val Pro Tyr Val Asp Arg Asn Ser Cys Lys Leu Ser Ser
385                 390                 395                 400

Ser Phe Ile Ile Thr Gln Asn Met Phe Cys Ala Gly Tyr Asp Thr Lys
                405                 410                 415

Gln Glu Asp Ala Cys Gln Gly Asp Ser Gly Gly Pro His Val Thr Arg
            420                 425                 430

Phe Lys Asp Thr Tyr Phe Val Thr Gly Ile Val Ser Trp Gly Glu Gly
        435                 440                 445

Cys Ala Arg Lys Gly Lys Tyr Gly Ile Tyr Thr Lys Val Thr Ala Phe
    450                 455                 460

Leu Lys Trp Ile Asp Arg Ser Met Lys Thr Arg Gly Leu Pro Lys Ala
465                 470                 475                 480

Lys Ser His Ala Pro Glu Val Ile Thr Ser Ser Pro Leu Lys Glu Asp
                485                 490                 495

Gln Val Asp Pro Arg Leu Ile Asp Gly Lys
            500                 505

<210> SEQ ID NO 22
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Gly Arg Pro Leu His Leu Val Leu Leu Ser Ala Ser Leu Ala Gly
1               5                   10                  15
```

```
Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
        35                  40                  45

Lys Lys Gly His Leu Glu Arg Glu Cys Met Glu Thr Cys Ser Tyr
50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
            115                 120                 125

Cys Ser Leu Asp Asn Gly Asp Cys Asp Gln Phe Cys His Glu Glu Gln
130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
            195                 200                 205

Asp Pro Thr Glu Asn Pro Phe Asp Leu Leu Asp Phe Asn Gln Thr Gln
210                 215                 220

Pro Glu Arg Gly Asp Asn Asn Leu Thr Arg Phe Asn Asp Phe Thr Arg
225                 230                 235                 240

Ile Val Gly Gly Gln Glu Cys Lys Asp Gly Glu Cys Pro Trp Gln Ala
                245                 250                 255

Leu Leu Ile Asn Glu Glu Asn Glu Gly Phe Cys Gly Gly Thr Ile Leu
            260                 265                 270

Ser Glu Phe Tyr Ile Leu Thr Ala Ala His Cys Leu Tyr Gln Ala Lys
            275                 280                 285

Arg Phe Lys Val Arg Val Gly Asp Arg Asn Thr Glu Gln Glu Glu Gly
            290                 295                 300

Gly Glu Ala Val His Glu Val Glu Val Ile Lys His Asn Arg Phe
305                 310                 315                 320

Thr Lys Glu Thr Tyr Asp Phe Asp Ile Ala Val Leu Arg Leu Lys Thr
                325                 330                 335

Pro Ile Thr Phe Arg Met Asn Val Ala Pro Ala Cys Leu Pro Glu Arg
            340                 345                 350

Asp Trp Ala Glu Ser Thr Leu Met Thr Gln Lys Thr Gly Ile Val Ser
            355                 360                 365

Gly Phe Gly Arg Thr His Glu Lys Gly Arg Gln Ser Thr Arg Leu Lys
            370                 375                 380

Met Leu Glu Val Pro Tyr Val Asp Arg Asn Ser Cys Lys Leu Ser Ser
385                 390                 395                 400

Ser Phe Ile Ile Thr Gln Asn Met Phe Cys Ala Gly Tyr Asp Thr Lys
                405                 410                 415

Gln Glu Asp Ala Cys Gln Gly Asp Ser Gly Gly Pro His Val Thr Arg
            420                 425                 430
```

```
Phe Lys Asp Thr Tyr Phe Val Thr Gly Ile Val Ser Trp Gly Glu Gly
            435                 440                 445

Cys Ala Arg Lys Gly Lys Tyr Gly Ile Tyr Thr Lys Val Thr Ala Phe
        450                 455                 460

Leu Lys Trp Ile Asp Arg Ser Met Lys Thr Arg Gly Leu Pro Lys Ala
465                 470                 475                 480

Lys Ser His Ala Pro Glu Val Ile Thr Ser Pro Leu Lys Glu Asp
            485                 490                 495

Gln Val Asp Pro Arg Leu Ile Asp Gly Lys
            500                 505

<210> SEQ ID NO 23
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
210                 215                 220

Pro Glu Arg Gly Asp Asn Asn Leu Thr Arg Leu Ser Ser Met Thr Arg
225                 230                 235                 240

Ile Val Gly Gly Gln Glu Cys Lys Asp Gly Glu Cys Pro Trp Gln Ala
                245                 250                 255

Leu Leu Ile Asn Glu Glu Asn Glu Gly Phe Cys Gly Gly Thr Ile Leu
            260                 265                 270

Ser Glu Phe Tyr Ile Leu Thr Ala Ala His Cys Leu Tyr Gln Ala Lys
        275                 280                 285
```

```
Arg Phe Lys Val Arg Val Gly Asp Arg Asn Thr Glu Gln Glu Glu Gly
        290                 295                 300

Gly Glu Ala Val His Glu Val Glu Val Ile Lys His Asn Arg Phe
305                 310                 315                 320

Thr Lys Glu Thr Tyr Asp Phe Asp Ile Ala Val Leu Arg Leu Lys Thr
                    325                 330                 335

Pro Ile Thr Phe Arg Met Asn Val Ala Pro Ala Cys Leu Pro Glu Arg
                340                 345                 350

Asp Trp Ala Glu Ser Thr Leu Met Thr Gln Lys Thr Gly Ile Val Ser
            355                 360                 365

Gly Phe Gly Arg Thr His Glu Lys Gly Arg Gln Ser Thr Arg Leu Lys
        370                 375                 380

Met Leu Glu Val Pro Tyr Val Asp Arg Asn Ser Cys Lys Leu Ser Ser
385                 390                 395                 400

Ser Phe Ile Ile Thr Gln Asn Met Phe Cys Ala Gly Tyr Asp Thr Lys
                    405                 410                 415

Gln Glu Asp Ala Cys Gln Gly Asp Ser Gly Gly Pro His Val Thr Arg
                420                 425                 430

Phe Lys Asp Thr Tyr Phe Val Thr Gly Ile Val Ser Trp Gly Glu Gly
            435                 440                 445

Cys Ala Arg Lys Gly Lys Tyr Gly Ile Tyr Thr Lys Val Thr Ala Phe
450                 455                 460

Leu Lys Trp Ile Asp Arg Ser Met Lys Thr Arg Gly Leu Pro Lys Ala
465                 470                 475                 480

Lys Ser His Ala Pro Glu Val Ile Thr Ser Ser Pro Leu Lys Glu Asp
                    485                 490                 495

Gln Val Asp Pro Arg Leu Ile Asp Gly Lys
                500                 505

<210> SEQ ID NO 24
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
                20                  25                  30

Asn Ile Leu Ala Arg Val Arg Arg Ala Asn Ser Phe Leu Glu Glu Met
            35                  40                  45

Lys Lys Gly His Leu Glu Arg Glu Cys Met Glu Glu Thr Cys Ser Tyr
        50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
                100                 105                 110

Leu Glu Gly Phe Glu Gly Lys Asn Cys Glu Leu Phe Thr Arg Lys Leu
            115                 120                 125

Cys Ser Leu Asp Asn Gly Asp Cys Asp Gln Phe Cys His Glu Glu Gln
```

```
            130                 135                 140
Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
210                 215                 220

Pro Glu Arg Gly Asp Asn Asn Leu Thr Arg Pro Pro Ser Leu Thr Arg
225                 230                 235                 240

Ile Val Gly Gly Gln Glu Cys Lys Asp Gly Glu Cys Pro Trp Gln Ala
                245                 250                 255

Leu Leu Ile Asn Glu Glu Asn Glu Gly Phe Cys Gly Gly Thr Ile Leu
            260                 265                 270

Ser Glu Phe Tyr Ile Leu Thr Ala Ala His Cys Leu Tyr Gln Ala Lys
        275                 280                 285

Arg Phe Lys Val Arg Val Gly Asp Arg Asn Thr Glu Gln Glu Glu Gly
290                 295                 300

Gly Glu Ala Val His Glu Val Glu Val Val Ile Lys His Asn Arg Phe
305                 310                 315                 320

Thr Lys Glu Thr Tyr Asp Phe Asp Ile Ala Val Leu Arg Leu Lys Thr
                325                 330                 335

Pro Ile Thr Phe Arg Met Asn Val Ala Pro Ala Cys Leu Pro Glu Arg
            340                 345                 350

Asp Trp Ala Glu Ser Thr Leu Met Thr Gln Lys Thr Gly Ile Val Ser
        355                 360                 365

Gly Phe Gly Arg Thr His Glu Lys Gly Arg Gln Ser Thr Arg Leu Lys
370                 375                 380

Met Leu Glu Val Pro Tyr Val Asp Arg Asn Ser Cys Lys Leu Ser Ser
385                 390                 395                 400

Ser Phe Ile Ile Thr Gln Asn Met Phe Cys Ala Gly Tyr Asp Thr Lys
                405                 410                 415

Gln Glu Asp Ala Cys Gln Gly Asp Ser Gly Gly Pro His Val Thr Arg
            420                 425                 430

Phe Lys Asp Thr Tyr Phe Val Thr Gly Ile Val Ser Trp Gly Glu Gly
        435                 440                 445

Cys Ala Arg Lys Gly Lys Tyr Gly Ile Tyr Thr Lys Val Thr Ala Phe
        450                 455                 460

Leu Lys Trp Ile Asp Arg Ser Met Lys Thr Arg Gly Leu Pro Lys Ala
465                 470                 475                 480

Lys Ser His Ala Pro Glu Val Ile Thr Ser Ser Pro Leu Lys Glu Asp
                485                 490                 495

Gln Val Asp Pro Arg Leu Ile Asp Gly Lys
            500                 505
```

<210> SEQ ID NO 25
<211> LENGTH: 506
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
        35                  40                  45

Lys Lys Gly His Leu Glu Arg Glu Cys Met Glu Thr Cys Ser Tyr
50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
210                 215                 220

Pro Glu Arg Gly Asp Asn Asn Leu Thr Arg Leu Ser Cys Gly Gln Arg
225                 230                 235                 240

Ile Val Gly Gly Gln Glu Cys Lys Asp Gly Glu Cys Pro Trp Gln Ala
                245                 250                 255

Leu Leu Ile Asn Glu Glu Asn Glu Gly Phe Cys Gly Gly Thr Ile Leu
            260                 265                 270

Ser Glu Phe Tyr Ile Leu Thr Ala Ala His Cys Leu Tyr Gln Ala Lys
        275                 280                 285

Arg Phe Lys Val Arg Val Gly Asp Arg Asn Thr Glu Gln Glu Glu Gly
290                 295                 300

Gly Glu Ala Val His Glu Val Glu Val Val Ile Lys His Asn Arg Phe
305                 310                 315                 320

Thr Lys Glu Thr Tyr Asp Phe Asp Ile Ala Val Leu Arg Leu Lys Thr
                325                 330                 335

Pro Ile Thr Phe Arg Met Asn Val Ala Pro Ala Cys Leu Pro Glu Arg
            340                 345                 350

Asp Trp Ala Glu Ser Thr Leu Met Thr Gln Lys Thr Gly Ile Val Ser
        355                 360                 365

Gly Phe Gly Arg Thr His Glu Lys Gly Arg Gln Ser Thr Arg Leu Lys
            370                 375                 380

Met Leu Glu Val Pro Tyr Val Asp Arg Asn Ser Cys Lys Leu Ser Ser
385                 390                 395                 400

Ser Phe Ile Ile Thr Gln Asn Met Phe Cys Ala Gly Tyr Asp Thr Lys

```
                    405                 410                 415
Gln Glu Asp Ala Cys Gln Gly Asp Ser Gly Gly Pro His Val Thr Arg
                420                 425                 430

Phe Lys Asp Thr Tyr Phe Val Thr Gly Ile Val Ser Trp Gly Glu Gly
            435                 440                 445

Cys Ala Arg Lys Gly Lys Tyr Gly Ile Tyr Thr Lys Val Thr Ala Phe
        450                 455                 460

Leu Lys Trp Ile Asp Arg Ser Met Lys Thr Arg Gly Leu Pro Lys Ala
465                 470                 475                 480

Lys Ser His Ala Pro Glu Val Ile Thr Ser Ser Pro Leu Lys Glu Asp
                485                 490                 495

Gln Val Asp Pro Arg Leu Ile Asp Gly Lys
                500                 505

<210> SEQ ID NO 26
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
                20                  25                  30

Asn Ile Leu Ala Arg Val Arg Arg Ala Asn Ser Phe Leu Glu Glu Met
            35                  40                  45

Lys Lys Gly His Leu Glu Arg Glu Cys Met Glu Glu Thr Cys Ser Tyr
        50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Asp Ser Ile Thr Trp Lys Pro
            180                 185                 190

Tyr Asp Ala Ala Asp Leu Asp Pro Thr Glu Asn Pro Phe Asp Leu Leu
        195                 200                 205

Asp Phe Asn Gln Thr Gln Pro Glu Arg Gly Asp Asn Asn Leu Thr Arg
210                 215                 220

Asp Phe Leu Ala Glu Gly Gly Val Arg Ile Val Gly Gly Gln Glu
225                 230                 235                 240

Cys Lys Asp Gly Glu Cys Pro Trp Gln Ala Leu Leu Ile Asn Glu Glu
                245                 250                 255
```

```
Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Gly Gly Glu Ala Val His Glu
    290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
    370                 375                 380

Val Asp Arg Asn Ser Cys Lys Leu Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys Glu Asp Gln Val Asp Pro Arg Leu
                485                 490                 495

Ile Asp Gly Lys
            500

<210> SEQ ID NO 27
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110
```

```
Leu Glu Gly Phe Glu Gly Lys Asn Cys Glu Leu Phe Thr Arg Lys Leu
            115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Asp Ser Ile Thr Trp Lys Pro
                180                 185                 190

Tyr Asp Ala Ala Asp Leu Asp Pro Thr Glu Asn Pro Phe Asp Leu Leu
                195                 200                 205

Asp Phe Asn Gln Thr Gln Pro Glu Arg Gly Asp Asn Asn Leu Thr Arg
    210                 215                 220

Asp Phe Leu Ala Glu Gly Leu Thr Pro Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
                260                 265                 270

Thr Ala Ala His Cys Leu Tyr Gln Ala Lys Arg Phe Lys Val Arg Val
                275                 280                 285

Gly Asp Arg Asn Thr Glu Gln Glu Glu Gly Gly Glu Ala Val His Glu
                290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
                340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
        370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
                420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys Glu Asp Gln Val Asp Pro Arg Leu
                485                 490                 495

Ile Asp Gly Lys
            500

<210> SEQ ID NO 28
<211> LENGTH: 500
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Asp Ser Ile Thr Trp Lys Pro
            180                 185                 190

Tyr Asp Ala Ala Asp Leu Asp Pro Thr Glu Asn Pro Phe Asp Leu Leu
        195                 200                 205

Asp Phe Asn Gln Thr Gln Pro Glu Arg Gly Asp Asn Asn Leu Thr Arg
    210                 215                 220

Lys Ala Thr Asn Ala Thr Leu Ser Pro Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Glu Gly Gly Glu Ala Val His Glu
    290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
    370                 375                 380
```

```
Val Asp Arg Asn Ser Cys Lys Leu Ser Ser Phe Ile Ile Thr Gln
385                 390                 395                 400

Asn Met Phe Cys Ala Gly Tyr Asp Thr Lys Gln Glu Asp Ala Cys Gln
            405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
            435                 440                 445

Tyr Gly Ile Tyr Thr Lys Val Thr Ala Phe Leu Lys Trp Ile Asp Arg
            450                 455                 460

Ser Met Lys Thr Arg Gly Leu Pro Lys Ala Lys Ser His Ala Pro Glu
465                 470                 475                 480

Val Ile Thr Ser Ser Pro Leu Lys Glu Asp Gln Val Asp Pro Arg Leu
            485                 490                 495

Ile Asp Gly Lys
            500

<210> SEQ ID NO 29
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
            35                  40                  45

Lys Lys Gly His Leu Glu Arg Glu Cys Met Glu Glu Thr Cys Ser Tyr
50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
            115                 120                 125

Cys Ser Leu Asp Asn Gly Asp Cys Asp Gln Phe Cys His Glu Glu Gln
130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Asp Ser Ile Thr Trp Lys Pro
            180                 185                 190

Tyr Asp Ala Ala Asp Leu Asp Pro Thr Glu Asn Pro Phe Asp Leu Leu
            195                 200                 205

Asp Phe Asn Gln Thr Gln Pro Glu Arg Gly Asp Asn Asn Leu Thr Arg
            210                 215                 220

Lys Ala Thr Gln Ala Thr Leu Ser Pro Arg Ile Val Gly Gly Gln Glu
```

```
                       225                 230                 235                 240

Cys Lys Asp Gly Glu Cys Pro Trp Gln Ala Leu Leu Ile Asn Glu Glu
                        245                 250                 255

Asn Glu Gly Phe Cys Gly Gly Thr Ile Leu Ser Glu Phe Tyr Ile Leu
                        260                 265                 270

Thr Ala Ala His Cys Leu Tyr Gln Ala Lys Arg Phe Lys Val Arg Val
                        275                 280                 285

Gly Asp Arg Asn Thr Glu Gln Glu Glu Gly Glu Ala Val His Glu
                        290                 295                 300

Val Glu Val Val Ile Lys His Asn Arg Phe Thr Lys Glu Thr Tyr Asp
        305                 310                 315                 320

Phe Asp Ile Ala Val Leu Arg Leu Lys Thr Pro Ile Thr Phe Arg Met
                        325                 330                 335

Asn Val Ala Pro Ala Cys Leu Pro Glu Arg Asp Trp Ala Glu Ser Thr
                        340                 345                 350

Leu Met Thr Gln Lys Thr Gly Ile Val Ser Gly Phe Gly Arg Thr His
                        355                 360                 365

Glu Lys Gly Arg Gln Ser Thr Arg Leu Lys Met Leu Glu Val Pro Tyr
                        370                 375                 380

Val Asp Arg Asn Ser Cys Lys Leu Ser Ser Ser Phe Ile Ile Thr Gln
        385                 390                 395                 400

Asn Met Phe Cys Ala Gly Tyr Asp Thr Lys Gln Glu Asp Ala Cys Gln
                        405                 410                 415

Gly Asp Ser Gly Gly Pro His Val Thr Arg Phe Lys Asp Thr Tyr Phe
                        420                 425                 430

Val Thr Gly Ile Val Ser Trp Gly Glu Gly Cys Ala Arg Lys Gly Lys
                        435                 440                 445

Tyr Gly Ile Tyr Thr Lys Val Thr Ala Phe Leu Lys Trp Ile Asp Arg
                        450                 455                 460

Ser Met Lys Thr Arg Gly Leu Pro Lys Ala Lys Ser His Ala Pro Glu
        465                 470                 475                 480

Val Ile Thr Ser Ser Pro Leu Lys Glu Asp Gln Val Asp Pro Arg Leu
                        485                 490                 495

Ile Asp Gly Lys
                        500

<210> SEQ ID NO 30
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Gly Arg Pro Leu His Leu Val Leu Leu Ser Ala Ser Leu Ala Gly
        1               5                   10                  15

Leu Leu Leu Leu Gly Glu Ser Leu Phe Ile Arg Arg Glu Gln Ala Asn
                        20                  25                  30

Asn Ile Leu Ala Arg Val Arg Arg Ala Asn Ser Phe Leu Glu Glu Met
                        35                  40                  45

Lys Lys Gly His Leu Glu Arg Glu Cys Met Glu Glu Thr Cys Ser Tyr
                        50                  55                  60

Glu Glu Ala Arg Glu Val Phe Glu Asp Ser Asp Lys Thr Asn Glu Phe
        65                  70                  75                  80
```

-continued

```
Trp Asn Lys Tyr Lys Asp Gly Asp Gln Cys Glu Thr Ser Pro Cys Gln
                85                  90                  95
Asn Gln Gly Lys Cys Lys Asp Gly Leu Gly Glu Tyr Thr Cys Thr Cys
            100                 105                 110
Leu Glu Gly Phe Glu Gly Lys Asn Cys Glu Leu Phe Thr Arg Lys Leu
        115                 120                 125
Cys Ser Leu Asp Asn Gly Asp Cys Asp Gln Phe Cys His Glu Glu Gln
    130                 135                 140
Asn Ser Val Val Cys Ser Cys Ala Arg Gly Tyr Thr Leu Ala Asp Asn
145                 150                 155                 160
Gly Lys Ala Cys Ile Pro Thr Gly Pro Tyr Pro Cys Gly Lys Gln Thr
                165                 170                 175
Leu Glu Arg Arg Lys Arg Ser Val Ala Gln Ala Thr Ser Asp Ser Ile
            180                 185                 190
Thr Trp Lys Pro Tyr Asp Ala Ala Asp Leu Asp Pro Thr Glu Asn Pro
        195                 200                 205
Phe Asp Leu Leu Asp Phe Asn Gln Thr Gln Pro Glu Arg Gly Asp Asn
    210                 215                 220
Asn Leu Thr Arg Thr Ser Lys Leu Thr Arg Ile Val Gly Gly Gln Glu
225                 230                 235                 240
Cys Lys Asp Gly Glu Cys Pro Trp Gln Ala Leu Leu Ile Asn Glu Glu
                245                 250                 255
Asn Glu Gly Phe Cys Gly Gly Thr Ile Leu Ser Glu Phe Tyr Ile Leu
            260                 265                 270
Thr Ala Ala His Cys Leu Tyr Gln Ala Lys Arg Phe Lys Val Arg Val
        275                 280                 285
Gly Asp Arg Asn Thr Glu Gln Glu Glu Gly Gly Glu Ala Val His Glu
    290                 295                 300
Val Glu Val Val Ile Lys His Asn Arg Phe Thr Lys Glu Thr Tyr Asp
305                 310                 315                 320
Phe Asp Ile Ala Val Leu Arg Leu Lys Thr Pro Ile Thr Phe Arg Met
                325                 330                 335
Asn Val Ala Pro Ala Cys Leu Pro Glu Arg Asp Trp Ala Glu Ser Thr
            340                 345                 350
Leu Met Thr Gln Lys Thr Gly Ile Val Ser Gly Phe Gly Arg Thr His
        355                 360                 365
Glu Lys Gly Arg Gln Ser Thr Arg Leu Lys Met Leu Glu Val Pro Tyr
    370                 375                 380
Val Asp Arg Asn Ser Cys Lys Leu Ser Ser Phe Ile Ile Thr Gln
385                 390                 395                 400
Asn Met Phe Cys Ala Gly Tyr Asp Thr Lys Gln Glu Asp Ala Cys Gln
                405                 410                 415
Gly Asp Ser Gly Gly Pro His Val Thr Arg Phe Lys Asp Thr Tyr Phe
            420                 425                 430
Val Thr Gly Ile Val Ser Trp Gly Glu Gly Cys Ala Arg Lys Gly Lys
        435                 440                 445
Tyr Gly Ile Tyr Thr Lys Val Thr Ala Phe Leu Lys Trp Ile Asp Arg
    450                 455                 460
Ser Met Lys Thr Arg Gly Leu Pro Lys Ala Lys Ser His Ala Pro Glu
465                 470                 475                 480
Val Ile Thr Ser Ser Pro Leu Lys Glu Asp Gln Val Asp Pro Arg Leu
                485                 490                 495
Ile Asp Gly Lys
```

<210> SEQ ID NO 31
<211> LENGTH: 500
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

```
Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Asp Ser Ile
            180                 185                 190

Thr Trp Lys Pro Tyr Asp Ala Ala Asp Leu Asp Pro Thr Glu Asn Pro
        195                 200                 205

Phe Asp Leu Leu Asp Phe Asn Gln Thr Gln Pro Glu Arg Gly Asp Asn
    210                 215                 220

Asn Leu Thr Arg Phe Asn Asp Phe Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Gly Gly Glu Ala Val His Glu
    290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350
```

```
Leu Met Thr Gln Lys Thr Gly Ile Val Ser Gly Phe Gly Arg Thr His
            355                 360                 365

Glu Lys Gly Arg Gln Ser Thr Arg Leu Lys Met Leu Glu Val Pro Tyr
        370                 375                 380

Val Asp Arg Asn Ser Cys Lys Leu Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
            435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys Glu Asp Gln Val Asp Pro Arg Leu
                485                 490                 495

Ile Asp Gly Lys
            500

<210> SEQ ID NO 32
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Asp Ser Ile
            180                 185                 190

Thr Trp Lys Pro Tyr Asp Ala Ala Asp Leu Asp Pro Thr Glu Asn Pro
        195                 200                 205
```

```
Phe Asp Leu Leu Asp Phe Asn Gln Thr Gln Pro Glu Arg Gly Asp Asn
            210                 215                 220

Asn Leu Thr Arg Leu Ser Ser Met Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Glu Gly Glu Ala Val His Glu
        290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
370                 375                 380

Val Asp Arg Asn Ser Cys Lys Leu Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys Glu Asp Gln Val Asp Pro Arg Leu
                485                 490                 495

Ile Asp Gly Lys
            500

<210> SEQ ID NO 33
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
        35                  40                  45

Lys Lys Gly His Leu Glu Arg Glu Cys Met Glu Glu Thr Cys Ser Tyr
```

```
            50                  55                  60
Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
            115                 120                 125

Cys Ser Leu Asp Asn Gly Asp Cys Asp Gln Phe Cys His Glu Glu Gln
            130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Asp Ser Ile
            180                 185                 190

Thr Trp Lys Pro Tyr Asp Ala Ala Asp Leu Asp Pro Thr Glu Asn Pro
            195                 200                 205

Phe Asp Leu Leu Asp Phe Asn Gln Thr Gln Pro Glu Arg Gly Asp Asn
210                 215                 220

Asn Leu Thr Arg Pro Pro Ser Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
            275                 280                 285

Gly Asp Arg Asn Thr Glu Gln Glu Glu Gly Gly Glu Ala Val His Glu
            290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
            355                 360                 365

Glu Lys Gly Arg Gln Ser Thr Arg Leu Lys Met Leu Glu Val Pro Tyr
370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
            435                 440                 445

Tyr Gly Ile Tyr Thr Lys Val Thr Ala Phe Leu Lys Trp Ile Asp Arg
            450                 455                 460

Ser Met Lys Thr Arg Gly Leu Pro Lys Ala Lys Ser His Ala Pro Glu
465                 470                 475                 480
```

-continued

```
Val Ile Thr Ser Ser Pro Leu Lys Glu Asp Gln Val Asp Pro Arg Leu
            485                 490                 495

Ile Asp Gly Lys
        500

<210> SEQ ID NO 34
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
        35                  40                  45

Lys Lys Gly His Leu Glu Arg Glu Cys Met Glu Glu Thr Cys Ser Tyr
50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Asp Ser Ile
            180                 185                 190

Thr Trp Lys Pro Tyr Asp Ala Ala Asp Leu Asp Pro Thr Glu Asn Pro
        195                 200                 205

Phe Asp Leu Leu Asp Phe Asn Gln Thr Gln Pro Glu Arg Gly Asp Asn
210                 215                 220

Asn Leu Thr Arg Leu Ser Cys Gly Gln Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Glu Gly Glu Ala Val His Glu
290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
```

```
                      325                 330                 335
Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
    370                 375                 380

Val Asp Arg Asn Ser Cys Lys Leu Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys Glu Asp Gln Val Asp Pro Arg Leu
                485                 490                 495

Ile Asp Gly Lys
            500

<210> SEQ ID NO 35
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
atgggaagac ccctgcatct ggtgctgctg tccgcctcac tggctgggct gctgctgctg      60
ggagaatctc tgtttatccg acgggagcag gctaacaata tcctggcaag agtgcgagaa     120
gccaactctt tcctggagga aatgaagaaa ggccacctgg agcgggaatg catggaggaa     180
acctgtagtt acgaggaagc cagagaggtg ttcgaagact cagataagac aaacgagttt     240
tggaataagt acaaagacgg cgatcagtgc gaaactagcc atgtcagaac caggggaag     300 tgcaaagatg gactgggcga gtacacctgc acatgtctgg agggattcga aggcaagaat     360
tgcgaactgt ttaccagaaa gctgtgctcc ctggataacg gcgactgcga tcagttttgt     420
catgaggaac agaattccgt ggtctgctct tgtgccaggg gatacacact ggctgacaat     480
ggcaaggcat gcatccccac cggcccctat ccttgtggga gcagacact  ggagaggcgc     540 aaaaggtcag tggctcaggc aactagctcc tctggcgagg ccccgatag cattacctgg     600 aaaccttatg acgccgctga cctggacccc acagagaacc cctttgacct gctggacttc     660
aaccagacac agcctgaaag aggcgataac aatctgacta ggatcgtggg aggacaggag     720
tgcaaggacg gagaatgtcc atggcaggcc ctgctgatta cgaggaaaa tgagggattc     780 tgcggaggca ctatcctgag cgagttctac attctgaccg cagcccactg tctgtatcag     840
gctaagcgat caaagtgcg ggtcggcgac agaaacaccg agcaggagga agggggagaa     900
gcagtgcacg aggtcgaagt ggtcatcaag cataatcgct tcactaaaga gacctacgac     960
tttgatatcg ctgtgctgcg cctgaagaca cctattactt tccgaatgaa cgtcgcccct    1020
```

```
gcttgcctgc cagagcgaga ttgggccgaa agcaccctga tgacacagaa aactggcatc    1080
gtgagcgggt ttggacggac acatgagaag ggcaggcagt ccactcgcct gaaaatgctg    1140
gaagtgccct acgtcgaccg gaactcttgt aagctgagta gcagcttcat cattacccag    1200
aatatgtttt gcgccgggta tgacacaaag caggaggatg cttgtcaggg agacagtggc    1260
gggcctcacg tgactaggtt caaagatact tattttgtga ccggcatcgt cagctgggga    1320
gagggatgcg cacgcaaggg gaaatacgga atctatacca aggtgacagc ctttctgaaa    1380
tggattgacc gatctatgaa gacccggggg ctgccaaagg caaaaagtca tgcccccgag    1440
gtcattacca gttcccctct gaaagaagac caggtggacc caaggctgat tgacggcaag    1500
```

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gggactttcc tacttggcag t                                              21

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ttcactgcat tctagttgtg gt                                             22

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtggagactg aagttaggcc ag                                             22

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cttcatttcc tccaggaaag agttggc                                        27

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cagatggctg gcaactagaa                                            20

<210> SEQ ID NO 41
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tccttctgcc aggaagtcct gtgtctggtt gaagtccagc aggtca               46

<210> SEQ ID NO 42
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tcaggccctc ggccaggaag tcctgtgtct ggttgaagtc cagcaggtca           50

<210> SEQ ID NO 43
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tggcgttggt ggccttctgt gtctggttga agtccagcag gtcaa                45

<210> SEQ ID NO 44
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
agggtggcct gggtggcctt ctgtgtctgg ttgaagtcca gcaggtca             48

<210> SEQ ID NO 45
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tggtcagctt gctggtgcct ctttcaggct gtgtctggtt ga                   42

<210> SEQ ID NO 46
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46

```
tggtgaagtc gttgaagcct ctttcaggct gtgtctggtt gaag           44
```

<210> SEQ ID NO 47
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47

```
tggtcatgct gctcaggcct ctttcaggct gtgtctggtt gaagt          45
```

<210> SEQ ID NO 48
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48

```
tggtcaggct gggagggcct ctttcaggct gtgtctggtt gaag           44
```

<210> SEQ ID NO 49
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49

```
tctggccgca ggacaggcct ctttcaggct gtgtctggtt gaag           44
```

<210> SEQ ID NO 50
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50

```
ctccttctgc caggaagtcc ctagtcagat tgttatcgcc tctttcaggc     50
```

<210> SEQ ID NO 51
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51

```
gtcaggccct cggccaggaa gtccctagtc agattgttat cgcctctttc aggc  54
```

<210> SEQ ID NO 52
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52

```
agggtggcgt tggtggcctt cctagtcaga ttgttatcgc tctttcagg c    51
```

<210> SEQ ID NO 53
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
agggtggcct gggtggcctt cctagtcaga ttgttatcgc ctctttcagg c        51

<210> SEQ ID NO 54
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tcagcttgct ggtcctagtc agattgttat cgcctctttc aggc                 44

<210> SEQ ID NO 55
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ggtgaagtcg ttgaacctag tcagattgtt atcgcctctt tcaggc               46

<210> SEQ ID NO 56
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
atgctgctca gcctagtcag attgttatcg cctctttcag gc                   42

<210> SEQ ID NO 57
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gtcaggctgg gaggcctagt cagattgtta tcgcctcttt caggc                45

<210> SEQ ID NO 58
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tctggccgca ggacagccta gtcagattgt tatcgcctct ttcaggc              47

```
<210> SEQ ID NO 59
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gcagaaggag gaggagtgag gatcgtggga ggacaggagt gca            43

<210> SEQ ID NO 60
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
agggcctgac ccctaggatc gtgggaggac aggagtgcaa gga            43

<210> SEQ ID NO 61
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
aggccaccaa cgccaccctg tccctagga tcgtgggagg acaggagtgc aagga       55

<210> SEQ ID NO 62
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
caggccaccc tgagccctag gatcgtggga ggacaggagt gcaag          45

<210> SEQ ID NO 63
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
accagcaagc tgaccaggat cgtgggagga caggagtgca agga           44

<210> SEQ ID NO 64
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
caacgacttc accaggatcg tgggaggaca ggagtgcaag ga             42
```

```
<210> SEQ ID NO 65
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tgagcagcat gaccaggatc gtgggaggac aggagtgcaa gga          43

<210> SEQ ID NO 66
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cctcccagcc tgaccaggat cgtgggagga caggagtgca agga         44

<210> SEQ ID NO 67
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tgtcctgcgg ccagaggatc gtgggaggac aggagtgcaa gga          43

<210> SEQ ID NO 68
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
tcttccattt cagctagcaa gcttgccgcc ac                      32

<210> SEQ ID NO 69
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
agctctagac aattgattta aatggatcct cacttgccgt c            41

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
accagctgct agcaagcttg ccg                                23

<210> SEQ ID NO 71
```

```
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gaaactattt aaatggatcc tcacttgccg tcaatcagc                             39

<210> SEQ ID NO 72
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ccaggtaatg ctatcagcca ctgacctttt gcgcctctc                             39

<210> SEQ ID NO 73
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tcagtggctg atagcattac ctggaaacct tatgacgc                              38

<210> SEQ ID NO 74
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gctagttgcc tgagccactg acctttttg                                        28

<210> SEQ ID NO 75
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gctcaggcaa ctagcgatag cattacctgg aaaccttatg acgc                       44

<210> SEQ ID NO 76
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
atgggaagac ccctgcatct ggtgctgctg tccgcctcac tggctgggct gctgctgctg      60
ggagaatctc tgtttatccg acgggagcag gctaacaata tcctggcaag agtgcggaga     120
gccaactctt tcctggagga aatgaagaaa ggccacctgg agcgggaatg catggaggaa     180
```

```
acctgtagtt acgaggaagc cagagaggtg ttcgaagact cagataagac aaacgagttt      240
tggaataagt acaaagacgg cgatcagtgc gaaactagcc catgtcagaa ccaggggaag      300
tgcaaagatg gactgggcga gtacacctgc acatgtctgg agggattcga aggcaagaat      360
tgcgaactgt ttaccagaaa gctgtgctcc ctggataacg gcgactgcga tcagttttgt      420
catgaggaac agaattccgt ggtctgctct tgtgccaggg gatacacact ggctgacaat      480
ggcaaggcat gcatccccac cggcccctat ccttgtggga agcagacact ggagaggcgc      540
aaaaggtcag tggctcaggc aactagctcc tctggcgagg ccccgatag cattacctgg       600 aaaccttatg acgccgctga cctggacccc acagagaacc cctttgacct gctggacttc      660
aaccagacac aggacttcct ggcagaagga ggaggagtga ggatcgtggg aggacaggag      720
tgcaaggacg gagaatgtcc atggcaggcc ctgctgatta cgaggaaaa tgagggattc        780 tgcggaggca ctatcctgag cgagttctac attctgaccg cagcccactg tctgtatcag      840
gctaagcgat tcaaagtgcg ggtcggcgac agaaacaccg agcaggagga agggggagaa      900
gcagtgcacg aggtcgaagt ggtcatcaag cataatcgct tcactaaaga gacctacgac      960
tttgatatcg ctgtgctgcg cctgaagaca cctattactt tccgaatgaa cgtcgcccct     1020
gcttgcctgc cagagcgaga ttgggccgaa agcaccctga tgacacagaa aactggcatc     1080
gtgagcgggt ttggacggac acatgagaag ggcaggcagt ccactcgcct gaaaatgctg     1140
gaagtgccct acgtcgaccg gaactcttgt aagctgagta gcagcttcat cattacccag     1200
aatatgtttt gcgccgggta tgacacaaag caggaggatg cttgtcaggg agacagtggc     1260
gggcctcacg tgactaggtt caaagatact tattttgtga ccggcatcgt cagctgggga     1320
gagggatgcg cacgcaaggg gaaatacgga atctatacca aggtgacagc ctttctgaaa     1380
tggattgacc gatctatgaa gacccggggg ctgccaaagg caaaaagtca tgcccccgag     1440
gtcattacca gttcccctct gaaagaagac caggtggacc caaggctgat tgacggcaag     1500
```

<210> SEQ ID NO 77
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

```
atgggaagac ccctgcatct ggtgctgctg tccgcctcac tggctgggct gctgctgctg       60
ggagaatctc tgtttatccg acgggagcag gctaacaata tcctggcaag agtgcggaga      120
gccaactctt tcctggagga aatgaagaaa ggccacctgg agcgggaatg catggaggaa      180
acctgtagtt acgaggaagc cagagaggtg ttcgaagact cagataagac aaacgagttt      240
tggaataagt acaaagacgg cgatcagtgc gaaactagcc catgtcagaa ccaggggaag      300
tgcaaagatg gactgggcga gtacacctgc acatgtctgg agggattcga aggcaagaat      360
tgcgaactgt ttaccagaaa gctgtgctcc ctggataacg gcgactgcga tcagttttgt      420
catgaggaac agaattccgt ggtctgctct tgtgccaggg gatacacact ggctgacaat      480
ggcaaggcat gcatccccac cggcccctat ccttgtggga agcagacact ggagaggcgc      540
aaaaggtcag tggctcaggc aactagctcc tctggcgagg ccccgatag cattacctgg       600 aaaccttatg acgccgctga cctggacccc acagagaacc cctttgacct gctggacttc      660
aaccagacac aggacttcct ggccgagggc ctgacccta ggatcgtggg aggacaggag        720
```

```
tgcaaggacg gagaatgtcc atggcaggcc ctgctgatta acgaggaaaa tgagggattc      780
tgcggaggca ctatcctgag cgagttctac attctgaccg cagcccactg tctgtatcag      840
gctaagcgat tcaaagtgcg ggtcggcgac agaaacaccg agcaggagga agggggagaa      900
gcagtgcacg aggtcgaagt ggtcatcaag cataatcgct tcactaaaga gacctacgac      960
tttgatatcg ctgtgctgcg cctgaagaca cctattactt tccgaatgaa cgtcgcccct     1020
gcttgcctgc cagagcgaga ttgggccgaa agcaccctga tgacacagaa aactggcatc     1080
gtgagcgggt ttggacggac acatgagaag ggcaggcagt ccactcgcct gaaaatgctg     1140
gaagtgccct acgtcgaccg gaactcttgt aagctgagta gcagcttcat cattacccag     1200
aatatgtttt gcgccgggta tgacacaaag caggaggatg cttgtcaggg agacagtggc     1260
gggcctcacg tgactaggtt caaagatact tattttgtga ccggcatcgt cagctgggga     1320
gagggatgcg cacgcaaggg gaaatacgga atctatacca aggtgacagc ctttctgaaa     1380
tggattgacc gatctatgaa gacccggggg ctgccaaagg caaaaagtca tgcccccgag     1440
gtcattacca gttcccctct gaaagaagac caggtggacc caaggctgat tgacggcaag     1500
```

<210> SEQ ID NO 78
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78

```
atgggaagac ccctgcatct ggtgctgctg tccgcctcac tggctgggct gctgctgctg       60
ggagaatctc tgtttatccg acgggagcag gctaacaata tcctggcaag agtgcggaga      120
gccaactctt tcctggagga aatgaagaaa ggccacctgg agcgggaatg catggaggaa      180
acctgtagtt acgaggaagc cagagaggtg ttcgaagact cagataagac aaacgagttt      240
tggaataagt acaaagacgg cgatcagtgc gaaactagcc catgtcagaa ccaggggaag      300
tgcaaagatg gactgggcga gtacacctgc acatgtctgg agggattcga aggcaagaat      360
tgcgaactgt ttaccagaaa gctgtgctcc ctggataacg gcgactgcga tcagttttgt      420
catgaggaac agaattccgt ggtctgctct tgtgccaggg gatacacact ggctgacaat      480
ggcaaggcat gcatccccac cggcccctat ccttgtggga gcagacact ggagaggcgc       540 aaaaggtcag tggctcaggc aactagctcc tctggcgagg ccccgatag cattacctgg       600 aaaccttatg cgccgctga cctggacccc acagagaacc cctttgacct gctggacttc       660
aaccagacac agaaggccac caacgccacc ctgtccccta ggatcgtggg aggacaggag      720
tgcaaggacg gagaatgtcc atggcaggcc ctgctgatta acgaggaaaa tgagggattc      780
tgcggaggca ctatcctgag cgagttctac attctgaccg cagcccactg tctgtatcag      840
gctaagcgat tcaaagtgcg ggtcggcgac agaaacaccg agcaggagga agggggagaa      900
gcagtgcacg aggtcgaagt ggtcatcaag cataatcgct tcactaaaga gacctacgac      960
tttgatatcg ctgtgctgcg cctgaagaca cctattactt tccgaatgaa cgtcgcccct     1020
gcttgcctgc cagagcgaga ttgggccgaa agcaccctga tgacacagaa aactggcatc     1080
gtgagcgggt ttggacggac acatgagaag ggcaggcagt ccactcgcct gaaaatgctg     1140
gaagtgccct acgtcgaccg gaactcttgt aagctgagta gcagcttcat cattacccag     1200
aatatgtttt gcgccgggta tgacacaaag caggaggatg cttgtcaggg agacagtggc     1260
```

```
gggcctcacg tgactaggtt caaagatact tattttgtga ccggcatcgt cagctgggga   1320
gagggatgcg cacgcaaggg gaaatacgga atctatacca aggtgacagc ctttctgaaa   1380
tggattgacc gatctatgaa gacccggggg ctgccaaagg caaaaagtca tgcccccgag   1440
gtcattacca gttcccctct gaaagaagac caggtggacc caaggctgat tgacggcaag   1500
```

<210> SEQ ID NO 79
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

```
atgggaagac ccctgcatct ggtgctgctg tccgcctcac tggctgggct gctgctgctg    60
ggagaatctc tgtttatccg acgggagcag gctaacaata tcctggcaag agtgcggaga   120
gccaactctt tcctggagga aatgaagaaa ggccacctgg agcgggaatg catggaggaa   180
acctgtagtt acgaggaagc cagagaggtg ttcgaagact cagataagac aaacgagttt   240
tggaataagt acaaagacgg cgatcagtgc gaaactagcc atgtcagaa ccaggggaag   300 tgcaaagatg gactgggcga gtacacctgc acatgtctgg agggattcga aggcaagaat   360
tgcgaactgt ttaccagaaa gctgtgctcc ctggataacg gcgactgcga tcagttttgt   420
catgaggaac agaattccgt ggtctgctct tgtgccaggg gatacacact ggctgacaat   480
ggcaaggcat gcatccccac cggcccctat ccttgtggga gcagacact ggagaggcgc   540 aaaaggtcag tggctcaggc aactagctcc ctggcgagg ccccgatag cattacctgg   600 aaaccttatg acgccgctga cctggacccc acagagaacc cctttgacct gctggacttc   660
aaccagacac agaaggccac ccaggccacc ctgagcccta ggatcgtggg aggacaggag   720
tgcaaggacg gagaatgtcc atggcaggcc ctgctgatta cgaggaaaa tgagggattc   780 tgcggaggca ctatcctgag cgagttctac attctgaccg cagcccactg tctgtatcag   840
gctaagcgat tcaaagtgcg ggtcggcgac agaaacaccg agcaggagga agggggagaa   900
gcagtgcacg aggtcgaagt ggtcatcaag cataatcgct tcactaaaga gacctacgac   960
tttgatatcg ctgtgctgcg cctgaagaca cctattactt tccgaatgaa cgtcgcccct  1020
gcttgcctgc cagagcgaga ttgggccgaa agcaccctga tgacacagaa aactggcatc  1080
gtgagcgggt ttggacggac acatgagaag ggcaggcagt ccactcgcct gaaaatgctg  1140
gaagtgccct acgtcgaccg gaactcttgt aagctgagta gcagcttcat cattacccag  1200
aatatgtttt gcgccgggta tgacacaaag caggaggatg cttgtcaggg agacagtggc  1260
gggcctcacg tgactaggtt caaagatact tattttgtga ccggcatcgt cagctgggga  1320
gagggatgcg cacgcaaggg gaaatacgga atctatacca aggtgacagc ctttctgaaa  1380
tggattgacc gatctatgaa gacccggggg ctgccaaagg caaaaagtca tgcccccgag  1440
gtcattacca gttcccctct gaaagaagac caggtggacc caaggctgat tgacggcaag  1500
```

<210> SEQ ID NO 80
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

```
atgggaagac ccctgcatct ggtgctgctg tccgcctcac tggctgggct gctgctgctg      60
ggagaatctc tgtttatccg acgggagcag gctaacaata tcctggcaag agtgcggaga     120
gccaactctt tcctggagga aatgaagaaa ggccacctgg agcgggaatg catggaggaa     180
acctgtagtt acgaggaagc cagagaggtg ttcgaagact cagataagac aaacgagttt     240
tggaataagt acaaagacgg cgatcagtgc gaaactagcc catgtcagaa ccaggggaag     300
tgcaaagatg gactgggcga gtacacctgc acatgtctgg agggattcga aggcaagaat     360
tgcgaactgt ttaccagaaa gctgtgctcc ctggataacg gcgactgcga tcagttttgt     420
catgaggaac agaattccgt ggtctgctct tgtgccaggg gatacacact ggctgacaat     480
ggcaaggcat gcatccccac cggcccctat ccttgtggga agcagacact ggagaggcgc     540
aaaaggtcag tggctcaggc aactagctcc tctggcgagg ccccgatag cattacctgg      600
aaaccttatg acgccgctga cctggacccc acagagaacc cctttgacct gctggacttc     660
aaccagacac agcctgaaag aggcaccagc aagctgacca ggatcgtggg aggacaggag     720
tgcaaggacg gagaatgtcc atggcaggcc ctgctgatta acgaggaaaa tgagggattc     780
tgcggaggca ctatcctgag cgagttctac attctgaccg cagcccactg tctgtatcag     840
gctaagcgat tcaaagtgcg ggtcggcgac agaaacaccg agcaggagga agggggagaa     900
gcagtgcacg aggtcgaagt ggtcatcaag cataatcgct tcactaaaga gacctacgac     960
tttgatatcg ctgtgctgcg cctgaagaca cctattactt tccgaatgaa cgtcgcccct    1020
gcttgcctgc cagagcgaga ttgggccgaa agcaccctga tgacacagaa aactggcatc    1080
gtgagcgggt ttggacggac acatgagaag ggcaggcagt ccactcgcct gaaaatgctg    1140
gaagtgccct acgtcgaccg gaactcttgt aagctgagta gcagcttcat cattacccag    1200
aatatgtttt gcgccgggta tgacacaaag caggaggatg cttgtcaggg agacagtggc    1260
gggcctcacg tgactaggtt caaagatact tattttgtga ccggcatcgt cagctgggga    1320
gagggatgcg cacgcaaggg gaaatacgga atctatacca aggtgacagc ctttctgaaa    1380
tggattgacc gatctatgaa gacccggggg ctgccaaagg caaaaagtca tgccccgag    1440
gtcattacca gttcccctct gaaagaagac caggtggacc caaggctgat tgacggcaag    1500
```

<210> SEQ ID NO 81
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

```
atgggaagac ccctgcatct ggtgctgctg tccgcctcac tggctgggct gctgctgctg      60
ggagaatctc tgtttatccg acgggagcag gctaacaata tcctggcaag agtgcggaga     120
gccaactctt tcctggagga aatgaagaaa ggccacctgg agcgggaatg catggaggaa     180
acctgtagtt acgaggaagc cagagaggtg ttcgaagact cagataagac aaacgagttt     240
tggaataagt acaaagacgg cgatcagtgc gaaactagcc catgtcagaa ccaggggaag     300
tgcaaagatg gactgggcga gtacacctgc acatgtctgg agggattcga aggcaagaat     360
tgcgaactgt ttaccagaaa gctgtgctcc ctggataacg gcgactgcga tcagttttgt     420
catgaggaac agaattccgt ggtctgctct tgtgccaggg gatacacact ggctgacaat     480
```

```
ggcaaggcat gcatccccac cggcccctat ccttgtggga agcagacact ggagaggcgc    540
aaaaggtcag tggctcaggc aactagctcc tctggcgagg ccccgatag cattacctgg     600 aaaccttatg acgccgctga cctggacccc acagagaacc cctttgacct gctggacttc    660
aaccagacac agcctgaaag aggcttcaac gacttcacca ggatcgtggg aggacaggag    720
tgcaaggacg gagaatgtcc atggcaggcc ctgctgatta acgaggaaaa tgagggattc    780
tgcggaggca ctatcctgag cgagttctac attctgaccg cagcccactg tctgtatcag    840
gctaagcgat tcaaagtgcg ggtcggcgac agaaacaccg agcaggagga agggggagaa    900
gcagtgcacg aggtcgaagt ggtcatcaag cataatcgct tcactaaaga gacctacgac    960
tttgatatcg ctgtgctgcg cctgaagaca cctattactt tccgaatgaa cgtcgcccct   1020
gcttgcctgc cagagcgaga ttgggccgaa agcaccctga tgacacagaa aactggcatc   1080
gtgagcgggt ttggacggac acatgagaag ggcaggcagt ccactcgcct gaaaatgctg   1140
gaagtgccct acgtcgaccg gaactcttgt aagctgagta gcagcttcat cattacccag   1200
aatatgtttt gcgccgggta tgacacaaag caggaggatg cttgtcaggg agacagtggc   1260
gggcctcacg tgactaggtt caaagatact tattttgtga ccggcatcgt cagctgggga   1320
gagggatgcg cacgcaaggg gaaatacgga atctatacca aggtgacagc ctttctgaaa   1380
tggattgacc gatctatgaa gacccggggg ctgccaaagg caaaaagtca tgcccccgag   1440
gtcattacca gttcccctct gaaagaagac caggtggacc caaggctgat tgacggcaag   1500
```

<210> SEQ ID NO 82
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82

```
atgggaagac ccctgcatct ggtgctgctg tccgcctcac tggctgggct gctgctgctg     60
ggagaatctc tgtttatccg acgggagcag gctaacaata tcctggcaag agtgcggaga    120
gccaactctt cctggagga atgaagaaa ggccacctgg agcgggaatg catggaggaa     180
acctgtagtt acgaggaagc cagagaggtg ttcgaagact cagataagac aaacgagttt    240
tggaataagt acaaagacgg cgatcagtgc gaaactagcc atgtcagaa ccaggggaag     300 tgcaaagatg gactgggcga gtacacctgc acatgtctgg agggattcga aggcaagaat    360
tgcgaactgt ttaccagaaa gctgtgctcc ctggataacg gcgactgcga tcagttttgt    420
catgaggaac agaattccgt ggtctgctct tgtgccaggg gatacacact ggctgacaat    480
ggcaaggcat gcatccccac cggcccctat ccttgtggga agcagacact ggagaggcgc    540
aaaaggtcag tggctcaggc aactagctcc tctggcgagg ccccgatag cattacctgg     600 aaaccttatg acgccgctga cctggacccc acagagaacc cctttgacct gctggacttc    660
aaccagacac agcctgaaag aggcctgagc agcatgacca ggatcgtggg aggacaggag    720
tgcaaggacg gagaatgtcc atggcaggcc ctgctgatta acgaggaaaa tgagggattc    780
tgcggaggca ctatcctgag cgagttctac attctgaccg cagcccactg tctgtatcag    840
gctaagcgat tcaaagtgcg ggtcggcgac agaaacaccg agcaggagga agggggagaa    900
gcagtgcacg aggtcgaagt ggtcatcaag cataatcgct tcactaaaga gacctacgac    960
tttgatatcg ctgtgctgcg cctgaagaca cctattactt tccgaatgaa cgtcgcccct   1020
```

| | |
|---|---|
| gcttgcctgc cagagcgaga ttgggccgaa agcaccctga tgacacagaa aactggcatc | 1080 |
| gtgagcgggt ttggacggac acatgagaag ggcaggcagt ccactcgcct gaaaatgctg | 1140 |
| gaagtgccct acgtcgaccg gaactcttgt aagctgagta gcagcttcat cattacccag | 1200 |
| aatatgtttt gcgccgggta tgacacaaag caggaggatg cttgtcaggg agacagtggc | 1260 |
| gggcctcacg tgactaggtt caaagatact tattttgtga ccggcatcgt cagctgggga | 1320 |
| gagggatgcg cacgcaaggg gaaatacgga atctatacca aggtgacagc ctttctgaaa | 1380 |
| tggattgacc gatctatgaa gacccggggg ctgccaaagg caaaaagtca tgccccgag | 1440 |
| gtcattacca gttcccctct gaaagaagac caggtggacc caaggctgat tgacggcaag | 1500 |

<210> SEQ ID NO 83
<211> LENGTH: 1500
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 83

| | |
|---|---|
| atgggaagac ccctgcatct ggtgctgctg tccgcctcac tggctgggct gctgctgctg | 60 |
| ggagaatctc tgtttatccg acgggagcag gctaacaata tcctggcaag agtgcggaga | 120 |
| gccaactctt tcctggagga aatgaagaaa ggccacctgg agcgggaatg catggaggaa | 180 |
| acctgtagtt acgaggaagc cagagaggtg ttcgaagact cagataagac aaacgagttt | 240 |
| tggaataagt acaaagacgg cgatcagtgc gaaactagcc catgtcagaa ccaggggaag | 300 |
| tgcaaagatg gactgggcga gtacacctgc acatgtctgg agggattcga aggcaagaat | 360 |
| tgcgaactgt ttaccagaaa gctgtgctcc ctggataacg gcgactgcga tcagttttgt | 420 |
| catgaggaac agaattccgt ggtctgctct tgtgccaggg gatacacact ggctgacaat | 480 |
| ggcaaggcat gcatccccac cggccctat ccttgtggga agcagacact ggagaggcgc | 540 |
| aaaaggtcag tggctcaggc aactagctcc tctggcgagg cccccgatag cattacctgg | 600 |
| aaaccttatg acgccgctga cctgaccccc acagagaacc cctttgacct gctggacttc | 660 |
| aaccagacac agcctgaaag aggccctccc agcctgacca ggatcgtggg aggacaggag | 720 |
| tgcaaggacg gagaatgtcc atggcaggcc ctgctgatta cgaggaaaa tgagggattc | 780 |
| tgcggaggca ctatcctgag cgagttctac attctgaccg cagcccactg tctgtatcag | 840 |
| gctaagcgat tcaaagtgcg ggtcggcgac agaaacaccg agcaggagga aggggagaa | 900 |
| gcagtgcacg aggtcgaagt ggtcatcaag cataatcgct tcactaaaga gacctacgac | 960 |
| tttgatatcg ctgtgctgcg cctgaagaca ccattactt tccgaatgaa cgtcgcccct | 1020 |
| gcttgcctgc cagagcgaga ttgggccgaa agcaccctga tgacacagaa aactggcatc | 1080 |
| gtgagcgggt ttggacggac acatgagaag ggcaggcagt ccactcgcct gaaaatgctg | 1140 |
| gaagtgccct acgtcgaccg gaactcttgt aagctgagta gcagcttcat cattacccag | 1200 |
| aatatgtttt gcgccgggta tgacacaaag caggaggatg cttgtcaggg agacagtggc | 1260 |
| gggcctcacg tgactaggtt caaagatact tattttgtga ccggcatcgt cagctgggga | 1320 |
| gagggatgcg cacgcaaggg gaaatacgga atctatacca aggtgacagc ctttctgaaa | 1380 |
| tggattgacc gatctatgaa gacccggggg ctgccaaagg caaaaagtca tgccccgag | 1440 |
| gtcattacca gttcccctct gaaagaagac caggtggacc caaggctgat tgacggcaag | 1500 |

<210> SEQ ID NO 84

<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84

```
atgggaagac ccctgcatct ggtgctgctg tccgcctcac tggctgggct gctgctgctg      60
ggagaatctc tgtttatccg acgggagcag gctaacaata tcctggcaag agtgcggaga     120
gccaactctt tcctggagga aatgaagaaa ggccacctgg agcgggaatg catggaggaa     180
acctgtagtt acgaggaagc cagagaggtg ttcgaagact cagataagac aaacgagttt     240
tggaataagt acaaagacgg cgatcagtgc gaaactagcc atgtcagaa ccaggggaag      300
tgcaaagatg gactgggcga gtacacctgc acatgtctgg agggattcga aggcaagaat     360
tgcgaactgt ttaccagaaa gctgtgctcc ctggataacg gcgactgcga tcagttttgt     420
catgaggaac agaattccgt ggtctgctct tgtgccaggg gatacacact ggctgacaat     480
ggcaaggcat gcatccccac cggcccctat ccttgtggga agcagacact ggagaggcgc     540
aaaaggtcag tggctcaggc aactagctcc tctggcgagg cccccgatag cattacctgg     600
aaaccttatg acgccgctga cctggacccc acagagaacc cctttgacct gctggacttc     660
aaccagacac agcctgaaag aggcctgtcc tgcggccaga ggatcgtggg aggacaggag     720
tgcaaggacg gagaatgtcc atggcaggcc ctgctgatta cgaggaaaa tgagggattc      780
tgcgaggcca ctatcctgag cgagttctac attctgaccg cagcccactg tctgtatcag     840
gctaagcgat tcaaagtgcg ggtcggcgac agaaacaccg agcaggagga aggggagaa      900
gcagtgcacg aggtcgaagt ggtcatcaag cataatcgct tcactaaaga gacctacgac     960
tttgatatcg ctgtgctgcg cctgaagaca cctattactt tccgaatgaa cgtcgcccct    1020
gcttgcctgc cagagcgaga ttgggccgaa agcaccctga tgacacagaa aactggcatc    1080
gtgagcgggt ttggacggac acatgagaag ggcaggcagt ccactcgcct gaaaatgctg    1140
gaagtgccct acgtcgaccg gaactcttgt aagctgagta gcagcttcat cattacccag    1200
aatatgtttt gcgccgggta tgacacaaag caggaggatg cttgtcaggg agacagtggc    1260
gggcctcacg tgactaggtt caaagatact tattttgtga ccggcatcgt cagctgggga    1320
gagggatgcg cacgcaaggg gaaatacgga atctatacca aggtgacagc ctttctgaaa    1380
tggattgacc gatctatgaa gacccggggg ctgccaaagg caaaaagtca tgccccgag     1440
gtcattacca gttcccctct gaagaagac caggtggacc caaggctgat tgacggcaag     1500
```

<210> SEQ ID NO 85
<211> LENGTH: 1530
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85

```
atgggaagac ccctgcatct ggtgctgctg tccgcctcac tggctgggct gctgctgctg      60
ggagaatctc tgtttatccg acgggagcag gctaacaata tcctggcaag agtgcggaga     120
gccaactctt tcctggagga aatgaagaaa ggccacctgg agcgggaatg catggaggaa     180
acctgtagtt acgaggaagc cagagaggtg ttcgaagact cagataagac aaacgagttt     240
tggaataagt acaaagacgg cgatcagtgc gaaactagcc atgtcagaa ccaggggaag      300
```

```
tgcaaagatg gactgggcga gtacacctgc acatgtctgg agggattcga aggcaagaat    360
tgcgaactgt ttaccagaaa gctgtgctcc ctggataacg gcgactgcga tcagttttgt    420
catgaggaac agaattccgt ggtctgctct tgtgccaggg gatacacact ggctgacaat    480
ggcaaggcat gcatccccac cggcccctat ccttgtggga agcagacact ggagaggcgc    540
aaaaggtcag tggctcaggc aactagctcc tctggcgagg cccccgatag cattacctgg    600
aaaccttatg acgccgctga cctggacccc acagagaacc cctttgacct gctggacttc    660
aaccagacac agcctgaaag aggcgataac aatctgacta gggacttcct ggcagaagga    720
ggaggagtga ggatcgtggg aggacaggag tgcaaggacg gagaatgtcc atggcaggcc    780
ctgctgatta acgaggaaaa tgagggattc tgcggaggca ctatcctgag cgagttctac    840
attctgaccg cagcccactg tctgtatcag gctaagcgat tcaaagtgcg ggtcggcgac    900
agaaacaccg agcaggagga aggggagaa gcagtgcacg aggtcgaagt ggtcatcaag    960
cataatcgct tcactaaaga gacctacgac tttgatatcg ctgtgctgcg cctgaagaca    1020
cctattactt tccgaatgaa cgtcgcccct gcttgcctgc cagagcgaga ttgggccgaa    1080 agcacctga tgacacagaa aactggcatc gtgagcgggt ttggacggac acatgagaag    1140
ggcaggcagt ccactcgcct gaaaatgctg gaagtgccct acgtcgaccg gaactcttgt    1200
aagctgagta gcagcttcat cattacccag aatatgtttt gcgccgggta tgacacaaag    1260
caggaggatg cttgtcaggg agacagtggc gggcctcacg tgactaggtt caaagatact    1320
tattttgtga ccggcatcgt cagctgggga gagggatgcg cacgcaaggg gaaatacgga    1380 atctataccα aggtgacagc ctttctgaaa tggattgacc gatctatgaa gacccggggg    1440
ctgccaaagg caaaaagtca tgcccccgag gtcattacca gttcccctct gaaagaagac    1500
caggtggacc caaggctgat tgacggcaag                                    1530

<210> SEQ ID NO 86
<211> LENGTH: 1530
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
atgggaagac ccctgcatct ggtgctgctg tccgcctcac tggctgggct gctgctgctg    60
ggagaatctc tgtttatccg acgggagcag gctaacaata tcctggcaag agtgcggaga    120
gccaactctt tcctggagga aatgaagaaa ggccacctgg agcgggaatg catggaggaa    180
acctgtagtt acgaggaagc cagagaggtg ttcgaagact cagataagac aaacgagttt    240
tggaataagt acaaagacgg cgatcagtgc gaaactagcc catgtcagaa ccaggggaag    300
tgcaaagatg gactgggcga gtacacctgc acatgtctgg agggattcga aggcaagaat    360
tgcgaactgt ttaccagaaa gctgtgctcc ctggataacg gcgactgcga tcagttttgt    420
catgaggaac agaattccgt ggtctgctct tgtgccaggg gatacacact ggctgacaat    480
ggcaaggcat gcatccccac cggcccctat ccttgtggga agcagacact ggagaggcgc    540
aaaaggtcag tggctcaggc aactagctcc tctggcgagg cccccgatag cattacctgg    600
aaaccttatg acgccgctga cctggacccc acagagaacc cctttgacct gctggacttc    660
aaccagacac agcctgaaag aggcgataac aatctgacta gggacttcct ggccgagggc    720 ctgacccta ggatcgtggg aggacaggag tgcaaggacg gagaatgtcc atggcaggcc    780
```

```
ctgctgatta acgaggaaaa tgagggattc tgcggaggca ctatcctgag cgagttctac      840
attctgaccg cagcccactg tctgtatcag gctaagcgat tcaaagtgcg ggtcggcgac      900
agaaacaccg agcaggagga aggggggagaa gcagtgcacg aggtcgaagt ggtcatcaag     960
cataatcgct tcactaaaga gacctacgac tttgatatcg ctgtgctgcg cctgaagaca     1020
cctattactt tccgaatgaa cgtcgcccct gcttgcctgc cagagcgaga ttgggccgaa     1080
agcaccctga tgacacagaa aactggcatc gtgagcgggt ttggacggac acatgagaag    1140
ggcaggcagt ccactcgcct gaaaatgctg gaagtgccct acgtcgaccg gaactcttgt     1200
aagctgagta gcagcttcat cattacccag aatatgtttt gcgccgggta tgacacaaag    1260
caggaggatg cttgtcaggg agacagtggc gggcctcacg tgactaggtt caaagatact     1320
tattttgtga ccggcatcgt cagctgggga gagggatgcg cacgcaaggg gaaatacgga    1380
atctatacca aggtgacagc ctttctgaaa tggattgacc gatctatgaa gacccggggg    1440
ctgccaaagg caaaaagtca tgcccccgag gtcattacca gttcccctct gaaagaagac    1500
caggtggacc caaggctgat tgacggcaag                                      1530

<210> SEQ ID NO 87
<211> LENGTH: 1530
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
atgggaagac ccctgcatct ggtgctgctg tccgcctcac tggctgggct gctgctgctg       60
ggagaatctc tgtttatccg acgggagcag gctaacaata tcctggcaag agtgcgagaa     120
gccaactctt tcctggagga aatgaagaaa ggccacctgg agcgggaatg catggaggaa     180
acctgtagtt acgaggaagc cagagaggtg ttcgaagact cagataagac aaacgagttt     240
tggaataagt acaaagacgg cgatcagtgc gaaactagcc catgtcagaa ccaggggaag     300
tgcaaagatg gactgggcga gtacacctgc acatgtctgg agggattcga aggcaagaat     360
tgcgaactgt ttaccagaaa gctgtgctcc ctggataacg gcgactgcga tcagttttgt     420
catgaggaac agaattccgt ggtctgctct tgtgccaggg gatacacact ggctgacaat     480
ggcaaggcat gcatccccac cggcccctat ccttgtggga gcagacact ggagaggcgc      540 aaaaggtcag tggctcaggc aactagctcc tctggcgagg cccccgatag cattacctgg    600
aaaccttatg cgccgctga cctggacccc acagagaacc cctttgacct gctggacttc      660
aaccagacac agcctgaaag aggcgataac aatctgacta ggaaggccac caacgccacc      720
ctgtccccta ggatcgtggg aggacaggag tgcaaggacg gagaatgtcc atggcaggcc    780
ctgctgatta acgaggaaaa tgagggattc tgcggaggca ctatcctgag cgagttctac    840
attctgaccg cagcccactg tctgtatcag gctaagcgat tcaaagtgcg ggtcggcgac    900
agaaacaccg agcaggagga aggggggagaa gcagtgcacg aggtcgaagt ggtcatcaag    960
cataatcgct tcactaaaga gacctacgac tttgatatcg ctgtgctgcg cctgaagaca    1020
cctattactt tccgaatgaa cgtcgcccct gcttgcctgc cagagcgaga ttgggccgaa    1080
agcaccctga tgacacagaa aactggcatc gtgagcgggt ttggacggac acatgagaag   1140
ggcaggcagt ccactcgcct gaaaatgctg gaagtgccct acgtcgaccg gaactcttgt    1200
aagctgagta gcagcttcat cattacccag aatatgtttt gcgccgggta tgacacaaag   1260
```

| | | |
|---|---|---|
| caggaggatg cttgtcaggg agacagtggc gggcctcacg tgactaggtt caaagatact | | 1320 |
| tattttgtga ccggcatcgt cagctgggga gagggatgcg cacgcaaggg gaaatacgga | | 1380 |
| atctatacca aggtgacagc ctttctgaaa tggattgacc gatctatgaa gacccggggg | | 1440 |
| ctgccaaagg caaaaagtca tgcccccgag gtcattacca gttcccctct gaagaagac | | 1500 |
| caggtggacc caaggctgat tgacggcaag | | 1530 |

<210> SEQ ID NO 88
<211> LENGTH: 1530
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 88

| | | |
|---|---|---|
| atgggaagac ccctgcatct ggtgctgctg tccgcctcac tggctgggct gctgctgctg | | 60 |
| ggagaatctc tgtttatccg acgggagcag gctaacaata tcctggcaag agtgcggaga | | 120 |
| gccaactctt tcctggagga aatgaagaaa ggccacctgg agcgggaatg catggaggaa | | 180 |
| acctgtagtt acgaggaagc cagagaggtg ttcgaagact cagataagac aaacgagttt | | 240 |
| tggaataagt acaaagacgg cgatcagtgc gaaactagcc catgtcagaa ccaggggaag | | 300 |
| tgcaaagatg gactgggcga gtacacctgc acatgtctgg agggattcga aggcaagaat | | 360 |
| tgcgaactgt ttaccagaaa gctgtgctcc ctggataacg gcgactgcga tcagttttgt | | 420 |
| catgaggaac agaattccgt ggtctgctct tgtgccaggg gatacacact ggctgacaat | | 480 |
| ggcaaggcat gcatccccac cggcccctat ccttgtggga gcagacact ggagaggcgc | | 540 |
| aaaaggtcag tggctcaggc aactagctcc tctggcgagg ccccgatag cattacctgg | | 600 |
| aaaccttatg acgccgctga cctggacccc acagagaacc cctttgacct gctggacttc | | 660 |
| aaccagacac agcctgaaag aggcgataac aatctgacta ggaaggccac ccaggccacc | | 720 |
| ctgagcccta ggatcgtggg aggacaggag tgcaaggacg agaatgtcc atggcaggcc | | 780 |
| ctgctgatta acgaggaaaa tgagggattc tgcggaggca ctatcctgag cgagttctac | | 840 |
| attctgaccg cagcccactg tctgtatcag gctaagcgat caaagtgcg ggtcggcgac | | 900 |
| agaaacaccg agcaggagga aggggagaa gcagtgcacg aggtcgaagt ggtcatcaag | | 960 |
| cataatcgct tcactaaaga gacctacgac tttgatatcg ctgtgctgcg cctgaagaca | | 1020 |
| cctattactt tccgaatgaa cgtcgcccct gcttgcctgc cagagcgaga ttgggccgaa | | 1080 |
| agcaccctga tgacacagaa aactggcatc gtgagcgggt ttggacggac acatgagaag | | 1140 |
| ggcaggcagt ccactcgcct gaaaatgctg gaagtgccct acgtcgaccg gaactcttgt | | 1200 |
| aagctgagta gcagcttcat cattacccag aatatgtttt gcgccgggta tgacacaaag | | 1260 |
| caggaggatg cttgtcaggg agacagtggc gggcctcacg tgactaggtt caaagatact | | 1320 |
| tattttgtga ccggcatcgt cagctgggga gagggatgcg cacgcaaggg gaaatacgga | | 1380 |
| atctatacca aggtgacagc ctttctgaaa tggattgacc gatctatgaa gacccggggg | | 1440 |
| ctgccaaagg caaaaagtca tgcccccgag gtcattacca gttcccctct gaagaagac | | 1500 |
| caggtggacc caaggctgat tgacggcaag | | 1530 |

<210> SEQ ID NO 89
<211> LENGTH: 1518
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 89

```
atgggaagac ccctgcatct ggtgctgctg tccgcctcac tggctgggct gctgctgctg      60
ggagaatctc tgtttatccg acgggagcag gctaacaata tcctggcaag agtgcggaga     120
gccaactctt tcctggagga aatgaagaaa ggccacctgg agcggaatg catggaggaa      180
acctgtagtt acgaggaagc cagagaggtg ttcgaagact cagataagac aaacgagttt     240
tggaataagt acaaagacgg cgatcagtgc gaaactagcc catgtcagaa ccaggggaag     300
tgcaaagatg gactgggcga gtacacctgc acatgtctgg agggattcga aggcaagaat     360
tgcgaactgt ttaccagaaa gctgtgctcc ctggataacg gcgactgcga tcagttttgt     420
catgaggaac agaattccgt ggtctgctct tgtgccaggg gatacacact ggctgacaat     480
ggcaaggcat gcatccccac cggcccctat ccttgtggga agcagacact ggagaggcgc     540
aaaaggtcag tggctcaggc aactagctcc tctggcgagg cccccgatag cattacctgg     600
aaaccttatg acgccgctga cctggacccc acagagaacc cctttgacct gctggacttc     660
aaccagacac agcctgaaag aggcgataac aatctgacta ggaccagcaa gctgaccagg     720
atcgtgggag acaggagtg caaggacgga gaatgtccat ggcaggccct gctgattaac     780
gaggaaaatg agggattctg cggaggcact atcctgagcg agttctacat tctgaccgca     840
gcccactgtc tgtatcaggc taagcgattc aaagtgcggg tcggcgacag aaacaccgag     900
caggaggaag gggagaagc agtgcacgag gtcgaagtgg tcatcaagca taatcgcttc     960
actaaagaga cctacgactt tgatatcgct gtgctgcgcc tgaagacacc tattactttc    1020
cgaatgaacg tcgcccctgc ttgcctgcca gagcgagatt gggccgaaag cacctgatg    1080
acacagaaaa ctggcatcgt gagcgggttt ggacggacac atgagaaggg caggcagtcc    1140
actcgcctga aaatgctgga agtgcccac gtcgaccgga actcttgtaa gctgagtagc    1200
agcttcatca ttacccagaa tatgttttgc gccgggtatg acacaaagca ggaggatgct    1260
tgtcagggag acagtggcgg gcctcacgtg actaggttca agatactta ttttgtgacc    1320
ggcatcgtca gctggggaga gggatgcgca cgcaagggga aatacggaat ctataccaag    1380
gtgacagcct ttctgaaatg gattgaccga tctatgaaga cccgggggct gccaaaggca    1440
aaaagtcatg cccccgaggt cattaccagt tcccctctga agaagacca ggtggaccca    1500
aggctgattg acggcaag                                                 1518
```

<210> SEQ ID NO 90
<211> LENGTH: 1518
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 90

```
atgggaagac ccctgcatct ggtgctgctg tccgcctcac tggctgggct gctgctgctg      60
ggagaatctc tgtttatccg acgggagcag gctaacaata tcctggcaag agtgcggaga     120
gccaactctt tcctggagga aatgaagaaa ggccacctgg agcggaatg catggaggaa      180
acctgtagtt acgaggaagc cagagaggtg ttcgaagact cagataagac aaacgagttt     240
tggaataagt acaaagacgg cgatcagtgc gaaactagcc catgtcagaa ccaggggaag     300
```

```
tgcaaagatg gactgggcga gtacacctgc acatgtctgg agggattcga aggcaagaat    360
tgcgaactgt ttaccagaaa gctgtgctcc ctggataacg cgactgcga tcagttttgt    420 catgaggaac agaattccgt ggtctgctct tgtgccaggg gatacacact ggctgacaat    480
ggcaaggcat gcatccccac cggcccctat ccttgtggga agcagacact ggagaggcgc    540
aaaaggtcag tggctcaggc aactagctcc tctggcgagg cccccgatag cattacctgg    600
aaaccttatg acgccgctga cctggacccc acagagaacc cctttgacct gctggacttc    660
aaccagacac agcctgaaag aggcgataac aatctgacta ggttcaacga cttcaccagg    720
atcgtgggag acaggagtg caaggacgga gaatgtccat ggcaggccct gctgattaac    780
gaggaaaatg agggattctg cggaggcact atcctgagcg agttctacat tctgaccgca    840
gcccactgtc tgtatcaggc taagcgattc aaagtgcggg tcggcgacag aaacaccgag    900
caggaggaag ggggagaagc agtgcacgag gtcgaagtgg tcatcaagca taatcgcttc    960
actaaagaga cctacgactt tgatatcgct gtgctgcgcc tgaagacacc tattactttc   1020
cgaatgaacg tcgcccctgc ttgcctgcca gagcgagatt gggccgaaag caccctgatg   1080
acacagaaaa ctggcatcgt gagcgggttt ggacggacac atgagaaggg caggcagtcc   1140
actcgcctga aaatgctgga agtgccctac gtcgaccgga actcttgtaa gctgagtagc   1200
agcttcatca ttacccagaa tatgttttgc gccgggtatg acacaaagca ggaggatgct   1260
tgtcagggag acagtggcgg gcctcacgtg actaggttca aagatactta ttttgtgacc   1320
ggcatcgtca gctggggaga gggatgcgca cgcaagggga atacggaat ctataccaag   1380 gtgacagcct ttctgaaatg gattgaccga tctatgaaga cccggggggct gccaaaggca   1440 aaaagtcatg cccccgaggt cattaccagt tcccctctga agaagacca ggtggaccca   1500 aggctgattg acggcaag                                                 1518

<210> SEQ ID NO 91
<211> LENGTH: 1518
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
atgggaagac ccctgcatct ggtgctgctg tccgcctcac tggctgggct gctgctgctg     60
ggagaatctc tgtttatccg acgggagcag gctaacaata tcctggcaag agtgcggaga    120
gccaactctt tcctggagga aatgaagaaa ggccacctgg agcgggaatg catggaggaa    180
acctgtagtt acgaggaagc cagagaggtg ttcgaagact cagataagac aaacgagttt    240
tggaataagt acaaagacgg cgatcagtgc gaaactagcc atgtcagaa ccaggggaag    300 tgcaaagatg gactgggcga gtacacctgc acatgtctgg agggattcga aggcaagaat    360
tgcgaactgt ttaccagaaa gctgtgctcc ctggataacg cgactgcga tcagttttgt    420 catgaggaac agaattccgt ggtctgctct tgtgccaggg gatacacact ggctgacaat    480
ggcaaggcat gcatccccac cggcccctat ccttgtggga agcagacact ggagaggcgc    540
aaaaggtcag tggctcaggc aactagctcc tctggcgagg cccccgatag cattacctgg    600
aaaccttatg acgccgctga cctggacccc acagagaacc cctttgacct gctggacttc    660
aaccagacac agcctgaaag aggcgataac aatctgacta ggctgagcag catgaccagg    720
atcgtgggag acaggagtg caaggacgga gaatgtccat ggcaggccct gctgattaac    780
```

| | |
|---|---|
| gaggaaaatg agggattctg cggaggcact atcctgagcg agttctacat tctgaccgca | 840 |
| gcccactgtc tgtatcaggc taagcgattc aaagtgcggg tcggcgacag aaacaccgag | 900 |
| caggaggaag ggggagaagc agtgcacgag gtcgaagtgg tcatcaagca taatcgcttc | 960 |
| actaaagaga cctacgactt tgatatcgct gtgctgcgcc tgaagacacc tattactttc | 1020 |
| cgaatgaacg tcgcccctgc ttgcctgcca gagcgagatt gggccgaaag caccctgatg | 1080 |
| acacagaaaa ctggcatcgt gagcgggttt ggacggacac atgagaaggg caggcagtcc | 1140 |
| actcgcctga aaatgctgga agtgccctac gtcgaccgga actcttgtaa gctgagtagc | 1200 |
| agcttcatca ttacccagaa tatgttttgc gccgggtatg acacaaagca ggaggatgct | 1260 |
| tgtcagggag acagtggcgg gcctcacgtg actaggttca agatactta ttttgtgacc | 1320 |
| ggcatcgtca gctggggaga gggatgcgca cgcaagggga aatacggaat ctataccaag | 1380 |
| gtgacagcct ttctgaaatg gattgaccga tctatgaaga cccgggggct gccaaaggca | 1440 |
| aaaagtcatg cccccgaggt cattaccagt tcccctctga agaagacca ggtggaccca | 1500 |
| aggctgattg acggcaag | 1518 |

<210> SEQ ID NO 92
<211> LENGTH: 1518
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92

| | |
|---|---|
| atgggaagac ccctgcatct ggtgctgctg tccgcctcac tggctgggct gctgctgctg | 60 |
| ggagaatctc tgtttatccg acgggagcag gctaacaata tcctggcaag agtgcggaga | 120 |
| gccaactctt tcctggagga aatgaagaaa ggccacctgg agcgggaatg catggaggaa | 180 |
| acctgtagtt acgaggaagc cagagaggtg ttcgaagact cagataagac aaacgagttt | 240 |
| tggaataagt acaaagacgg cgatcagtgc gaaactagcc atgtcagaa ccaggggaag | 300 |
| tgcaaagatg gactgggcga gtacacctgc acatgtctgg agggattcga aggcaagaat | 360 |
| tgcgaactgt ttaccagaaa gctgtgctcc ctggataacg gcgactgcga tcagttttgt | 420 |
| catgaggaac agaattccgt ggtctgctct tgtgccaggg gatacacact ggctgacaat | 480 |
| ggcaaggcat gcatccccac cggcccctat ccttgtggga gcagacact ggagaggcgc | 540 |
| aaaaggtcag tggctcaggc aactagctcc tctggcgagg ccccgatag cattacctgg | 600 |
| aaaccttatg acgccgctga cctggacccc acagagaacc ctttgacct gctggacttc | 660 |
| aaccagacac agcctgaaag aggcgataac aatctgacta ggcctcccag cctgaccagg | 720 |
| atcgtgggag acaggagtg caaggacgga gaatgtccat ggcaggccct gctgattaac | 780 |
| gaggaaaatg agggattctg cggaggcact atcctgagcg agttctacat tctgaccgca | 840 |
| gcccactgtc tgtatcaggc taagcgattc aaagtgcggg tcggcgacag aaacaccgag | 900 |
| caggaggaag ggggagaagc agtgcacgag gtcgaagtgg tcatcaagca taatcgcttc | 960 |
| actaaagaga cctacgactt tgatatcgct gtgctgcgcc tgaagacacc tattactttc | 1020 |
| cgaatgaacg tcgcccctgc ttgcctgcca gagcgagatt gggccgaaag caccctgatg | 1080 |
| acacagaaaa ctggcatcgt gagcgggttt ggacggacac atgagaaggg caggcagtcc | 1140 |
| actcgcctga aaatgctgga agtgccctac gtcgaccgga actcttgtaa gctgagtagc | 1200 |
| agcttcatca ttacccagaa tatgttttgc gccgggtatg acacaaagca ggaggatgct | 1260 |

```
tgtcagggag acagtggcgg gcctcacgtg actaggttca aagatactta ttttgtgacc    1320
ggcatcgtca gctggggaga gggatgcgca cgcaaggga aatacggaat ctataccaag    1380
gtgacagcct ttctgaaatg gattgaccga tctatgaaga cccgggggct gccaaaggca    1440
aaaagtcatg cccccgaggt cattaccagt tccctctga aagaagacca ggtggaccca    1500
aggctgattg acggcaag                                                  1518
```

<210> SEQ ID NO 93
<211> LENGTH: 1518
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 93

```
atgggaagac ccctgcatct ggtgctgctg tccgcctcac tggctgggct gctgctgctg    60
ggagaatctc tgtttatccg acgggagcag gctaacaata tcctggcaag agtgcggaga    120
gccaactctt tcctggagga aatgaagaaa ggccacctgg agcgggaatg catggaggaa    180
acctgtagtt acgaggaagc cagagaggtg ttcgaagact cagataagac aaacgagttt    240
tggaataagt acaaagacgg cgatcagtgc gaaactagcc catgtcagaa ccaggggaag    300
tgcaaagatg gactgggcga gtacacctgc acatgtctgg agggattcga aggcaagaat    360
tgcgaactgt ttaccagaaa gctgtgctcc ctggataacg gcgactgcga tcagttttgt    420
catgaggaac agaattccgt ggtctgctct tgtgccaggg gatacacact ggctgacaat    480
ggcaaggcat gcatccccac cggcccctat ccttgtggga gcagacact ggagaggcgc     540 aaaaggtcag tggctcaggc aactagctcc tctggcgagg ccccgatag cattacctgg    600 aaaccttatg acgccgctga cctggacccc acagagaacc cctttgacct gctggacttc    660
aaccagacac agcctgaaag aggcgataac aatctgacta ggctgtcctg cggccagagg    720
atcgtgggag gacaggagtg caaggacgga gaatgtccat ggcaggccct gctgattaac    780
gaggaaaatg agggattctg cggaggcact atcctgagcg agttctacat tctgaccgca    840
gcccactgtc tgtatcaggc taagcgattc aaagtgcggg tcggcgacag aaacaccgag    900
caggaggaag gggagaagc agtgcacgag gtcgaagtgg tcatcaagca taatcgcttc    960
actaaagaga cctacgactt tgatatcgct gtgctgcgcc tgaagacacc tattactttc    1020
cgaatgaacg tcgccctgc ttgcctgcca gagcgagatt gggccgaaag caccctgatg    1080
acacagaaaa ctggcatcgt gagcgggttt ggacggacac atgagaaggg caggcagtcc    1140
actcgcctga aaatgctgga agtgccctac gtcgaccgga actcttgtaa gctgagtagc    1200
agcttcatca ttacccagaa tatgttttgc gccgggtatg acacaaagca ggaggatgct    1260
tgtcagggag acagtggcgg gcctcacgtg actaggttca aagatactta ttttgtgacc    1320
ggcatcgtca gctggggaga gggatgcgca cgcaaggga aatacggaat ctataccaag    1380
gtgacagcct ttctgaaatg gattgaccga tctatgaaga cccgggggct gccaaaggca    1440
aaaagtcatg cccccgaggt cattaccagt tccctctga aagaagacca ggtggaccca    1500
aggctgattg acggcaag                                                  1518
```

<210> SEQ ID NO 94
<211> LENGTH: 1500
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 94

| | | | | | |
|---|---|---|---|---|---|
| atgggaagac | ccctgcatct | ggtgctgctg | tccgcctcac | tggctgggct | gctgctgctg | 60 |
| ggagaatctc | tgtttatccg | acgggagcag | gctaacaata | tcctggcaag | agtgcggaga | 120 |
| gccaactctt | tcctggagga | aatgaagaaa | ggccacctgg | agcgggaatg | catggaggaa | 180 |
| acctgtagtt | acgaggaagc | cagagaggtg | ttcgaagact | cagataagac | aaacgagttt | 240 |
| tggaataagt | acaaagacgg | cgatcagtgc | gaaactagcc | catgtcagaa | ccaggggaag | 300 |
| tgcaaagatg | gactgggcga | gtacacctgc | acatgtctgg | agggattcga | aggcaagaat | 360 |
| tgcgaactgt | ttaccagaaa | gctgtgctcc | ctggataacg | gcgactgcga | tcagttttgt | 420 |
| catgaggaac | agaattccgt | ggtctgctct | tgtgccaggg | gatacacact | ggctgacaat | 480 |
| ggcaaggcat | gcatccccac | cggcccctat | ccttgtggga | agcagacact | ggagaggcgc | 540 |
| aaaaggtcag | tggctgatag | cattacctgg | aaaccttatg | acgccgctga | cctggacccc | 600 |
| acagagaacc | cctttgacct | gctggacttc | aaccagacac | agcctgaaag | aggcgataac | 660 |
| aatctgacta | gggacttcct | ggcagaagga | ggaggagtga | ggatcgtggg | aggacaggag | 720 |
| tgcaaggacg | gagaatgtcc | atggcaggcc | ctgctgatta | acgaggaaaa | tgagggattc | 780 |
| tgcgaggca | ctatcctgag | cgagttctac | attctgaccg | cagcccactg | tctgtatcag | 840 |
| gctaagcgat | tcaaagtgcg | ggtcggcgac | agaaacaccg | agcaggagga | aggggagaa | 900 |
| gcagtgcacg | aggtcgaagt | ggtcatcaag | cataatcgct | tcactaaaga | gacctacgac | 960 |
| tttgatatcg | ctgtgctgcg | cctgaagaca | cctattactt | tccgaatgaa | cgtcgcccct | 1020 |
| gcttgcctgc | cagagcgaga | ttgggccgaa | agcaccctga | tgacacagaa | aactggcatc | 1080 |
| gtgagcgggt | ttggacggac | acatgagaag | ggcaggcagt | ccactcgcct | gaaaatgctg | 1140 |
| gaagtgccct | acgtcgaccg | gaactcttgt | aagctgagta | gcagcttcat | cattacccag | 1200 |
| aatatgtttt | gcgccgggta | tgacacaaag | caggaggatg | cttgtcaggg | agacagtggc | 1260 |
| gggcctcacg | tgactaggtt | caaagatact | tattttgtga | ccggcatcgt | cagctggggc | 1320 |
| gagggatgcg | cacgcaaggg | gaaatacgga | atctatacca | aggtgacagc | ctttctgaaa | 1380 |
| tggattgacc | gatctatgaa | gacccggggg | ctgccaaagg | caaaaagtca | tgcccccgag | 1440 |
| gtcattacca | gttcccctct | gaaagaagac | caggtggacc | caaggctgat | tgacggcaag | 1500 |

<210> SEQ ID NO 95
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95

| | | | | | |
|---|---|---|---|---|---|
| atgggaagac | ccctgcatct | ggtgctgctg | tccgcctcac | tggctgggct | gctgctgctg | 60 |
| ggagaatctc | tgtttatccg | acgggagcag | gctaacaata | tcctggcaag | agtgcggaga | 120 |
| gccaactctt | tcctggagga | aatgaagaaa | ggccacctgg | agcgggaatg | catggaggaa | 180 |
| acctgtagtt | acgaggaagc | cagagaggtg | ttcgaagact | cagataagac | aaacgagttt | 240 |
| tggaataagt | acaaagacgg | cgatcagtgc | gaaactagcc | catgtcagaa | ccaggggaag | 300 |
| tgcaaagatg | gactgggcga | gtacacctgc | acatgtctgg | agggattcga | aggcaagaat | 360 |
| tgcgaactgt | ttaccagaaa | gctgtgctcc | ctggataacg | gcgactgcga | tcagttttgt | 420 |

```
catgaggaac agaattccgt ggtctgctct tgtgccaggg gatacacact ggctgacaat    480
ggcaaggcat gcatccccac cggccccctat ccttgtggga agcagacact ggagaggcgc    540
aaaaggtcag tggctgatag cattacctgg aaaccttatg acgccgctga cctggacccc    600
acagagaacc cctttgacct gctggacttc aaccagacac agcctgaaag aggcgataac    660
aatctgacta gggacttcct ggccgagggc ctgacccccta ggatcgtggg aggacaggag    720
tgcaaggacg gagaatgtcc atggcaggcc ctgctgatta acgaggaaaa tgagggattc    780
tgcggaggca ctatcctgag cgagttctac attctgaccg cagcccactg tctgtatcag    840
gctaagcgat tcaaagtgcg ggtcggcgac agaaacaccg agcaggagga agggggagaa    900
gcagtgcacg aggtcgaagt ggtcatcaag cataatcgct tcactaaaga gacctacgac    960
tttgatatcg ctgtgctgcg cctgaagaca cctattactt tccgaatgaa cgtcgcccct   1020
gcttgcctgc cagagcgaga ttgggccgaa agcaccctga tgacacagaa aactggcatc   1080
gtgagcgggt ttggacggac acatgagaag ggcaggcagt ccactcgcct gaaaatgctg   1140
gaagtgccct acgtcgaccg gaactcttgt aagctgagta gcagcttcat cattacccag   1200
aatatgtttt gcgccgggta tgacacaaag caggaggatg cttgtcaggg agacagtggc   1260
gggcctcacg tgactaggtt caaagatact tattttgtga ccggcatcgt cagctgggga   1320
gagggatgcg cacgcaaggg gaaatacgga atctatacca aggtgacagc ctttctgaaa   1380
tggattgacc gatctatgaa gacccggggg ctgccaaagg caaaaagtca tgcccccgag   1440
gtcattacca gttcccctct gaaagaagac caggtggacc caaggctgat tgacggcaag   1500
```

<210> SEQ ID NO 96
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96

```
atgggaagac ccctgcatct ggtgctgctg tccgcctcac tggctgggct gctgctgctg     60
ggagaatctc tgtttatccg acgggagcag gctaacaata tcctggcaag agtgcggaga    120
gccaactctt tcctggagga aatgaagaaa ggccacctgg agcggaatg catgaggaa     180 acctgtagtt acgaggaagc cagagaggtg ttcgaagact cagataagac aaacgagttt    240
tggaataagt acaaagacgg cgatcagtgc gaaactagcc atgtcagaa ccaggggaag    300 tgcaaagatg gactgggcga gtacacctgc acatgtctgg agggattcga aggcaagaat    360
tgcgaactgt ttaccagaaa gctgtgctcc ctggataacg gcgactgcga tcagttttgt    420
catgaggaac agaattccgt ggtctgctct tgtgccaggg gatacacact ggctgacaat    480
ggcaaggcat gcatccccac cggccccctat ccttgtggga agcagacact ggagaggcgc    540
aaaaggtcag tggctgatag cattacctgg aaaccttatg acgccgctga cctggacccc    600
acagagaacc cctttgacct gctggacttc aaccagacac agcctgaaag aggcgataac    660
aatctgacta ggaaggccac caacgccacc ctgtccccta ggatcgtggg aggacaggag    720
tgcaaggacg gagaatgtcc atggcaggcc ctgctgatta acgaggaaaa tgagggattc    780
tgcggaggca ctatcctgag cgagttctac attctgaccg cagcccactg tctgtatcag    840
gctaagcgat tcaaagtgcg ggtcggcgac agaaacaccg agcaggagga agggggagaa    900
gcagtgcacg aggtcgaagt ggtcatcaag cataatcgct tcactaaaga gacctacgac    960
```

```
tttgatatcg ctgtgctgcg cctgaagaca cctattactt tccgaatgaa cgtcgcccct    1020
gcttgcctgc cagagcgaga ttgggccgaa agcaccctga tgacacagaa aactggcatc    1080
gtgagcgggt ttggacggac acatgagaag ggcaggcagt ccactcgcct gaaaatgctg    1140
gaagtgccct acgtcgaccg gaactcttgt aagctgagta gcagcttcat cattacccag    1200
aatatgtttt gcgccgggta tgacacaaag caggaggatg cttgtcaggg agacagtggc    1260
gggcctcacg tgactaggtt caaagatact tattttgtga ccggcatcgt cagctgggga    1320
gagggatgcg cacgcaaggg gaaatacgga atctatacca aggtgacagc ctttctgaaa    1380
tggattgacc gatctatgaa gacccggggg ctgccaaagg caaaaagtca tgcccccgag    1440
gtcattacca gttcccctct gaaagaagac caggtggacc caaggctgat tgacggcaag    1500
```

<210> SEQ ID NO 97
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97

```
atgggaagac ccctgcatct ggtgctgctg tccgcctcac tggctgggct gctgctgctg      60
ggagaatctc tgtttatccg acgggagcag gctaacaata tcctggcaag agtgcgagaa    120
gccaactctt tcctggagga aatgaagaaa ggccacctgg agcgggaatg catggaggaa    180
acctgtagtt acgaggaagc cagagaggtg ttcgaagact cagataagac aaacgagttt    240
tggaataagt acaaagacgg cgatcagtgc gaaactagcc atgtcagaa ccaggggaag    300 tgcaaagatg gactgggcga gtacacctgc acatgtctgg agggattcga aggcaagaat    360
tgcgaactgt ttaccagaaa gctgtgctcc ctggataacg gcgactgcga tcagttttgt    420
catgaggaac agaattccgt ggtctgctct tgtgccaggg gatacacact ggctgacaat    480
ggcaaggcat gcatccccac cggcccctat ccttgtggga gcagacact ggagaggcgc    540 aaaaggtcag tggctgatag cattacctgg aaaccttatg acgccgctga cctggacccc    600
acagagaacc cctttgacct gctggacttc aaccagacac agcctgaaag aggcgataac    660
aatctgacta ggaaggccac ccaggccacc ctgagcccta ggatcgtggg aggacaggag    720
tgcaaggacg gagaatgtcc atggcaggcc ctgctgatta acgaggaaaa tgagggattc    780 tgcgaggca ctatcctgag cgagttctac attctgaccg cagcccactg tctgtatcag    840
gctaagcgat tcaaagtgcg ggtcggcgac agaaacaccg agcaggagga aggggggagaa    900 gcagtgcacg aggtcgaagt ggtcatcaag cataatcgct tcactaaaga gacctacgac    960
tttgatatcg ctgtgctgcg cctgaagaca cctattactt tccgaatgaa cgtcgcccct    1020
gcttgcctgc cagagcgaga ttgggccgaa agcaccctga tgacacagaa aactggcatc    1080
gtgagcgggt ttggacggac acatgagaag ggcaggcagt ccactcgcct gaaaatgctg    1140
gaagtgccct acgtcgaccg gaactcttgt aagctgagta gcagcttcat cattacccag    1200
aatatgtttt gcgccgggta tgacacaaag caggaggatg cttgtcaggg agacagtggc    1260
gggcctcacg tgactaggtt caaagatact tattttgtga ccggcatcgt cagctgggga    1320
gagggatgcg cacgcaaggg gaaatacgga atctatacca aggtgacagc ctttctgaaa    1380
tggattgacc gatctatgaa gacccggggg ctgccaaagg caaaaagtca tgcccccgag    1440
gtcattacca gttcccctct gaaagaagac caggtggacc caaggctgat tgacggcaag    1500
```

<210> SEQ ID NO 98
<211> LENGTH: 1500
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 98

```
atgggaagac ccctgcatct ggtgctgctg tccgcctcac tggctgggct gctgctgctg      60
ggagaatctc tgtttatccg acgggagcag gctaacaata tcctggcaag agtgcggaga     120
gccaactctt tcctggagga aatgaagaaa ggccacctgg agcgggaatg catggaggaa     180
acctgtagtt acgaggaagc cagagaggtg ttcgaagact cagataagac aaacgagttt     240
tggaataagt acaaagacgg cgatcagtgc gaaactagcc atgtcagaa ccaggggaag      300
tgcaaagatg gactgggcga gtacacctgc acatgtctgg agggattcga aggcaagaat     360
tgcgaactgt ttaccagaaa gctgtgctcc ctggataacg gcgactgcga tcagttttgt     420
catgaggaac agaattccgt ggtctgctct tgtgccaggg atacacact ggctgacaat      480
ggcaaggcat gcatccccac cggccccat ccttgtggga gcagacact ggagaggcgc       540
aaaaggtcag tggctcaggc aactagcgat agcattacct ggaaacctta tgacgccgct     600
gacctggacc ccacagagaa cccctttgac ctgctggact caaccagac acagcctgaa      660
agaggcgata caatctgac taggaccagc aagctgacca ggatcgtggg aggacaggag      720
tgcaaggacg gagaatgtcc atggcaggcc ctgctgatta cgaggaaaa tgagggattc      780
tgcggaggca ctatcctgag cgagttctac attctgaccg cagcccactg tctgtatcag     840
gctaagcgat tcaaagtgcg ggtcggcgac agaaacaccg agcaggagga aggggagaa      900
gcagtgcacg aggtcgaagt ggtcatcaag cataatcgct tcactaaaga gacctacgac     960
tttgatatcg ctgtgctgcg cctgaagaca cctattactt tccgaatgaa cgtcgcccct    1020
gcttgcctgc cagagcgaga ttgggccgaa agcaccctga tgacacagaa aactggcatc    1080
gtgagcgggt ttggacggac acatgagaag ggcaggcagt ccactcgcct gaaaatgctg    1140
gaagtgccct acgtcgaccg gaactcttgt aagctgagta gcagcttcat cattacccag    1200
aatatgtttt gcgccgggta tgacacaaag caggaggatg cttgtcaggg agacagtggc    1260
gggcctcacg tgactaggtt caaagatact tattttgtga ccggcatcgt cagctgggga    1320
gagggatgcg cacgcaaggg gaaatacgga atctatacca aggtgacagc ctttctgaaa    1380
tggattgacc gatctatgaa gacccggggg ctgccaaagg caaaaagtca tgcccccgag    1440
gtcattacca gttcccctct gaaagaagac caggtggacc aaggctgat tgacggcaag     1500
```

<210> SEQ ID NO 99
<211> LENGTH: 1500
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 99

```
atgggaagac ccctgcatct ggtgctgctg tccgcctcac tggctgggct gctgctgctg      60
ggagaatctc tgtttatccg acgggagcag gctaacaata tcctggcaag agtgcggaga     120
gccaactctt tcctggagga aatgaagaaa ggccacctgg agcgggaatg catggaggaa     180
```

```
acctgtagtt acgaggaagc cagagaggtg ttcgaagact cagataagac aaacgagttt      240
tggaataagt acaaagacgg cgatcagtgc gaaactagcc catgtcagaa ccaggggaag      300
tgcaaagatg gactgggcga gtacacctgc acatgtctgg agggattcga aggcaagaat      360
tgcgaactgt ttaccagaaa gctgtgctcc ctggataacg gcgactgcga tcagttttgt      420
catgaggaac agaattccgt ggtctgctct tgtgccaggg gatacacact ggctgacaat      480
ggcaaggcat gcatccccac cggcccctat ccttgtggga agcagacact ggagaggcgc      540
aaaaggtcag tggctcaggc aactagcgat agcattacct ggaaacctta tgacgccgct      600
gacctggacc ccacagagaa cccctttgac ctgctggact caaccagac acagcctgaa       660 agaggcgata caatctgac taggttcaac gacttcacca ggatcgtggg aggacaggag      720
tgcaaggacg gagaatgtcc atggcaggcc ctgctgatta cgaggaaaa tgagggattc       780 tgcggaggca ctatcctgag cgagttctac attctgaccg cagcccactg tctgtatcag      840
gctaagcgat tcaaagtgcg ggtcggcgac agaaacaccg agcaggagga aggggagaa       900 gcagtgcacg aggtcgaagt ggtcatcaag cataatcgct tcactaaaga gacctacgac      960
tttgatatcg ctgtgctgcg cctgaagaca cctattactt tccgaatgaa cgtcgccct      1020 gcttgcctgc cagagcgaga ttgggccgaa agcaccctga tgcacagaa aactggcatc      1080 gtgagcgggt ttggacggac acatgagaag ggcaggcagt ccactcgcct gaaaatgctg      1140
gaagtgccct acgtcgaccg gaactcttgt aagctgagta gcagcttcat cattacccag      1200
aatatgtttt gcgccgggta tgacacaaag caggaggatg cttgtcaggg agacagtggc      1260
gggcctcacg tgactaggtt caaagatact tattttgtga ccggcatcgt cagctgggga      1320
gagggatgcg cacgcaaggg gaaatacgga atctatacca aggtgacagc ctttctgaaa      1380
tggattgacc gatctatgaa gacccggggg ctgccaaagg caaaaagtca tgcccccgag      1440
gtcattacca gttcccctct gaaagaagac caggtggacc caaggctgat tgacggcaag      1500
```

<210> SEQ ID NO 100
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

```
atgggaagac ccctgcatct ggtgctgctg tccgcctcac tggctgggct gctgctgctg       60
ggagaatctc tgtttatccg acgggagcag gctaacaata tcctggcaag agtgcgagaa      120
gccaactctt tcctggagga aatgaagaaa ggccacctgg agcgggaatg catggaggaa      180
acctgtagtt acgaggaagc cagagaggtg ttcgaagact cagataagac aaacgagttt      240
tggaataagt acaaagacgg cgatcagtgc gaaactagcc catgtcagaa ccaggggaag      300
tgcaaagatg gactgggcga gtacacctgc acatgtctgg agggattcga aggcaagaat      360
tgcgaactgt ttaccagaaa gctgtgctcc ctggataacg gcgactgcga tcagttttgt      420
catgaggaac agaattccgt ggtctgctct tgtgccaggg gatacacact ggctgacaat      480
ggcaaggcat gcatccccac cggcccctat ccttgtggga agcagacact ggagaggcgc      540
aaaaggtcag tggctcaggc aactagcgat agcattacct ggaaacctta tgacgccgct      600
gacctggacc ccacagagaa cccctttgac ctgctggact caaccagac acagcctgaa       660 agaggcgata caatctgac taggctgagc agcatgacca ggatcgtggg aggacaggag       720
```

```
tgcaaggacg gagaatgtcc atggcaggcc ctgctgatta acgaggaaaa tgagggattc      780
tgcggaggca ctatcctgag cgagttctac attctgaccg cagcccactg tctgtatcag      840
gctaagcgat tcaaagtgcg ggtcggcgac agaaacaccg agcaggagga agggggagaa      900
gcagtgcacg aggtcgaagt ggtcatcaag cataatcgct tcactaaaga gacctacgac      960
tttgatatcg ctgtgctgcg cctgaagaca cctattactt tccgaatgaa cgtcgcccct     1020
gcttgcctgc cagagcgaga ttgggccgaa agcaccctga tgacacagaa aactggcatc     1080
gtgagcgggt ttggacggac acatgagaag ggcaggcagt ccactcgcct gaaaatgctg     1140
gaagtgccct acgtcgaccg gaactcttgt aagctgagta gcagcttcat cattacccag     1200
aatatgtttt gcgccgggta tgacacaaag caggaggatg cttgtcaggg agacagtggc     1260
gggcctcacg tgactaggtt caaagatact tattttgtga ccggcatcgt cagctgggga     1320
gagggatgcg cacgcaaggg gaaatacgga atctatacca aggtgacagc ctttctgaaa     1380
tggattgacc gatctatgaa gacccggggg ctgccaaagg caaaaagtca tgcccccgag     1440
gtcattacca gttcccctct gaaagaagac caggtggacc aaggctgat tgacggcaag     1500
```

<210> SEQ ID NO 101
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

```
atgggaagac ccctgcatct ggtgctgctg tccgcctcac tggctgggct gctgctgctg       60
ggagaatctc tgtttatccg acgggagcag gctaacaata tcctggcaag agtgcggaga      120
gccaactctt tcctggagga aatgaagaaa ggccacctgg agcgggaatg catggaggaa      180
acctgtagtt acgaggaagc cagagaggtg ttcgaagact cagataagac aaacgagttt      240
tggaataagt acaaagacgg cgatcagtgc gaaactagcc atgtcagaa ccaggggaag      300 tgcaaagatg gactgggcga gtacacctgc acatgtctgg agggattcga aggcaagaat      360
tgcgaactgt ttaccagaaa gctgtgctcc ctggataacg gcgactgcga tcagttttgt      420
catgaggaac agaattccgt ggtctgctct tgtgccaggg gatacacact ggctgacaat      480
ggcaaggcat gcatccccac cggccccat ccttgtggga gcagacact ggagaggcgc       540 aaaaggtcag tggctcaggc aactagcgat agcattacct ggaaacctta tgacgccgct      600
gacctggacc ccacagagaa cccctttgac ctgctggact caaccagac acagcctgaa      660 agaggcgata caatctgac taggcctccc agcctgacca ggatcgtggg aggacaggag      720
tgcaaggacg gagaatgtcc atggcaggcc ctgctgatta acgaggaaaa tgagggattc      780
tgcggaggca ctatcctgag cgagttctac attctgaccg cagcccactg tctgtatcag      840
gctaagcgat tcaaagtgcg ggtcggcgac agaaacaccg agcaggagga agggggagaa      900
gcagtgcacg aggtcgaagt ggtcatcaag cataatcgct tcactaaaga gacctacgac      960
tttgatatcg ctgtgctgcg cctgaagaca cctattactt tccgaatgaa cgtcgcccct     1020
gcttgcctgc cagagcgaga ttgggccgaa agcaccctga tgacacagaa aactggcatc     1080
gtgagcgggt ttggacggac acatgagaag ggcaggcagt ccactcgcct gaaaatgctg     1140
gaagtgccct acgtcgaccg gaactcttgt aagctgagta gcagcttcat cattacccag     1200
aatatgtttt gcgccgggta tgacacaaag caggaggatg cttgtcaggg agacagtggc     1260
```

```
gggcctcacg tgactaggtt caaagatact tattttgtga ccggcatcgt cagctgggga     1320
gagggatgcg cacgcaaggg gaaatacgga atctatacca aggtgacagc ctttctgaaa     1380
tggattgacc gatctatgaa gacccggggg ctgccaaagg caaaaagtca tgcccccgag     1440
gtcattacca gttcccctct gaagaagac caggtggacc caaggctgat tgacggcaag     1500
```

<210> SEQ ID NO 102
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102

```
atgggaagac ccctgcatct ggtgctgctg tccgcctcac tggctgggct gctgctgctg      60
ggagaatctc tgtttatccg acgggagcag gctaacaata tcctggcaag agtgcggaga     120
gccaactctt tcctggagga aatgaagaaa ggccacctgg agcggaatg catggaggaa     180 acctgtagtt acgaggaagc cagagaggtg ttcgaagact cagataagac aaacgagttt     240
tggaataagt acaaagacgg cgatcagtgc gaaactagcc atgtcagaa ccaggggaag     300 tgcaaagatg gactgggcga gtacacctgc acatgtctgg agggattcga aggcaagaat     360
tgcgaactgt ttaccagaaa gctgtgctcc ctggataacg gcgactgcga tcagttttgt     420
catgaggaac agaattccgt ggtctgctct tgtgccaggg gatacacact ggctgacaat     480
ggcaaggcat gcatccccac cggcccctat ccttgtggga gcagacact ggagaggcgc     540 aaaaggtcag tggctcaggc aactagcgat agcattacct ggaaacctta tgacgccgct     600
gacctggacc ccacagagaa ccccctttgac ctgctggact tcaaccagac acagcctgaa     660
agaggcgata acaatctgac taggctgtcc tgcggccaga ggatcgtggg aggacaggag     720
tgcaaggacg gagaatgtcc atggcaggcc ctgctgatta cgaggaaaa tgagggattc     780 tgcggaggca ctatcctgag cgagttctac attctgaccg cagcccactg tctgtatcag     840
gctaagcgat tcaaagtgcg ggtcggcgac agaaacaccg agcaggagga aggggagaa     900 gcagtgcacg aggtcgaagt ggtcatcaag cataatcgct tcactaaaga gacctacgac     960
tttgatatcg ctgtgctgcg cctgaagaca cctattactt tccgaatgaa cgtcgcccct    1020
gcttgcctgc cagagcgaga ttgggccgaa agcaccctga tgcacagaa aactggcatc    1080 gtgagcgggt ttggacggac acatgagaag ggcaggcagt ccactcgcct gaaaatgctg    1140
gaagtgccct acgtcgaccg gaactcttgt aagctgagta gcagcttcat cattacccag    1200
aatatgtttt gcgccgggta tgacacaaag caggaggatg cttgtcaggg agacagtggc    1260
gggcctcacg tgactaggtt caaagatact tattttgtga ccggcatcgt cagctgggga    1320
gagggatgcg cacgcaaggg gaaatacgga atctatacca aggtgacagc ctttctgaaa    1380
tggattgacc gatctatgaa gacccggggg ctgccaaagg caaaaagtca tgcccccgag    1440
gtcattacca gttcccctct gaagaagac caggtggacc caaggctgat tgacggcaag    1500
```

<210> SEQ ID NO 103
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

```
Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
                20                  25                  30

Asp Ser Asp Lys Thr Asn Glu Phe Trp Asn Lys Tyr Lys Asp Gly Asp
            35                  40                  45

Gln Cys Glu Thr Ser Pro Cys Gln Asn Gln Gly Lys Cys Lys Asp Gly
        50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Gln Ala Thr Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
            180                 185                 190

Thr Arg Ile Val Gly Gly Gln Glu Cys Lys Asp Gly Glu Cys Pro Trp
        195                 200                 205

Gln Ala Leu Leu Ile Asn Glu Glu Asn Glu Gly Phe Cys Gly Gly Thr
    210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
        275                 280                 285

Lys Thr Pro Ile Thr Phe Arg Met Asn Val Ala Pro Ala Cys Leu Pro
    290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
        355                 360                 365

Thr Lys Gln Glu Asp Ala Cys Gln Gly Asp Ser Gly Gly Pro His Val
    370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415
```

Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
            435                 440                 445

Glu Asp Gln Val Asp Pro Arg Leu Ile Asp Gly Lys
    450                 455                 460

<210> SEQ ID NO 104
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Asp Phe Leu Ala Glu Gly Gly Gly
            180                 185                 190

Val Arg Ile Val Gly Gly Gln Glu Cys Lys Asp Gly Glu Cys Pro Trp
        195                 200                 205

Gln Ala Leu Leu Ile Asn Glu Glu Asn Glu Gly Phe Cys Gly Gly Thr
    210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
        275                 280                 285

Lys Thr Pro Ile Thr Phe Arg Met Asn Val Ala Pro Ala Cys Leu Pro
    290                 295                 300

Glu Arg Asp Trp Ala Glu Ser Thr Leu Met Thr Gln Lys Thr Gly Ile
305                 310                 315                 320

```
Val Ser Gly Phe Gly Arg Thr His Glu Lys Gly Arg Gln Ser Thr Arg
            325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
            355                 360                 365

Thr Lys Gln Glu Asp Ala Cys Gln Gly Asp Ser Gly Gly Pro His Val
            370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
            405                 410                 415

Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
            435                 440                 445

Glu Asp Gln Val Asp Pro Arg Leu Ile Asp Gly Lys
            450                 455                 460

<210> SEQ ID NO 105
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Asp Phe Leu Ala Glu Gly Leu Thr
            180                 185                 190

Pro Arg Ile Val Gly Gly Gln Glu Cys Lys Asp Gly Glu Cys Pro Trp
        195                 200                 205

Gln Ala Leu Leu Ile Asn Glu Glu Asn Glu Gly Phe Cys Gly Gly Thr
```

```
            210                 215                 220
Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
                260                 265                 270

Arg Phe Thr Lys Glu Thr Tyr Asp Phe Asp Ile Ala Val Leu Arg Leu
                275                 280                 285

Lys Thr Pro Ile Thr Phe Arg Met Asn Val Ala Pro Ala Cys Leu Pro
        290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
                340                 345                 350

Ser Ser Ser Phe Ile Ile Thr Gln Asn Met Phe Cys Ala Gly Tyr Asp
                355                 360                 365

Thr Lys Gln Glu Asp Ala Cys Gln Gly Asp Ser Gly Gly Pro His Val
        370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
                420                 425                 430

Lys Ala Lys Ser His Ala Pro Glu Val Ile Thr Ser Ser Pro Leu Lys
                435                 440                 445

Glu Asp Gln Val Asp Pro Arg Leu Ile Asp Gly Lys
        450                 455                 460

<210> SEQ ID NO 106
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
                20                  25                  30

Asp Ser Asp Lys Thr Asn Glu Phe Trp Asn Lys Tyr Lys Asp Gly Asp
            35                  40                  45

Gln Cys Glu Thr Ser Pro Cys Gln Asn Gln Gly Lys Cys Lys Asp Gly
        50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
                100                 105                 110
```

```
Arg Gly Tyr Thr Leu Ala Asp Asn Gly Lys Ala Cys Ile Pro Thr Gly
            115                 120                 125

Pro Tyr Pro Cys Gly Lys Gln Thr Leu Glu Arg Lys Arg Ser Val
    130                 135                 140

Ala Gln Ala Thr Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Lys Ala Thr Asn Ala Thr Leu Ser
                180                 185                 190

Pro Arg Ile Val Gly Gly Gln Glu Cys Lys Asp Gly Glu Cys Pro Trp
            195                 200                 205

Gln Ala Leu Leu Ile Asn Glu Glu Asn Glu Gly Phe Cys Gly Gly Thr
210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
            275                 280                 285

Lys Thr Pro Ile Thr Phe Arg Met Asn Val Ala Pro Ala Cys Leu Pro
        290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
        355                 360                 365

Thr Lys Gln Glu Asp Ala Cys Gln Gly Asp Ser Gly Gly Pro His Val
    370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
        435                 440                 445

Glu Asp Gln Val Asp Pro Arg Leu Ile Asp Gly Lys
    450                 455                 460

<210> SEQ ID NO 107
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Ala Asn Ser Phe Leu Glu Glu Met Lys Lys Gly His Leu Glu Arg Glu
1               5                   10                  15
```

```
Cys Met Glu Glu Thr Cys Ser Tyr Glu Glu Ala Arg Glu Val Phe Glu
             20                  25                  30

Asp Ser Asp Lys Thr Asn Glu Phe Trp Asn Lys Tyr Lys Asp Gly Asp
             35                  40                  45

Gln Cys Glu Thr Ser Pro Cys Gln Asn Gln Gly Lys Cys Lys Asp Gly
 50                  55                  60

Leu Gly Glu Tyr Thr Cys Thr Cys Leu Glu Gly Phe Glu Gly Lys Asn
 65                  70                  75                  80

Cys Glu Leu Phe Thr Arg Lys Leu Cys Ser Leu Asp Asn Gly Asp Cys
                 85                  90                  95

Asp Gln Phe Cys His Glu Glu Gln Asn Ser Val Val Cys Ser Cys Ala
                100                 105                 110

Arg Gly Tyr Thr Leu Ala Asp Asn Gly Lys Ala Cys Ile Pro Thr Gly
                115                 120                 125

Pro Tyr Pro Cys Gly Lys Gln Thr Leu Glu Arg Arg Lys Arg Ser Val
     130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Lys Ala Thr Gln Ala Thr Leu Ser
                180                 185                 190

Pro Arg Ile Val Gly Gly Gln Glu Cys Lys Asp Gly Glu Cys Pro Trp
         195                 200                 205

Gln Ala Leu Leu Ile Asn Glu Glu Asn Glu Gly Phe Cys Gly Gly Thr
         210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
                260                 265                 270

Arg Phe Thr Lys Glu Thr Tyr Asp Phe Asp Ile Ala Val Leu Arg Leu
                275                 280                 285

Lys Thr Pro Ile Thr Phe Arg Met Asn Val Ala Pro Ala Cys Leu Pro
     290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
                340                 345                 350

Ser Ser Ser Phe Ile Ile Thr Gln Asn Met Phe Cys Ala Gly Tyr Asp
                355                 360                 365

Thr Lys Gln Glu Asp Ala Cys Gln Gly Asp Ser Gly Gly Pro His Val
     370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
                420                 425                 430
```

```
Lys Ala Lys Ser His Ala Pro Glu Val Ile Thr Ser Ser Pro Leu Lys
            435                 440                 445

Glu Asp Gln Val Asp Pro Arg Leu Ile Asp Gly Lys
    450                 455                 460

<210> SEQ ID NO 108
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Ala Asn Ser Phe Leu Glu Glu Met Lys Lys Gly His Leu Glu Arg Glu
1               5                   10                  15

Cys Met Glu Glu Thr Cys Ser Tyr Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Gln Ala Thr Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Thr Ser Lys Leu
            180                 185                 190

Thr Arg Ile Val Gly Gly Gln Glu Cys Lys Asp Gly Glu Cys Pro Trp
        195                 200                 205

Gln Ala Leu Leu Ile Asn Glu Glu Asn Glu Gly Phe Cys Gly Gly Thr
    210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
        275                 280                 285

Lys Thr Pro Ile Thr Phe Arg Met Asn Val Ala Pro Ala Cys Leu Pro
    290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335
```

```
Leu Lys Met Leu Glu Val Pro Tyr Val Asp Arg Asn Ser Cys Lys Leu
        340                 345                 350

Ser Ser Ser Phe Ile Ile Thr Gln Asn Met Phe Cys Ala Gly Tyr Asp
        355                 360                 365

Thr Lys Gln Glu Asp Ala Cys Gln Gly Asp Ser Gly Gly Pro His Val
        370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
                420                 425                 430

Lys Ala Lys Ser His Ala Pro Glu Val Ile Thr Ser Ser Pro Leu Lys
                435                 440                 445

Glu Asp Gln Val Asp Pro Arg Leu Ile Asp Gly Lys
        450                 455                 460

<210> SEQ ID NO 109
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
                20                  25                  30

Asp Ser Asp Lys Thr Asn Glu Phe Trp Asn Lys Tyr Lys Asp Gly Asp
            35                  40                  45

Gln Cys Glu Thr Ser Pro Cys Gln Asn Gln Gly Lys Cys Lys Asp Gly
        50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
                100                 105                 110

Arg Gly Tyr Thr Leu Ala Asp Asn Gly Lys Ala Cys Ile Pro Thr Gly
            115                 120                 125

Pro Tyr Pro Cys Gly Lys Gln Thr Leu Glu Arg Arg Lys Arg Ser Val
        130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Phe Asn Asp Phe
                180                 185                 190

Thr Arg Ile Val Gly Gly Gln Glu Cys Lys Asp Gly Glu Cys Pro Trp
            195                 200                 205

Gln Ala Leu Leu Ile Asn Glu Glu Asn Glu Gly Phe Cys Gly Gly Thr
        210                 215                 220

Ile Leu Ser Glu Phe Tyr Ile Leu Thr Ala Ala His Cys Leu Tyr Gln
```

Ala Lys Arg Phe Lys Val Arg Val Gly Asp Arg Asn Thr Glu Gln Glu
225                 230                 235                 240

Glu Gly Gly Glu Ala Val His Glu Val Glu Val Ile Lys His Asn
        245                 250                 255

Arg Phe Thr Lys Glu Thr Tyr Asp Phe Asp Ile Ala Val Leu Arg Leu
    260                 265                 270

Lys Thr Pro Ile Thr Phe Arg Met Asn Val Ala Pro Ala Cys Leu Pro
275                 280                 285

Glu Arg Asp Trp Ala Glu Ser Thr Leu Met Thr Gln Lys Thr Gly Ile
290                 295                 300

Val Ser Gly Phe Gly Arg Thr His Glu Lys Gly Arg Gln Ser Thr Arg
305                 310                 315                 320

Leu Lys Met Leu Glu Val Pro Tyr Val Asp Arg Asn Ser Cys Lys Leu
            325                 330                 335

Ser Ser Ser Phe Ile Ile Thr Gln Asn Met Phe Cys Ala Gly Tyr Asp
        340                 345                 350

Thr Lys Gln Glu Asp Ala Cys Gln Gly Asp Ser Gly Gly Pro His Val
    355                 360                 365

Thr Arg Phe Lys Asp Thr Tyr Phe Val Thr Gly Ile Val Ser Trp Gly
370                 375                 380

Glu Gly Cys Ala Arg Lys Gly Lys Tyr Gly Ile Tyr Thr Lys Val Thr
385                 390                 395                 400

Ala Phe Leu Lys Trp Ile Asp Arg Ser Met Lys Thr Arg Gly Leu Pro
            405                 410                 415

Lys Ala Lys Ser His Ala Pro Glu Val Ile Thr Ser Ser Pro Leu Lys
        420                 425                 430

Glu Asp Gln Val Asp Pro Arg Leu Ile Asp Gly Lys
    435                 440                 445

<210> SEQ ID NO 110
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
            85                  90                  95

Asp Gln Phe Cys His Glu Glu Gln Asn Ser Val Val Cys Ser Cys Ala
        100                 105                 110

Arg Gly Tyr Thr Leu Ala Asp Asn Gly Lys Ala Cys Ile Pro Thr Gly
    115                 120                 125

Pro Tyr Pro Cys Gly Lys Gln Thr Leu Glu Arg Arg Lys Arg Ser Val
130                 135                 140

Ala Gln Ala Thr Ser Ser Gly Glu Ala Pro Asp Ser Ile Thr Trp
145                 150                 155                 160

Lys Pro Tyr Asp Ala Asp Leu Asp Pro Thr Glu Asn Pro Phe Asp
            165                 170                 175

Leu Leu Asp Phe Asn Gln Thr Gln Pro Glu Arg Gly Leu Ser Ser Met
            180                 185                 190

Thr Arg Ile Val Gly Gly Gln Glu Cys Lys Asp Gly Glu Cys Pro Trp
            195                 200                 205

Gln Ala Leu Leu Ile Asn Glu Glu Asn Glu Gly Phe Cys Gly Gly Thr
210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
            245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
            275                 280                 285

Lys Thr Pro Ile Thr Phe Arg Met Asn Val Ala Pro Ala Cys Leu Pro
290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
            325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
            355                 360                 365

Thr Lys Gln Glu Asp Ala Cys Gln Gly Asp Ser Gly Gly Pro His Val
            370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
            405                 410                 415

Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
            435                 440                 445

Glu Asp Gln Val Asp Pro Arg Leu Ile Asp Gly Lys
450                 455                 460

<210> SEQ ID NO 111
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

```
Asp Ser Asp Lys Thr Asn Glu Phe Trp Asn Lys Tyr Lys Asp Gly Asp
         35                  40                  45

Gln Cys Glu Thr Ser Pro Cys Gln Asn Gln Gly Lys Cys Lys Asp Gly
 50                  55                  60

Leu Gly Glu Tyr Thr Cys Thr Cys Leu Glu Gly Phe Glu Gly Lys Asn
 65                  70                  75                  80

Cys Glu Leu Phe Thr Arg Lys Leu Cys Ser Leu Asp Asn Gly Asp Cys
                 85                  90                  95

Asp Gln Phe Cys His Glu Gln Asn Ser Val Val Cys Ser Cys Ala
                100                 105                 110

Arg Gly Tyr Thr Leu Ala Asp Asn Gly Lys Ala Cys Ile Pro Thr Gly
                115                 120                 125

Pro Tyr Pro Cys Gly Lys Gln Thr Leu Glu Arg Arg Lys Arg Ser Val
                130                 135                 140

Ala Gln Ala Thr Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Pro Pro Ser Leu
                180                 185                 190

Thr Arg Ile Val Gly Gly Gln Glu Cys Lys Asp Gly Glu Cys Pro Trp
                195                 200                 205

Gln Ala Leu Leu Ile Asn Glu Glu Asn Glu Gly Phe Cys Gly Gly Thr
                210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
                260                 265                 270

Arg Phe Thr Lys Glu Thr Tyr Asp Phe Asp Ile Ala Val Leu Arg Leu
                275                 280                 285

Lys Thr Pro Ile Thr Phe Arg Met Asn Val Ala Pro Ala Cys Leu Pro
                290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
                340                 345                 350

Ser Ser Ser Phe Ile Ile Thr Gln Asn Met Phe Cys Ala Gly Tyr Asp
                355                 360                 365

Thr Lys Gln Glu Asp Ala Cys Gln Gly Asp Ser Gly Gly Pro His Val
                370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
                420                 425                 430

Lys Ala Lys Ser His Ala Pro Glu Val Ile Thr Ser Ser Pro Leu Lys
                435                 440                 445
```

```
Glu Asp Gln Val Asp Pro Arg Leu Ile Asp Gly Lys
    450                 455                 460
```

<210> SEQ ID NO 112
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

```
Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Leu Ser Cys Gly
            180                 185                 190

Gln Arg Ile Val Gly Gly Gln Glu Cys Lys Asp Gly Glu Cys Pro Trp
        195                 200                 205

Gln Ala Leu Leu Ile Asn Glu Glu Asn Glu Gly Phe Cys Gly Gly Thr
    210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
        275                 280                 285

Lys Thr Pro Ile Thr Phe Arg Met Asn Val Ala Pro Ala Cys Leu Pro
    290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350
```

```
Ser Ser Ser Phe Ile Ile Thr Gln Asn Met Phe Cys Ala Gly Tyr Asp
        355                 360                 365

Thr Lys Gln Glu Asp Ala Cys Gln Gly Asp Ser Gly Gly Pro His Val
370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
                420                 425                 430

Lys Ala Lys Ser His Ala Pro Glu Val Ile Thr Ser Ser Pro Leu Lys
                435                 440                 445

Glu Asp Gln Val Asp Pro Arg Leu Ile Asp Gly Lys
450                 455                 460

<210> SEQ ID NO 113
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
                100                 105                 110

Arg Gly Tyr Thr Leu Ala Asp Asn Gly Lys Ala Cys Ile Pro Thr Gly
            115                 120                 125

Pro Tyr Pro Cys Gly Lys Gln Thr Leu Glu Arg Arg Lys Arg Ser Val
        130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
                180                 185                 190

Thr Arg Asp Phe Leu Ala Glu Gly Gly Val Arg Ile Val Gly Gly
            195                 200                 205

Gln Glu Cys Lys Asp Gly Glu Cys Pro Trp Gln Ala Leu Leu Ile Asn
        210                 215                 220

Glu Glu Asn Glu Gly Phe Cys Gly Gly Thr Ile Leu Ser Glu Phe Tyr
225                 230                 235                 240

Ile Leu Thr Ala Ala His Cys Leu Tyr Gln Ala Lys Arg Phe Lys Val
```

```
                    245                 250                 255
Arg Val Gly Asp Arg Asn Thr Glu Gln Glu Glu Gly Gly Glu Ala Val
                260                 265                 270

His Glu Val Glu Val Val Ile Lys His Asn Arg Phe Thr Lys Glu Thr
            275                 280                 285

Tyr Asp Phe Asp Ile Ala Val Leu Arg Leu Lys Thr Pro Ile Thr Phe
        290                 295                 300

Arg Met Asn Val Ala Pro Ala Cys Leu Pro Glu Arg Asp Trp Ala Glu
305                 310                 315                 320

Ser Thr Leu Met Thr Gln Lys Thr Gly Ile Val Ser Gly Phe Gly Arg
                325                 330                 335

Thr His Glu Lys Gly Arg Gln Ser Thr Arg Leu Lys Met Leu Glu Val
            340                 345                 350

Pro Tyr Val Asp Arg Asn Ser Cys Lys Leu Ser Ser Ser Phe Ile Ile
        355                 360                 365

Thr Gln Asn Met Phe Cys Ala Gly Tyr Asp Thr Lys Gln Glu Asp Ala
    370                 375                 380

Cys Gln Gly Asp Ser Gly Gly Pro His Val Thr Arg Phe Lys Asp Thr
385                 390                 395                 400

Tyr Phe Val Thr Gly Ile Val Ser Trp Gly Glu Gly Cys Ala Arg Lys
                405                 410                 415

Gly Lys Tyr Gly Ile Tyr Thr Lys Val Thr Ala Phe Leu Lys Trp Ile
            420                 425                 430

Asp Arg Ser Met Lys Thr Arg Gly Leu Pro Lys Ala Lys Ser His Ala
        435                 440                 445

Pro Glu Val Ile Thr Ser Ser Pro Leu Lys Glu Asp Gln Val Asp Pro
    450                 455                 460

Arg Leu Ile Asp Gly Lys
465                 470

<210> SEQ ID NO 114
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125
```

Pro Tyr Pro Cys Gly Lys Gln Thr Leu Glu Arg Arg Lys Arg Ser Val
130                 135                 140

Ala Gln Ala Thr Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
                180                 185                 190

Thr Arg Asp Phe Leu Ala Glu Gly Leu Thr Pro Arg Ile Val Gly Gly
                195                 200                 205

Gln Glu Cys Lys Asp Gly Glu Cys Pro Trp Gln Ala Leu Leu Ile Asn
210                 215                 220

Glu Glu Asn Glu Gly Phe Cys Gly Gly Thr Ile Leu Ser Glu Phe Tyr
225                 230                 235                 240

Ile Leu Thr Ala Ala His Cys Leu Tyr Gln Ala Lys Arg Phe Lys Val
                245                 250                 255

Arg Val Gly Asp Arg Asn Thr Glu Gln Glu Glu Gly Gly Glu Ala Val
                260                 265                 270

His Glu Val Glu Val Val Ile Lys His Asn Arg Phe Thr Lys Glu Thr
                275                 280                 285

Tyr Asp Phe Asp Ile Ala Val Leu Arg Leu Lys Thr Pro Ile Thr Phe
                290                 295                 300

Arg Met Asn Val Ala Pro Ala Cys Leu Pro Glu Arg Asp Trp Ala Glu
305                 310                 315                 320

Ser Thr Leu Met Thr Gln Lys Thr Gly Ile Val Ser Gly Phe Gly Arg
                325                 330                 335

Thr His Glu Lys Gly Arg Gln Ser Thr Arg Leu Lys Met Leu Glu Val
                340                 345                 350

Pro Tyr Val Asp Arg Asn Ser Cys Lys Leu Ser Ser Ser Phe Ile Ile
                355                 360                 365

Thr Gln Asn Met Phe Cys Ala Gly Tyr Asp Thr Lys Gln Glu Asp Ala
                370                 375                 380

Cys Gln Gly Asp Ser Gly Gly Pro His Val Thr Arg Phe Lys Asp Thr
385                 390                 395                 400

Tyr Phe Val Thr Gly Ile Val Ser Trp Gly Glu Gly Cys Ala Arg Lys
                405                 410                 415

Gly Lys Tyr Gly Ile Tyr Thr Lys Val Thr Ala Phe Leu Lys Trp Ile
                420                 425                 430

Asp Arg Ser Met Lys Thr Arg Gly Leu Pro Lys Ala Lys Ser His Ala
                435                 440                 445

Pro Glu Val Ile Thr Ser Ser Pro Leu Lys Glu Asp Gln Val Asp Pro
450                 455                 460

Arg Leu Ile Asp Gly Lys
465                 470

<210> SEQ ID NO 115
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Ala Asn Ser Phe Leu Glu Glu Met Lys Lys Gly His Leu Glu Arg Glu
1               5                   10                  15

```
Cys Met Glu Glu Thr Cys Ser Tyr Glu Glu Ala Arg Glu Val Phe Glu
        20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
        50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                    85                  90                  95

Asp Gln Phe Cys His Glu Glu Gln Asn Ser Val Val Cys Ser Cys Ala
                100                 105                 110

Arg Gly Tyr Thr Leu Ala Asp Asn Gly Lys Ala Cys Ile Pro Thr Gly
                115                 120                 125

Pro Tyr Pro Cys Gly Lys Gln Thr Leu Glu Arg Arg Lys Arg Ser Val
                130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
                180                 185                 190

Thr Arg Lys Ala Thr Asn Ala Thr Leu Ser Pro Arg Ile Val Gly Gly
                195                 200                 205

Gln Glu Cys Lys Asp Gly Glu Cys Pro Trp Gln Ala Leu Leu Ile Asn
            210                 215                 220

Glu Glu Asn Glu Gly Phe Cys Gly Gly Thr Ile Leu Ser Glu Phe Tyr
225                 230                 235                 240

Ile Leu Thr Ala Ala His Cys Leu Tyr Gln Ala Lys Arg Phe Lys Val
                245                 250                 255

Arg Val Gly Asp Arg Asn Thr Glu Gln Glu Glu Gly Gly Glu Ala Val
                260                 265                 270

His Glu Val Glu Val Val Ile Lys His Asn Arg Phe Thr Lys Glu Thr
                275                 280                 285

Tyr Asp Phe Asp Ile Ala Val Leu Arg Leu Lys Thr Pro Ile Thr Phe
290                 295                 300

Arg Met Asn Val Ala Pro Ala Cys Leu Pro Glu Arg Asp Trp Ala Glu
305                 310                 315                 320

Ser Thr Leu Met Thr Gln Lys Thr Gly Ile Val Ser Gly Phe Gly Arg
                325                 330                 335

Thr His Glu Lys Gly Arg Gln Ser Thr Arg Leu Lys Met Leu Glu Val
                340                 345                 350

Pro Tyr Val Asp Arg Asn Ser Cys Lys Leu Ser Ser Phe Ile Ile
                355                 360                 365

Thr Gln Asn Met Phe Cys Ala Gly Tyr Asp Thr Lys Gln Glu Asp Ala
                370                 375                 380

Cys Gln Gly Asp Ser Gly Gly Pro His Val Thr Arg Phe Lys Asp Thr
385                 390                 395                 400

Tyr Phe Val Thr Gly Ile Val Ser Trp Gly Glu Gly Cys Ala Arg Lys
                    405                 410                 415

Gly Lys Tyr Gly Ile Tyr Thr Lys Val Thr Ala Phe Leu Lys Trp Ile
                420                 425                 430
```

Asp Arg Ser Met Lys Thr Arg Gly Leu Pro Lys Ala Lys Ser His Ala
            435                 440                 445

Pro Glu Val Ile Thr Ser Ser Pro Leu Lys Glu Asp Gln Val Asp Pro
    450                 455                 460

Arg Leu Ile Asp Gly Lys
465             470

<210> SEQ ID NO 116
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
            35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65              70                  75                  80

Cys Glu Leu Phe Thr Arg Lys Leu Cys Ser Leu Asp Asn Gly Asp Cys
            85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
            115                 120                 125

Pro Tyr Pro Cys Gly Lys Gln Thr Leu Glu Arg Arg Lys Arg Ser Val
    130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
            180                 185                 190

Thr Arg Lys Ala Thr Gln Ala Thr Leu Ser Pro Arg Ile Val Gly Gly
        195                 200                 205

Gln Glu Cys Lys Asp Gly Glu Cys Pro Trp Gln Ala Leu Leu Ile Asn
    210                 215                 220

Glu Glu Asn Glu Gly Phe Cys Gly Gly Thr Ile Leu Ser Glu Phe Tyr
225                 230                 235                 240

Ile Leu Thr Ala Ala His Cys Leu Tyr Gln Ala Lys Arg Phe Lys Val
                245                 250                 255

Arg Val Gly Asp Arg Asn Thr Glu Gln Glu Glu Gly Gly Glu Ala Val
            260                 265                 270

His Glu Val Glu Val Val Ile Lys His Asn Arg Phe Thr Lys Glu Thr
        275                 280                 285

Tyr Asp Phe Asp Ile Ala Val Leu Arg Leu Lys Thr Pro Ile Thr Phe
    290                 295                 300

Arg Met Asn Val Ala Pro Ala Cys Leu Pro Glu Arg Asp Trp Ala Glu
305                 310                 315                 320

Ser Thr Leu Met Thr Gln Lys Thr Gly Ile Val Ser Gly Phe Gly Arg
            325                 330                 335

Thr His Glu Lys Gly Arg Gln Ser Thr Arg Leu Lys Met Leu Glu Val
            340                 345                 350

Pro Tyr Val Asp Arg Asn Ser Cys Lys Leu Ser Ser Phe Ile Ile
            355                 360                 365

Thr Gln Asn Met Phe Cys Ala Gly Tyr Asp Thr Lys Gln Glu Asp Ala
        370                 375                 380

Cys Gln Gly Asp Ser Gly Pro His Val Thr Arg Phe Lys Asp Thr
385                 390                 395                 400

Tyr Phe Val Thr Gly Ile Val Ser Trp Gly Glu Gly Cys Ala Arg Lys
                405                 410                 415

Gly Lys Tyr Gly Ile Tyr Thr Lys Val Thr Ala Phe Leu Lys Trp Ile
                420                 425                 430

Asp Arg Ser Met Lys Thr Arg Gly Leu Pro Lys Ala Lys Ser His Ala
            435                 440                 445

Pro Glu Val Ile Thr Ser Ser Pro Leu Lys Glu Asp Gln Val Asp Pro
    450                 455                 460

Arg Leu Ile Asp Gly Lys
465                 470

<210> SEQ ID NO 117
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
            180                 185                 190

Thr Arg Thr Ser Lys Leu Thr Arg Ile Val Gly Gly Gln Glu Cys Lys

```
                195                 200                 205
Asp Gly Glu Cys Pro Trp Gln Ala Leu Leu Ile Asn Glu Glu Asn Glu
        210                 215                 220

Gly Phe Cys Gly Gly Thr Ile Leu Ser Glu Phe Tyr Ile Leu Thr Ala
225                 230                 235                 240

Ala His Cys Leu Tyr Gln Ala Lys Arg Phe Lys Val Arg Val Gly Asp
                245                 250                 255

Arg Asn Thr Glu Gln Glu Glu Gly Glu Ala Val His Glu Val Glu
        260                 265                 270

Val Val Ile Lys His Asn Arg Phe Thr Lys Glu Thr Tyr Asp Phe Asp
                275                 280                 285

Ile Ala Val Leu Arg Leu Lys Thr Pro Ile Thr Phe Arg Met Asn Val
        290                 295                 300

Ala Pro Ala Cys Leu Pro Glu Arg Asp Trp Ala Glu Ser Thr Leu Met
305                 310                 315                 320

Thr Gln Lys Thr Gly Ile Val Ser Gly Phe Gly Arg Thr His Glu Lys
                325                 330                 335

Gly Arg Gln Ser Thr Arg Leu Lys Met Leu Glu Val Pro Tyr Val Asp
        340                 345                 350

Arg Asn Ser Cys Lys Leu Ser Ser Phe Ile Ile Thr Gln Asn Met
        355                 360                 365

Phe Cys Ala Gly Tyr Asp Thr Lys Gln Glu Asp Ala Cys Gln Gly Asp
        370                 375                 380

Ser Gly Gly Pro His Val Thr Arg Phe Lys Asp Thr Tyr Phe Val Thr
385                 390                 395                 400

Gly Ile Val Ser Trp Gly Gly Cys Ala Arg Lys Gly Lys Tyr Gly
                405                 410                 415

Ile Tyr Thr Lys Val Thr Ala Phe Leu Lys Trp Ile Asp Arg Ser Met
        420                 425                 430

Lys Thr Arg Gly Leu Pro Lys Ala Lys Ser His Ala Pro Glu Val Ile
        435                 440                 445

Thr Ser Ser Pro Leu Lys Glu Asp Gln Val Asp Pro Arg Leu Ile Asp
        450                 455                 460

Gly Lys
465

<210> SEQ ID NO 118
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
                20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
        50                  55                  60

Leu Gly Glu Tyr Thr Cys Thr Cys Leu Glu Gly Phe Glu Gly Lys Asn
65              70                  75                  80
```

```
Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
            115                 120                 125

Pro Tyr Pro Cys Gly Lys Gln Thr Leu Glu Arg Arg Lys Arg Ser Val
            130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
            180                 185                 190

Thr Arg Phe Asn Asp Phe Thr Arg Ile Val Gly Gly Gln Glu Cys Lys
            195                 200                 205

Asp Gly Glu Cys Pro Trp Gln Ala Leu Leu Ile Asn Glu Glu Asn Glu
210                 215                 220

Gly Phe Cys Gly Gly Thr Ile Leu Ser Glu Phe Tyr Ile Leu Thr Ala
225                 230                 235                 240

Ala His Cys Leu Tyr Gln Ala Lys Arg Phe Lys Val Arg Val Gly Asp
            245                 250                 255

Arg Asn Thr Glu Gln Glu Glu Gly Gly Glu Ala Val His Glu Val Glu
            260                 265                 270

Val Val Ile Lys His Asn Arg Phe Thr Lys Glu Thr Tyr Asp Phe Asp
            275                 280                 285

Ile Ala Val Leu Arg Leu Lys Thr Pro Ile Thr Phe Arg Met Asn Val
290                 295                 300

Ala Pro Ala Cys Leu Pro Glu Arg Asp Trp Ala Glu Ser Thr Leu Met
305                 310                 315                 320

Thr Gln Lys Thr Gly Ile Val Ser Gly Phe Gly Arg Thr His Glu Lys
            325                 330                 335

Gly Arg Gln Ser Thr Arg Leu Lys Met Leu Glu Val Pro Tyr Val Asp
            340                 345                 350

Arg Asn Ser Cys Lys Leu Ser Ser Ser Phe Ile Ile Thr Gln Asn Met
            355                 360                 365

Phe Cys Ala Gly Tyr Asp Thr Lys Gln Glu Asp Ala Cys Gln Gly Asp
            370                 375                 380

Ser Gly Gly Pro His Val Thr Arg Phe Lys Asp Thr Tyr Phe Val Thr
385                 390                 395                 400

Gly Ile Val Ser Trp Gly Glu Gly Cys Ala Arg Lys Gly Lys Tyr Gly
            405                 410                 415

Ile Tyr Thr Lys Val Thr Ala Phe Leu Lys Trp Ile Asp Arg Ser Met
            420                 425                 430

Lys Thr Arg Gly Leu Pro Lys Ala Lys Ser His Ala Pro Glu Val Ile
            435                 440                 445

Thr Ser Ser Pro Leu Lys Glu Asp Gln Val Asp Pro Arg Leu Ile Asp
450                 455                 460

Gly Lys
465

<210> SEQ ID NO 119
<211> LENGTH: 466
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 119

```
Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
            180                 185                 190

Thr Arg Leu Ser Ser Met Thr Arg Ile Val Gly Gly Gln Glu Cys Lys
        195                 200                 205

Asp Gly Glu Cys Pro Trp Gln Ala Leu Leu Ile Asn Glu Glu Asn Glu
210                 215                 220

Gly Phe Cys Gly Gly Thr Ile Leu Ser Glu Phe Tyr Ile Leu Thr Ala
225                 230                 235                 240

Ala His Cys Leu Tyr Gln Ala Lys Arg Phe Lys Val Arg Val Gly Asp
                245                 250                 255

Arg Asn Thr Glu Gln Glu Glu Gly Gly Glu Ala Val His Glu Val Glu
            260                 265                 270

Val Val Ile Lys His Asn Arg Phe Thr Lys Glu Thr Tyr Asp Phe Asp
        275                 280                 285

Ile Ala Val Leu Arg Leu Lys Thr Pro Ile Thr Phe Arg Met Asn Val
290                 295                 300

Ala Pro Ala Cys Leu Pro Glu Arg Asp Trp Ala Glu Ser Thr Leu Met
305                 310                 315                 320

Thr Gln Lys Thr Gly Ile Val Ser Gly Phe Gly Arg Thr His Glu Lys
                325                 330                 335

Gly Arg Gln Ser Thr Arg Leu Lys Met Leu Glu Val Pro Tyr Val Asp
            340                 345                 350

Arg Asn Ser Cys Lys Leu Ser Ser Ser Phe Ile Ile Thr Gln Asn Met
        355                 360                 365

Phe Cys Ala Gly Tyr Asp Thr Lys Gln Glu Asp Ala Cys Gln Gly Asp
370                 375                 380
```

```
Ser Gly Gly Pro His Val Thr Arg Phe Lys Asp Thr Tyr Phe Val Thr
385                 390                 395                 400

Gly Ile Val Ser Trp Gly Glu Gly Cys Ala Arg Lys Gly Lys Tyr Gly
                405                 410                 415

Ile Tyr Thr Lys Val Thr Ala Phe Leu Lys Trp Ile Asp Arg Ser Met
                420                 425                 430

Lys Thr Arg Gly Leu Pro Lys Ala Lys Ser His Ala Pro Glu Val Ile
            435                 440                 445

Thr Ser Ser Pro Leu Lys Glu Asp Gln Val Asp Pro Arg Leu Ile Asp
        450                 455                 460

Gly Lys
465

<210> SEQ ID NO 120
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
            180                 185                 190

Thr Arg Pro Pro Ser Leu Thr Arg Ile Val Gly Gly Gln Glu Cys Lys
        195                 200                 205

Asp Gly Glu Cys Pro Trp Gln Ala Leu Leu Ile Asn Glu Glu Asn Glu
    210                 215                 220

Gly Phe Cys Gly Gly Thr Ile Leu Ser Glu Phe Tyr Ile Leu Thr Ala
225                 230                 235                 240

Ala His Cys Leu Tyr Gln Ala Lys Arg Phe Lys Val Arg Val Gly Asp
                245                 250                 255

Arg Asn Thr Glu Gln Glu Glu Gly Gly Glu Ala Val His Glu Val Glu
            260                 265                 270
```

```
Val Val Ile Lys His Asn Arg Phe Thr Lys Glu Thr Tyr Asp Phe Asp
            275                 280                 285

Ile Ala Val Leu Arg Leu Lys Thr Pro Ile Thr Phe Arg Met Asn Val
290                 295                 300

Ala Pro Ala Cys Leu Pro Glu Arg Asp Trp Ala Glu Ser Thr Leu Met
305                 310                 315                 320

Thr Gln Lys Thr Gly Ile Val Ser Gly Phe Gly Arg Thr His Glu Lys
                325                 330                 335

Gly Arg Gln Ser Thr Arg Leu Lys Met Leu Glu Val Pro Tyr Val Asp
                340                 345                 350

Arg Asn Ser Cys Lys Leu Ser Ser Ser Phe Ile Ile Thr Gln Asn Met
            355                 360                 365

Phe Cys Ala Gly Tyr Asp Thr Lys Gln Glu Asp Ala Cys Gln Gly Asp
370                 375                 380

Ser Gly Gly Pro His Val Thr Arg Phe Lys Asp Thr Tyr Phe Val Thr
385                 390                 395                 400

Gly Ile Val Ser Trp Gly Glu Gly Cys Ala Arg Lys Gly Lys Tyr Gly
                405                 410                 415

Ile Tyr Thr Lys Val Thr Ala Phe Leu Lys Trp Ile Asp Arg Ser Met
                420                 425                 430

Lys Thr Arg Gly Leu Pro Lys Ala Lys Ser His Ala Pro Glu Val Ile
                435                 440                 445

Thr Ser Ser Pro Leu Lys Glu Asp Gln Val Asp Pro Arg Leu Ile Asp
            450                 455                 460

Gly Lys
465

<210> SEQ ID NO 121
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
                20                  25                  30

Asp Ser Asp Lys Thr Asn Glu Phe Trp Asn Lys Tyr Lys Asp Gly Asp
            35                  40                  45

Gln Cys Glu Thr Ser Pro Cys Gln Asn Gln Gly Lys Cys Lys Asp Gly
        50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Gln Ala Thr Ser Ser Ser Gly Glu Ala Pro Asp Ser Ile Thr Trp
```

```
            145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
            180                 185                 190

Thr Arg Leu Ser Cys Gly Gln Arg Ile Val Gly Gln Glu Cys Lys
        195                 200                 205

Asp Gly Glu Cys Pro Trp Gln Ala Leu Leu Ile Asn Glu Glu Asn Glu
    210                 215                 220

Gly Phe Cys Gly Gly Thr Ile Leu Ser Glu Phe Tyr Ile Leu Thr Ala
225                 230                 235                 240

Ala His Cys Leu Tyr Gln Ala Lys Arg Phe Lys Val Arg Val Gly Asp
                245                 250                 255

Arg Asn Thr Glu Gln Glu Glu Gly Gly Glu Ala Val His Glu Val Glu
            260                 265                 270

Val Val Ile Lys His Asn Arg Phe Thr Lys Glu Thr Tyr Asp Phe Asp
        275                 280                 285

Ile Ala Val Leu Arg Leu Lys Thr Pro Ile Thr Phe Arg Met Asn Val
    290                 295                 300

Ala Pro Ala Cys Leu Pro Glu Arg Asp Trp Ala Glu Ser Thr Leu Met
305                 310                 315                 320

Thr Gln Lys Thr Gly Ile Val Ser Gly Phe Gly Arg Thr His Glu Lys
                325                 330                 335

Gly Arg Gln Ser Thr Arg Leu Lys Met Leu Glu Val Pro Tyr Val Asp
            340                 345                 350

Arg Asn Ser Cys Lys Leu Ser Ser Ser Phe Ile Ile Thr Gln Asn Met
        355                 360                 365

Phe Cys Ala Gly Tyr Asp Thr Lys Gln Glu Asp Ala Cys Gln Gly Asp
    370                 375                 380

Ser Gly Gly Pro His Val Thr Arg Phe Lys Asp Thr Tyr Phe Val Thr
385                 390                 395                 400

Gly Ile Val Ser Trp Gly Glu Gly Cys Ala Arg Lys Gly Lys Tyr Gly
                405                 410                 415

Ile Tyr Thr Lys Val Thr Ala Phe Leu Lys Trp Ile Asp Arg Ser Met
            420                 425                 430

Lys Thr Arg Gly Leu Pro Lys Ala Lys Ser His Ala Pro Glu Val Ile
        435                 440                 445

Thr Ser Ser Pro Leu Lys Glu Asp Gln Val Asp Pro Arg Leu Ile Asp
    450                 455                 460

Gly Lys
465

<210> SEQ ID NO 122
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30
```

```
Asp Ser Asp Lys Thr Asn Glu Phe Trp Asn Lys Tyr Lys Asp Gly Asp
         35                  40                  45
Gln Cys Glu Thr Ser Pro Cys Gln Asn Gln Gly Lys Cys Lys Asp Gly
 50                  55                  60
Leu Gly Glu Tyr Thr Cys Thr Cys Leu Glu Gly Phe Glu Gly Lys Asn
 65                  70                  75                  80
Cys Glu Leu Phe Thr Arg Lys Leu Cys Ser Leu Asp Asn Gly Asp Cys
                 85                  90                  95
Asp Gln Phe Cys His Glu Glu Gln Asn Ser Val Val Cys Ser Cys Ala
            100                 105                 110
Arg Gly Tyr Thr Leu Ala Asp Asn Gly Lys Ala Cys Ile Pro Thr Gly
        115                 120                 125
Pro Tyr Pro Cys Gly Lys Gln Thr Leu Glu Arg Arg Lys Arg Ser Val
    130                 135                 140
Ala Asp Ser Ile Thr Trp Lys Pro Tyr Asp Ala Ala Asp Leu Asp Pro
145                 150                 155                 160
Thr Glu Asn Pro Phe Asp Leu Leu Asp Phe Asn Gln Thr Gln Pro Glu
                165                 170                 175
Arg Gly Asp Asn Asn Leu Thr Arg Asp Phe Leu Ala Glu Gly Gly Gly
            180                 185                 190
Val Arg Ile Val Gly Gly Gln Glu Cys Lys Asp Gly Glu Cys Pro Trp
        195                 200                 205
Gln Ala Leu Leu Ile Asn Glu Glu Asn Glu Gly Phe Cys Gly Gly Thr
    210                 215                 220
Ile Leu Ser Glu Phe Tyr Ile Leu Thr Ala Ala His Cys Leu Tyr Gln
225                 230                 235                 240
Ala Lys Arg Phe Lys Val Arg Val Gly Asp Arg Asn Thr Glu Gln Glu
                245                 250                 255
Glu Gly Gly Glu Ala Val His Glu Val Glu Val Val Ile Lys His Asn
            260                 265                 270
Arg Phe Thr Lys Glu Thr Tyr Asp Phe Asp Ile Ala Val Leu Arg Leu
        275                 280                 285
Lys Thr Pro Ile Thr Phe Arg Met Asn Val Ala Pro Ala Cys Leu Pro
    290                 295                 300
Glu Arg Asp Trp Ala Glu Ser Thr Leu Met Thr Gln Lys Thr Gly Ile
305                 310                 315                 320
Val Ser Gly Phe Gly Arg Thr His Glu Lys Gly Arg Gln Ser Thr Arg
                325                 330                 335
Leu Lys Met Leu Glu Val Pro Tyr Val Asp Arg Asn Ser Cys Lys Leu
            340                 345                 350
Ser Ser Ser Phe Ile Ile Thr Gln Asn Met Phe Cys Ala Gly Tyr Asp
        355                 360                 365
Thr Lys Gln Glu Asp Ala Cys Gln Gly Asp Ser Gly Gly Pro His Val
    370                 375                 380
Thr Arg Phe Lys Asp Thr Tyr Phe Val Thr Gly Ile Val Ser Trp Gly
385                 390                 395                 400
Glu Gly Cys Ala Arg Lys Gly Lys Tyr Gly Ile Tyr Thr Lys Val Thr
                405                 410                 415
Ala Phe Leu Lys Trp Ile Asp Arg Ser Met Lys Thr Arg Gly Leu Pro
            420                 425                 430
Lys Ala Lys Ser His Ala Pro Glu Val Ile Thr Ser Ser Pro Leu Lys
        435                 440                 445
Glu Asp Gln Val Asp Pro Arg Leu Ile Asp Gly Lys
```

<210> SEQ ID NO 123
<211> LENGTH: 460
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 123

```
Ala Asn Ser Phe Leu Glu Glu Met Lys Lys Gly His Leu Glu Arg Glu
1               5                   10                  15
Cys Met Glu Glu Thr Cys Ser Tyr Glu Ala Arg Glu Val Phe Glu
            20                  25                  30
Asp Ser Asp Lys Thr Asn Glu Phe Trp Asn Lys Tyr Lys Asp Gly Asp
        35                  40                  45
Gln Cys Glu Thr Ser Pro Cys Gln Asn Gln Gly Lys Cys Lys Asp Gly
    50                  55                  60
Leu Gly Glu Tyr Thr Cys Thr Cys Leu Glu Gly Phe Glu Gly Lys Asn
65                  70                  75                  80
Cys Glu Leu Phe Thr Arg Lys Leu Cys Ser Leu Asp Asn Gly Asp Cys
                85                  90                  95
Asp Gln Phe Cys His Glu Glu Gln Asn Ser Val Val Cys Ser Cys Ala
            100                 105                 110
Arg Gly Tyr Thr Leu Ala Asp Asn Gly Lys Ala Cys Ile Pro Thr Gly
        115                 120                 125
Pro Tyr Pro Cys Gly Lys Gln Thr Leu Glu Arg Arg Lys Arg Ser Val
    130                 135                 140
Ala Asp Ser Ile Thr Trp Lys Pro Tyr Asp Ala Ala Asp Leu Asp Pro
145                 150                 155                 160
Thr Glu Asn Pro Phe Asp Leu Leu Asp Phe Asn Gln Thr Gln Pro Glu
                165                 170                 175
Arg Gly Asp Asn Asn Leu Thr Arg Asp Phe Leu Ala Glu Gly Leu Thr
            180                 185                 190
Pro Arg Ile Val Gly Gly Gln Glu Cys Lys Asp Gly Glu Cys Pro Trp
        195                 200                 205
Gln Ala Leu Leu Ile Asn Glu Glu Asn Glu Gly Phe Cys Gly Gly Thr
    210                 215                 220
Ile Leu Ser Glu Phe Tyr Ile Leu Thr Ala Ala His Cys Leu Tyr Gln
225                 230                 235                 240
Ala Lys Arg Phe Lys Val Arg Val Gly Asp Arg Asn Thr Glu Gln Glu
                245                 250                 255
Glu Gly Gly Glu Ala Val His Glu Val Glu Val Val Ile Lys His Asn
            260                 265                 270
Arg Phe Thr Lys Glu Thr Tyr Asp Phe Asp Ile Ala Val Leu Arg Leu
        275                 280                 285
Lys Thr Pro Ile Thr Phe Arg Met Asn Val Ala Pro Ala Cys Leu Pro
    290                 295                 300
Glu Arg Asp Trp Ala Glu Ser Thr Leu Met Thr Gln Lys Thr Gly Ile
305                 310                 315                 320
Val Ser Gly Phe Gly Arg Thr His Glu Lys Gly Arg Gln Ser Thr Arg
                325                 330                 335
Leu Lys Met Leu Glu Val Pro Tyr Val Asp Arg Asn Ser Cys Lys Leu
            340                 345                 350
```

```
Ser Ser Ser Phe Ile Ile Thr Gln Asn Met Phe Cys Ala Gly Tyr Asp
            355                 360                 365

Thr Lys Gln Glu Asp Ala Cys Gln Gly Asp Ser Gly Gly Pro His Val
    370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
    435                 440                 445

Glu Asp Gln Val Asp Pro Arg Leu Ile Asp Gly Lys
    450                 455                 460

<210> SEQ ID NO 124
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Asp Ser Ile Thr Trp Lys Pro Tyr Asp Ala Ala Asp Leu Asp Pro
145                 150                 155                 160

Thr Glu Asn Pro Phe Asp Leu Leu Asp Phe Asn Gln Thr Gln Pro Glu
                165                 170                 175

Arg Gly Asp Asn Asn Leu Thr Arg Lys Ala Thr Asn Ala Thr Leu Ser
            180                 185                 190

Pro Arg Ile Val Gly Gly Gln Glu Cys Lys Asp Gly Glu Cys Pro Trp
        195                 200                 205

Gln Ala Leu Leu Ile Asn Glu Glu Asn Glu Gly Phe Cys Gly Gly Thr
    210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255
```

```
Glu Gly Gly Glu Ala Val His Glu Val Glu Val Ile Lys His Asn
                260                 265                 270

Arg Phe Thr Lys Glu Thr Tyr Asp Phe Asp Ile Ala Val Leu Arg Leu
            275                 280                 285

Lys Thr Pro Ile Thr Phe Arg Met Asn Val Ala Pro Ala Cys Leu Pro
        290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
        355                 360                 365

Thr Lys Gln Glu Asp Ala Cys Gln Gly Asp Ser Gly Gly Pro His Val
    370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
        435                 440                 445

Glu Asp Gln Val Asp Pro Arg Leu Ile Asp Gly Lys
    450                 455                 460

<210> SEQ ID NO 125
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Asp Ser Ile Thr Trp Lys Pro Tyr Asp Ala Ala Asp Leu Asp Pro
```

145                 150                 155                 160

Thr Glu Asn Pro Phe Asp Leu Leu Asp Phe Asn Gln Thr Gln Pro Glu
                165                 170                 175

Arg Gly Asp Asn Asn Leu Thr Arg Lys Ala Thr Gln Ala Thr Leu Ser
                180                 185                 190

Pro Arg Ile Val Gly Gly Gln Glu Cys Lys Asp Gly Glu Cys Pro Trp
                195                 200                 205

Gln Ala Leu Leu Ile Asn Glu Glu Asn Glu Gly Phe Cys Gly Gly Thr
                210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
                260                 265                 270

Arg Phe Thr Lys Glu Thr Tyr Asp Phe Asp Ile Ala Val Leu Arg Leu
                275                 280                 285

Lys Thr Pro Ile Thr Phe Arg Met Asn Val Ala Pro Ala Cys Leu Pro
                290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
                340                 345                 350

Ser Ser Ser Phe Ile Ile Thr Gln Asn Met Phe Cys Ala Gly Tyr Asp
                355                 360                 365

Thr Lys Gln Glu Asp Ala Cys Gln Gly Asp Ser Gly Gly Pro His Val
                370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
                420                 425                 430

Lys Ala Lys Ser His Ala Pro Glu Val Ile Thr Ser Ser Pro Leu Lys
                435                 440                 445

Glu Asp Gln Val Asp Pro Arg Leu Ile Asp Gly Lys
                450                 455                 460

<210> SEQ ID NO 126
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
                20                  25                  30

Asp Ser Asp Lys Thr Asn Glu Phe Trp Asn Lys Tyr Lys Asp Gly Asp
                35                  40                  45

```
Gln Cys Glu Thr Ser Pro Cys Gln Asn Gln Gly Lys Cys Lys Asp Gly
 50                  55                  60

Leu Gly Glu Tyr Thr Cys Thr Cys Leu Glu Gly Phe Glu Gly Lys Asn
 65                  70                  75                  80

Cys Glu Leu Phe Thr Arg Lys Leu Cys Ser Leu Asp Asn Gly Asp Cys
                 85                  90                  95

Asp Gln Phe Cys His Glu Glu Gln Asn Ser Val Val Cys Ser Cys Ala
                100                 105                 110

Arg Gly Tyr Thr Leu Ala Asp Asn Gly Lys Ala Cys Ile Pro Thr Gly
                115                 120                 125

Pro Tyr Pro Cys Gly Lys Gln Thr Leu Glu Arg Arg Lys Arg Ser Val
            130                 135                 140

Ala Gln Ala Thr Ser Asp Ser Ile Thr Trp Lys Pro Tyr Asp Ala Ala
145                 150                 155                 160

Asp Leu Asp Pro Thr Glu Asn Pro Phe Asp Leu Leu Asp Phe Asn Gln
                165                 170                 175

Thr Gln Pro Glu Arg Gly Asp Asn Asn Leu Thr Arg Thr Ser Lys Leu
            180                 185                 190

Thr Arg Ile Val Gly Gly Gln Glu Cys Lys Asp Gly Glu Cys Pro Trp
            195                 200                 205

Gln Ala Leu Leu Ile Asn Glu Glu Asn Glu Gly Phe Cys Gly Gly Thr
210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
            275                 280                 285

Lys Thr Pro Ile Thr Phe Arg Met Asn Val Ala Pro Ala Cys Leu Pro
290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
                340                 345                 350

Ser Ser Ser Phe Ile Ile Thr Gln Asn Met Phe Cys Ala Gly Tyr Asp
            355                 360                 365

Thr Lys Gln Glu Asp Ala Cys Gln Gly Asp Ser Gly Gly Pro His Val
            370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
                420                 425                 430

Lys Ala Lys Ser His Ala Pro Glu Val Ile Thr Ser Ser Pro Leu Lys
            435                 440                 445

Glu Asp Gln Val Asp Pro Arg Leu Ile Asp Gly Lys
450                 455                 460
```

```
<210> SEQ ID NO 127
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
130                 135                 140

Ala Gln Ala Thr Ser Ser Ser Ile Thr Trp Lys Pro Tyr Asp Ala Ala
145                 150                 155                 160

Asp Leu Asp Pro Thr Glu Asn Pro Phe Asp Leu Leu Asp Phe Asn Gln
                165                 170                 175

Thr Gln Pro Glu Arg Gly Asp Asn Asn Leu Thr Arg Phe Asn Asp Phe
            180                 185                 190

Thr Arg Ile Val Gly Gly Gln Glu Cys Lys Asp Gly Glu Cys Pro Trp
        195                 200                 205

Gln Ala Leu Leu Ile Asn Glu Glu Asn Glu Gly Phe Cys Gly Gly Thr
210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
        275                 280                 285

Lys Thr Pro Ile Thr Phe Arg Met Asn Val Ala Pro Ala Cys Leu Pro
290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
        355                 360                 365
```

```
Thr Lys Gln Glu Asp Ala Cys Gln Gly Asp Ser Gly Gly Pro His Val
    370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
                420                 425                 430

Lys Ala Lys Ser His Ala Pro Glu Val Ile Thr Ser Ser Pro Leu Lys
                435                 440                 445

Glu Asp Gln Val Asp Pro Arg Leu Ile Asp Gly Lys
450                 455                 460

<210> SEQ ID NO 128
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
                20                  25                  30

Asp Ser Asp Lys Thr Asn Glu Phe Trp Asn Lys Tyr Lys Asp Gly Asp
            35                  40                  45

Gln Cys Glu Thr Ser Pro Cys Gln Asn Gln Gly Lys Cys Lys Asp Gly
50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
                100                 105                 110

Arg Gly Tyr Thr Leu Ala Asp Asn Gly Lys Ala Cys Ile Pro Thr Gly
            115                 120                 125

Pro Tyr Pro Cys Gly Lys Gln Thr Leu Glu Arg Arg Lys Arg Ser Val
130                 135                 140

Ala Gln Ala Thr Ser Asp Ser Ile Thr Trp Lys Pro Tyr Asp Ala Ala
145                 150                 155                 160

Asp Leu Asp Pro Thr Glu Asn Pro Phe Asp Leu Leu Asp Phe Asn Gln
                165                 170                 175

Thr Gln Pro Glu Arg Gly Asp Asn Asn Leu Thr Arg Leu Ser Ser Met
                180                 185                 190

Thr Arg Ile Val Gly Gly Gln Glu Cys Lys Asp Gly Glu Cys Pro Trp
            195                 200                 205

Gln Ala Leu Leu Ile Asn Glu Glu Asn Glu Gly Phe Cys Gly Gly Thr
210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
                260                 265                 270
```

Arg Phe Thr Lys Glu Thr Tyr Asp Phe Asp Ile Ala Val Leu Arg Leu
            275                 280                 285

Lys Thr Pro Ile Thr Phe Arg Met Asn Val Ala Pro Ala Cys Leu Pro
        290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
            355                 360                 365

Thr Lys Gln Glu Asp Ala Cys Gln Gly Asp Ser Gly Gly Pro His Val
        370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
            435                 440                 445

Glu Asp Gln Val Asp Pro Arg Leu Ile Asp Gly Lys
        450                 455                 460

<210> SEQ ID NO 129
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Gln Ala Thr Ser Asp Ser Ile Thr Trp Lys Pro Tyr Asp Ala Ala
145                 150                 155                 160

Asp Leu Asp Pro Thr Glu Asn Pro Phe Asp Leu Leu Asp Phe Asn Gln

```
              165                 170                 175
Thr Gln Pro Glu Arg Gly Asp Asn Asn Leu Thr Arg Pro Pro Ser Leu
            180                 185                 190

Thr Arg Ile Val Gly Gly Gln Glu Cys Lys Asp Gly Glu Cys Pro Trp
        195                 200                 205

Gln Ala Leu Leu Ile Asn Glu Glu Asn Glu Gly Phe Cys Gly Gly Thr
    210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
            245                 250                 255

Glu Gly Gly Glu Ala Val His Glu Val Glu Val Val Ile Lys His Asn
        260                 265                 270

Arg Phe Thr Lys Glu Thr Tyr Asp Phe Asp Ile Ala Val Leu Arg Leu
    275                 280                 285

Lys Thr Pro Ile Thr Phe Arg Met Asn Val Ala Pro Ala Cys Leu Pro
290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
            325                 330                 335

Leu Lys Met Leu Glu Val Pro Tyr Val Asp Arg Asn Ser Cys Lys Leu
        340                 345                 350

Ser Ser Ser Phe Ile Ile Thr Gln Asn Met Phe Cys Ala Gly Tyr Asp
    355                 360                 365

Thr Lys Gln Glu Asp Ala Cys Gln Gly Asp Ser Gly Gly Pro His Val
370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
            405                 410                 415

Ala Phe Leu Lys Trp Ile Asp Arg Ser Met Lys Thr Arg Gly Leu Pro
        420                 425                 430

Lys Ala Lys Ser His Ala Pro Glu Val Ile Thr Ser Ser Pro Leu Lys
    435                 440                 445

Glu Asp Gln Val Asp Pro Arg Leu Ile Asp Gly Lys
450                 455                 460

<210> SEQ ID NO 130
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60
```

```
Leu Gly Glu Tyr Thr Cys Thr Cys Leu Glu Gly Phe Glu Gly Lys Asn
 65                  70                  75                  80

Cys Glu Leu Phe Thr Arg Lys Leu Cys Ser Leu Asp Asn Gly Asp Cys
                 85                  90                  95

Asp Gln Phe Cys His Glu Gln Asn Ser Val Val Cys Ser Cys Ala
            100                 105                 110

Arg Gly Tyr Thr Leu Ala Asp Asn Gly Lys Ala Cys Ile Pro Thr Gly
            115                 120                 125

Pro Tyr Pro Cys Gly Lys Gln Thr Leu Glu Arg Arg Lys Arg Ser Val
130                 135                 140

Ala Gln Ala Thr Ser Asp Ser Ile Thr Trp Lys Pro Tyr Asp Ala Ala
145                 150                 155                 160

Asp Leu Asp Pro Thr Glu Asn Pro Phe Asp Leu Leu Asp Phe Asn Gln
                165                 170                 175

Thr Gln Pro Glu Arg Gly Asp Asn Asn Leu Thr Arg Leu Ser Cys Gly
            180                 185                 190

Gln Arg Ile Val Gly Gly Gln Glu Cys Lys Asp Gly Glu Cys Pro Trp
            195                 200                 205

Gln Ala Leu Leu Ile Asn Glu Glu Asn Glu Gly Phe Cys Gly Gly Thr
210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
            275                 280                 285

Lys Thr Pro Ile Thr Phe Arg Met Asn Val Ala Pro Ala Cys Leu Pro
290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
            355                 360                 365

Thr Lys Gln Glu Asp Ala Cys Gln Gly Asp Ser Gly Gly Pro His Val
370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
435                 440                 445

Glu Asp Gln Val Asp Pro Arg Leu Ile Asp Gly Lys
450                 455                 460

<210> SEQ ID NO 131
<211> LENGTH: 1380
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 131

```
gccaactctt tcctggagga aatgaagaaa ggccacctgg agcgggaatg catggaggaa      60
acctgtagtt acgaggaagc cagagaggtg ttcgaagact cagataagac aaacgagttt     120
tggaataagt acaaagacgg cgatcagtgc gaaactagcc catgtcagaa ccaggggaag     180
tgcaaagatg gactgggcga gtacacctgc acatgtctgg agggattcga aggcaagaat     240
tgcgaactgt ttaccagaaa gctgtgctcc ctggataacg gcgactgcga tcagttttgt     300
catgaggaac agaattccgt ggtctgctct tgtgccaggg atacacact ggctgacaat      360
ggcaaggcat gcatccccac cggcccctat ccttgtggga agcagacact ggagaggcgc     420
aaaaggtcag tggctcaggc aactagctcc tctggcgagg cccccgatag cattacctgg     480
aaaccttatg acgccgctga cctggacccc acagagaacc cctttgacct gctggacttc     540
aaccagacac agcctgaaag aggcgataac aatctgacta ggatcgtggg aggacaggag     600
tgcaaggacg gagaatgtcc atggcaggcc ctgctgatta cgaggaaaa tgagggattc      660
tgcggaggca ctatcctgag cgagttctac attctgaccg cagcccactg tctgtatcag     720
gctaagcgat tcaaagtgcg ggtcggcgac agaaacaccg agcaggagga aggggagaa      780
gcagtgcacg aggtcgaagt ggtcatcaag cataatcgct tcactaaaga gacctacgac     840
tttgatatcg ctgtgctgcg cctgaagaca cctattactt tccgaatgaa cgtcgcccct     900
gcttgcctgc cagagcgaga ttgggccgaa agcaccctga tgacacagaa aactggcatc     960
gtgagcgggt ttggacggac acatgagaag ggcaggcagt ccactcgcct gaaaatgctg    1020
gaagtgccct acgtcgaccg gaactcttgt aagctgagta gcagcttcat cattacccag    1080
aatatgtttt gcgccgggta tgacacaaag caggaggatg cttgtcaggg agacagtggc    1140
gggcctcacg tgactaggtt caaagatact tattttgtga ccggcatcgt cagctgggga    1200
gagggatgcg cacgcaaggg gaaatacgga atctatacca aggtgacagc ctttctgaaa    1260
tggattgacc gatctatgaa gacccggggg ctgccaaagg caaaaagtca tgcccccgag    1320
gtcattacca gttcccctct gaaagaagac caggtggacc caaggctgat tgacggcaag    1380
```

<210> SEQ ID NO 132
<211> LENGTH: 1380
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 132

```
gccaactctt tcctggagga aatgaagaaa ggccacctgg agcgggaatg catggaggaa      60
acctgtagtt acgaggaagc cagagaggtg ttcgaagact cagataagac aaacgagttt     120
tggaataagt acaaagacgg cgatcagtgc gaaactagcc catgtcagaa ccaggggaag     180
tgcaaagatg gactgggcga gtacacctgc acatgtctgg agggattcga aggcaagaat     240
tgcgaactgt ttaccagaaa gctgtgctcc ctggataacg gcgactgcga tcagttttgt     300
catgaggaac agaattccgt ggtctgctct tgtgccaggg atacacact ggctgacaat      360
ggcaaggcat gcatccccac cggcccctat ccttgtggga agcagacact ggagaggcgc     420
aaaaggtcag tggctcaggc aactagctcc tctggcgagg cccccgatag cattacctgg     480
```

```
aaaccttatg acgccgctga cctggacccc acagagaacc cctttgacct gctggacttc    540
aaccagacac aggacttcct ggcagaagga ggaggagtga ggatcgtggg aggacaggag    600
tgcaaggacg gagaatgtcc atggcaggcc ctgctgatta acgaggaaaa tgagggattc    660
tgcggaggca ctatcctgag cgagttctac attctgaccg cagcccactg tctgtatcag    720
gctaagcgat tcaaagtgcg ggtcggcgac agaaacaccg agcaggagga aggggagaa     780 gcagtgcacg aggtcgaagt ggtcatcaag cataatcgct tcactaaaga gacctacgac    840
tttgatatcg ctgtgctgcg cctgaagaca cctattactt tccgaatgaa cgtcgcccct    900
gcttgcctgc cagagcgaga ttgggccgaa agcaccctga tgacacagaa aactggcatc    960
gtgagcgggt ttggacggac acatgagaag ggcaggcagt ccactcgcct gaaaatgctg   1020
gaagtgccct acgtcgaccg gaactcttgt aagctgagta gcagcttcat cattacccag   1080
aatatgtttt gcgccgggta tgacacaaag caggaggatg cttgtcaggg agacagtggc   1140
gggcctcacg tgactaggtt caaagatact tattttgtga ccggcatcgt cagctgggga   1200
gagggatgcg cacgcaaggg gaaatacgga atctatacca aggtgacagc ctttctgaaa   1260
tggattgacc gatctatgaa gacccggggg ctgccaaagg caaaaagtca tgccccgag    1320 gtcattacca gttcccctct gaaagaagac caggtggacc aaggctgat tgacggcaag    1380
```

<210> SEQ ID NO 133
<211> LENGTH: 1380
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133

```
gccaactctt tcctggagga aatgaagaaa ggccacctgg agcgggaatg catggaggaa     60
acctgtagtt acgaggaagc cagagaggtg ttcgaagact cagataagac aaacgagttt    120
tggaataagt acaaagacgg cgatcagtgc gaaactagcc catgtcagaa ccaggggaag    180
tgcaaagatg gactgggcga gtacacctgc acatgtctgg agggattcga aggcaagaat    240
tgcgaactgt ttaccagaaa gctgtgctcc ctggataacg gcgactgcga tcagttttgt    300
catgaggaac agaattccgt ggtctgctct tgtgccaggg gatacacact ggctgacaat    360
ggcaaggcat gcatccccac cggcccctat ccttgtggga agcagacact ggagaggcgc    420
aaaaggtcag tggctcaggc aactagctcc tctggcgagg cccccgatag cattacctgg    480
aaaccttatg acgccgctga cctggacccc acagagaacc cctttgacct gctggacttc    540
aaccagacac aggacttcct ggccgagggc ctgaccccta ggatcgtggg aggacaggag    600
tgcaaggacg gagaatgtcc atggcaggcc ctgctgatta acgaggaaaa tgagggattc    660
tgcggaggca ctatcctgag cgagttctac attctgaccg cagcccactg tctgtatcag    720
gctaagcgat tcaaagtgcg ggtcggcgac agaaacaccg agcaggagga aggggagaa     780 gcagtgcacg aggtcgaagt ggtcatcaag cataatcgct tcactaaaga gacctacgac    840
tttgatatcg ctgtgctgcg cctgaagaca cctattactt tccgaatgaa cgtcgcccct    900
gcttgcctgc cagagcgaga ttgggccgaa agcaccctga tgacacagaa aactggcatc    960
gtgagcgggt ttggacggac acatgagaag ggcaggcagt ccactcgcct gaaaatgctg   1020
gaagtgccct acgtcgaccg gaactcttgt aagctgagta gcagcttcat cattacccag   1080
aatatgtttt gcgccgggta tgacacaaag caggaggatg cttgtcaggg agacagtggc   1140
```

```
gggcctcacg tgactaggtt caaagatact tattttgtga ccggcatcgt cagctgggga    1200
gagggatgcg cacgcaaggg gaaatacgga atctatacca aggtgacagc ctttctgaaa    1260
tggattgacc gatctatgaa gacccggggg ctgccaaagg caaaaagtca tgccccgag     1320 gtcattacca gttccctct gaaagaagac caggtggacc caaggctgat tgacggcaag    1380
```

<210> SEQ ID NO 134
<211> LENGTH: 1380
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134

```
gccaactctt tcctggagga aatgaagaaa ggccacctgg agcgggaatg catggaggaa      60
acctgtagtt acgaggaagc cagagaggtg ttcgaagact cagataagac aaacgagttt    120
tggaataagt acaaagacgg cgatcagtgc gaaactagcc atgtcagaa ccaggggaag     180 tgcaaagatg gactgggcga gtacacctgc acatgtctgg agggattcga aggcaagaat    240
tgcgaactgt ttaccagaaa gctgtgctcc ctggataacg gcgactgcga tcagttttgt    300
catgaggaac agaattccgt ggtctgctct tgtgccaggg gatacacact ggctgacaat    360
ggcaaggcat gcatccccac cggccctat ccttgtggga gcagacact ggagaggcgc      420 aaaaggtcag tggctcaggc aactagctcc tctggcgagg ccccgatag cattacctgg    480 aaaccttatg acgccgctga cctggacccc acagagaacc cctttgacct gctggacttc    540
aaccagacac agaaggccac caacgccacc ctgtcccta ggatcgtggg aggacaggag     600
tgcaaggacg gagaatgtcc atggcaggcc ctgctgatta cgaggaaaa tgagggattc     660 tgcggaggca ctatcctgag cgagttctac attctgaccg cagcccactg tctgtatcag    720
gctaagcgat tcaaagtgcg ggtcggcgac agaaacaccg agcaggagga aggggagaa     780 gcagtgcacg aggtcgaagt ggtcatcaag cataatcgct tcactaaaga gacctacgac    840
tttgatatcg ctgtgctgcg cctgaagaca cctattactt tccgaatgaa cgtcgcccct    900
gcttgcctgc cagagcgaga ttgggccgaa agcaccctga tgacacagaa aactggcatc    960
gtgagcgggt ttggacggac acatgagaag ggcaggcagt ccactcgcct gaaaatgctg   1020
gaagtgccct acgtcgaccg gaactcttgt aagctgagta gcagcttcat cattacccag   1080
aatatgtttt gcgccgggta tgacacaaag caggaggatg cttgtcaggg agacagtggc   1140
gggcctcacg tgactaggtt caaagatact tattttgtga ccggcatcgt cagctgggga   1200
gagggatgcg cacgcaaggg gaaatacgga atctatacca aggtgacagc ctttctgaaa   1260
tggattgacc gatctatgaa gacccggggg ctgccaaagg caaaaagtca tgccccgag    1320 gtcattacca gttccctct gaaagaagac caggtggacc caaggctgat tgacggcaag   1380
```

<210> SEQ ID NO 135
<211> LENGTH: 1380
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135

```
gccaactctt tcctggagga aatgaagaaa ggccacctgg agcgggaatg catggaggaa      60
```

| | |
|---|---|
| acctgtagtt acgaggaagc cagagaggtg ttcgaagact cagataagac aaacgagttt | 120 |
| tggaataagt acaaagacgg cgatcagtgc gaaactagcc catgtcagaa ccaggggaag | 180 |
| tgcaaagatg gactgggcga gtacacctgc acatgtctgg agggattcga aggcaagaat | 240 |
| tgcgaactgt ttaccagaaa gctgtgctcc ctggataacg gcgactgcga tcagttttgt | 300 |
| catgaggaac agaattccgt ggtctgctct tgtgccaggg gatacacact ggctgacaat | 360 |
| ggcaaggcat gcatccccac cggcccctat ccttgtggga agcagacact ggagaggcgc | 420 |
| aaaaggtcag tggctcaggc aactagctcc tctggcgagg ccccgatag cattacctgg | 480 |
| aaaccttatg acgccgctga cctggacccc acagagaacc ctttgacct gctggacttc | 540 |
| aaccagacac agaaggccac ccaggccacc ctgagcccta ggatcgtggg aggacaggag | 600 |
| tgcaaggacg gagaatgtcc atggcaggcc ctgctgatta acgaggaaaa tgagggattc | 660 |
| tgcggaggca ctatcctgag cgagttctac attctgaccg cagcccactg tctgtatcag | 720 |
| gctaagcgat tcaaagtgcg ggtcggcgac agaaacaccg agcaggagga aggggagaa | 780 |
| gcagtgcacg aggtcgaagt ggtcatcaag cataatcgct tcactaaaga gacctacgac | 840 |
| tttgatatcg ctgtgctgcg cctgaagaca cctattactt tccgaatgaa cgtcgcccct | 900 |
| gcttgcctgc cagagcgaga ttgggccgaa agcaccctga tgcacagaa aactggcatc | 960 |
| gtgagcgggt ttggacggac acatgagaag ggcaggcagt ccactcgcct gaaaatgctg | 1020 |
| gaagtgccct acgtcgaccg gaactcttgt aagctgagta gcagcttcat cattacccag | 1080 |
| aatatgtttt gcgccgggta tgacacaaag caggaggatg cttgtcaggg agacagtggc | 1140 |
| gggcctcacg tgactaggtt caaagatact tattttgtga ccggcatcgt cagctgggga | 1200 |
| gagggatgcg cacgcaaggg gaaatacgga atctatacca aggtgacagc ctttctgaaa | 1260 |
| tggattgacc gatctatgaa gacccggggg ctgccaaagg caaaaagtca tgcccccgag | 1320 |
| gtcattacca gttcccctct gaaagaagac caggtggacc caaggctgat tgacggcaag | 1380 |

<210> SEQ ID NO 136
<211> LENGTH: 1380
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 136

| | |
|---|---|
| gccaactctt tcctggagga aatgaagaaa ggccacctgg agcgggaatg catggaggaa | 60 |
| acctgtagtt acgaggaagc cagagaggtg ttcgaagact cagataagac aaacgagttt | 120 |
| tggaataagt acaaagacgg cgatcagtgc gaaactagcc catgtcagaa ccaggggaag | 180 |
| tgcaaagatg gactgggcga gtacacctgc acatgtctgg agggattcga aggcaagaat | 240 |
| tgcgaactgt ttaccagaaa gctgtgctcc ctggataacg gcgactgcga tcagttttgt | 300 |
| catgaggaac agaattccgt ggtctgctct tgtgccaggg gatacacact ggctgacaat | 360 |
| ggcaaggcat gcatccccac cggcccctat ccttgtggga agcagacact ggagaggcgc | 420 |
| aaaaggtcag tggctcaggc aactagctcc tctggcgagg ccccgatag cattacctgg | 480 |
| aaaccttatg acgccgctga cctggacccc acagagaacc ctttgacct gctggacttc | 540 |
| aaccagacac agcctgaaag aggcaccagc aagctgacca ggatcgtggg aggacaggag | 600 |
| tgcaaggacg gagaatgtcc atggcaggcc ctgctgatta acgaggaaaa tgagggattc | 660 |
| tgcggaggca ctatcctgag cgagttctac attctgaccg cagcccactg tctgtatcag | 720 |

| | |
|---|---|
| gctaagcgat tcaaagtgcg gtcggcgac agaaacaccg agcaggagga aggggagaa | 780 |
| gcagtgcacg aggtcgaagt ggtcatcaag cataatcgct tcactaaaga gacctacgac | 840 |
| tttgatatcg ctgtgctgcg cctgaagaca cctattactt tccgaatgaa cgtcgcccct | 900 |
| gcttgcctgc cagagcgaga ttgggccgaa agcaccctga tgacacagaa aactggcatc | 960 |
| gtgagcgggt ttggacggac acatgagaag ggcaggcagt ccactcgcct gaaaatgctg | 1020 |
| gaagtgccct acgtcgaccg gaactcttgt aagctgagta gcagcttcat cattacccag | 1080 |
| aatatgtttt gcgccgggta tgacacaaag caggaggatg cttgtcaggg agacagtggc | 1140 |
| gggcctcacg tgactaggtt caaagatact tattttgtga ccggcatcgt cagctgggga | 1200 |
| gagggatgcg cacgcaaggg gaaatacgga atctatacca aggtgacagc ctttctgaaa | 1260 |
| tggattgacc gatctatgaa gacccggggg ctgccaaagg caaaaagtca tgcccccgag | 1320 |
| gtcattacca gttcccctct gaagaagac caggtggacc caaggctgat tgacggcaag | 1380 |

<210> SEQ ID NO 137
<211> LENGTH: 1380
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 137

| | |
|---|---|
| gccaactctt tcctggagga aatgaagaaa ggccacctgg agcgggaatg catggaggaa | 60 |
| acctgtagtt acgaggaagc cagagaggtg ttcgaagact cagataagac aaacgagttt | 120 |
| tggaataagt acaaagacgg cgatcagtgc gaaactagcc catgtcagaa ccaggggaag | 180 |
| tgcaaagatg gactgggcga gtacacctgc acatgtctgg agggattcga aggcaagaat | 240 |
| tgcgaactgt ttaccagaaa gctgtgctcc ctggataacg gcgactgcga tcagttttgt | 300 |
| catgaggaac agaattccgt ggtctgtctc tgtgccaggg gatacacact ggctgacaat | 360 |
| ggcaaggcat gcatccccac cggcccctat ccttgtggga agcagacact ggagaggcgc | 420 |
| aaaaggtcag tggctcaggc aactagctcc tctggcgagg cccccgatag cattacctgg | 480 |
| aaaccttatg acgccgctga cctggacccc acagagaacc cctttgacct gctggacttc | 540 |
| aaccagacac agcctgaaag aggcttcaac gacttcacca ggatcgtggg aggacaggag | 600 |
| tgcaaggacg gagaatgtcc atggcaggcc tgctgattaa cgaggaaaaa tgagggattc | 660 |
| tgcggaggca ctatcctgag cgagttctac attctgaccg cagcccactg tctgtatcag | 720 |
| gctaagcgat tcaaagtgcg gtcggcgac agaaacaccg agcaggagga aggggagaa | 780 |
| gcagtgcacg aggtcgaagt ggtcatcaag cataatcgct tcactaaaga gacctacgac | 840 |
| tttgatatcg ctgtgctgcg cctgaagaca cctattactt tccgaatgaa cgtcgcccct | 900 |
| gcttgcctgc cagagcgaga ttgggccgaa agcaccctga tgacacagaa aactggcatc | 960 |
| gtgagcgggt ttggacggac acatgagaag ggcaggcagt ccactcgcct gaaaatgctg | 1020 |
| gaagtgccct acgtcgaccg gaactcttgt aagctgagta gcagcttcat cattacccag | 1080 |
| aatatgtttt gcgccgggta tgacacaaag caggaggatg cttgtcaggg agacagtggc | 1140 |
| gggcctcacg tgactaggtt caaagatact tattttgtga ccggcatcgt cagctgggga | 1200 |
| gagggatgcg cacgcaaggg gaaatacgga atctatacca aggtgacagc ctttctgaaa | 1260 |
| tggattgacc gatctatgaa gacccggggg ctgccaaagg caaaaagtca tgcccccgag | 1320 |
| gtcattacca gttcccctct gaagaagac caggtggacc caaggctgat tgacggcaag | 1380 |

<210> SEQ ID NO 138
<211> LENGTH: 1380
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 138

| | |
|---|---|
| gccaactctt tcctggagga aatgaagaaa ggccacctgg agcgggaatg catggaggaa | 60 |
| acctgtagtt acgaggaagc cagagaggtg ttcgaagact cagataagac aaacgagttt | 120 |
| tggaataagt acaaagacgg cgatcagtgc gaaactagcc catgtcagaa ccaggggaag | 180 |
| tgcaaagatg gactgggcga gtacacctgc acatgtctgg agggattcga aggcaagaat | 240 |
| tgcgaactgt ttaccagaaa gctgtgctcc ctggataacg gcgactgcga tcagttttgt | 300 |
| catgaggaac agaattccgt ggtctgctct tgtgccaggg gatacacact ggctgacaat | 360 |
| ggcaaggcat gcatccccac cggccccctat ccttgtggga agcagacact ggagaggcgc | 420 |
| aaaaggtcag tggctcaggc aactagctcc tctggcgagg cccccgatag cattacctgg | 480 |
| aaaccttatg acgccgctga cctggacccc acagagaacc cctttgacct gctggacttc | 540 |
| aaccagacac agcctgaaag aggcctgagc agcatgacca ggatcgtggg aggacaggag | 600 |
| tgcaaggacg gagaatgtcc atggcaggcc ctgctgatta acgaggaaaa tgagggattc | 660 |
| tgcggaggca ctatcctgag cgagttctac attctgaccg cagcccactg tctgtatcag | 720 |
| gctaagcgat tcaaagtgcg ggtcggcgac agaaacaccg agcaggagga aggggagaa | 780 |
| gcagtgcacg aggtcgaagt ggtcatcaag cataatcgct tcactaaaga gacctacgac | 840 |
| tttgatatcg ctgtgctgcg cctgaagaca cctattactt tccgaatgaa cgtcgcccct | 900 |
| gcttgcctgc cagagcgaga ttgggccgaa agcaccctga tgacacagaa aactggcatc | 960 |
| gtgagcgggt ttggacggac acatgagaag ggcaggcagt ccactcgcct gaaaatgctg | 1020 |
| gaagtgccct acgtcgaccg gaactcttgt aagctgagta gcagcttcat cattacccag | 1080 |
| aatatgtttt gcgccgggta tgacacaaag caggaggatg cttgtcaggg agacagtggc | 1140 |
| gggcctcacg tgactaggtt caaagatact tattttgtga ccggcatcgt cagctgggga | 1200 |
| gagggatgcg cacgcaaggg gaaatacgga atctatacca aggtgacagc ctttctgaaa | 1260 |
| tggattgacc gatctatgaa gacccggggg ctgccaaagg caaaaagtca tgcccccgag | 1320 |
| gtcattacca gttcccctct gaaagaagac caggtggacc caaggctgat tgacggcaag | 1380 |

<210> SEQ ID NO 139
<211> LENGTH: 1380
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 139

| | |
|---|---|
| gccaactctt tcctggagga aatgaagaaa ggccacctgg agcgggaatg catggaggaa | 60 |
| acctgtagtt acgaggaagc cagagaggtg ttcgaagact cagataagac aaacgagttt | 120 |
| tggaataagt acaaagacgg cgatcagtgc gaaactagcc catgtcagaa ccaggggaag | 180 |
| tgcaaagatg gactgggcga gtacacctgc acatgtctgg agggattcga aggcaagaat | 240 |
| tgcgaactgt ttaccagaaa gctgtgctcc ctggataacg gcgactgcga tcagttttgt | 300 |
| catgaggaac agaattccgt ggtctgctct tgtgccaggg gatacacact ggctgacaat | 360 |

```
ggcaaggcat gcatccccac cggcccctat ccttgtggga agcagacact ggagaggcgc    420
aaaaggtcag tggctcaggc aactagctcc tctggcgagg cccccgatag cattacctgg    480
aaaccttatg acgccgctga cctggacccc acagagaacc cctttgacct gctggacttc    540
aaccagacac agcctgaaag aggccctccc agcctgacca ggatcgtggg aggacaggag    600
tgcaaggacg gagaatgtcc atggcaggcc ctgctgatta acgaggaaaa tgagggattc    660
tgcggaggca ctatcctgag cgagttctac attctgaccg cagcccactg tctgtatcag    720
gctaagcgat tcaaagtgcg ggtcggcgac agaaacaccg agcaggagga aggggagaa    780 gcagtgcacg aggtcgaagt ggtcatcaag cataatcgct tcactaaaga gacctacgac    840
tttgatatcg ctgtgctgcg cctgaagaca cctattactt tccgaatgaa cgtcgcccct    900
gcttgcctgc cagagcgaga ttgggccgaa agcaccctga tgacacagaa actggcatc    960 gtgagcgggt ttggacggac acatgagaag ggcaggcagt ccactcgcct gaaaatgctg    1020
gaagtgccct acgtcgaccg gaactcttgt aagctgagta gcagcttcat cattacccag    1080
aatatgtttt gcgccgggta tgacacaaag caggaggatg cttgtcaggg agacagtggc    1140
gggcctcacg tgactaggtt caaagatact tattttgtga ccggcatcgt cagctgggga    1200
gagggatgcg cacgcaaggg gaaatacgga atctatacca aggtgacagc ctttctgaaa    1260
tggattgacc gatctatgaa gacccggggg ctgccaaagg caaaaagtca tgccccccgag   1320 gtcattacca gttcccctct gaaagaagac caggtggacc aaggctgat tgacggcaag   1380
```

<210> SEQ ID NO 140
<211> LENGTH: 1380
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140

```
gccaactctt tcctggagga aatgaagaaa ggccacctgg agcgggaatg catggaggaa    60
acctgtagtt acgaggaagc cagagaggtg ttcgaagact cagataagac aaacgagttt    120
tggaataagt acaaagacgg cgatcagtgc gaaactagcc catgtcagaa ccaggggaag    180
tgcaaagatg gactgggcga gtacacctgc acatgtctgg agggattcga aggcaagaat    240
tgcgaactgt ttaccagaaa gctgtgctcc ctggataacg gcgactgcga tcagttttgt    300
catgaggaac agaattccgt ggtctgctct tgtgccaggg gatacacact ggctgacaat    360
ggcaaggcat gcatccccac cggcccctat ccttgtggga agcagacact ggagaggcgc    420
aaaaggtcag tggctcaggc aactagctcc tctggcgagg cccccgatag cattacctgg    480
aaaccttatg acgccgctga cctggacccc acagagaacc cctttgacct gctggacttc    540
aaccagacac agcctgaaag aggcctgtcc tgcggccaga ggatcgtggg aggacaggag    600
tgcaaggacg gagaatgtcc atggcaggcc ctgctgatta acgaggaaaa tgagggattc    660
tgcggaggca ctatcctgag cgagttctac attctgaccg cagcccactg tctgtatcag    720
gctaagcgat tcaaagtgcg ggtcggcgac agaaacaccg agcaggagga aggggagaa    780 gcagtgcacg aggtcgaagt ggtcatcaag cataatcgct tcactaaaga gacctacgac    840
tttgatatcg ctgtgctgcg cctgaagaca cctattactt tccgaatgaa cgtcgcccct    900
gcttgcctgc cagagcgaga ttgggccgaa agcaccctga tgacacagaa actggcatc    960 gtgagcgggt ttggacggac acatgagaag ggcaggcagt ccactcgcct gaaaatgctg    1020
```

```
gaagtgccct acgtcgaccg gaactcttgt aagctgagta gcagcttcat cattacccag   1080
aatatgtttt gcgccgggta tgacacaaag caggaggatg cttgtcaggg agacagtggc   1140
gggcctcacg tgactaggtt caaagatact tattttgtga ccggcatcgt cagctgggga   1200
gagggatgcg cacgcaaggg gaaatacgga atctatacca aggtgacagc ctttctgaaa   1260
tggattgacc gatctatgaa gacccggggg ctgccaaagg caaaaagtca tgccccgag    1320 gtcattacca gttcccctct gaaagaagac caggtggacc caaggctgat tgacggcaag   1380
```

<210> SEQ ID NO 141
<211> LENGTH: 1410
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 141

```
gccaactctt tcctggagga aatgaagaaa ggccacctgg agcgggaatg catggaggaa    60
acctgtagtt acgaggaagc cagagaggtg ttcgaagact cagataagac aaacgagttt   120
tggaataagt acaaagacgg cgatcagtgc gaaactagcc catgtcagaa ccaggggaag   180
tgcaaagatg gactgggcga gtacacctgc acatgtctgg agggattcga aggcaagaat   240
tgcgaactgt ttaccagaaa gctgtgctcc ctggataacg gcgactgcga tcagttttgt   300
catgaggaac agaattccgt ggtctgctct tgtgccaggg gatacacact ggctgacaat   360
ggcaaggcat gcatccccac cggccccat ccttgtggga gcagacact ggagaggcgc    420 aaaaggtcag tggctcaggc aactagctcc tctggcgagg cccccgatag cattacctgg   480
aaaccttatg acgccgctga cctggacccc acagagaacc cctttgacct gctggacttc   540
aaccagacac agcctgaaag aggcgataac aatctgacta gggacttcct ggcagaagga   600
ggaggagtga ggatcgtggg aggacaggag tgcaaggacg gagaatgtcc atggcaggcc   660
ctgctgatta acgaggaaaa tgagggattc tgcggaggca ctatcctgag cgagttctac   720
attctgaccg cagcccactg tctgtatcag gctaagcgat tcaaagtgcg ggtcggcgac   780
agaaacaccg agcaggagga aggggagaa gcagtgcacg aggtcgaagt ggtcatcaag   840
cataatcgct tcactaaaga gacctacgac tttgatatcg ctgtgctgcg cctgaagaca   900
cctattactt tccgaatgaa cgtcgcccct gcttgcctgc cagagcgaga ttgggccgaa   960
agcaccctga tgacacagaa aactggcatc gtgagcgggt ttggacggac acatgagaag  1020
ggcaggcagt ccactcgcct gaaaatgctg gaagtgccct acgtcgaccg gaactcttgt  1080
aagctgagta gcagcttcat cattacccag aatatgtttt gcgccgggta tgacacaaag  1140
caggaggatg cttgtcaggg agacagtggc gggcctcacg tgactaggtt caaagatact  1200
tattttgtga ccggcatcgt cagctgggga gagggatgcg cacgcaaggg gaaatacgga  1260
atctatacca aggtgacagc ctttctgaaa tggattgacc gatctatgaa gacccggggg  1320
ctgccaaagg caaaaagtca tgccccgag gtcattacca gttcccctct gaaagaagac   1380
caggtggacc caaggctgat tgacggcaag                                    1410
```

<210> SEQ ID NO 142
<211> LENGTH: 1410
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 142

```
gccaactctt tcctggagga aatgaagaaa ggccacctgg agcgggaatg catggaggaa      60
acctgtagtt acgaggaagc cagagaggtg ttcgaagact cagataagac aaacgagttt     120
tggaataagt acaaagacgg cgatcagtgc gaaactagcc catgtcagaa ccaggggaag     180
tgcaaagatg gactgggcga gtacacctgc acatgtctgg agggattcga aggcaagaat     240
tgcgaactgt ttaccagaaa gctgtgctcc ctggataacg gcgactgcga tcagttttgt     300
catgaggaac agaattccgt ggtctgctct tgtgccaggg gatacacact ggctgacaat     360
ggcaaggcat gcatccccac cggcccctat ccttgtggga agcagacact ggagaggcgc     420
aaaaggtcag tggctcaggc aactagctcc tctggcgagg cccccgatag cattacctgg     480
aaaccttatg acgccgctga cctggacccc acagagaacc cctttgacct gctggacttc     540
aaccagacac agcctgaaag aggcgataac aatctgacta gggacttcct ggccgagggc     600
ctgaccccta ggatcgtggg aggacaggag tgcaaggacg agaatgtcc atggcaggcc      660
ctgctgatta cgaggaaaa tgagggattc tgcggaggca ctatcctgag cgagttctac     720
attctgaccg cagcccactg tctgtatcag gctaagcgat tcaaagtgcg ggtcggcgac     780
agaaacaccg agcaggagga aggggagaa gcagtgcacg aggtcgaagt ggtcatcaag     840
cataatcgct tcactaaaga gacctacgac tttgatatcg ctgtgctgcg cctgaagaca     900
cctattactt tccgaatgaa cgtcgcccct gcttgcctgc agagcgaga ttgggccgaa      960
agcaccctga tgacacagaa aactggcatc gtgagcgggt ttggacggac acatgagaag    1020
ggcaggcagt ccactcgcct gaaaatgctg gaagtgccct acgtcgaccg gaactcttgt    1080
aagctgagta gcagcttcat cattacccag aatatgtttt cgccgggta tgacacaaag    1140
caggaggatg cttgtcaggg agacagtggc gggcctcacg tgactaggtt caaagatact    1200
tattttgtga ccggcatcgt cagctgggga gagggatgcg cacgcaaggg gaaatacgga    1260
atctatacca aggtgacagc cttttctgaaa tggattgacc gatctatgaa gacccggggg    1320
ctgccaaagg caaaaagtca tgcccccgag gtcattacca gttcccctct gaaagaagac    1380
caggtggacc caaggctgat tgacggcaag                                      1410
```

<210> SEQ ID NO 143
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143

```
gccaactctt tcctggagga aatgaagaaa ggccacctgg agcgggaatg catggaggaa      60
acctgtagtt acgaggaagc cagagaggtg ttcgaagact cagataagac aaacgagttt     120
tggaataagt acaaagacgg cgatcagtgc gaaactagcc catgtcagaa ccaggggaag     180
tgcaaagatg gactgggcga gtacacctgc acatgtctgg agggattcga aggcaagaat     240
tgcgaactgt ttaccagaaa gctgtgctcc ctggataacg gcgactgcga tcagttttgt     300
catgaggaac agaattccgt ggtctgctct tgtgccaggg gatacacact ggctgacaat     360
ggcaaggcat gcatccccac cggcccctat ccttgtggga agcagacact ggagaggcgc     420
aaaaggtcag tggctcaggc aactagctcc tctggcgagg cccccgatag cattacctgg     480
```

```
aaaccttatg acgccgctga cctggacccc acagagaacc cctttgacct gctggacttc      540
aaccagacac agcctgaaag aggcgataac aatctgacta ggaaggccac caacgccacc      600
ctgtccccta ggatcgtggg aggacaggag tgcaaggacg agaatgtcc atggcaggcc       660 ctgctgatta acgaggaaaa tgagggattc tgcggaggca ctatcctgag cgagttctac      720
attctgaccg cagcccactg tctgtatcag gctaagcgat tcaaagtgcg ggtcggcgac      780
agaaacaccg agcaggagga aggggagaa gcagtgcacg aggtcgaagt ggtcatcaag       840
cataatcgct tcactaaaga gacctacgac tttgatatcg ctgtgctgcg cctgaagaca      900
cctattactt tccgaatgaa cgtcgcccct gcttgcctgc cagagcgaga ttgggccgaa      960
agcaccctga tgacacagaa aactggcatc gtgagcgggt ttggacggac acatgagaag     1020
ggcaggcagt ccactcgcct gaaaatgctg gaagtgccct acgtcgaccg gaactcttgt     1080
aagctgagta gcagcttcat cattacccag aatatgtttt gcgccgggta tgacacaaag     1140
caggaggatg cttgtcaggg agacagtggc gggcctcacg tgactaggtt caaagatact     1200
tattttgtga ccggcatcgt cagctgggga gagggatgcg cacgcaaggg gaaatacgga     1260
atctatacca aggtgacagc ctttctgaaa tggattgacc gatctatgaa gacccggggg     1320
ctgccaaagg caaaaagtca tgcccccgag gtcattacca gttcccctct gaaagaagac     1380
caggtggacc caaggctgat tgacggcaag                                      1410
```

<210> SEQ ID NO 144
<211> LENGTH: 1410
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 144

```
gccaactctt tcctggagga aatgaagaaa ggccacctgg agcgggaatg catggaggaa       60
acctgtagtt acgaggaagc cagagaggtg ttcgaagact cagataagac aaacgagttt      120
tggaataagt acaaagacgg cgatcagtgc gaaactagcc atgtcagaa ccaggggaag       180 tgcaaagatg gactgggcga gtacacctgc acatgtctgg agggattcga aggcaagaat      240
tgcgaactgt ttaccagaaa gctgtgctcc ctggataacg gcgactgcga tcagttttgt      300
catgaggaac agaattccgt ggtctgctct tgtgccaggg gatacacact ggctgacaat      360
ggcaaggcat gcatccccac cggcccctat ccttgtggga gcagacact ggagaggcgc      420 aaaaggtcag tggctcaggc aactagctcc tctggcgagg cccccgatag cattaccctgg    480 aaaccttatg acgccgctga cctggacccc acagagaacc cctttgacct gctggacttc     540
aaccagacac agcctgaaag aggcgataac aatctgacta ggaaggccac ccaggccacc     600
ctgagcccta ggatcgtggg aggacaggag tgcaaggacg agaatgtcc atggcaggcc      660 ctgctgatta acgaggaaaa tgagggattc tgcggaggca ctatcctgag cgagttctac     720
attctgaccg cagcccactg tctgtatcag gctaagcgat tcaaagtgcg ggtcggcgac     780
agaaacaccg agcaggagga aggggagaa gcagtgcacg aggtcgaagt ggtcatcaag      840
cataatcgct tcactaaaga gacctacgac tttgatatcg ctgtgctgcg cctgaagaca     900
cctattactt tccgaatgaa cgtcgcccct gcttgcctgc cagagcgaga ttgggccgaa     960
agcaccctga tgacacagaa aactggcatc gtgagcgggt ttggacggac acatgagaag    1020
ggcaggcagt ccactcgcct gaaaatgctg gaagtgccct acgtcgaccg gaactcttgt    1080
```

| | |
|---|---|
| aagctgagta gcagcttcat cattacccag aatatgtttt gcgccgggta tgacacaaag | 1140 |
| caggaggatg cttgtcaggg agacagtggc gggcctcacg tgactaggtt caaagatact | 1200 |
| tattttgtga ccggcatcgt cagctgggga gagggatgcg cacgcaaggg gaaatacgga | 1260 |
| atctatacca aggtgacagc ctttctgaaa tggattgacc gatctatgaa gacccggggg | 1320 |
| ctgccaaagg caaaaagtca tgcccccgag gtcattacca gttcccctct gaagaagac | 1380 |
| caggtggacc caaggctgat tgacggcaag | 1410 |

<210> SEQ ID NO 145
<211> LENGTH: 1398
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 145

| | |
|---|---|
| gccaactctt tcctggagga aatgaagaaa ggccacctgg agcgggaatg catggaggaa | 60 |
| acctgtagtt acgaggaagc cagagaggtg ttcgaagact cagataagac aaacgagttt | 120 |
| tggaataagt acaaagacgg cgatcagtgc gaaactagcc catgtcagaa ccaggggaag | 180 |
| tgcaaagatg gactgggcga gtacacctgc acatgtctgg agggattcga aggcaagaat | 240 |
| tgcgaactgt ttaccagaaa gctgtgctcc ctggataacg cgactgcga tcagttttgt | 300 |
| catgaggaac agaattccgt ggtctgctct tgtgccaggg gatacacact ggctgacaat | 360 |
| ggcaaggcat gcatccccac cggccctat ccttgtggga agcagacact ggagaggcgc | 420 |
| aaaaggtcag tggctcaggc aactagctcc tctggcgagg ccccgatag cattacctgg | 480 |
| aaaccttatg acgccgctga cctgaccccc acagagaacc cctttgacct gctggacttc | 540 |
| aaccagacac agcctgaaag aggcgataac aatctgacta ggaccagcaa gctgaccagg | 600 |
| atcgtgggag acaggagtg caaggacgga gaatgtccat ggcaggccct gctgattaac | 660 |
| gaggaaaatg agggattctg cggaggcact atcctgagcg agttctacat tctgaccgca | 720 |
| gcccactgtc tgtatcaggc taagcgattc aaagtgcggg tcggcgacag aaacaccgag | 780 |
| caggaggaag ggggagaagc agtgcacgag gtcgaagtgg tcatcaagca taatcgcttc | 840 |
| actaaagaga cctacgactt tgatatcgct gtgctgcgcc tgaagacacc tattactttc | 900 |
| cgaatgaacg tcgcccctgc ttgcctgcca gagcgagatt gggccgaaag caccctgatg | 960 |
| acacagaaaa ctggcatcgt gagcgggttt ggacggacac atgagaaggg caggcagtcc | 1020 |
| actcgcctga aaatgctgga agtgcccta gtcgaccgga actcttgtaa gctgagtagc | 1080 |
| agcttcatca ttacccagaa tatgttttgc gccgggtatg acacaaagca ggaggatgct | 1140 |
| tgtcagggag acagtggcgg gcctcacgtg actaggttca agatactta ttttgtgacc | 1200 |
| ggcatcgtca gctggggaga gggatgcgca cgcaaggga aatacggaat ctataccaag | 1260 |
| gtgacagcct ttctgaaatg gattgaccga tctatgaaga cccggggct gccaaaggca | 1320 |
| aaaagtcatg cccccgaggt cattaccagt tcccctctga agaagacca ggtggaccca | 1380 |
| aggctgattg acggcaag | 1398 |

<210> SEQ ID NO 146
<211> LENGTH: 1398
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 146

```
gccaactctt tcctggagga aatgaagaaa ggccacctgg agcgggaatg catggaggaa      60
acctgtagtt acgaggaagc cagagaggtg ttcgaagact cagataagac aaacgagttt     120
tggaataagt acaaagacgg cgatcagtgc gaaactagcc catgtcagaa ccaggggaag     180
tgcaaagatg gactgggcga gtacacctgc acatgtctgg agggattcga aggcaagaat     240
tgcgaactgt ttaccagaaa gctgtgctcc ctggataacg cgactgcga tcagttttgt      300
catgaggaac agaattccgt ggtctgctct tgtgccaggg gatacacact ggctgacaat     360
ggcaaggcat gcatccccac cggcccctat ccttgtggga agcagacact ggagaggcgc     420
aaaaggtcag tggctcaggc aactagctcc tctggcgagg cccccgatag cattacctgg     480
aaaccttatg acgccgctga cctggacccc acagagaacc cctttgacct gctggacttc     540
aaccagacac agcctgaaag aggcgataac aatctgacta ggttcaacga cttcaccagg     600
atcgtgggag acaggagtg caaggacgga gaatgtccat ggcaggccct gctgattaac      660
gaggaaaatg agggattctg cggaggcact atcctgagcg agttctacat tctgaccgca     720
gcccactgtc tgtatcaggc taagcgattc aaagtgcggg tcggcgacag aaacaccgag     780
caggaggaag ggggagaagc agtgcacgag gtcgaagtgg tcatcaagca taatcgcttc     840
actaaagaga cctacgactt tgatatcgct gtgctgcgcc tgaagacacc tattactttc     900
cgaatgaacg tcgcccctgc ttgcctgcca gagcgagatt gggccgaaag caccctgatg     960
acacagaaaa ctggcatcgt gagcgggttt ggacggacac atgagaaggg caggcagtcc    1020
actcgcctga aaatgctgga agtgccctac gtcgaccgga actcttgtaa gctgagtagc    1080
agcttcatca ttacccagaa tatgttttgc gccgggtatg acacaaagca ggaggatgct    1140
tgtcagggag acagtggcgg gcctcacgtg actaggttca agatactta ttttgtgacc     1200
ggcatcgtca gctggggaga gggatgcgca cgcaaggga aatacggaat ctataccaag     1260
gtgacagcct ttctgaaatg gattgaccga tctatgaaga cccgggggct gccaaaggca    1320
aaaagtcatg cccccgaggt cattaccagt tcccctctga agaagacca ggtggaccca      1380
aggctgattg acggcaag                                                  1398
```

<210> SEQ ID NO 147
<211> LENGTH: 1398
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 147

```
gccaactctt tcctggagga aatgaagaaa ggccacctgg agcgggaatg catggaggaa      60
acctgtagtt acgaggaagc cagagaggtg ttcgaagact cagataagac aaacgagttt     120
tggaataagt acaaagacgg cgatcagtgc gaaactagcc catgtcagaa ccaggggaag     180
tgcaaagatg gactgggcga gtacacctgc acatgtctgg agggattcga aggcaagaat     240
tgcgaactgt ttaccagaaa gctgtgctcc ctggataacg cgactgcga tcagttttgt      300
catgaggaac agaattccgt ggtctgctct tgtgccaggg gatacacact ggctgacaat     360
ggcaaggcat gcatccccac cggcccctat ccttgtggga agcagacact ggagaggcgc     420
aaaaggtcag tggctcaggc aactagctcc tctggcgagg cccccgatag cattacctgg     480
aaaccttatg acgccgctga cctggacccc acagagaacc cctttgacct gctggacttc     540
```

```
aaccagacac agcctgaaag aggcgataac aatctgacta ggctgagcag catgaccagg    600
atcgtgggag dacaggagtg caaggacgga gaatgtccat ggcaggccct gctgattaac    660
gaggaaaatg agggattctg cggaggcact atcctgagcg agttctacat tctgaccgca    720
gcccactgtc tgtatcaggc taagcgattc aaagtgcggg tcggcgacag aaacaccgag    780
caggaggaag ggggagaagc agtgcacgag gtcgaagtgg tcatcaagca taatcgcttc    840
actaaagaga cctacgactt tgatatcgct gtgctgcgcc tgaagacacc tattactttc    900
cgaatgaacg tcgcccctgc ttgcctgcca gagcgagatt gggccgaaag caccctgatg    960
acacagaaaa ctggcatcgt gagcgggttt ggacggacac atgagaaggg caggcagtcc   1020
actcgcctga aaatgctgga agtgccctac gtcgaccgga actcttgtaa gctgagtagc   1080
agcttcatca ttacccagaa tatgtttttgc gccgggtatg acacaaagca ggaggatgct   1140
tgtcagggag acagtggcgg gcctcacgtg actaggttca agatactta tttttgtgacc   1200 ggcatcgtca gctggggaga gggatgcgca cgcaaggga aatacggaat ctataccaag   1260
gtgacagcct ttctgaaatg gattgaccga tctatgaaga cccggggggct gccaaaggca   1320 aaaagtcatg cccccgaggt cattaccagt tcccctctga agaagacca ggtggaccca    1380 aggctgattg acggcaag                                                 1398

<210> SEQ ID NO 148
<211> LENGTH: 1398
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 148
gccaactctt tcctggagga aatgaagaaa ggccacctgg agcgggaatg catggaggaa     60
acctgtagtt acgaggaagc cagagaggtg ttcgaagact cagataagac aaacgagttt    120
tggaataagt acaaagacgg cgatcagtgc gaaactagcc catgtcagaa ccaggggaag    180
tgcaaagatg gactgggcga gtacacctgc acatgtctgg agggattcga aggcaagaat    240
tgcgaactgt ttaccagaaa gctgtgctcc ctggataacg gcgactgcga tcagttttgt    300
catgaggaac agaattccgt ggtctgctct tgtgccaggg gatacacact ggctgacaat    360
ggcaaggcat gcatccccac cggcccctat ccttgtggga agcagacact ggagaggcgc    420
aaaaggtcag tggctcaggc aactagctcc tctggcgagg cccccgatag cattacctgg    480
aaaccttatg acgccgctga cctggacccc acagagaacc cctttgacct gctggacttc    540
aaccagacac agcctgaaag aggcgataac aatctgacta ggcctcccag cctgaccagg    600
atcgtgggag dacaggagtg caaggacgga gaatgtccat ggcaggccct gctgattaac    660
gaggaaaatg agggattctg cggaggcact atcctgagcg agttctacat tctgaccgca    720
gcccactgtc tgtatcaggc taagcgattc aaagtgcggg tcggcgacag aaacaccgag    780
caggaggaag ggggagaagc agtgcacgag gtcgaagtgg tcatcaagca taatcgcttc    840
actaaagaga cctacgactt tgatatcgct gtgctgcgcc tgaagacacc tattactttc    900
cgaatgaacg tcgcccctgc ttgcctgcca gagcgagatt gggccgaaag caccctgatg    960
acacagaaaa ctggcatcgt gagcgggttt ggacggacac atgagaaggg caggcagtcc   1020
actcgcctga aaatgctgga agtgccctac gtcgaccgga actcttgtaa gctgagtagc   1080
agcttcatca ttacccagaa tatgtttttgc gccgggtatg acacaaagca ggaggatgct   1140
```

```
tgtcagggag acagtggcgg gcctcacgtg actaggttca aagatactta ttttgtgacc    1200
ggcatcgtca gctggggaga gggatgcgca cgcaaggggga aatacggaat ctataccaag   1260
gtgacagcct ttctgaaatg gattgaccga tctatgaaga cccggggggct gccaaaggca   1320 aaaagtcatg cccccgaggt cattaccagt tccctctga aagaagacca ggtggaccca    1380
aggctgattg acggcaag                                                 1398
```

<210> SEQ ID NO 149
<211> LENGTH: 1398
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 149

```
gccaactctt tcctggagga aatgaagaaa ggccacctgg agcgggaatg catggaggaa    60
acctgtagtt acgaggaagc cagagaggtg ttcgaagact cagataagac aaacgagttt    120
tggaataagt acaaagacgg cgatcagtgc gaaactagcc catgtcagaa ccaggggaag   180
tgcaaagatg gactgggcga gtacacctgc acatgtctgg agggattcga aggcaagaat   240
tgcgaactgt ttaccagaaa gctgtgctcc ctggataacg gcgactgcga tcagttttgt   300
catgaggaac agaattccgt ggtctgctct tgtgccaggg gatacacact ggctgacaat   360
ggcaaggcat gcatccccac cggcccctat ccttgtggga gcagacact ggagaggcgc   420 aaaaggtcag tggctcaggc aactagctcc tctggcgagg cccccgatag cattacctgg   480
aaaccttatg acgccgctga cctggacccc acagagaacc cctttgacct gctggacttc   540
aaccagacac agcctgaaag aggcgataac aatctgacta ggctgtcctg cggccagagg   600
atcgtgggag acaggagtg caaggacgga gaatgtccat ggcaggccct gctgattaac   660
gaggaaaatg agggattctg cggaggcact atcctgagcg agttctacat tctgaccgca   720
gcccactgtc tgtatcaggc taagcgattc aaagtgcggg tcggcgacag aaacaccgag   780
caggaggaag gggagaagc agtgcacgag gtcgaagtgg tcatcaagca taatcgcttc   840
actaaagaga cctacgactt tgatatcgct gtgctgcgcc tgaagacacc tattactttc   900
cgaatgaacg tcgcccctgc ttgcctgcca gagcgagatt gggccgaaag caccctgatg   960
acacagaaaa ctggcatcgt gagcgggttt ggacggacac atgagaaggg caggcagtcc   1020
actcgcctga aaatgctgga agtgccctac gtcgaccgga actcttgtaa gctgagtagc   1080
agcttcatca ttacccagaa tatgttttgc gccgggtatg acacaaagca ggaggatgct   1140
tgtcagggag acagtggcgg gcctcacgtg actaggttca aagatactta ttttgtgacc   1200
ggcatcgtca gctggggaga gggatgcgca cgcaaggggga aatacggaat ctataccaag   1260
gtgacagcct ttctgaaatg gattgaccga tctatgaaga cccggggggct gccaaaggca   1320 aaaagtcatg cccccgaggt cattaccagt tccctctga aagaagacca ggtggaccca    1380
aggctgattg acggcaag                                                 1398
```

<210> SEQ ID NO 150
<211> LENGTH: 1380
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 150

```
gccaactctt tcctggagga aatgaagaaa ggccacctgg agcgggaatg catggaggaa      60
acctgtagtt acgaggaagc cagagaggtg ttcgaagact cagataagac aaacgagttt     120
tggaataagt acaaagacgg cgatcagtgc gaaactagcc catgtcagaa ccaggggaag     180
tgcaaagatg gactgggcga gtacacctgc acatgtctgg agggattcga aggcaagaat     240
tgcgaactgt ttaccagaaa gctgtgctcc ctggataacg gcgactgcga tcagttttgt     300
catgaggaac agaattccgt ggtctgctct tgtgccaggg gatacacact ggctgacaat     360
ggcaaggcat gcatccccac cggcccctat ccttgtggga agcagacact ggagaggcgc     420
aaaaggtcag tggctgatag cattacctgg aaaccttatg acgccgctga cctggacccc     480
acagagaacc cctttgacct gctggacttc aaccagacac agcctgaaag aggcgataac     540
aatctgacta gggacttcct ggcagaagga ggaggagtga ggatcgtggg aggacaggag     600
tgcaaggacg gagaatgtcc atggcaggcc ctgctgatta cgaggaaaa tgagggattc     660
tgcggaggca ctatcctgag cgagttctac attctgaccg cagcccactg tctgtatcag     720
gctaagcgat tcaaagtgcg ggtcggcgac agaaacaccg agcaggagga aggggagaa     780
gcagtgcacg aggtcgaagt ggtcatcaag cataatcgct tcactaaaga gacctacgac     840
tttgatatcg ctgtgctgcg cctgaagaca cctattactt tccgaatgaa cgtcgcccct     900
gcttgcctgc cagagcgaga ttgggccgaa agcaccctga tgcacagaa aactggcatc     960
gtgagcgggt ttggacggac acatgagaag ggcaggcagt ccactcgcct gaaaatgctg    1020
gaagtgcccc tacgtcgaccg gaactcttgt aagctgagta gcagcttcat cattacccag    1080
aatatgtttt gcgccgggta tgacacaaag caggaggatg cttgtcaggg agacagtggc    1140
gggcctcacg tgactaggtt caaagatact tattttgtga ccggcatcgt cagctgggga    1200
gagggatgcg cacgcaaggg gaaatacgga atctatacca aggtgacagc ctttctgaaa    1260
tggattgacc gatctatgaa gacccggggg ctgccaaagg caaaaagtca tgcccccgag    1320
gtcattacca gttcccctct gaaagaagac caggtggacc caaggctgat tgacggcaag    1380
```

<210> SEQ ID NO 151
<211> LENGTH: 1380
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 151

```
gccaactctt tcctggagga aatgaagaaa ggccacctgg agcgggaatg catggaggaa      60
acctgtagtt acgaggaagc cagagaggtg ttcgaagact cagataagac aaacgagttt     120
tggaataagt acaaagacgg cgatcagtgc gaaactagcc catgtcagaa ccaggggaag     180
tgcaaagatg gactgggcga gtacacctgc acatgtctgg agggattcga aggcaagaat     240
tgcgaactgt ttaccagaaa gctgtgctcc ctggataacg gcgactgcga tcagttttgt     300
catgaggaac agaattccgt ggtctgctct tgtgccaggg gatacacact ggctgacaat     360
ggcaaggcat gcatccccac cggcccctat ccttgtggga agcagacact ggagaggcgc     420
aaaaggtcag tggctgatag cattacctgg aaaccttatg acgccgctga cctggacccc     480
acagagaacc cctttgacct gctggacttc aaccagacac agcctgaaag aggcgataac     540
aatctgacta gggacttcct ggccgagggc ctgacccta ggatcgtggg aggacaggag     600
```

```
tgcaaggacg agaatgtcc atggcaggcc ctgctgatta acgaggaaaa tgagggattc    660
tgcggaggca ctatcctgag cgagttctac attctgaccg cagcccactg tctgtatcag    720
gctaagcgat tcaaagtgcg ggtcggcgac agaaacaccg agcaggagga aggggagaa    780 gcagtgcacg aggtcgaagt ggtcatcaag cataatcgct tcactaaaga gacctacgac    840
tttgatatcg ctgtgctgcg cctgaagaca cctattactt tccgaatgaa cgtcgcccct    900
gcttgcctgc cagagcgaga ttgggccgaa agcaccctga tgacacagaa aactggcatc    960
gtgagcgggt ttggacggac acatgagaag ggcaggcagt ccactcgcct gaaaatgctg   1020
gaagtgccct acgtcgaccg gaactcttgt aagctgagta gcagcttcat cattacccag   1080
aatatgtttt gcgccgggta tgacacaaag caggaggatg cttgtcaggg agacagtggc   1140
gggcctcacg tgactaggtt caaagatact tattttgtga ccggcatcgt cagctgggga   1200
gagggatgcg cacgcaaggg gaaatacgga atctatacca aggtgacagc ctttctgaaa   1260
tggattgacc gatctatgaa gacccggggg ctgccaaagg caaaaagtca tgcccccgag   1320
gtcattacca gttcccctct gaaagaagac caggtggacc aaggctgat tgacggcaag   1380
```

<210> SEQ ID NO 152
<211> LENGTH: 1380
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 152

```
gccaactctt tcctggagga aatgaagaaa ggccacctgg agcgggaatg catggaggaa     60
acctgtagtt acgaggaagc cagagaggtg ttcgaagact cagataagac aaacgagttt    120
tggaataagt acaaagacgg cgatcagtgc gaaactagcc catgtcagaa ccaggggaag    180
tgcaaagatg gactgggcga gtacacctgc acatgtctgg agggattcga aggcaagaat    240
tgcgaactgt ttaccagaaa gctgtgctcc ctggataacg gcgactgcga tcagttttgt    300
catgaggaac agaattccgt ggtctgtctc tgtgccaggg gatacacact ggctgacaat    360
ggcaaggcat gcatccccac cggcccctat ccttgtggga agcagacact ggagaggcgc    420
aaaaggtcag tggctgatag cattacctgg aaaccttatg acgccgctga cctggacccc    480
acagagaacc cctttgacct gctggacttc aaccagacac agcctgaaag aggcgataac    540
aatctgacta ggaaggccac caacgccacc ctgtccccta ggatcgtggg aggacaggag    600
tgcaaggacg agaatgtcc atggcaggcc ctgctgatta acgaggaaaa tgagggattc    660
tgcggaggca ctatcctgag cgagttctac attctgaccg cagcccactg tctgtatcag    720
gctaagcgat tcaaagtgcg ggtcggcgac agaaacaccg agcaggagga aggggagaa    780 gcagtgcacg aggtcgaagt ggtcatcaag cataatcgct tcactaaaga gacctacgac    840
tttgatatcg ctgtgctgcg cctgaagaca cctattactt tccgaatgaa cgtcgcccct    900
gcttgcctgc cagagcgaga ttgggccgaa agcaccctga tgacacagaa aactggcatc    960
gtgagcgggt ttggacggac acatgagaag ggcaggcagt ccactcgcct gaaaatgctg   1020
gaagtgccct acgtcgaccg gaactcttgt aagctgagta gcagcttcat cattacccag   1080
aatatgtttt gcgccgggta tgacacaaag caggaggatg cttgtcaggg agacagtggc   1140
gggcctcacg tgactaggtt caaagatact tattttgtga ccggcatcgt cagctgggga   1200
gagggatgcg cacgcaaggg gaaatacgga atctatacca aggtgacagc ctttctgaaa   1260
```

| | |
|---|---|
| tggattgacc gatctatgaa gacccggggg ctgccaaagg caaaaagtca tgcccccgag | 1320 |
| gtcattacca gttcccctct gaaagaagac caggtggacc caaggctgat tgacggcaag | 1380 |

<210> SEQ ID NO 153
<211> LENGTH: 1380
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 153

| | |
|---|---|
| gccaactctt tcctggagga aatgaagaaa ggccacctgg agcgggaatg catggaggaa | 60 |
| acctgtagtt acgaggaagc cagagaggtg ttcgaagact cagataagac aaacgagttt | 120 |
| tggaataagt acaaagacgg cgatcagtgc gaaactagcc catgtcagaa ccaggggaag | 180 |
| tgcaaagatg gactgggcga gtacacctgc acatgtctgg agggattcga aggcaagaat | 240 |
| tgcgaactgt ttaccagaaa gctgtgctcc ctggataacg gcgactgcga tcagttttgt | 300 |
| catgaggaac agaattccgt ggtctgctct tgtgccaggg gatacacact ggctgacaat | 360 |
| ggcaaggcat gcatccccac cggcccctat ccttgtggga gcagacact ggagaggcgc | 420 |
| aaaaggtcag tggctgatag cattacctgg aaaccttatg acgccgctga cctggacccc | 480 |
| acagagaacc cctttgacct gctggacttc aaccagacac agcctgaaag aggcgataac | 540 |
| aatctgacta ggaaggccac ccaggccacc ctgagcccta ggatcgtggg aggacaggag | 600 |
| tgcaaggacg gagaatgtcc atggcaggcc ctgctgatta acgaggaaaa tgagggattc | 660 |
| tgcggaggca ctatcctgag cgagttctac attctgaccg cagcccactg tctgtatcag | 720 |
| gctaagcgat tcaaagtgcg ggtcggcgac agaaacaccg agcaggagga aggggggagaa | 780 |
| gcagtgcacg aggtcgaagt ggtcatcaag cataatcgct tcactaaaga gacctacgac | 840 |
| tttgatatcg ctgtgctgcg cctgaagaca cctattactt tccgaatgaa cgtcgcccct | 900 |
| gcttgcctgc cagagcgaga ttgggccgaa agcaccctga tgacacagaa aactggcatc | 960 |
| gtgagcgggt ttggacggac acatgagaag ggcaggcagt ccactcgcct gaaaatgctg | 1020 |
| gaagtgccct acgtcgaccg gaactcttgt aagctgagta gcagcttcat cattacccag | 1080 |
| aatatgtttt gcgccgggta tgacacaaag caggaggatg cttgtcaggg agacagtggc | 1140 |
| gggcctcacg tgactaggtt caagagatact tattttgtga ccggcatcgt cagctgggga | 1200 |
| gagggatgcg cacgcaaggg gaaatacgga atctatacca aggtgacagc ctttctgaaa | 1260 |
| tggattgacc gatctatgaa gacccggggg ctgccaaagg caaaaagtca tgcccccgag | 1320 |
| gtcattacca gttcccctct gaaagaagac caggtggacc caaggctgat tgacggcaag | 1380 |

<210> SEQ ID NO 154
<211> LENGTH: 1380
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 154

| | |
|---|---|
| gccaactctt tcctggagga aatgaagaaa ggccacctgg agcgggaatg catggaggaa | 60 |
| acctgtagtt acgaggaagc cagagaggtg ttcgaagact cagataagac aaacgagttt | 120 |
| tggaataagt acaaagacgg cgatcagtgc gaaactagcc catgtcagaa ccaggggaag | 180 |
| tgcaaagatg gactgggcga gtacacctgc acatgtctgg agggattcga aggcaagaat | 240 |

```
tgcgaactgt tnaccagaaa gctgtgctcc ctggataacg gcgactgcga tcagttttgt      300
catgaggaac agaattccgt ggtctgctct tgtgccaggg gatacacact ggctgacaat      360
ggcaaggcat gcatccccac cggcccctat ccttgtggga agcagacact ggagaggcgc      420
aaaaggtcag tggctcaggc aactagcgat agcattacct ggaaacctta tgacgccgct      480
gacctggacc ccacagagaa ccccttttgac ctgctggact tcaaccagac acagcctgaa     540
agaggcgata acaatctgac taggaccagc aagctgacca ggatcgtggg aggacaggag      600
tgcaaggacg gagaatgtcc atggcaggcc ctgctgatta acgaggaaaa tgagggattc      660
tgcggaggca ctatcctgag cgagttctac attctgaccg cagcccactg tctgtatcag      720
gctaagcgat tcaaagtgcg ggtcggcgac agaaacaccg agcaggagga aggggagaa      780 gcagtgcacg aggtcgaagt ggtcatcaag cataatcgct tcactaaaga gacctacgac      840
tttgatatcg ctgtgctgcg cctgaagaca cctattactt tccgaatgaa cgtcgcccct      900
gcttgcctgc cagagcgaga ttgggccgaa agcaccctga tgacacagaa aactggcatc      960
gtgagcgggt ttggacggac acatgagaag ggcaggcagt ccactcgcct gaaaatgctg      1020 gaagtgcccct acgtcgaccg gaactcttgt aagctgagta gcagcttcat cattacccag      1080
aatatgtttt gcgccgggta tgacacaaag caggaggatg cttgtcaggg agacagtggc      1140
gggcctcacg tgactaggtt caaagatact tattttgtga ccggcatcgt cagctgggga      1200
gagggatgcg cacgcaaggg gaaatacgga atctatacca aggtgacagc ctttctgaaa      1260
tggattgacc gatctatgaa gacccggggg ctgccaaagg caaaaagtca tgcccccgag      1320
gtcattacca gttcccctct gaaagaagac caggtggacc caaggctgat tgacggcaag      1380
```

<210> SEQ ID NO 155
<211> LENGTH: 1380
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 155

```
gccaactctt tcctggagga aatgaagaaa ggccacctgg agcgggaatg catggaggaa      60
acctgtagtt acgaggaagc cagagaggtg ttcgaagact cagataagac aaacgagttt      120
tggaataagt acaaagacgg cgatcagtgc gaaactagcc catgtcagaa ccaggggaag      180
tgcaaagatg gactgggcga gtacacctgc acatgtctgg agggattcga aggcaagaat      240
tgcgaactgt ttaccagaaa gctgtgctcc ctggataacg gcgactgcga tcagttttgt      300
catgaggaac agaattccgt ggtctgctct tgtgccaggg gatacacact ggctgacaat      360
ggcaaggcat gcatccccac cggcccctat ccttgtggga agcagacact ggagaggcgc      420
aaaaggtcag tggctcaggc aactagcgat agcattacct ggaaacctta tgacgccgct      480
gacctggacc ccacagagaa ccccttttgac ctgctggact tcaaccagac acagcctgaa     540
agaggcgata acaatctgac taggttcaac gacttcacca ggatcgtggg aggacaggag      600
tgcaaggacg gagaatgtcc atggcaggcc ctgctgatta acgaggaaaa tgagggattc      660
tgcggaggca ctatcctgag cgagttctac attctgaccg cagcccactg tctgtatcag      720
gctaagcgat tcaaagtgcg ggtcggcgac agaaacaccg agcaggagga aggggagaa      780 gcagtgcacg aggtcgaagt ggtcatcaag cataatcgct tcactaaaga gacctacgac      840
tttgatatcg ctgtgctgcg cctgaagaca cctattactt tccgaatgaa cgtcgcccct      900
```

```
gcttgcctgc cagagcgaga ttgggccgaa agcaccctga tgacacagaa aactggcatc    960
gtgagcgggt ttggacggac acatgagaag ggcaggcagt ccactcgcct gaaaatgctg   1020
gaagtgccct acgtcgaccg gaactcttgt aagctgagta gcagcttcat cattacccag   1080
aatatgtttt gcgccgggta tgacacaaag caggaggatg cttgtcaggg agacagtggc   1140
gggcctcacg tgactaggtt caaagatact tattttgtga ccggcatcgt cagctgggga   1200
gagggatgcg cacgcaaggg gaaatacgga atctatacca aggtgacagc ctttctgaaa   1260
tggattgacc gatctatgaa gacccggggg ctgccaaagg caaaaagtca tgcccccgag   1320
gtcattacca gttcccctct gaaagaagac caggtggacc caaggctgat tgacggcaag   1380
```

<210> SEQ ID NO 156
<211> LENGTH: 1380
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 156

```
gccaactctt tcctggagga aatgaagaaa ggccacctgg agcgggaatg catggaggaa     60
acctgtagtt acgaggaagc cagagaggtg ttcgaagact cagataagac aaacgagttt    120
tggaataagt acaaagacgg cgatcagtgc gaaactagcc atgtcagaa ccaggggaag    180 tgcaaagatg gactgggcga gtacacctgc acatgtctgg agggattcga aggcaagaat    240
tgcgaactgt ttaccagaaa gctgtgctcc ctggataacg gcgactgcga tcagttttgt    300
catgaggaac agaattccgt ggtctgctct tgtgccaggg gatacacact ggctgacaat    360
ggcaaggcat gcatccccac cggccccctat ccttgtggga gcagacact ggagaggcgc    420 aaaaggtcag tggctcaggc aactagcgat agcattacct ggaaacctta tgacgccgct    480
gacctggacc ccacagagaa ccccctttgac ctgctggact caaccagac acagcctgaa    540 agaggcgata caatctgac taggctgagc agcatgacca ggatcgtggg aggacaggag    600
tgcaaggacg gagaatgtcc atggcaggcc ctgctgatta acgaggaaaa tgagggattc    660
tgcggaggca ctatcctgag cgagttctac attctgaccg cagcccactg tctgtatcag    720
gctaagcgat tcaaagtgcg ggtcggcgac agaaacaccg agcaggagga agggggagaa    780
gcagtgcacg aggtcgaagt ggtcatcaag cataatcgct tcactaaaga gacctacgac    840
tttgatatcg ctgtgctgcg cctgaagaca cctattactt tccgaatgaa cgtcgcccct    900
gcttgcctgc cagagcgaga ttgggccgaa agcaccctga tgacacagaa aactggcatc    960
gtgagcgggt ttggacggac acatgagaag ggcaggcagt ccactcgcct gaaaatgctg   1020
gaagtgccct acgtcgaccg gaactcttgt aagctgagta gcagcttcat cattacccag   1080
aatatgtttt gcgccgggta tgacacaaag caggaggatg cttgtcaggg agacagtggc   1140
gggcctcacg tgactaggtt caaagatact tattttgtga ccggcatcgt cagctgggga   1200
gagggatgcg cacgcaaggg gaaatacgga atctatacca aggtgacagc ctttctgaaa   1260
tggattgacc gatctatgaa gacccggggg ctgccaaagg caaaaagtca tgcccccgag   1320
gtcattacca gttcccctct gaaagaagac caggtggacc caaggctgat tgacggcaag   1380
```

<210> SEQ ID NO 157
<211> LENGTH: 1380
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157

| | | | | | |
|---|---|---|---|---|---|
| gccaactctt | tcctggagga | aatgaagaaa | ggccacctgg | agcgggaatg | catggaggaa | 60 |
| acctgtagtt | acgaggaagc | cagagaggtg | ttcgaagact | cagataagac | aaacgagttt | 120 |
| tggaataagt | acaaagacgg | cgatcagtgc | gaaactagcc | catgtcagaa | ccaggggaag | 180 |
| tgcaaagatg | gactgggcga | gtacacctgc | acatgtctgg | agggattcga | aggcaagaat | 240 |
| tgcgaactgt | ttaccagaaa | gctgtgctcc | ctggataacg | gcgactgcga | tcagttttgt | 300 |
| catgaggaac | agaattccgt | ggtctgctct | tgtgccaggg | gatacacact | ggctgacaat | 360 |
| ggcaaggcat | gcatccccac | cggcccctat | ccttgtggga | agcagacact | ggagaggcgc | 420 |
| aaaaggtcag | tggctcaggc | aactagcgat | agcattacct | ggaaaccttga | tgacgccgct | 480 |
| gacctggacc | ccacagagaa | ccccttgac | ctgctggact | tcaaccagac | acagcctgaa | 540 |
| agaggcgata | acaatctgac | taggcctccc | agcctgacca | ggatcgtggg | aggacaggag | 600 |
| tgcaaggacg | gagaatgtcc | atggcaggcc | ctgctgatta | cgaggaaaa | tgagggattc | 660 |
| tgcggaggca | ctatcctgag | cgagttctac | attctgaccg | cagcccactg | tctgtatcag | 720 |
| gctaagcgat | tcaaagtgcg | ggtcggcgac | agaaacaccg | agcaggagga | aggggggagaa | 780 |
| gcagtgcacg | aggtcgaagt | ggtcatcaag | cataatcgct | tcactaaaga | gacctacgac | 840 |
| tttgatatcg | ctgtgctgcg | cctgaagaca | cctattactt | tccgaatgaa | cgtcgcccct | 900 |
| gcttgcctgc | cagagcgaga | ttgggccgaa | agcaccctga | tgacacagaa | aactggcatc | 960 |
| gtgagcgggt | ttggacggac | acatgagaag | ggcaggcagt | ccactcgcct | gaaaatgctg | 1020 |
| gaagtgccct | acgtcgaccg | gaactcttgt | aagctgagta | gcagcttcat | cattacccag | 1080 |
| aatatgtttt | gcgccgggta | tgacacaaag | caggaggatg | cttgtcaggg | agacagtggc | 1140 |
| gggcctcacg | tgactaggtt | caaagatact | tattttgtga | ccggcatcgt | cagctgggga | 1200 |
| gagggatgcg | cacgcaaggg | gaaatacgga | atctatacca | aggtgacagc | ctttctgaaa | 1260 |
| tggattgacc | gatctatgaa | gacccggggg | ctgccaaagg | caaaaagtca | tgcccccgag | 1320 |
| gtcattacca | gttcccctct | gaaagaagac | caggtggacc | caaggctgat | tgacggcaag | 1380 |

<210> SEQ ID NO 158
<211> LENGTH: 1380
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 158

| | | | | | |
|---|---|---|---|---|---|
| gccaactctt | tcctggagga | aatgaagaaa | ggccacctgg | agcgggaatg | catggaggaa | 60 |
| acctgtagtt | acgaggaagc | cagagaggtg | ttcgaagact | cagataagac | aaacgagttt | 120 |
| tggaataagt | acaaagacgg | cgatcagtgc | gaaactagcc | catgtcagaa | ccaggggaag | 180 |
| tgcaaagatg | gactgggcga | gtacacctgc | acatgtctgg | agggattcga | aggcaagaat | 240 |
| tgcgaactgt | ttaccagaaa | gctgtgctcc | ctggataacg | gcgactgcga | tcagttttgt | 300 |
| catgaggaac | agaattccgt | ggtctgctct | tgtgccaggg | gatacacact | ggctgacaat | 360 |
| ggcaaggcat | gcatccccac | cggcccctat | ccttgtggga | agcagacact | ggagaggcgc | 420 |
| aaaaggtcag | tggctcaggc | aactagcgat | agcattacct | ggaaacctta | tgacgccgct | 480 |

```
gacctggacc ccacagagaa cccctttgac ctgctggact tcaaccagac acagcctgaa    540
agaggcgata acaatctgac taggctgtcc tgcggccaga ggatcgtggg aggacaggag    600
tgcaaggacg gagaatgtcc atggcaggcc ctgctgatta acgaggaaaa tgagggattc    660
tgcggaggca ctatcctgag cgagttctac attctgaccg cagcccactg tctgtatcag    720
gctaagcgat tcaaagtgcg ggtcggcgac agaaacaccg agcaggagga aggggggagaa    780 gcagtgcacg aggtcgaagt ggtcatcaag cataatcgct tcactaaaga gacctacgac    840
tttgatatcg ctgtgctgcg cctgaagaca cctattactt tccgaatgaa cgtcgcccct    900
gcttgcctgc cagagcgaga ttgggccgaa agcaccctga tgacacagaa aactggcatc    960
gtgagcgggt ttggacggac acatgagaag ggcaggcagt ccactcgcct gaaaatgctg   1020
gaagtgccct acgtcgaccg gaactcttgt aagctgagta gcagcttcat cattacccag   1080
aatatgtttt gcgccgggta tgacacaaag caggaggatg cttgtcaggg agacagtggc   1140
gggcctcacg tgactaggtt caaagatact tattttgtga ccggcatcgt cagctgggga   1200
gagggatgcg cacgcaaggg gaaatacgga atctatacca aggtgacagc ctttctgaaa   1260
tggattgacc gatctatgaa gacccggggg ctgccaaagg caaaaagtca tgcccccgag   1320
gtcattacca gttcccctct gaaagaagac caggtggacc caaggctgat tgacggcaag   1380
```

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Asp Phe Leu Ala Glu Gly Leu Thr Pro Arg
1               5                   10

<210> SEQ ID NO 160
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Optionally glycosylated

<400> SEQUENCE: 160

Lys Ala Thr Asn Ala Thr Leu Ser Pro Arg
1               5                   10

<210> SEQ ID NO 161
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 161

Lys Ala Thr Xaa Ala Thr Leu Ser Pro Arg
1               5                   10

<210> SEQ ID NO 162
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Thr Ser Lys Leu Thr Arg
1               5

<210> SEQ ID NO 163
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Phe Asn Asp Phe Thr Arg
1               5

<210> SEQ ID NO 164
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Leu Ser Ser Met Thr Arg
1               5

<210> SEQ ID NO 165
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Pro Pro Ser Leu Thr Arg
1               5

<210> SEQ ID NO 166
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Leu Ser Cys Gly Gln Arg
1               5

<210> SEQ ID NO 167
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 167

Pro Glu Arg Gly Asp Asn Asn Leu Thr Arg Ile Val Gly Gly Gln
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(9)
<223> OTHER INFORMATION: Any amino acid

<400> SEQUENCE: 168

Xaa Xaa Xaa Xaa Xaa Xaa Xaa Xaa Xaa Arg Ile Val Gly Gly Gln
1               5                   10                  15

<210> SEQ ID NO 169
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(15)
<223> OTHER INFORMATION: Any amino acid

<400> SEQUENCE: 169

Asp Asn Asn Leu Thr Arg Xaa Xaa Xaa Xaa Xaa Xaa Xaa Xaa Xaa Arg
1               5                   10                  15

Ile Val Gly Gly Gln
            20
```

FACTOR X MUTANTS

SEQUENCE LISTING

The instant application contains a Sequence Listing which has been submitted electronically in ASCII format and is hereby incorporated by reference in its entirety. Said ASCII copy, created on Jul. 13, 2016, is named 102467-0708_SL.txt and is 378,295 bytes in size.

The present invention relates to factor X mutants, and to the use thereof in treating blood coagulation disorders.

Factor X is a protein present in the blood. This protein plays an important role in the coagulation cascade. Blood coagulation is a complex process which makes it possible to prevent blood flow via damaged vessels. As soon as a vessel is broken, the elements responsible for coagulation interact with one another to form a plug, the hemostatic plug, at the site where the vessel is broken. The coagulation factors are required in order to hold the hemostatic plug in place and to stabilize the clot.

The formation of a normal clot occurs in four steps:

Step 1 The blood vessel is damaged.

Step 2 The blood vessel contracts so as to restrict the blood supply to the damaged zone.

Step 3 The platelets adhere to the subendothelial space exposed during the damaging of the vessel and also to the stimulated blood vessel walls. The platelets spread, this is what is referred to as "platelet adhesion". These spread platelets release substances which activate other neighboring platelets such that they agglomerate at the seat of the lesion in order to form the hemostatic plug. This is what is referred to as "platelet aggregation".

Step 4 The surface of the activated platelets thus constitutes a surface on which blood coagulation can take place. The coagulation proteins which circulate in the blood (including factor X) are activated at the surface of platelets and form a fibrin clot.

These coagulation proteins (i.e. factors I, II, V, VIII, IX, X, XI, XII and XIII, and also Von Willebrand factor) operate in a chain reaction, i.e. the coagulation cascade.

Factor X in activated form (Xa) is involved more particularly in the activation of prothrombin (factor II) to thrombin (factor IIa), in particular when it is complexed with activated cofactor V so as to form the prothrombinase complex. This factor is an essential element in the coagulation cascade.

When this factor is lacking, bleeding occurs, such as epistaxis (nosebleeds), hemarthrosis (effusion of blood into a joint cavity) or gastrointestinal bleeding. Factor X deficiency is extremely rare. Its transmission is autosomal recessive, and its prevalence is 1/1 000 000.

FX activation occurs:

either very early during the step of initiation of the coagulation cascade by the factor VIIa/tissue factor complex, in a relatively ineffective reaction which results in the formation of traces of thrombin;

or during the step of amplification of the coagulation cascade resulting from positive feedback produced by the traces of thrombin, resulting in the activation of factors VIII and IX.

The latter two factors are missing in individuals suffering from hemophilia A and hemophilia B, thus causing a hemorrhagic disorder which can be fatal without treatment. The absence of these factors means that it is not possible to generate sufficient amounts of activated factor X to stop the hemorrhage.

Thus, there is a need for a modified factor X which can be activated by thrombin, and which would make it possible to have efficient coagulation in the absence of factor VIII and/or of factor IX, through the direct use of the traces of thrombin generated during the initiation of coagulation.

The inventors have identified specific factor X mutants (also called factor X variants), which are efficiently activated by thrombin, thus making it possible to restore coagulation in the absence of factor VIII, of factor IX and even of factor X. Indeed, as demonstrated in examples, these factor X mutants can be activated by thrombin, and allow efficient coagulation, even in the absence of endogenous factor VIII and/or factor IX and/or factor X.

The activation peptide cleavage sites generated in these factor X variants can also be the target of other coagulation proteases, such as factor VIIa, factor IXa, factor Xa, factor XIa, factor XIIa or kallikrein.

Moreover, a modification of the activation peptide of factor X can result in an additional modification of its pharmacological properties, other than the sole recognition by thrombin. This modification can confer on the factor X variant an improvement in specific activity, in stability, or in protease resistance, or else an increase in pharmacokinetics. In addition, the presence of additional glycosylations and phosphorylations, or on the contrary the absence of these modifications, compared with the wild-type molecule, may be caused by the modifications introduced into the activation peptide.

The present invention therefore relates to a protein comprising a mutated sequence of SEQ ID No. 1, said mutated sequence of SEQ ID No. 1 comprising at least one mutation A, A', B, C or C', in which: mutation A consists of the substitution of amino acids 43 to 52 of the sequence SEQ ID No. 1 with a sequence chosen from DFLAEGLTPR (SEQ ID NO: 159), KATN*ATLSPR (SEQ ID NO: 160) and KATXATLSPR (SEQ ID NO: 161), mutation A' consists of the substitution of amino acids 47 to 52 of the sequence SEQ ID No. 1 with a sequence chosen from TSKLTR (SEQ ID NO: 162), FNDFTR (SEQ ID NO: 163), LSSMTR (SEQ ID NO: 164), PPSLTR (SEQ ID NO: 165) and LSCGQR (SEQ ID NO: 166), mutation B consists of the insertion of a sequence chosen from DFLAEGLTPR (SEQ ID NO: 159), KATN*ATLSPR (SEQ ID NO: 160), KATXATLSPR (SEQ ID NO: 161), TSKLTR (SEQ ID NO: 162), FNDFTR (SEQ ID NO: 163), LSSMTR (SEQ ID NO: 164), PPSLTR (SEQ ID NO: 165) and LSCGQR (SEQ ID NO: 166), between amino acids 52 and 53 of the sequence SEQ ID No. 1, mutation C consists of the insertion of a sequence chosen from DFLAEGLTPR (SEQ ID NO: 159), KATN*ATLSPR (SEQ ID NO: 160) and KATXATLSPR (SEQ ID NO: 161), between amino acids 52 and 53 of the sequence SEQ ID No. 1, and of the deletion of amino acids 4 to 13 of the sequence SEQ ID No. 1, mutation C' consists of the insertion of a sequence chosen from TSKLTR (SEQ ID NO: 162), FNDFTR (SEQ ID NO: 163), LSSMTR (SEQ ID NO: 164), PPSLTR (SEQ ID NO: 165) and LSCGQR (SEQ ID NO: 166), between amino acids 52 and 53 of the sequence SEQ ID No. 1, and of the deletion of amino acids 4 to 9 of the sequence SEQ ID No. 1, where N* is an optionally glycosylated asparagine.

Another subject of the invention is a polynucleotide encoding said protein.

Another subject of the invention is an expression vector comprising said polynucleotide.

Another subject of the invention is a host cell comprising said expression vector or said polynucleotide.

Another subject of the invention is the use of said protein as a medicament. In particular, said protein may be used for the treatment of blood coagulation disorders, in particular hemorrhagic disorders, such as hemophilias A, B and C (factor XI deficiency), factor X deficiencies, or even emergency coagulation needs in order to substitute for factor VIIa. When a powerful and rapid procoagulant response is required, said protein can be used in combination with other hemostatic molecules, such as factor VIIa and/or fibrinogen, or even in combination with procoagulant compounds (platelet transfusion, procoagulant mixture such as FEIBA, Kaskadil, Kanokad, etc.), which will be able to reinforce the efficacy of the treatment.

As used herein, the terms "protein" and "polypeptide" are used interchangeably and refer to an amino acid sequence having more than 100 amino acids. As used herein, the term "protein" comprises amino acid sequences having between 100 and 1000 amino acids, preferably between 120 and 500 amino acids.

The present invention relates to a protein comprising a mutated sequence of SEQ ID No. 1, said mutated sequence of SEQ ID No. 1 comprising at least one mutation A, A', B, C or C', in which: mutation A consists of the substitution of amino acids 43 to 52 of the sequence SEQ ID No. 1 with a sequence chosen from DFLAEGLTPR (SEQ ID NO: 159), KATN*ATLSPR (SEQ ID NO: 160) and KATXATLSPR (SEQ ID NO: 161), mutation A' consists of the substitution of amino acids 47 to 52 of the sequence SEQ ID No. 1 with a sequence chosen from TSKLTR (SEQ ID NO: 162), FNDFTR (SEQ ID NO: 163), LSSMTR (SEQ ID NO: 164), PPSLTR (SEQ ID NO: 165) and LSCGQR (SEQ ID NO: 166), mutation B consists of the insertion of a sequence chosen from DFLAEGLTPR (SEQ ID NO: 159), KATN*ATLSPR (SEQ ID NO: 160), KATXATLSPR (SEQ ID NO: 161), TSKLTR (SEQ ID NO: 162), FNDFTR (SEQ ID NO: 163), LSSMTR (SEQ ID NO: 164), PPSLTR (SEQ ID NO: 165) and LSCGQR (SEQ ID NO: 166), between amino acids 52 and 53 of the sequence SEQ ID No. 1, mutation C consists of the insertion of a sequence chosen from DFLAEGLTPR (SEQ ID NO: 159), KATN*ATLSPR (SEQ ID NO: 160) and KATXATLSPR (SEQ ID NO: 161), between amino acids 52 and 53 of the sequence SEQ ID No. 1, and of the deletion of amino acids 4 to 13 of the sequence SEQ ID No. 1, mutation C' consists of the insertion of a sequence chosen from TSKLTR (SEQ ID NO: 162), FNDFTR (SEQ ID NO: 163), LSSMTR (SEQ ID NO: 164), PPSLTR (SEQ ID NO: 165) and LSCGQR (SEQ ID NO: 166), between amino acids 52 and 53 of the sequence SEQ ID No. 1, and of the deletion of amino acids 4 to 9 of the sequence SEQ ID No. 1, where N* is an optionally glycosylated asparagine.

Preferably, said protein comprises, preferably consists of, the sequence SEQ ID No. 7, with at least one mutation A, A', B, C or C' as described above.

The sequence SEQ ID No. 7 (500 amino acids) comprises all the sequence SEQ ID No. 1 (306 amino acids). More particularly, the sequence SEQ ID No. 7 comprises, in the N-terminal to C-terminal direction, a signal peptide and a propeptide (40 amino acids in total), the sequence SEQ ID No. 5, the sequence SEQ ID No. 1, then a tag (of the amino acids in position 489 to 500, i.e. a length of 12 amino acids), i.e. the HPC4 tag. The sequence SEQ ID No. 103 corresponds to the sequence SEQ ID No. 7 without signal peptide and without propeptide.

Said protein according to the invention is a mutated factor X which is effective in the treatment of coagulation disorders.

Factor X, also called Stuart-Prower factor, is encoded by the F 10 gene and refers to the serine protease EC3.4.21.6. The factor X is composed of a heavy chain of 306 amino acids and of a light chain of 139 amino acids.

Factor X is a protein of 488 amino acids, consisting of a signal peptide, a propeptide, and light and heavy chains.

Human factor X can be found in UniProtKB under accession number P00742. Its native structure is illustrated in FIG. 1.

The protein is translated in prepropeptide form. After cleavage of the signal peptide, the propeptide is finally cleaved, resulting in a light chain and a heavy chain (respectively of 142 and 306 amino acids) (zymogen). Following the triggering of coagulation, the heavy chain is finally activated by cleavage of the activation peptide, so as to contain only 254 amino acids (the first 52 amino acids are cleaved during the treatment): this is the heavy chain of factor Xa (SEQ ID No. 6).

The prepropeptide of human factor X corresponds to SEQ ID No. 4. The heavy chain corresponds to SEQ ID No. 1, and the light chain corresponds to SEQ ID No. 5. The activation peptide of the heavy chain corresponds to SEQ ID No. 3, and comprises 52 amino acids.

SEQ ID No. 2 is identical to amino acids 1 to 182 of SEQ ID No. 4.

SEQ ID No. 1 is identical to amino acids 183 to 488 of SEQ ID No. 4.

The heavy chain of factor Xa (SEQ ID No. 6) corresponds to SEQ ID No. 1, in which the peptide SEQ ID No. 3 has been cleaved.

The proteins according to the invention comprise mutated factor X proteins, in zymogen form, comprising, depending on the constructions, an activation peptide:
  modified by substitution of an identical number of residues at the same site included at the widest between residues 42 and 52; or
  having received an insertion of residues between residues 52 and 53; or
  having received an insertion of residues at the widest between residues 52 and 53, coupled to a deletion of an identical number of residues at the widest between residues 4 and 13.

The protein according to the invention may be a protein comprising a mutated sequence of SEQ ID No. 1, said mutated sequence of SEQ ID No. 1 comprising at least one mutation A, in which mutation A consists of the substitution of amino acids 43 to 52 of the sequence SEQ ID No. 1 with a sequence chosen from DFLAEGLTPR (SEQ ID NO: 159), KATN*ATLSPR (SEQ ID NO: 160) and KATXATLSPR (SEQ ID NO: 161), where N* is an optionally glycosylated asparagine. Preferably, the protein comprises the sequence SEQ ID No. 7 with at least one mutation A. Further preferably, in this case, the mutated protein comprises a sequence chosen from SEQ ID No. 9, SEQ ID No. 10 and SEQ ID No. 11.

The protein according to the invention may be a protein comprising a mutated sequence of SEQ ID No. 1, said mutated sequence of SEQ ID No. 1 comprising at least one mutation A', in which mutation A' consists of the substitution of amino acids 47 to 52 of the sequence SEQ ID No. 1 with the sequence chosen from TSKLTR (SEQ ID NO: 162), FNDFTR (SEQ ID NO: 163), LSSMTR (SEQ ID NO: 164), PPSLTR (SEQ ID NO: 165) and LSCGQR (SEQ ID NO: 166). Preferably, the protein comprises the sequence SEQ ID No. 7 with at least one mutation A'. Further preferably, in this case, the mutated protein comprises a sequence chosen from SEQ ID No. 12, SEQ ID No. 13, SEQ ID No. 14, SEQ ID No. 15 and SEQ ID No. 16.

The protein according to the invention may be a protein comprising a mutated sequence of SEQ ID No. 1, said mutated sequence of SEQ ID No. 1 comprising at least one mutation B, in which mutation B consists of the insertion of a sequence chosen from DFLAEGLTPR (SEQ ID NO: 159), KATN*ATLSPR (SEQ ID NO: 160), KATXATLSPR (SEQ ID NO: 161), TSKLTR (SEQ ID NO: 162), FNDFTR (SEQ ID NO: 163), LSSMTR (SEQ ID NO: 164), PPSLTR (SEQ ID NO: 165) and LSCGQR (SEQ ID NO: 166), between amino acids 52 and 53 of the sequence SEQ ID No. 1, where N* is an optionally glycosylated asparagine. Preferably, the protein comprises the sequence SEQ ID No. 7 with at least one mutation B. Further preferably, in this case, the mutated protein comprises a sequence chosen from SEQ ID No. 18, SEQ ID No. 19, SEQ ID No. 20, SEQ ID No. 21, SEQ ID No. 22, SEQ ID No. 23, SEQ ID No. 24 and SEQ ID No. 25.

The protein according to the invention may be a protein comprising a mutated sequence of SEQ ID No. 1, said mutated sequence of SEQ ID No. 1 comprising at least one mutation C, in which mutation C consists of the insertion of a sequence chosen from DFLAEGLTPR (SEQ ID NO: 159), KATN*ATLSPR (SEQ ID NO: 160) and KATXATLSPR (SEQ ID NO: 161), between amino acids 52 and 53 of the sequence SEQ ID No. 1, and of the deletion of amino acids 4 to 13 of the sequence SEQ ID No. 1, where N* is an optionally glycosylated asparagine. Preferably, the protein comprises the sequence SEQ ID No. 7 with at least one mutation C. Further preferably, in this case, the mutated protein comprises a sequence chosen from SEQ ID No. 27, SEQ ID No. 28 and SEQ ID No. 29.

The protein according to the invention may be a protein comprising a mutated sequence of SEQ ID No. 1, said mutated sequence of SEQ ID No. 1 comprising at least one mutation C', in which mutation C' consists of the insertion of a sequence chosen from TSKLTR (SEQ ID NO: 162), FNDFTR (SEQ ID NO: 163), LSSMTR (SEQ ID NO: 164), PPSLTR (SEQ ID NO: 165) and LSCGQR (SEQ ID NO: 166), between amino acids 52 and 53 of the sequence SEQ ID No. 1, and of the deletion of amino acids 4 to 9 of the sequence SEQ ID No. 1. Preferably, the protein comprises the sequence SEQ ID No. 7 with at least one mutation C'. Further preferably, in this case, the mutated protein comprises a sequence chosen from SEQ ID No. 30, SEQ ID No. 31, SEQ ID No. 32, SEQ ID No. 33 and SEQ ID No. 34.

Preferably, the protein according to the invention comprises, preferably consists of, a sequence chosen from SEQ ID No. 9 to 16, 18 to 25, 27 to 34, 105 to 112, 114 to 121 and 123 to 130.

The sequences described in the present application can be summarized as follows:

-continued

| SEQ ID No. | Protein |
|---|---|
| 1 | Human factor X heavy chain (306 amino acids), comprising the activation peptide |
| 2 | Human factor X signal peptide, propeptide and light chain (182 amino acids) |
| 3 | Heavy chain activation peptide (52 amino acids) |
| 4 | Human factor X prepropeptide (488 amino acids) |
| 5 | Human factor X light chain (142 amino acids) |
| 6 | Activated human factor X (FXa) heavy chain (254 amino acids) |
| 7 | FX-WT (corresponds to a human FX of which the nucleotide sequence has been optimized) |
| 8 | FX-control+ (mutant of SEQ ID No. 7 comprising the substitution of 10 amino acids with a sequence corresponding to the thrombin recognition site on fibrinogen = fibrinopeptide A) (comparative) |
| 9 | FX-IIa (mutant of SEQ ID No. 7 comprising a mutation A: insertion of the thrombin cleavage consensus site) |
| 10 | FX-PAR1 (mutant of SEQ ID No. 7 comprising a mutation A: insertion of the modified thrombin cleavage site on the PAR1 receptor) |
| 11 | FX-PAR1M (mutant of SEQ ID No. 7 comprising a mutation A: insertion of the modified thrombin cleavage site on the PAR1 receptor without glycosylation site) |
| 12 | FX-FXIa1 (mutant of SEQ ID No. 7 comprising a mutation A': insertion of FXIa cleavage site 1 on FIX) |
| 13 | FX-FXIa2 (mutant of SEQ ID No. 7 comprising a mutation A': insertion of FXIa cleavage site 2 on FIX) |
| 14 | FX-Kal1 (mutant of SEQ ID No. 7 comprising a mutation A': insertion of kallikrein cleavage site 1 on FXII) |
| 15 | FX-Kal2 (mutant of SEQ ID No. 7 comprising a mutation A': insertion of kallikrein cleavage site 2 on FXII) |
| 16 | FX-Kal3 (mutant of SEQ ID No. 7 comprising a mutation A': insertion of kallikrein cleavage site 3 on FXII) |
| 17 | FX-control+ (mutant of SEQ ID No. 7 comprising the insertion of a sequence corresponding to the thrombin recognition site on fibrinogen = fibrinopeptide A) (comparative) |
| 18 | FX-IIa (mutant of SEQ ID No. 7 comprising a mutation B: insertion of the thrombin cleavage consensus site) |
| 19 | FX-PAR1 (mutant of SEQ ID No. 7 comprising a mutation B: insertion of the modified thrombin cleavage site on the PAR1 receptor) |
| 20 | FX-PAR1M (mutant of SEQ ID No. 7 comprising a mutation B: insertion of the modified thrombin cleavage site on the PAR1 receptor without glycosylation site) |
| 21 | FX-FXIa1 (mutant of SEQ ID No. 7 comprising a mutation B: insertion of the FXIa cleavage site 1 on FIX) |
| 22 | FX-FXIa2 (mutant of SEQ ID No. 7 comprising a mutation B: insertion of the FXIa cleavage site 2 on FIX) |
| 23 | FX-Kal1 (mutant of SEQ ID No. 7 comprising a mutation B: insertion of kallikrein cleavage site 1 on FXII) |
| 24 | FX-Kal2 (mutant of SEQ ID No. 7 comprising a mutation B: insertion of kallikrein cleavage site 2 on FXII) |
| 25 | FX-Kal3 (mutant of SEQ ID No. 7 comprising a mutation B: insertion of kallikrein cleavage site 3 on FXII) |
| 26 | FX-control+ (mutant of SEQ ID No. 7 comprising the insertion of a sequence corresponding to the thrombin recognition site on fibrinogen = fibrinopeptide A, and the deletion of 10 amino acids) (comparative) |
| 27 | FX-IIa (mutant of SEQ ID No. 7 comprising a mutation C: insertion of the thrombin cleavage consensus site) |
| 28 | FX-PAR1 (mutant of SEQ ID No. 7 comprising a mutation C: insertion of the modified thrombin cleavage site on the PAR1 receptor) |
| 29 | FX-PAR1M (mutant of SEQ ID No. 7 comprising a mutation C: insertion of the modified thrombin cleavage site on the PAR1 receptor without glycosylation site) |
| 30 | FX-FXIa1 (mutant of SEQ ID No. 7 comprising a mutation C': insertion of FXIa cleavage site 1 on FIX) |
| 31 | FX-FXIa2 (mutant of SEQ ID No. 7 comprising a mutation C': insertion of FXIa cleavage site 2 on FIX) |
| 32 | FX-Kal1 (mutant of SEQ ID No. 7 comprising a mutation C': insertion of kallikrein cleavage site 1 on FXII) |
| 33 | FX-Kal2 (mutant of SEQ ID No. 7 comprising a mutation C': insertion of kallikrein cleavage site 2 on FXII) |
| 34 | FX-Kal3 (mutant of SEQ ID No. 7 comprising a mutation C': insertion of kallikrein cleavage site 3 on FXII) |
| 35 | Nucleic sequence encoding FX-WT (SEQ ID No. 7) |
| 36 to 75 | Primers |
| 76 to 102 | Nucleic sequences encoding respectively the proteins SEQ ID No. 8 to 34 |
| 103 to 130 | Protein sequences corresponding respectively to the proteins SEQ ID No. 7 to 34 without signal peptide and without propeptide |
| 131 to 158 | Nucleic sequences encoding respectively the proteins SEQ ID No. 103 to 130 |

A subject of the present invention is also a protein complex comprising:

a protein comprising a mutated sequence of SEQ ID No. 1 according to the invention, and at least one protein of sequence SEQ ID No. 2, said proteins being linked to one another by a disulfide bridge.

Another subject of the invention is a nucleic acid (polynucleotide) encoding said protein. Preferably, the nucleic acid is chosen from the sequences SEQ ID No. 77 to 84, 86 to 93, 95 to 102, 133 to 140, 142 to 149 and 151 to 158.

Another subject of the invention is an expression vector comprising said polynucleotide encoding said protein, or an expression cassette comprising said polynucleotide. According to the invention, the expression vectors appropriate for use according to the invention may comprise at least one expression-controlling element functionally linked to the nucleic acid sequence. The expression-controlling elements are inserted into the vector and make it possible to regulate the expression of the nucleic acid sequence. Examples of expression-controlling elements include in particular lac systems, the lambda phage promoter, yeast promoters or viral promoters. Other functional elements may be incorporated, such as a leader sequence, stop codons, polyadenylation signals and sequences required for the subsequent transcription and translation of the nucleic acid sequence in the host system. It will be understood by those skilled in the art that the correct combination of expression-controlling elements depends on the host system chosen. It will also be understood that the expression vector must contain the additional elements required for the subsequent transfer and replication of the expression vector containing the nucleic acid sequence into and in the host system.

Such vectors are easily constructed using conventional or commercially available methods.

Another subject of the invention is a recombinant cell comprising an expression vector as described above, or a polynucleotide as described above. According to the invention, examples of host cells which can be used are eukaryotic cells, such as animal, plant, insect and yeast cells; and prokaryotic cells, such as $E.$ $coli$. The means via which the vector carrying the gene can be introduced into the cells comprise in particular microinjection, electroporation, transduction or transfection by means of DEAE-dextran, lipofection, calcium phosphate or other procedures known to those skilled in the art. In one preferred embodiment, eukaryotic expression vectors which function in eukaryotic cells are used. Examples of such vectors include viral vectors, such as retroviruses, adenoviruses, herpes viruses, vaccinia virus, smallpox virus, poliovirus or lentiviruses, bacterial expression vectors or plasmids such as pcDNAS. The preferred eukaryotic cell lines include COS cells, CHO cells, HEK cells, BHK cells, PerC6 cells, HeLa cells, NIH/3T3 293 cells (ATCC # CRL1573), T2 cells, dendritic cells or monocytes.

The protein according to the invention may be produced in the milk of the transgenic animals.

In this case, according to a first aspect, the expression of a DNA sequence containing a gene encoding the protein according to the invention is controlled by a mammalian casein promoter or a mammalian whey promoter, said promoter not naturally controlling the transcription of said gene, and the DNA sequence also containing a sequence for secretion of the protein. The secretion sequence comprises a secretion signal interposed between the gene and the promoter.

The transgenic animal used is capable not only of producing the desired protein, but also of transmitting this capacity to its descendents. The secretion of the protein into the milk facilitates purification and avoids the use of blood products. The animal can thus be chosen from goats, doe rabbits, ewes or cows.

The protein according to the invention can be used as a medicament. Consequently, the protein according to the invention can be introduced into a pharmaceutical composition. In particular, the protein according to the invention can be used for the treatment of coagulation disorders, in particular hemorrhagic disorders.

The pharmaceutical composition of the invention can be combined with pharmaceutically acceptable excipients, and optionally sustained-release matrices, such as biodegradable polymers, for forming a therapeutic composition.

The pharmaceutical composition of the present invention can be administered orally, sublingually, subcutaneously, intramuscularly, intravenously, intra-arterially, intrathecally, intraocularly, intracerebrally, transdermally, locally or rectally. The active ingredient, alone or in combination with another active ingredient, can then be administered in unit administration form, as a mixture with conventional pharmaceutical carriers. Unit administration forms comprise oral forms, such as tablets, gel capsules, powders, granules and oral solutions or suspensions, sublingual and buccal administration forms, aerosols, subcutaneous implants, transdermal, topical, intraperitoneal, intramuscular, intravenous, subcutaneous and intrathecal administration forms, intranasal administration forms and rectal administration forms.

Preferably, the pharmaceutical composition contains a pharmaceutically acceptable vehicle for a formulation capable of being injected. This may involve in particular sterile, isotonic formulae, saline solutions (with monosodium or disodium phosphate, sodium chloride, potassium chloride, calcium chloride or magnesium chloride and the like, or mixtures of such salts), or lyophilized compositions, which, when sterilized water or physiological saline is added, as appropriate, enable the constitution of injectable solutes.

The pharmaceutical forms appropriate for injectable use comprise sterile aqueous solutions or dispersions, oily formulations, including sesame oil, and peanut oil, and sterile powders for the extemporaneous preparation of sterile injectable solutions or dispersions. In any event, the form must be sterile and must be fluid since it must be injected using a syringe. It must be stable under the manufacturing and storage conditions and must be preserved against the contaminating action of microorganisms, such as bacteria and fungi.

The dispersions according to the invention can be prepared in glycerol, liquid polyethylene glycols or mixtures thereof, or in oils. Under normal conditions of storage and use, these preparations contain a preservative for preventing microorganism growth. The pharmaceutically acceptable vehicle may be a solvent or dispersion medium containing, for example, water, ethanol, a polyol (for example, glycerol, propylene glycol, polyethylene glycol, and the like), appropriate mixtures thereof, and/or vegetable oils. Suitable fluidity may be maintained, for example, through the use of a surfactant, such as lecithin. The prevention of the action of microorganisms can be brought about by various antibacterial and antifungal agents, for example parabens, chlorobutanol, phenol, sorbic acid or else thimerosal. In many cases, it will be preferable to include isotonic agents, for example sugars or sodium chloride. Prolonged absorption of the injectable compositions can be brought about through the use, in the compositions, of absorption-delaying agents, for example aluminum monostearate or gelatin.

The sterile injectable solutions are prepared by incorporating the active substances in the required amount into the appropriate solvent with several of the other ingredients listed above, where appropriate followed by filtration sterilization. As a general rule, the dispersions are prepared by incorporating the various sterilized active ingredients into a sterile vehicle which contains the basic dispersion medium and the other ingredients required among those listed above. In the case of sterile powders for the preparation of sterile injectable solutions, the preferred preparation processes are drying under vacuum and lyophilization. During formulation, the solutions will be administered in a manner compatible with the dosage-regimen formulation and in a therapeutically effective amount. The formulations are easily administered in a variety of pharmaceutical forms, such as the injectable solutions described above, but drug-release capsules and the like can also be used. For parenteral administration in an aqueous solution for example, the solution must be suitably buffered and the liquid diluent made isotonic with a sufficient amount of saline solution or of glucose. These particular aqueous solutions are particularly suitable for intravenous, intramuscular, subcutaneous and intraperitoneal administration. In this regard, the sterile aqueous media which can be used are known to those skilled in the art. For example, a dose can be dissolved in 1 ml of isotonic NaCl solution and then added to 1000 ml of appropriate liquid, or injected on the proposed site of the infusion. Certain dosage-regimen variations will necessarily have to occur according to the condition of the subject treated.

The pharmaceutical composition of the invention may be formulated in a therapeutic mixture comprising approximately 0.0001 to 1.0 milligrams, or approximately 0.001 to 0.1 milligrams, or approximately 0.1 to 1.0 milligrams, or even approximately 10 milligrams per dose or more. Multiple doses can also be administered. The level of therapeutically effective dose specific for a particular patient will depend on a variety of factors, including the disorder which is treated and the seriousness of the disease, the activity of the specific compound used, the specific composition used, the age, body weight, general health, sex and diet of the patient, the time of the administration, the route of administration, the excretion rate of the specific compound used, the duration of the treatment, or else the medicaments used in parallel.

The following examples are given for the purpose of illustrating various embodiments of the invention.

Family 1 encompasses the mutants comprising mutations A or A' (SEQ ID NO: 168).

Family 2 groups together the mutants comprising mutation B (SEQ ID NO: 169).

Family 3 groups together the mutants comprising mutation C or C' (SEQ ID NO: 169).

Figure 3:
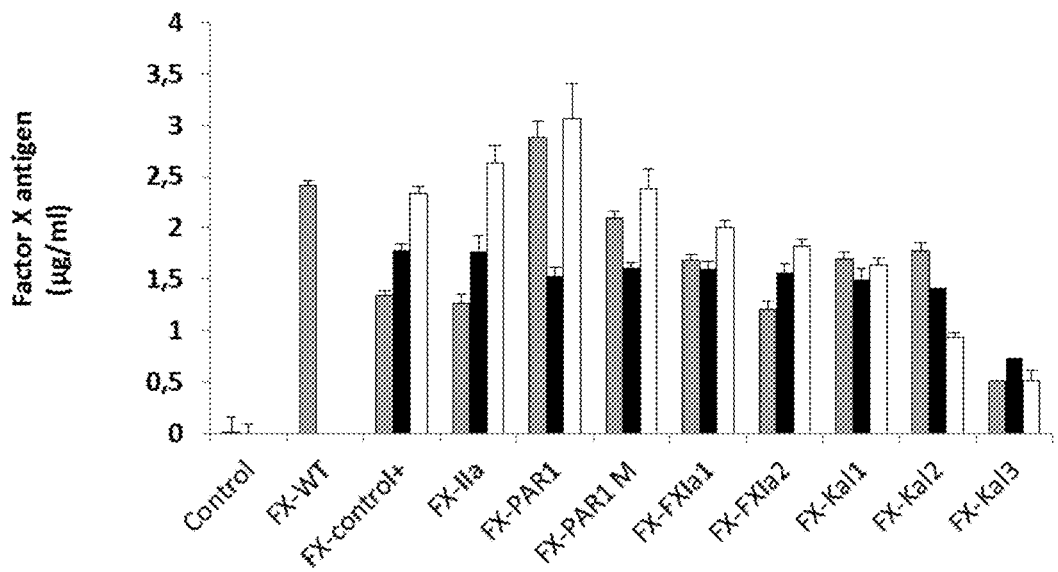

FIG. 3: Shows the level of expression of the variant factors produced in CHO

The three FX families were expressed following transfection in CHO. The day-7 supernatants were analyzed in triplicate with the Zymutest FX kit (Hyphen). The concentrations (μg/ml) are indicated along the y-axis. The standard deviations are indicated above the histograms. Family 1, grey bar; family 2, black bar; family 3, white bar.

Figure 4:
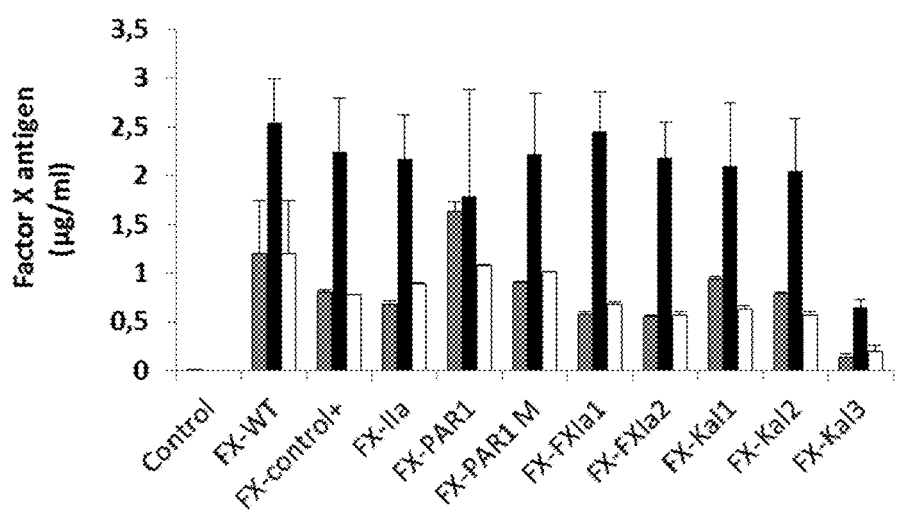

FIG. 4: Shows the level of expression of factors X and variants produced in HEK

The three FX families were expressed following transfection in HEK293S. The day-7 supernatants were analyzed in triplicate with the Zymutest FX kit (Hyphen). The concentrations (μg/ml) are indicated along the y-axis. The standard deviations are indicated above the histograms. Family 1, grey bar; family 2, black bar; family 3, white bar.

Figure 5:
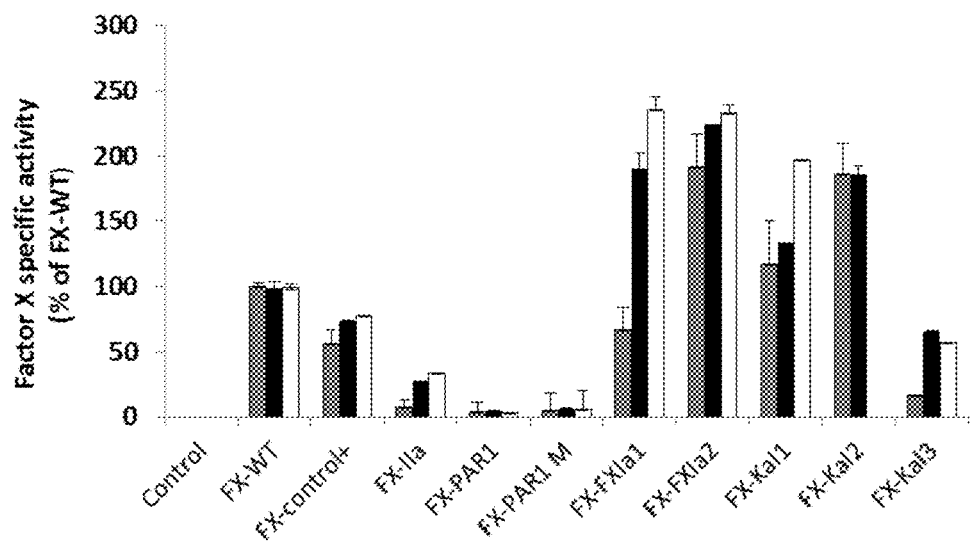

FIG. 5: Shows the chronometric activity of factors X and variants produced in CHO in factor-X-deficient plasma The three FX families were expressed following transfection in CHO-S. The day-7 supernatants were analyzed at least in duplicate by means of a TP test on a Star automated device (Stago). The coagulation times made it possible to calculate a specific activity (in s/(μg/ml)) and were then converted into percentage wild-type recombinant factor X activity. These values are given along the y-axis. The standard deviations are indicated above the histograms. Family 1, grey bar; family 2, black bar; family 3, white bar. * FX-Kal2 family 3, not done.

Figure 6:
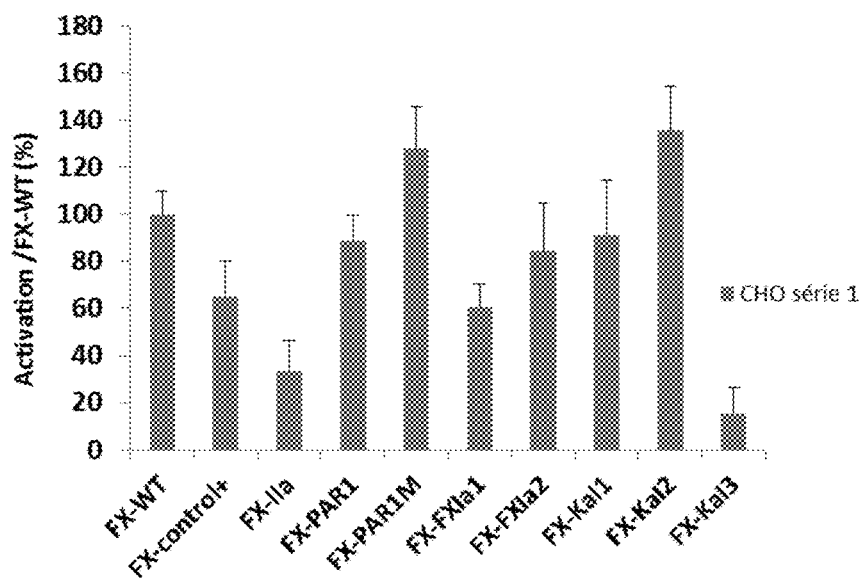

FIG. 6: Shows the activity of factor X variants of family 1 produced in CHO after activation by the RVV-X fraction The FX variants of family 1 were expressed following transfection in CHO-S. The day-7 supernatants were incubated at two FX concentrations (at least in duplicate) in the presence of the RVV-X fraction of Russell's viper venom. The appearance of FXa was measured by monitoring the hydrolysis of the pNAPEP 1025 substrate at 405 nM. The initial conversion rates (mODU/min/nM) were compared to that of FX-WT, fixed at 100%. The mean of the values at two concentrations is established and given on the y-axis. The standard deviations are indicated above the histograms.

Figure 7:
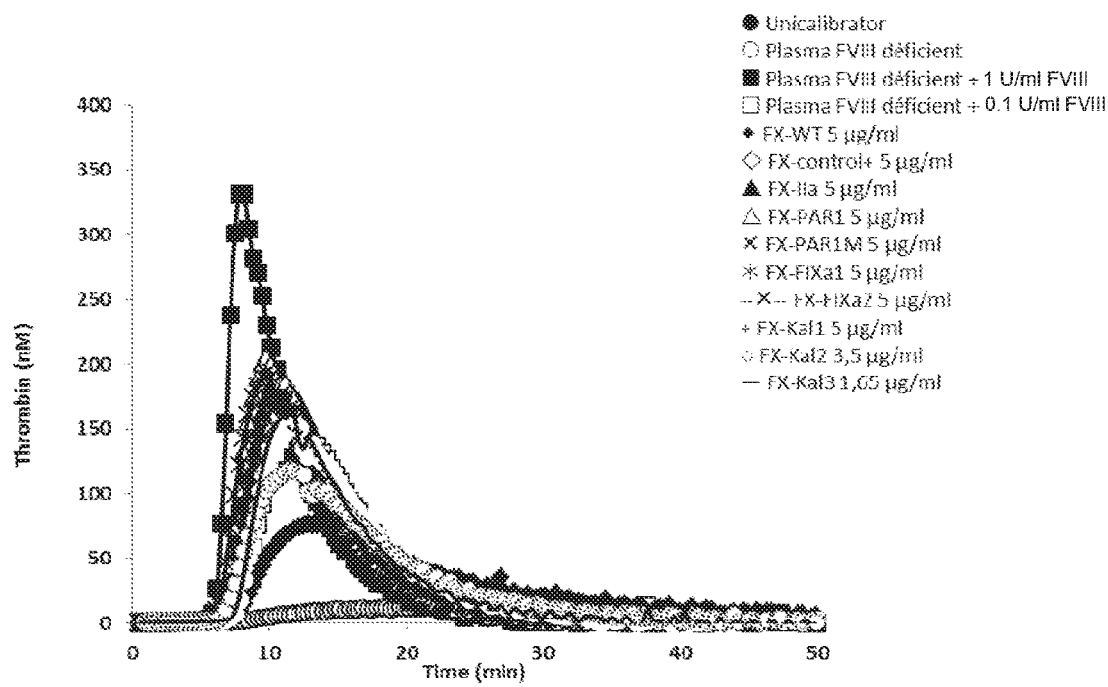

FIG. 7: Shows the thrombinograms obtained from the addition of FX or variants thereof of family 2 to a pool of factor VIII-deficient plasma following activation by tissue factor (1 pM)

along the x-axis: time (in minutes)
along the y-axis: maximum concentration of thrombin observed (in nM)

The normal plasma pool sample is represented by the black curve (●) and the factor FVIII-deficient plasma pool sample is represented by (○). The curves corresponding to the deficient plasma overloaded with 1 U/ml or 0.1 U/ml FVIII are represented by the symbols ■ and □ respectively. The symbols representing the wild-type FXs and the variants are the following: FX-WT (♦), FX– control+ (◊), FX-IIa (▲), FX-PAR1 (Δ), FX-PAR1M (× in solid line), FX-FIXa1 (∗), FX-FIXa2 (× with dashed curve), FX-Kal1 (⊢), FX-Kal2 (○) and FX-Kal3 (solid line without symbol). The factor X or variants thereof were used at 5 μg/ml except for FX-Kal2 and 3 which, for technical reasons, were used at 3.5 and 1.65 μg/ml respectively.

Figure 8:
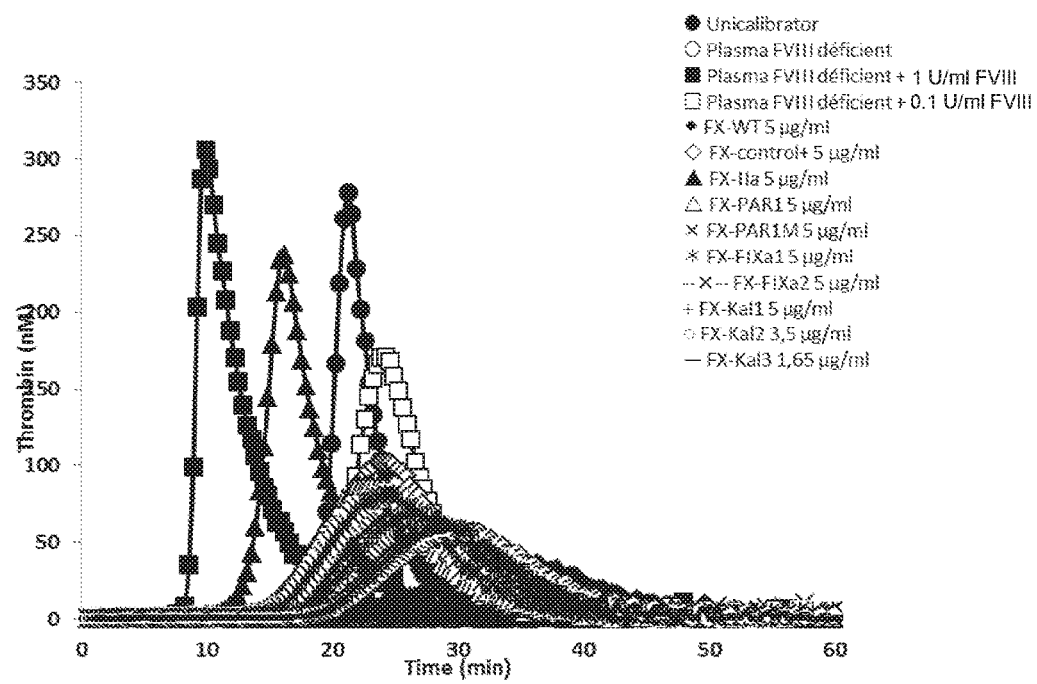

FIG. 8: Shows the thrombinograms obtained from the addition of FX or variants thereof of family 2 to a pool of factor VIII-deficient plasma following activation by cephalin along the x-axis: time (in minutes)
along the y-axis: maximum concentration of thrombin observed (in nM)

The normal plasma pool sample is represented by the black curve (●) and the factor FVIII-deficient plasma pool sample is represented by (○). The curves corresponding to the deficient plasma overloaded with 1 U/ml or 0.1 U/ml of FVIII are represented by the symbols ■ and □ respectively. The symbols representing the wild-type FXs and the variants are the following: FX-WT (♦), FX– control+ (◊), FX-IIa (▲), FX-PAR1 (Δ), FX-PAR1M (× in solid line), FX-FIXa1

(✱), FX-FIXa2 (× with dashed curve), FX-Kal1 (⊢), FX-Kal2 (○) and FX-Kal3 (solid line without symbol). The factor X or variants thereof were used at 5 µg/ml except for FX-Kal2 and 3 which, for technical reasons, were used at 3.5 and 1.65 µg/ml respectively.

Figure 9:
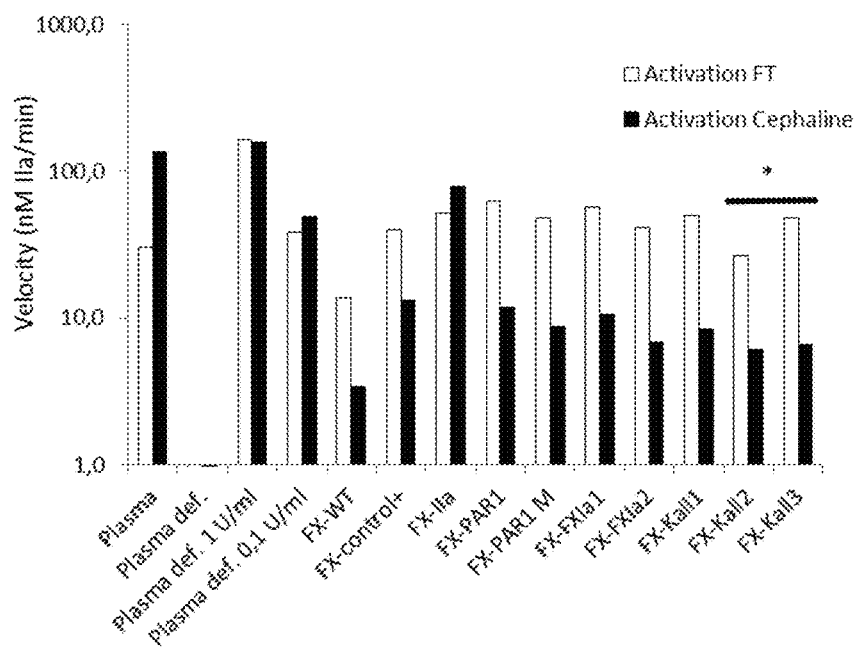

FIG. 9: Shows the velocities of the thrombograms obtained from the addition of FX or variants thereof of family 2 to a pool of factor VIII-deficient plasma, following activation by tissue factor or cephalin The values of the velocities (in nM/min of thrombin generated) arising from FIGS. 7 and 8 are presented. It should be noted that FX-Kal2 and 3 (*) were used at 3.5 and 1.65 µg/ml respectively instead of 5 µg/ml for the other FX and variants. White bars, values obtained by activation with tissue factor (1 pM); black bars, values obtained by activation with cephalin.

Figure 10:
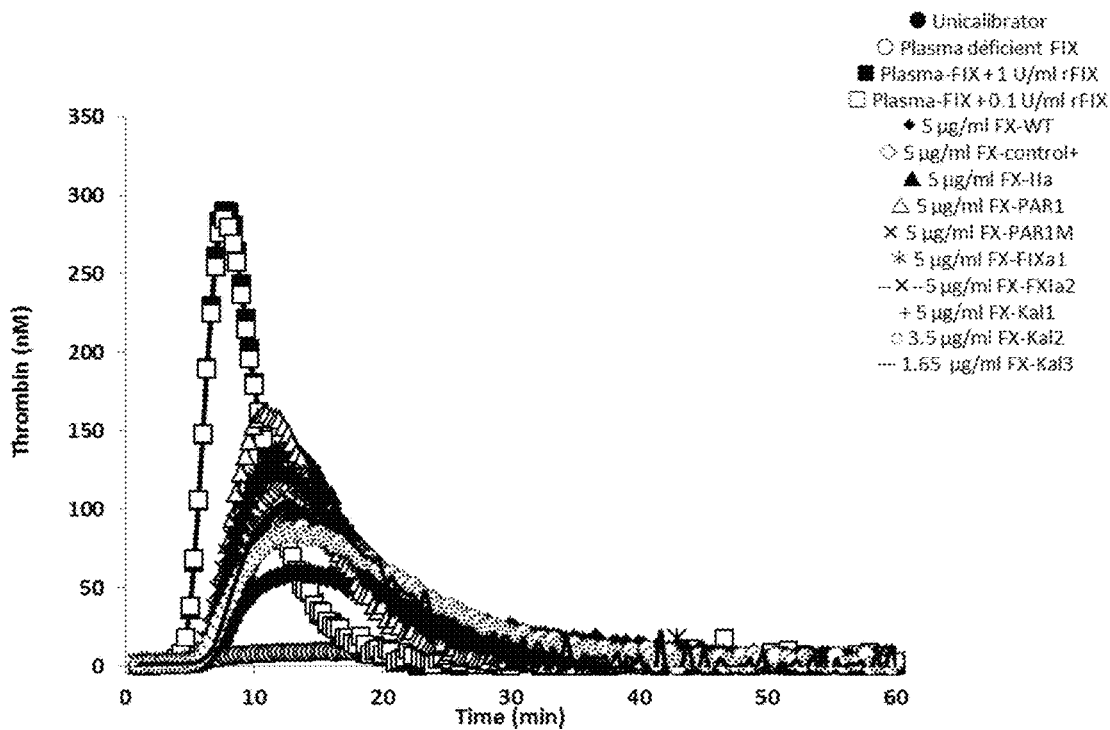

FIG. 10: Shows the thrombinograms obtained from the addition of FX or variants thereof of family 2 to a pool of factor IX-deficient plasma, following activation by tissue factor (1 pM)

along the x-axis: time (in minutes)

along the y-axis: maximum concentration of thrombin observed (in nM)

The normal plasma pool sample is represented by the black curve (●) and the factor FVIII-deficient plasma pool sample is represented by (○). The curves corresponding to the deficient plasma overloaded with 1 U/ml or 0.1 U/ml of FVIII are represented by the symbols ■ and □ respectively. The symbols representing the wild-type FXs and the variants are the following: FX-WT (♦), FX– control+ (◇), FX-IIa (▲), FX-PAR1 (Δ), FX-PAR1M (× in solid line), FX-FIXa1 (✱), FX-FIXa2 (× with dashed curve), FX-Kal1 (⊢), FX-Kal2 (○) and FX-Kal3 (solid line without symbol). The factor X or variants thereof were used at 5 µg/ml except for FX-Kal2 and 3 which, for technical reasons, were used at 3.5 and 1.65 µg/ml respectively.

Figure 11:
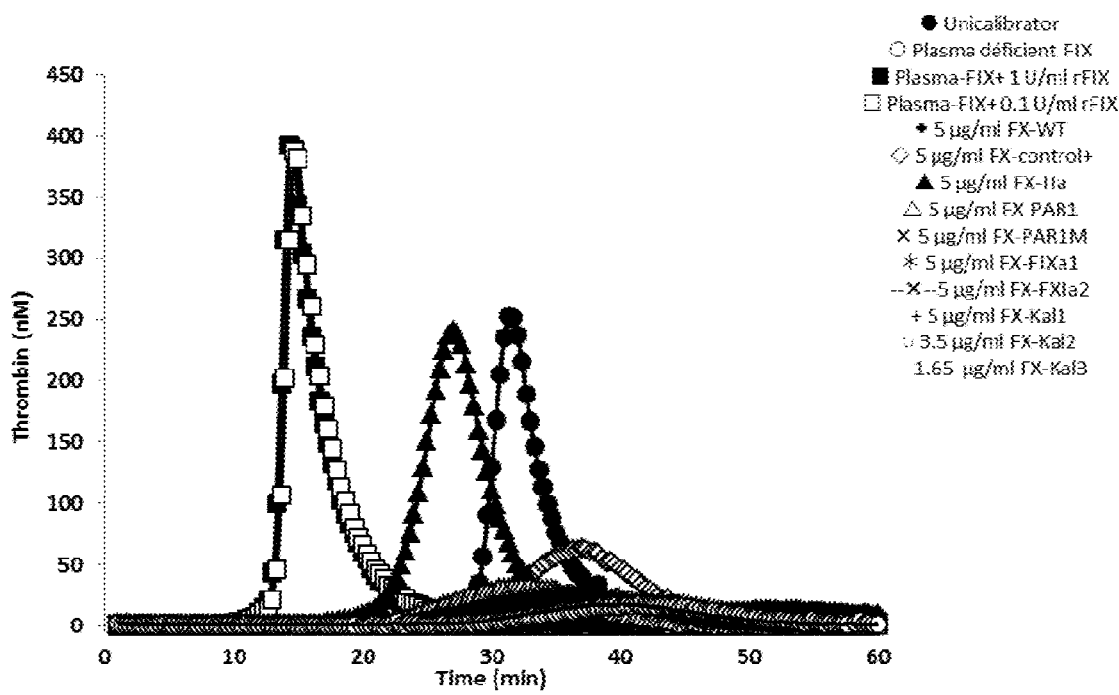

FIG. 11: Shows the thrombinograms obtained from the addition of FX or variants thereof of family 2 to a pool of factor IX-deficient plasma, following activation by cephalin along the x-axis: time (in minutes)

along the y-axis: maximum concentration of thrombin observed (in nM)

The normal plasma pool sample is represented by the black curve (●) and the factor FVIII-deficient plasma pool sample is represented by (○). The curves corresponding to the deficient plasma overloaded with 1 U/ml or 0.1 U/ml of FVIII are represented by the symbols ■ and □ respectively. The symbols representing the wild-type FXs and the variants are the following: FX-WT (♦), FX– control+ (◇), FX-IIa (▲), FX-PAR1 (Δ), FX-PAR1M (× in solid line), FX-FIXa1 (✱), FX-FIXa2 (× with dashed curve), FX-Kal1 (⊢), FX-Kal2 (○) and FX-Kal3 (solid line without symbol). The factor X or variants thereof were used at 5 µg/ml except for FX-Kal2 and 3 which, for technical reasons, were used at 3.5 and 1.65 µg/ml respectively.

Figure 12:
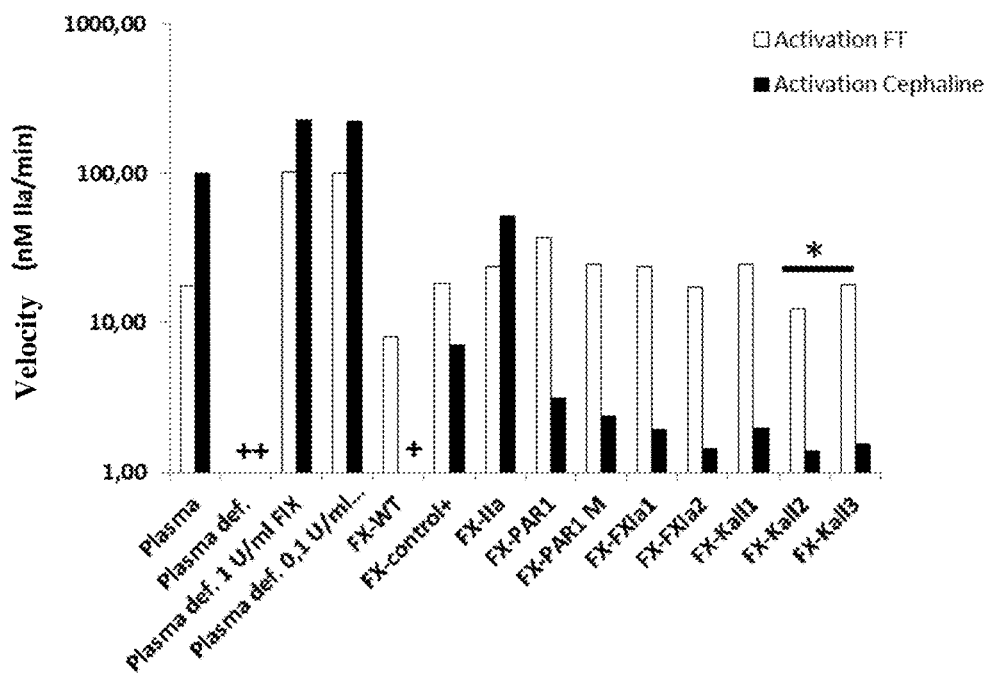

FIG. 12: Shows the velocities of the thrombograms obtained from the addition of FX or variants thereof of family 2 to a pool of factor IX-deficient plasma, following activation by tissue factor (1 pM) or cephalin.

The values of the velocities (in nM/min of thrombin generated) arising from FIGS. 10 and 11 are presented. It should be noted that FX-Kal2 and 3 (*) were used at 3.5 and 1.65 µg/ml respectively instead of 5 µg/ml for the other FX and variants. The results are presented in logarithmic scale. For greater readability, the values below 1 nM/min of thrombin generated are not represented (+). White bars, values obtained by activation with tissue factor (1 pM); black bars, values obtained by activation with cephalin.

Figure 13:
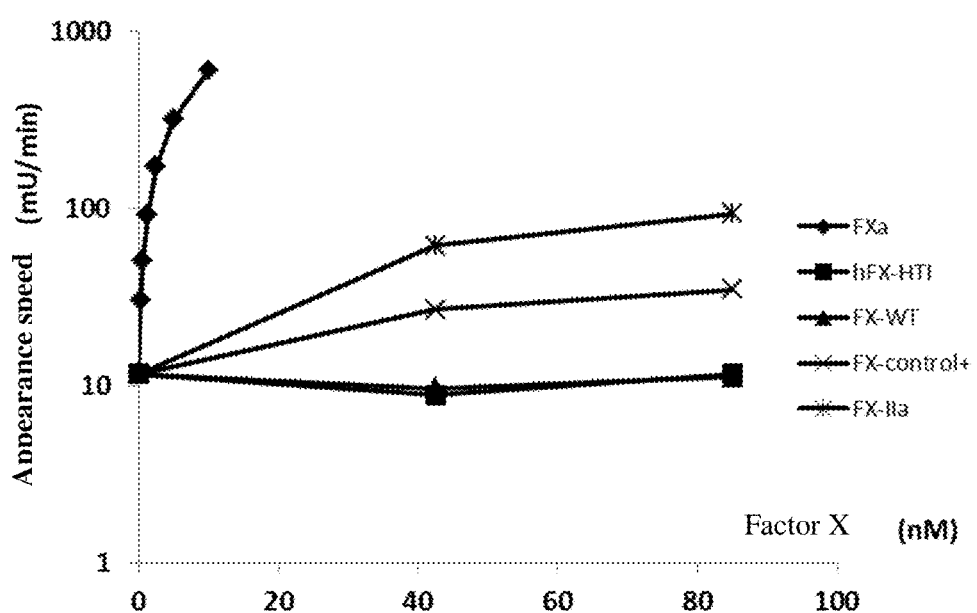

FIG. 13: Shows the thrombin activation of FX-WT and variants of family 2.

The activation of FX-WT and certain variants thereof of family 2 was carried out in the presence of thrombin (10 nM) in Hepes buffer containing Pefachrome FXa 8595 substrate. The appearance of the para-nitroanilide released by the FXa generated was monitored at 405 nm over time. Activated factor X, at various concentrations, was used as a positive control.

Figure 14:
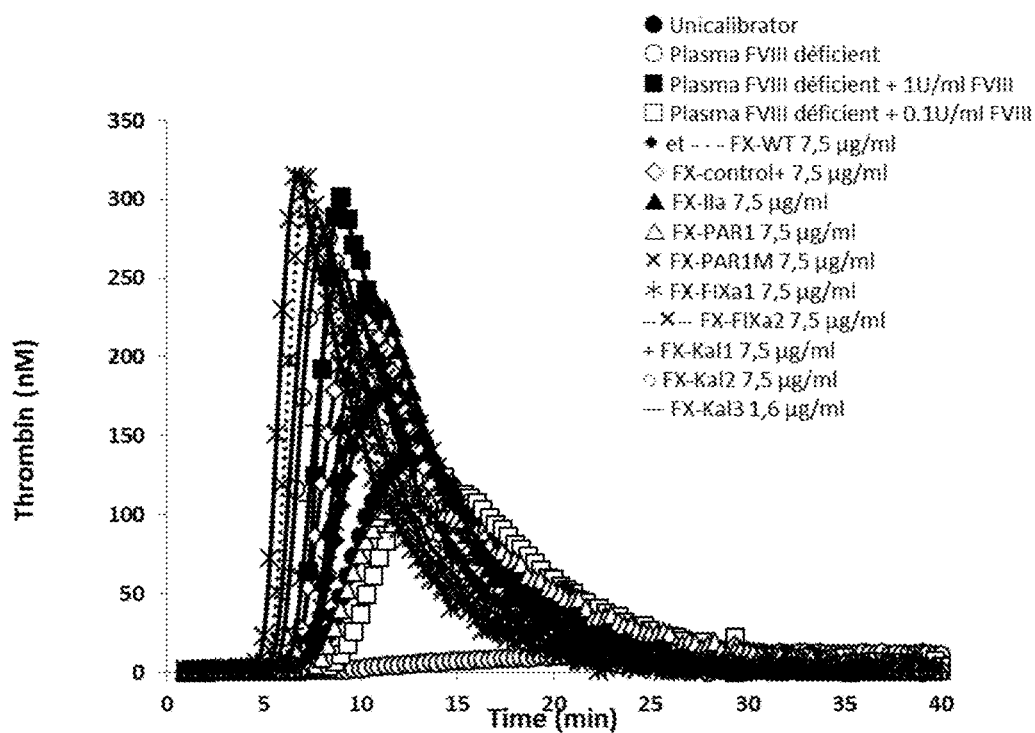

FIG. 14: Shows the thrombinograms obtained from the addition of FX or variants thereof of family 1 to a pool of factor VIII-deficient plasma, following activation by tissue factor along the x-axis: time (in minutes)

along the y-axis: maximum concentration of thrombin observed (in nM)

The normal plasma pool sample is represented by the black curve (●) and the FVIII-deficient plasma pool sample is represented by (○). The curves corresponding to the deficient plasma overloaded with 1 U/ml or 0.1 U/ml of FVIII are represented by the symbols ■ and □ respectively. The symbols representing the wild-type FXs and the variants are the following: FX-WT (♦), FX– control+ (◇), FX-IIa (▲), FX-PAR1 (Δ), FX-PAR1M (× in solid line), FX-FIXa1 (✱), FX-FIXa2 (× with dashed curve), FX-Kal1 (⊢), FX-Kal2 (○) and FX-Kal3 (solid line without symbol). The factor X or variants thereof were used at 7.5 µg/ml except for FX-Kal3 which, for technical reasons, was used at 1.65 µg/ml.

Figure 15:
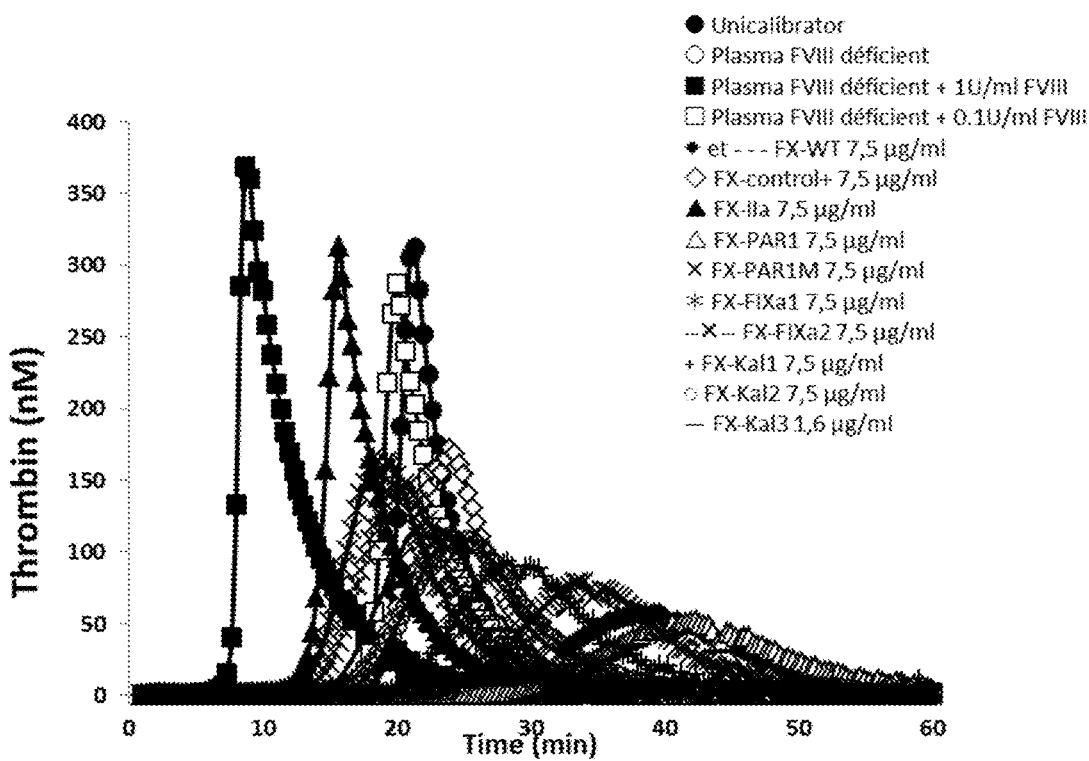

FIG. 15: Shows the thrombinograms obtained from the addition of FX or variants thereof of family 1 to a pool of factor VIII-deficient plasma, following activation by cephalin along the x-axis: time (in minutes)

along the y-axis: maximum concentration of thrombin observed (in nM)

The normal plasma pool sample is represented by the black curve (●) and the FVIII-deficient plasma pool sample is represented by (○). The curves corresponding to the deficient plasma overloaded with 1 U/ml or 0.1 U/ml of FVIII are represented by the symbols ■ and □ respectively. The symbols representing the wild-type FXs and the variants are the following: FX-WT (♦), FX– control+ (◇), FX-IIa (▲), FX-PAR1 (Δ), FX-PAR1M (× in solid line), FX-FIXa1 (✱), FX-FIXa2 (× with dashed curve), FX-Kal1 (⊢), FX-Kal2 (○) and FX-Kal3 (solid line without symbol). The factor X or variants thereof were used at 7.5 µg/ml except for FX-Kal3 which, for technical reasons, was used at 1.65 µg/ml.

Figure 16:
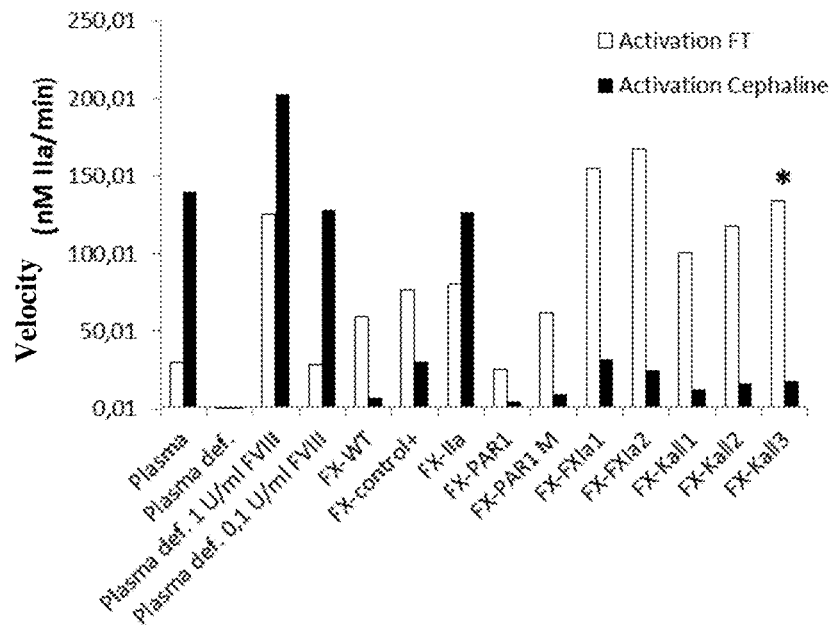

FIG. 16: Shows the velocities of the thrombograms obtained from the addition of FX or variants thereof of family 1 to a pool of factor VIII-deficient plasma, following activation by tissue factor (1 pM) or cephalin.

The values of the velocities (in nM/min of thrombin generated) arising from FIGS. 14 and 15 are presented. It should be noted that the FX-Kal3 (*) was used at 1.65 µg/ml instead of 7.5 µg/ml for the other FX and variants. The value of the FX-WT is the mean of the two experiments. For greater readability, the values below 1 nM/min of thrombin generated are not represented (+). White bars, values obtained by activation with tissue factor (1 pM); black bars, values obtained by activation with cephalin.

Figure 17:
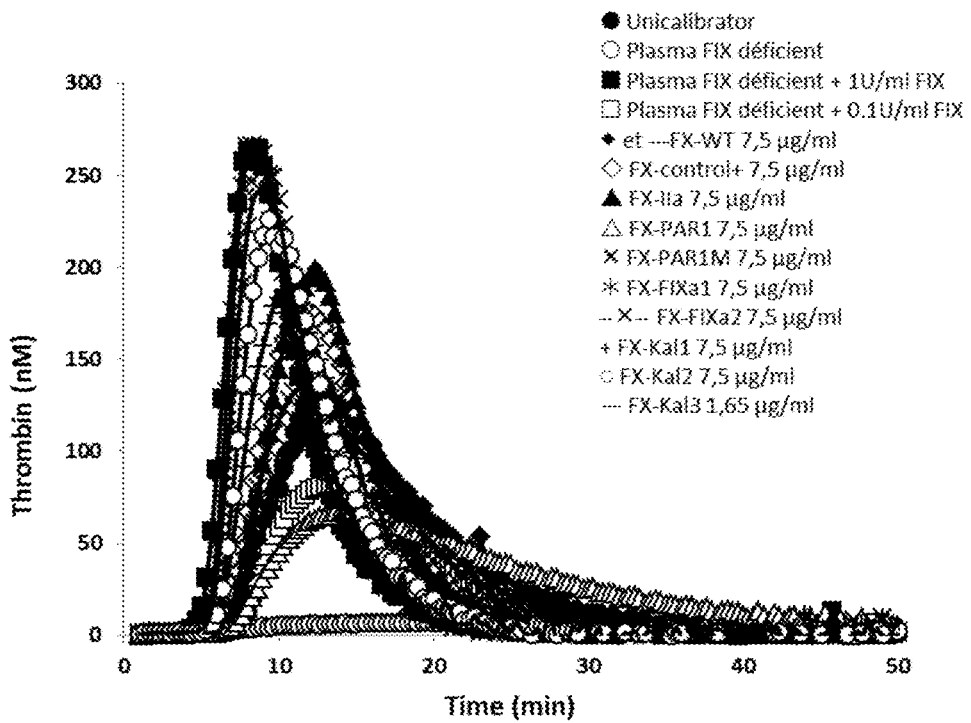

FIG. 17: Shows the thrombinograms obtained from the addition of FX or variants thereof of family 1 to a pool of factor IX-deficient plasma, following activation by tissue factor
along the x-axis: time (in minutes)
along the y-axis: maximum concentration of thrombin observed (in nM)
The normal plasma pool sample is represented by the black curve (●) and the FIX-deficient plasma pool sample is represented by (○). The curves corresponding to the deficient plasma overloaded with 1 U/ml or 0.1 U/ml of FIX are represented by the symbols ■ and □ respectively. The symbols representing the wild-type FXs and the variants are the following: FX-WT (♦), FX− control+ (◇), FX-IIa (▲), FX-PAR1 (Δ), FX-PAR1M (× in solid line), FX-FIXa1 (✳), FX-FIXa2 (× with dashed curve), FX-Kal1 (⊢), FX-Kal2 (○) and FX-Kal3 (solid line without symbol). The factor X or variants thereof were used at 7.5 μg/ml except for FX-Kal3 which, for technical reasons, was used at 1.65 μg/ml.

Figure 18:
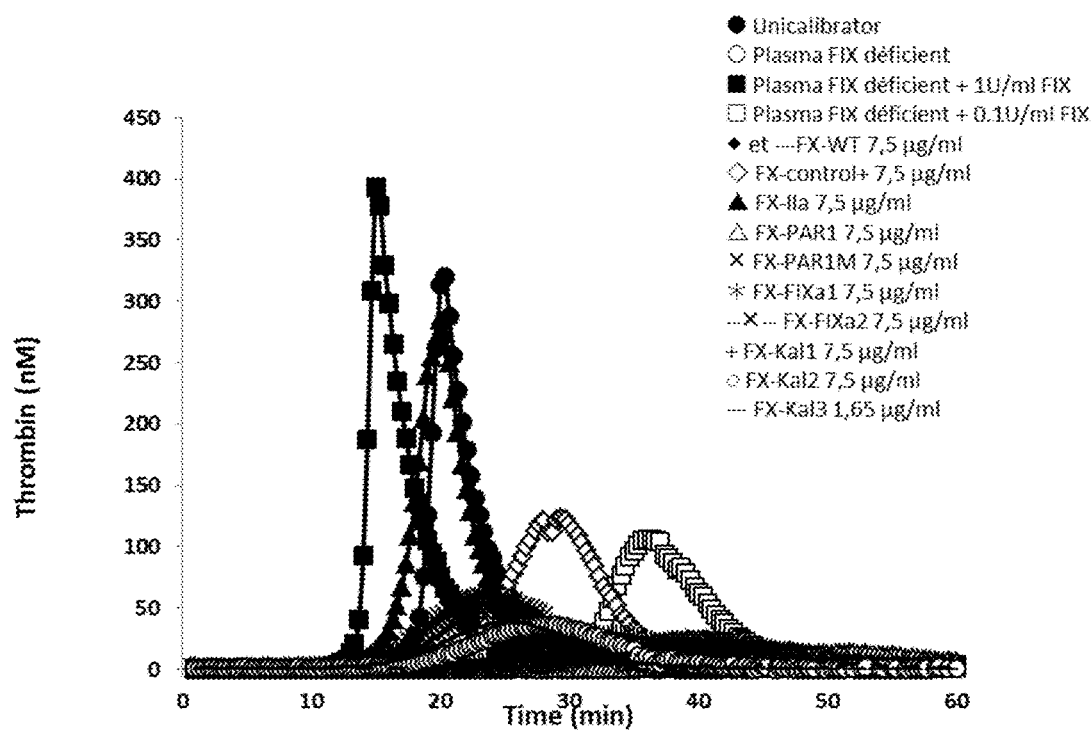

FIG. 18: Shows the thrombinograms obtained from the addition of FX or variants thereof of family 1 to a pool of factor IX-deficient plasma, following activation by cephalin
along the x-axis: time (in minutes)
along the y-axis: maximum concentration of thrombin observed (in nM)
The normal plasma pool sample is represented by the black curve (●) and the FIX-deficient plasma pool sample is represented by (○). The curves corresponding to the deficient plasma overloaded with 1 U/ml or 0.1 U/ml of FIX are represented by the symbols ■ and □ respectively. The symbols representing the wild-type FXs and the variants are the following: FX-WT (♦), FX− control+ (◇), FX-IIa (▲), FX-PAR1 (Δ), FX-PAR1M (× in solid line), FX-FIXa1 (✳), FX-FIXa2 (× with dashed curve), FX-Kal1 (⊢), FX-Kal2 (○) and FX-Kal3 (solid line without symbol). The factor X or variants thereof were used at 7.5 μg/ml except for FX-Kal3 which, for technical reasons, was used at 1.65 μg/ml.

Figure 19:
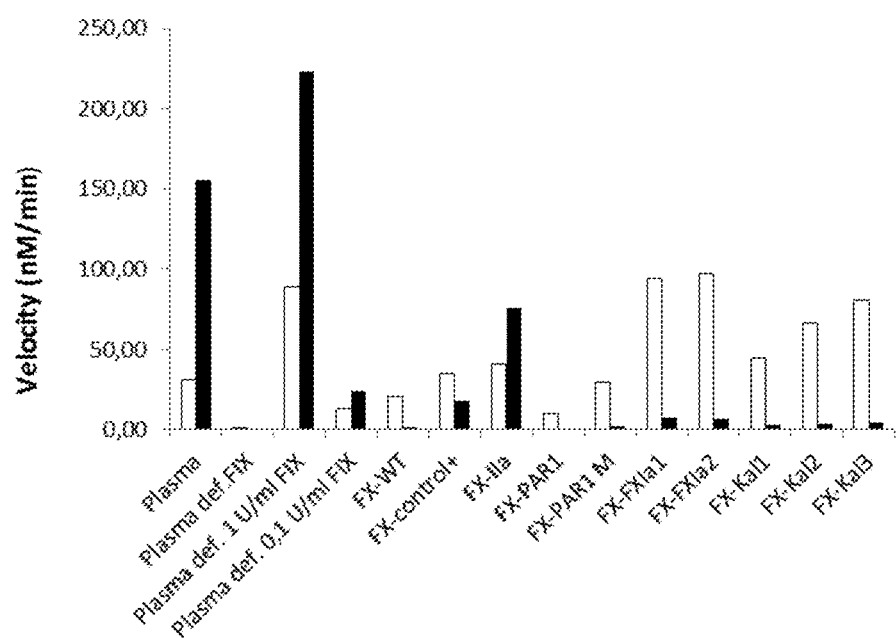

FIG. 19: Shows the velocities of the thrombograms obtained from the addition of FX or variants thereof of family 1 to a pool of factor IX-deficient plasma, following activation by tissue factor (1 pM) or cephalin.
The values of the velocities (in nM/min of thrombin generated) arising from FIGS. 17 and 18 are presented. It should be noted that FX-Kal3 (*) was used at 1.65 μg/ml instead of 7.5 μg/ml for the other FX and variants. The value of the FX-WT is the mean of the two experiments. For greater readability, the values below 1 nM/min of thrombin generated are not represented (+). White bars, values obtained by activation with tissue factor (1 pM); black bars, values obtained by activation with cephalin.

Figure 20:
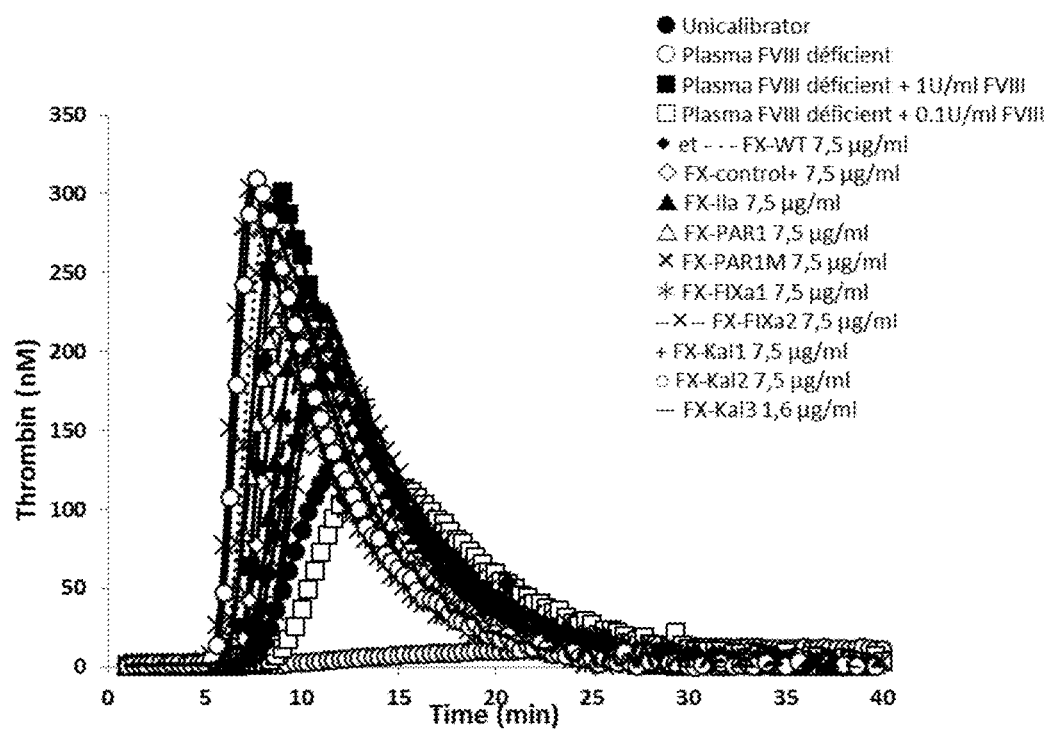

FIG. 20: Shows the thrombinograms obtained from the addition of FX or variants thereof of family 3 to a pool of factor VIII-deficient plasma, following activation by tissue factor
along the x-axis: time (in minutes)
along the y-axis: maximum concentration of thrombin observed (in nM)
The normal plasma pool sample is represented by the black curve (●) and the FVIII-deficient plasma pool sample is represented by (○). The curves corresponding to the deficient plasma overloaded with 1 U/ml or 0.1 U/ml of FVIII are represented by the symbols ■ and □ respectively. The symbols representing the wild-type FXs and the variants are the following: FX-WT (♦ and ---), FX− control+ (◇), FX-IIa (▲), FX-PAR1 (Δ), FX-PAR1M (× in solid line), FX-FIXa1 (✳), FX-FIXa2 (× with dashed curve), FX-Kal1 (⊢), FX-Kal2 (○) and FX-Kal3 (solid line without symbol). The factor X or variants thereof were used at 7.5 μg/ml except for FX-Kal3 which, for technical reasons, was used at 1.65 μg/ml.

Figure 21:
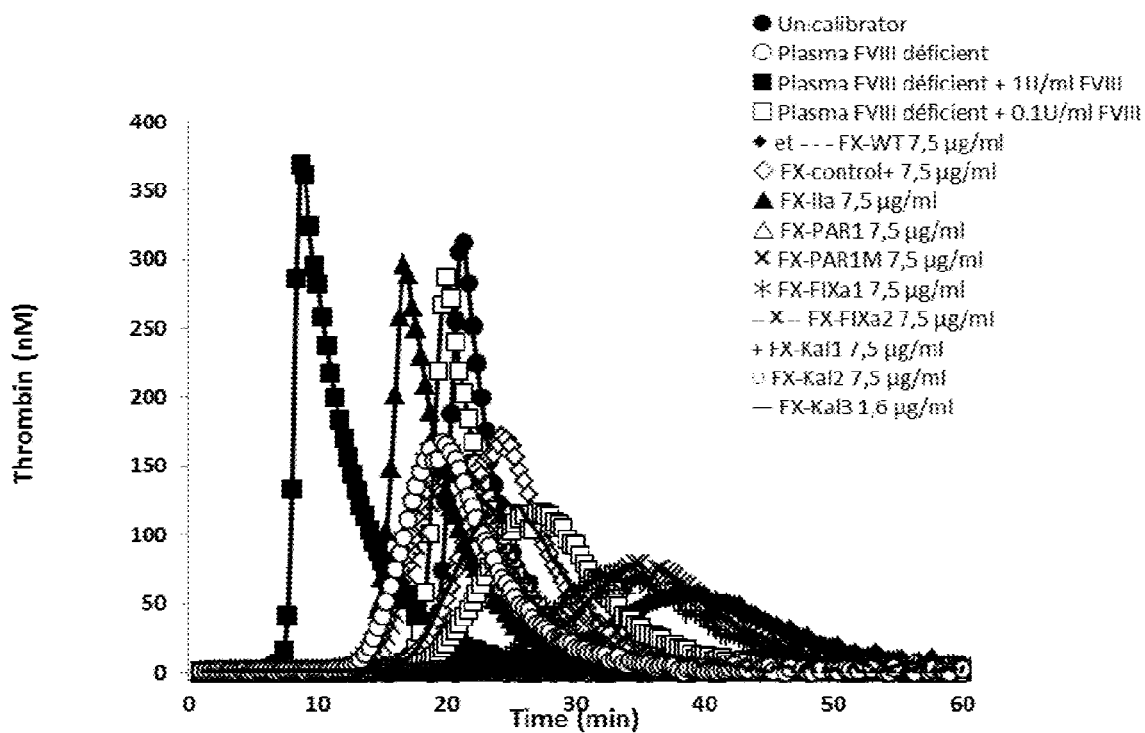

FIG. 21: Shows the thrombinograms obtained from the addition of FX or variants thereof of family 3 to a pool of factor VIII-deficient plasma, following activation by cephalin
along the x-axis: time (in minutes)
along the y-axis: maximum concentration of thrombin observed (in nM)
The normal plasma pool sample is represented by the black curve (●) and the FVIII-deficient plasma pool sample is represented by (○). The curves corresponding to the deficient plasma overloaded with 1 U/ml or 0.1 U/ml of FVIII are represented by the symbols ■ and □ respectively. The symbols representing the wild-type FXs and the variants are the following: FX-WT (♦ and ---), FX− control+ (◇), FX-IIa (▲), FX-PAR1 (Δ), FX-PAR1M (× in solid line), FX-FIXa1 (✳), FX-FIXa2 (× with dashed curve), FX-Kal1 (⊢), FX-Kal2 (○) and FX-Kal3 (solid line without symbol). The factor X or variants thereof were used at 7.5 μg/ml except for FX-Kal3 which, for technical reasons, was used at 1.65 μg/ml.

Figure 22:
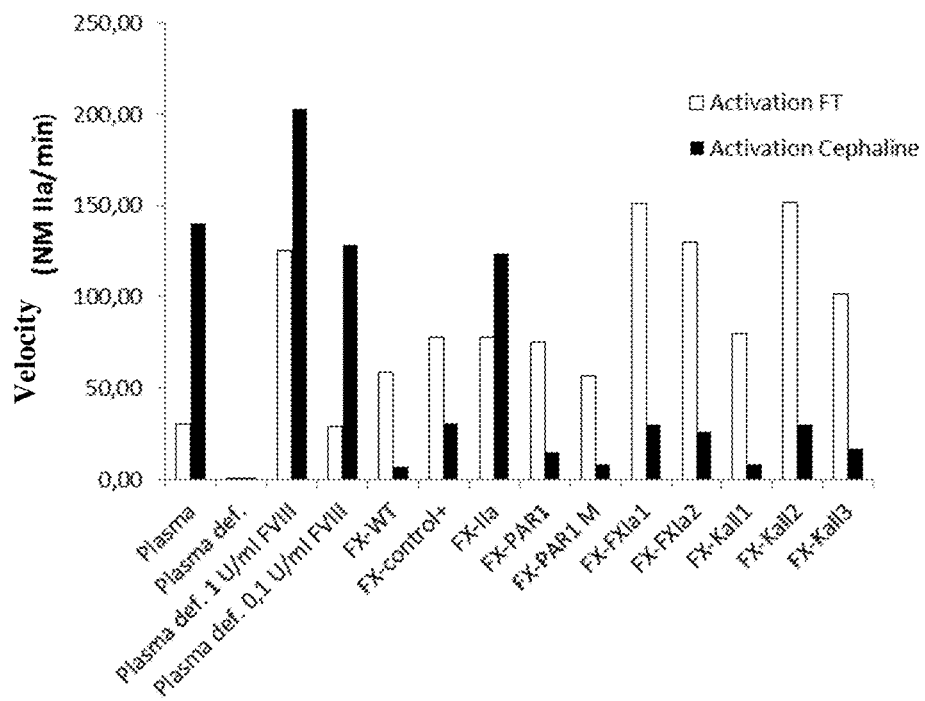

FIG. 22: Shows the velocities of the thrombograms obtained from the addition of FX or variants thereof of family 3 to a pool of factor VIII-deficient plasma, following activation by tissue factor (1 pM) or cephalin
The values of the velocities (in nM/min of thrombin generated) arising from FIGS. 20 and 21 are presented. It should be noted that FX-Kal3 (*) was used at 1.65 μg/ml instead of 7.5 μg/ml for the other FX and variants. The value of the FX-WT is the mean of the two experiments. White bars, values obtained by activation with tissue factor (1 pM); black bars, values obtained by activation with cephalin.

Figure 23:
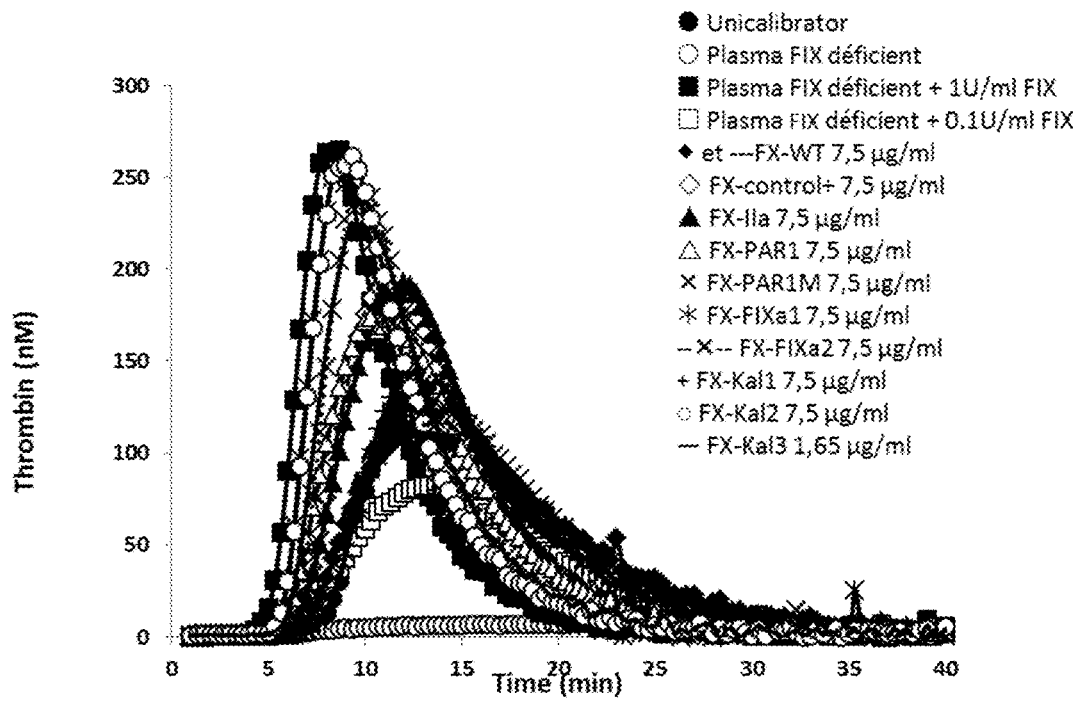

FIG. 23: Shows the thrombinograms obtained from the addition of FX or variants thereof of family 3 to a pool of factor IX-deficient plasma, following activation by tissue factor
along the x-axis: time (in minutes)
along the y-axis: maximum concentration of thrombin observed (in nM)
The normal plasma pool sample is represented by the black curve (●) and the FIX-deficient plasma pool sample is represented by (○). The curves corresponding to the deficient plasma overloaded with 1 U/ml or 0.1 U/ml of FIX are represented by the symbols ■ and □ respectively. The symbols representing the wild-type FXs and the variants are the following: FX-WT (♦), FX− control+ (◇), FX-IIa (▲), FX-PAR1 (Δ), FX-PAR1M (× in solid line), FX-FIXa1 (✳), FX-FIXa2 (× with dashed curve), FX-Kal1 (⊢), FX-Kal2 (○) and FX-Kal3 (solid line without symbol). The factor X or variants thereof were used at 7.5 μg/ml except for FX-Kal3 which, for technical reasons, was used at 1.65 μg/ml.

Figure 24:
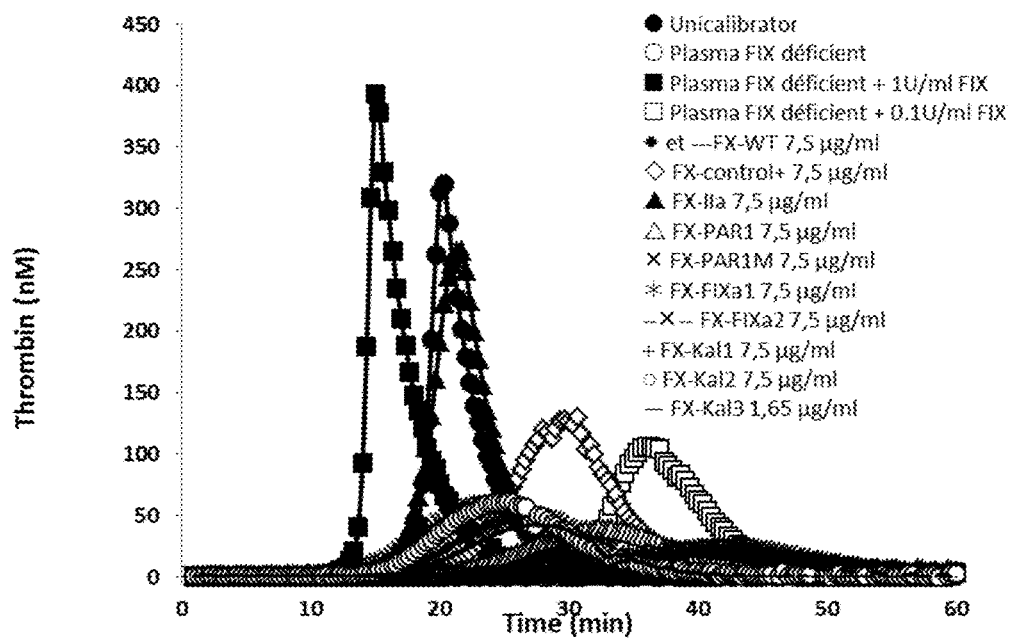

FIG. 24: Shows the thrombinograms obtained from the addition of FX or variants thereof of family 3 to a pool of factor IX-deficient plasma, following activation by cephalin
along the x-axis: time (in minutes)
along the y-axis: maximum concentration of thrombin observed (in nM)
The normal plasma pool sample is represented by the black curve (●) and the FIX-deficient plasma pool sample is represented by (○). The curves corresponding to the deficient plasma overloaded with 1 U/ml or 0.1 U/ml of FIX are represented by the symbols ■ and □ respectively. The symbols representing the wild-type FXs and the variants are the following: FX-WT (♦), FX– control+ (◇), FX-IIa (▲), FX-PAR1 (Δ), FX-PAR1M (× in solid line), FX-FIXa1 (✶), FX-FIXa2 (× with dashed curve), FX-Kal1 (⊢), FX-Kal2 (○) and FX-Kal3 (solid line without symbol). The factor X or variants thereof were used at 7.5 µg/ml except for FX-Kal3 which, for technical reasons, was used at 1.65 µg/ml.

Figure 25:
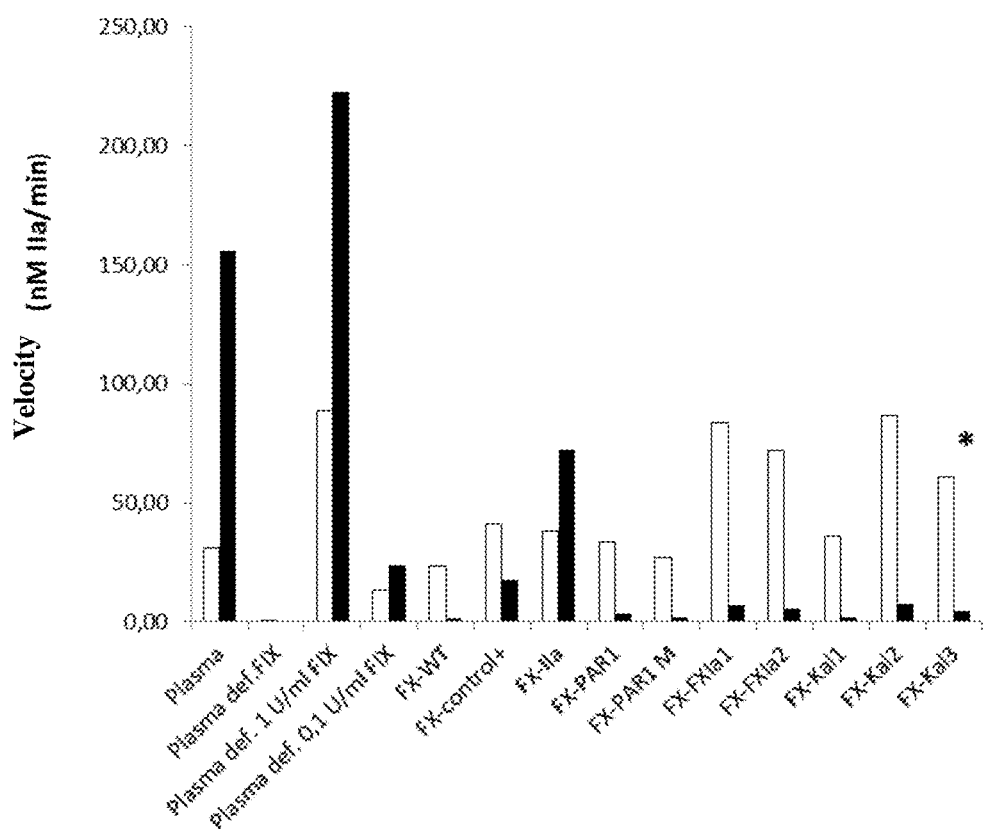

FIG. 25: Shows the velocities of the thrombograms obtained from the addition of FX or variants thereof of family 3 to a pool of factor IX-deficient plasma, following activation by tissue factor (1 pM) or cephalin The values of the velocities (in nM/min of thrombin generated) arising from FIGS. 23 and 24 are presented. It should be noted that FX-Kal3 (*) was used at 1.65 µg/ml instead of 7.5 µg/ml for the other FX and variants. The value of the FX-WT is the mean of the two experiments. White bars, values obtained by activation with tissue factor (1 pM); black bars, values obtained by activation with cephalin.

EXAMPLES

Example 1

Generation of the Complementary DNAs of the Factor X Variants

1—General Observations

The nucleotide and protein sequences of the various constructs are provided in the sequence listing, and are summarized in the table of the description. The wild-type FX molecule is called FX-WT (SEQ ID No. 7), it corresponds to a human FX, the nucleotide sequence of which has been optimized. This molecule will be used as a control for the three families of mutated molecules.

The mutated molecules are named according to the cleavage site placed upstream of the heavy chain. FX-control+ corresponds to the thrombin recognition site on fibrinogen, or fibrinopeptide A. The mutated molecules according to the invention are named, respectively, FX-IIa (thrombin cleavage consensus site), FX-PAR1 (modified thrombin cleavage site on the PAR1 receptor), FX-PAR1M (modified thrombin cleavage site on the PAR1 receptor without glycosylation site), FX-FXIa1 (FXIa cleavage site 1 on FIX), FX-FXIa2 (FXIa cleavage site 2 on FIX), FX-Kal 1 (kallikrein cleavage site 1 on FXII), FX-Kal2 (kallikrein cleavage site 2 on FXII) and FX-Kal3 (kallikrein cleavage site 3 on FXII).

Figure 1:
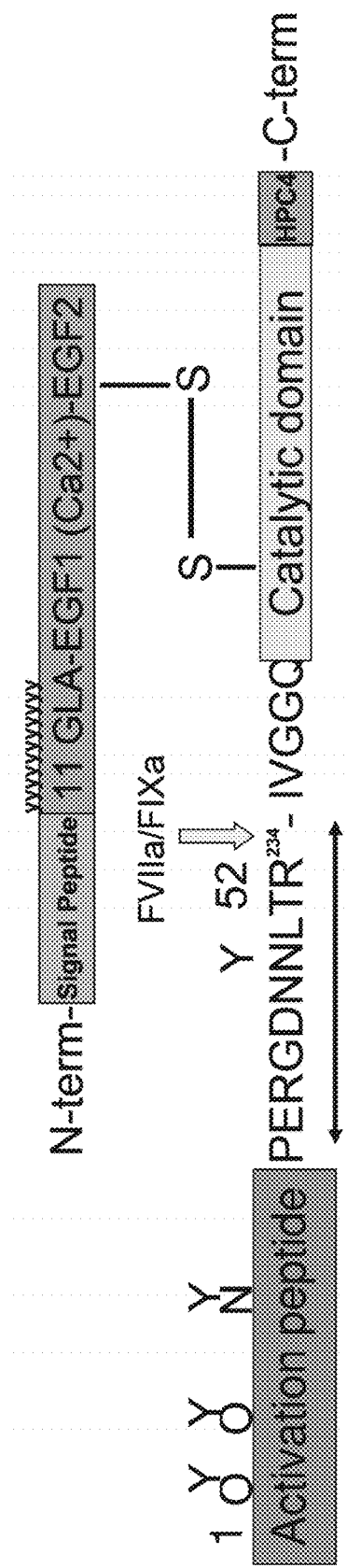
FIG. 1: Shows the structure of native human factor X. Figure discloses SEQ ID NO: 167.
Figure 2:
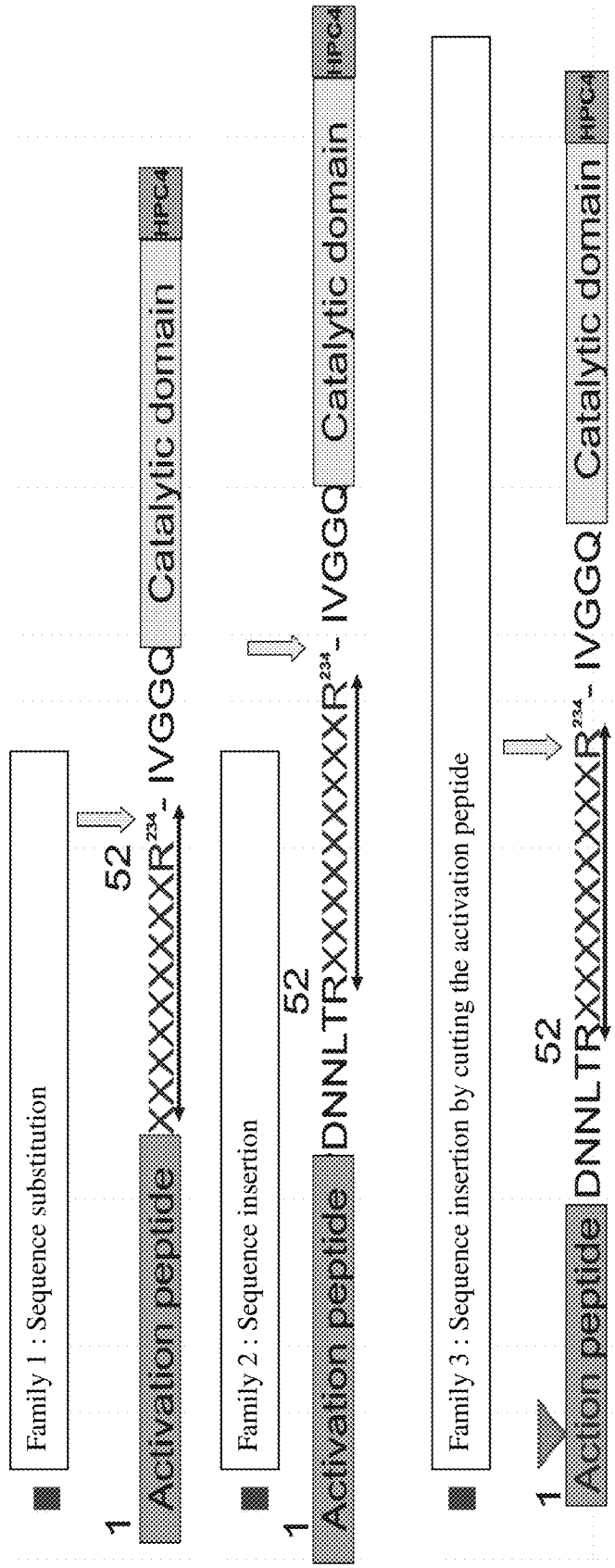
FIG. 2: Shows the mutant development strategies

As shown in FIG. 2, each of these sites is present in a different environment (family), namely:
either in family 1 which consists of the substitution of 6 or 10 amino acids upstream of the activation peptide cleavage site (mutation A or A');
or in family 2 which consists of the insertion of the same sequences upstream of the activation peptide cleavage site (mutation B);
or in family 3 which consists of the insertion of these sequences upstream of the activation peptide cleavage site, coupled to the deletion of a part of the activation peptide (mutation C or C').

Thus, the proteins of sequence SEQ ID No. 9 to 16 correspond to the sequence SEQ ID No. 7, into which a mutation A or A' has been inserted. These proteins therefore belong to family 1.

The proteins of sequence SEQ ID No. 18 to 25 correspond to the sequence SEQ ID No. 7, into which a mutation B has been inserted. These proteins therefore belong to family 2.

Finally, the proteins of sequence SEQ ID No. 27 to 34 correspond to the sequence SEQ ID No. 7, into which a mutation C or C' has been inserted. These proteins therefore belong to family 3.

The sequences SEQ ID No. 8, 17 and 26 correspond to an FX-control+, and are comparative.

2—Experimental Protocol

The sequences specific to each variant are introduced, by assembly or Infusion PCR, using primers judiciously designed so as to allow the insertion and/or the deletion of nucleotide sequences, into a synthetic nucleotide sequence encoding FX optimized for expression in Homo sapiens (SEQ ID No. 35).

2.1. Preparation of the pCEP4-FXWT4HS-gs Vector Encoding Human FX

The pUC57 cloning vector containing the synthetic gene optimized for expression in *Homo sapiens* and prepared by Genescript is digested, like the pCEP4 expression vector (Life Technologies), with the BamHI and HindIII enzymes. The insert corresponding to the FX gene (FXWT4HSgs) and the digested pCEP4 vector are purified using Nucleospin extract II (Clonetech Laboratories) before being ligated together using T4 ligase. The ligation product is used to transform Top10 bacteria (Life Technologies). The presence of the insert in the bacterial colonies is determined by digesting the plasmid with the BamHI and HindIII enzymes and passing the digestion product through agarose gel in order to detect therein a band of 1519 bp. The cDNA is verified by sequencing using the

```
CMVs1
(5'-GGGACTTTCCTACTTGGCAGT-3' SEQ ID No. 36)
and

SV40-3'UTR
(5'-TTCACTGCATTCTAGTTGTGGT-3' SEQ ID No. 37)
``` primers.

2.2—Preparation of the OptiCHO FXWT4HS Vector Encoding Human FX

For optimal expression of the variants, the latter and also the wild-type molecule are prepared in the OptiCHO vector.

Using the pCEP4-FXWT4HS-gs vector, the cDNA of the FXWT4HS sequence is amplified by PCR (kapa Hifi; Biosystems) with the 5'FXWT and 3'FX-SwaI primers.

The 1551-bp PCR product is purified using Nucleospin extract before being digested with the NheI and SwaI enzymes, just like the OptiCHO destination vector. They are again purified on Nucleospin extract after digestion.

The insert and the vector are ligated together using T4 ligase before the ligation product is integrated into competent Top10 bacteria. After bacterial amplification in the presence of ampicillin, bacterial colonies are sampled from a Petri dish and screened by PCR to search for a 296-bp amplicon with the 5'ef1a and 3FX primers, said amplicon being a sign of the presence of the insert encoding FX in the OptiCHO vector. The PCR screening is supplemented by a screening of the purified vectors by enzymatic digestion with the Nhe I and SwaI enzymes in order to search for a 1538-bp fragment on agarose gel. The OptiCHO-FXWT4HS vector is sequenced with the primers:

```
5'ef1a:
                                    (SEQ ID No. 38)
  5'-GTGGAGACTGAAGTTAGGCCAG-3'
```

-continued

3FX:
(SEQ ID No. 39)
5'-CTTCATTTCCTCCAGGAAAGAGTTGGC-3'

2BGHPA:
(SEQ ID No. 40)
5'-CAGATGGCTGGCAACTAGAA-3'

2.3. Preparation of the Family 1 Variants

The preparation of the inserts encoding the cDNAs of the family 1 variants is carried out according to table 1 by means of assembly PCR and ligation or by means of the Infusion technique using the primers listed in table 2. The template used for PCR1 and 2 is the OptiCHO-FXWT4HS vector. The PCR products are treated with DpnI in order to digest the parental DNA. The amplicons of interest are purified using Nucleospin extract.

For the OptiCHO-FX WTF1D, OptiCHO-FX WTF1G and OptiCHO-FX WTF1I molecules, the purified amplicons from PCR 1 and 2 were used as template and assembled by assembly PCR according to table 1. The purified PCR3 amplicons and also the vector digested with NheI and SwaI are assembled by ligation with T4 ligase.

TABLE 1

| Variant | PCR1 Primers | PCR1 Amplicon size | PCR2 Primers | PCR2 Amplicon size | Assembly PCR 3 after digestion of PCR1 and 2 Primers | Assembly PCR 3 after digestion of PCR1 and 2 Amplicon size |
|---|---|---|---|---|---|---|
| FXWT4HS F1D | 5'FXWT + 3'FX1d | 720 | 5'FX1d + 3'FX SwaI | 842 | 5'FXWT + 3'Fx SwaI | 1551 |
| FXWT4HS F1G | 5'FXWT + 3'FX1g | 716 | 5'FX1g + 3'FX SwaI | 841 | 5'FXWT + 3'Fx SwaI | 1551 |
| FXWT4HS F1I | 5'FXWT + 3'FX1i | 716 | 5'FX1i + 3'FX SwaI | 838 | 5'FXWT + 3'Fx SwaI | 1551 |

TABLE 2

| Primers | SEQ ID No. | Sequences |
|---|---|---|
| 3'FX1a | 41 | 5'-TCCTTCTGCCAGGAAGTCCTGTGTCTGGTTGAAGTCCAGCAGGTCA-3' |
| 3'FX1b | 42 | 5'-TCAGGCCCTCGGCCAGGAAGTCCTGTGTCTGGTTGAAGTCCAGCAGGTCA-3' |
| 3'FX1c | 43 | 5'-TGGCGTTGGTGGCCTTCTGTGTCTGGTTGAAGTCCAGCAGGTCAA-3' |
| 3'FX1d | 44 | 5'-AGGGTGGCCTGGGTGGCCTTCTGTGTCTGGTTGAAGTCCAGCAGGTCA-3' |
| 3'FX1e | 45 | 5'-TGGTCAGCTTGCTGGTGCCTCTTTCAGGCTGTGTCTGGTTGA-3' |
| 3'FX1f | 46 | 5'-TGGTGAAGTCGTTGAAGCCTCTTTCAGGCTGTGTCTGGTTGAAG-3' |
| 3'FX1g | 47 | 5'-TGGTCATGCTGCTCAGGCCTCTTTCAGGCTGTGTCTGGTTGAAGT-3' |
| 3'FX1h | 48 | 5'-TGGTCAGGCTGGGAGGGCCTCTTTCAGGCTGTGTCTGGTTGAAG-3' |
| 3'FX1i | 49 | 5'-TCTGGCCGCAGGACAGGCCTCTTTCAGGCTGTGTCTGGTTGAAG-3' |
| 3FX-2a | 50 | 5'-CTCCTTCTGCCAGGAAGTCCCTAGTCAGATTGTTATCGCCTCTTTCAGGC-3' |
| 3FX-2b | 51 | 5'-GTCAGGCCCTCGGCCAGGAAGTCCCTAGTCAGATTGTTATCGCCTCTTTCAGGC-3' |
| 3FX-2c | 52 | 5'-AGGGTGGCGTTGGTGGCCTTCCTAGTCAGATTGTTATCGCCTCTTTCAGGC-3' |
| 3FX-2d | 53 | 5'-AGGGTGGCCTGGGTGGCCTTCCTAGTCAGATTGTTATCGCCTCTTTCAGGC-3' |
| 3FX-2e | 54 | 5'-TCAGCTTGCTGGTCCTAGTCAGATTGTTATCGCCTCTTTCAGGC-3' |
| 3FX-2f | 55 | 5'-GGTGAAGTCGTTGAACCTAGTCAGATTGTTATCGCCTCTTTCAGGC-3' |
| 3FX-2g | 56 | 5'-ATGCTGCTCAGCCTAGTCAGATTGTTATCGCCTCTTTCAGGC-3' |
| 3FX-2h | 57 | 5'-GTCAGGCTGGGAGGCCTAGTCAGATTGTTATCGCCTCTTTCAGGC-3' |
| 3FX-2i | 58 | 5'-TCTGGCCGCAGGACAGCCTAGTCAGATTGTTATCGCCTCTTTCAGGC-3' |
| 5'FX1a | 59 | 5'-GCAGAAGGAGGAGGAGTGAGGATCGTGGGAGGACAGGAGTGCA-3' |
| 5'FX1b | 60 | 5'-AGGGCCTGACCCCTAGGATCGTGGGAGGACAGGAGTGCAAGGA-3' |
| 5'FX1cbis | 61 | 5'-AGGCCACCAACGCCACCCTGTCCCCTAGGATCGTGGGAGGACAGGAGTGCAAGGA-3' |
| 5'FX1d | 62 | 5'-CAGGCCACCCTGAGCCCTAGGATCGTGGGAGGACAGGAGTGCAAG-3' |
| 5'FX1e | 63 | 5'-ACCAGCAAGCTGACCAGGATCGTGGGAGGACAGGAGTGCAAGGA-3' |
| 5'FX1f | 64 | 5'-CAACGACTTCACCAGGATCGTGGGAGGACAGGAGTGCAAGGA-3' |
| 5'FX1g | 65 | 5'-TGAGCAGCATGACCAGGATCGTGGGAGGACAGGAGTGCAAGGA-3' |
| 5'FX1h | 66 | 5'-CCTCCCAGCCTGACCAGGATCGTGGGAGGACAGGAGTGCAAGGA-3' |
| 5'FX1i | 67 | 5'-TGTCCTGCGGCCAGAGGATCGTGGGAGGACAGGAGTGCAAGGA-3' |

TABLE 2-continued

| Primers | SEQ ID No. | Sequences |
|---|---|---|
| 5' fusion FX | 68 | 5'-TCTTCCATTTCAGCTAGCAAGCTTGCCGCCAC-3' |
| 3 fusion FX | 69 | 5'-AGCTCTAGACAATTGATTTAAATGGATCCTCACTTGCCGTC-3' |
| 5'FXWT | 70 | 5'-ACCAGCTGCTAGCAAGCTTGCCG-3' |
| 3'FX-SwaI | 71 | 5'-GAAACTATTTAAATGGATCCTCACTTGCCGTCAATCAGC-3' |
| 3FXF3 | 72 | 5'-CCAGGTAATGCTATCAGCCACTGACCTTTTGCGCCTCTC-3' |
| 5FXF3 | 73 | 5'-TCAGTGGCTGATAGCATTACCTGGAAACCTTATGACGC-3' |
| 3FXF3bis | 74 | 5'-GCTAGTTGCCTGAGCCACTGACCTTTTG-3' |
| 5FXF3bis | 75 | 5'-GCTCAGGCAACTAGCGATAGCATTACCTGGAAACCTTATGACGC-3' |
| 5'ef1a | 38 | 5'-GTGGAGACTGAAGTTAGGCCAG-3' |
| 3FX | 39 | 5'-CTTCATTTCCTCCAGGAAAGAGTTGGC-3' |
| 2BGHPA | 40 | 5'-CAGATGGCTGGCAACTAGAA-3' |

For the OptiCHO-FX WTF1a, OptiCHO-FX WTF1b, OptiCHO-FX WTF1c, OptiCHO-FX WTF1e, OptiCHO-FX WTF1f and OptiCHO-FX WTF1h molecules, the purified amplicons from PCR 1 and 2 were generated by PCR according to the conditions of table 3. The purified amplicons of PCR 1 and 2 are assembled by Infusion with the vector predigested with NheI and SwaI and purified using Nucleospin Extract.

TABLE 3

| | | PCR1 | | PCR2 | |
|---|---|---|---|---|---|
| Variant | Primers | | Amplicon size | Primers | Amplicon size |
| FX4hsF1a | 5'fusionFX + 3'FX1a | | 718 | 5'FX1A + 3fusionFX | 842 |
| FX4hsF1b | 5'fusionFX3'F + X1b | | 722 | 5'FX1b + 3fusionFX | 838 |
| FX4hsF1c | 5'fusionFX + 3'FX1c | | 718 | 5'FX1cbis + 3fusionFX | 859 |
| FX4hsF1e | 5'fusionFX + 3'FX1e | | 714 | 5'FX1e + 3fusionFX | 839 |
| FX4hsF1f | 5'fusionFX + 3'FX1f | | 716 | 5'FX1f + 3fusionFX | 814 |
| FX4hsF1h | 5'fusionFX + 3'FX1h | | 716 | 5'FX1h + 3fusionFX | 839 |

For each variant, the final vector is inserted by bacterial transformation into Top10 bacteria. After bacterial amplification in the presence of ampicillin, bacterial colonies are sampled from a Petri dish and screened by PCR in order to search for a 296-bp amplicon with the 5'ef1a and 3FX primers, said amplicon being a sign of the presence of the insert encoding FX in the OptiCHO vector. The OptiCHO-FX WTF1a to OptiCHO-FX WTF li vectors are sequenced with the primers:

5'ef1a

2BGHPA.

2.4—Preparation of the Family 2 Variants

The preparation of the inserts encoding the cDNAs of the family 2 variants is carried out according to table 4 by means of the technique of PCR and assembly by Infusion using the primers listed in table 2. The template used for PCR1 and 2 is the OptiCHO-FXWT4HS vector. The PCR products are treated with DpnI in order to digest the parental DNA. The amplicons are purified using Nucleospin extract. The purified amplicons of PCR 1 and 2 are assembled by Infusion with the OptiCHO vector predigested with NheI and SwaI and purified using Nucleospin Extract.

TABLE 4

| | PCR1 | | | PCR 2 | | |
|---|---|---|---|---|---|---|
| | 5' primers | 3' primers | Amplicon size | 5' primers | 3' primers | Amplicon size |
| Fx-a | 5'fusionFX | 3FX-2a | 781 | 5'FX-1a | 3fusion FX | 851 |
| Fx-b | 5'fusionFX | 3FX-2b | 758 | 5'FX-1b | 3fusion FX | 847 |
| Fx-c | 5'fusionFX | 3FX-2c | 755 | 5'FX-1c | 3fusion FX | 850 |
| Fx-d | 5'fusionFX | 3FX-2d | 755 | 5'FX-1d | 3fusion FX | 851 |
| Fx-e | 5'fusionFX | 3FX-2 e | 748 | 5'FX-1e | 3fusion FX | 848 |
| Fx-f | 5'fusionFX | 3FX-2f | 750 | 5FX-1f | 3fusion FX | 846 |
| Fx-g | 5'fusionFX | 3FX-2g | 746 | 5'FX-1g | 3fusion FX | 847 |
| Fx-h | 5'fusionFX | 3FX-2h | 749 | 5'FX-1h | 3fusion FX | 848 |
| Fx-i | 5'fusionFX | 3FX-2i | 751 | 5'FX-1i | 3fusion FX | 847 |

For each variant, the final vector is inserted by bacterial transformation into Top10 bacteria. After bacterial amplification in the presence of ampicillin, bacterial colonies are sampled from a Petri dish and screened by PCR in order to search for a 296-bp amplicon with the 5'ef1a and 3FX primers, said amplicon being a sign of the presence of the insert encoding FX in the OptiCHO vector. The OptiCHO-FX WTF2a to OptiCHO-FX WTF2i vectors are sequenced with the primers:
5'ef1a
2BGHPA.

2.5.—Preparation of the Family 3 Variants

Family 3 contains deletions in the activation peptide that it is necessary to prepare before being able to insert therein the enzymatic cleavage sites. In this respect, two intermediate vectors are prepared, OptiCHO FXWT F3AD for the family 3 variants F3a to F3d, and OptiCHO FXWT F3EI for the family 3 variants F3e to F3i.

The inserts of the intermediate vectors are constructed by assembly PCR according to table 5 using the OptiCHO FXWT4HS-gs vector as template and the 5'FXWT, 3'FX-SwaI, 3FXF3, 5FXF3, 3FXF3bis and 5FXF3bis primers listed in table 2.

TABLE 5

| Intermediate vector | PCR1 | | PCR2 | | Assembly PCR 3 after digestion of PCR1 and 2 | |
|---|---|---|---|---|---|---|
| | Primers | Amplicon size | Primers | Amplicon size | Primers | Amplicon size |
| OptiCHO FXWT F3AD | 5'FXWT + 3FXF3 | 598 | 3FX-SwaI + 5FXF3 | 947 | 5'FXWT + 3FX-SwaI | 1521 |
| OptiCHO FXWT F3EI | 5'FXWT + 3FXF3bis | 595 | 3FX-SwaI + 5FXF3bis | 953 | 5'FXWT + 3FX-SwaI | 1533 |

The assembly PCR products are purified using Nucleospin extract before being digested, just like the OptiCHO destination vector, with the NheI and SwaI enzymes. They are again purified on Nucleospin extract after digestion.

The insert and the vector are ligated together using T4 ligase before the ligation product is integrated into competent Top10 bacteria. After bacterial amplification in the presence of ampicillin, bacterial colonies are sampled from a Petri dish and screened by PCR in order to search for a 296-bp amplicon with the 5'ef1a and 3FX primers, said amplicon being a sign of the presence of the insert encoding the FX variant in the OptiCHO vector.

The OptiCHO FXWT F3AD and OptiCHO FXWT F3EI intermediate vectors are sequenced with the primers:
5'ef1a
3FX
2BGHPA.

With the exception of the OptiCHO FXWT F3A molecule, the preparation of the inserts encoding the cDNAs of the series 3 variants is carried out according to table 6 by assembly PCR using the primers listed in table 2. The template used for PCR1 and 2 is the OptiCHO FXWT F3AD vector for the family 3 variants F3a to F3d, and OptiCHO FXWT F3EI for the family 3 variants F3e to F3i. The amplicons are purified using Nucleospin extract. The purified amplicons of PCR 1 and 2 are assembled by assembly PCR with the OptiCHO vector predigested with NheI and SwaI and purified using Nucleospin extract.

TABLE 6

| | PCR1 | | PCR2 | | Assembly PCR 3 after digestion of PCR1 and 2 | |
|---|---|---|---|---|---|---|
| | Primers | Amplicon size | Primers | Amplicon size | Primers | Amplicon size |
| Fx-b | 5'FXWT + 3FX-2b | 723 | 5FX-1b + 3'FX-SwaI | 838 | 5'FXWT + 3'FX-SwaI | 1551 |
| Fx-c | 5'FXWT + 3FX-2c | 720 | 5FX-1c + 3'FX-SwaI | 841 | 5'FXWT + 3'FX-SwaI | 1551 |
| Fx-d | 5'FXWT + 3FX-2d | 720 | 5FX-1d + 3'FX-SwaI | 842 | 5'FXWT + 3'FX-SwaI | 1551 |

TABLE 6-continued

|  | PCR1 |  | PCR2 |  | Assembly PCR 3 after digestion of PCR1 and 2 |  |
|---|---|---|---|---|---|---|
|  | Primers | Amplicon size | Primers | Amplicon size | Primers | Amplicon size |
| Fx-e | 5'FXWT + 3FX-2e | 713 | 5FX-1e + 3'FX-SwaI | 725 | 5'FXWT + 3'FX-SwaI | 1551 |
| Fx-f | 5'FXWT + 3FX-2f | 715 | 5FX-1f + 3'FX-SwaI | 727 | 5'FXWT + 3'FX-SwaI | 1551 |
| Fx-g | 5'FXWT + 3FX-2g | 711 | 5FX-1g + 3'FX-SwaI | 723 | 5'FXWT + 3'FX-SwaI | 1551 |
| Fx-h | 5'FXWT + 3FX-2h | 714 | 5FX-1h + 3'FX-SwaI | 726 | 5'FXWT + 3'FX-SwaI | 1551 |
| Fx-i | 5'FXWT + 3FX-2i | 716 | 5FX-1i + 3'FX-SwaI | 728 | 5'FXWT + 3'FX-SwaI | 1551 |

The assembly PCR products are purified using Nucleospin extract before being digested, just like the OptiCHO destination vector, with the NheI and SwaI enzymes. They are again purified on Nucleospin extract after digestion.

The insert and the vector are ligated together using T4 ligase before the ligation product is inserted into competent Top10 bacteria. After bacterial amplification in the presence of ampicillin, bacterial colonies are sampled from a Petri dish and screened by PCR in order to search for a 296-bp amplicon with the 5'ef1a and 3FX primers, said amplicon being a sign of the presence of the insert encoding the FX variant in the OptiCHO vector.

The final family 3 vectors are sequenced with the primers:
5'ef1a
2BGHPA

Example 2

Production of Recombinant Factors X

1—Experimental Protocol
1.1—Reagents
ProCHO4 (Lonza) and Freestyle™ F17 (Gibco) culture medium.
L-glutamine (Gibco).
CHO-S cell transfection medium: Opti-Pro SFM (Gibco).
HEK cell transfection medium: Opti-MEM (Gibco).
Vitamin K1 (Sigma).
1.2—Protocol
The wild-type factor X and variants thereof are produced in CHO-S or HEK-293-Freestyle eukaryotic cells (Invitrogen) in transient expression.

The CHO-S cells are cultured in ProCHO4 medium and the HEK 293F cells in F17 medium, supplemented respectively with 4 mM and 8 mM of L-glutamine. The 2 cell lines are cultured under conditions shaken at 135 rpm in a controlled atmosphere (8% $CO_2$) at 37° C. On the day before the day of transfection, the cells are seeded at a density of $7 \times 10^5$ cells/ml.

On the day of the transfection, the DNA (20-30 µg) and 30 µg of transfection agent (TA) are preincubated separately in Opti-Pro medium for CHO-S and Opti-MEM for HEK 293F for 5 minutes and then mixed and incubated for 20 minutes in order to allow the formation of the DNA/TA complex. The whole thing is added to a cell preparation of $1 \times 10^6$ cells/ml in a volume of 30 ml.

In the case of the co-transfections of the FXs with native vitamin K epoxide reductase (VKOR), the 2 vectors are added at various ratios in order to obtain a total amount of DNA of 20-30 µg. The VKOR enzyme enables production of active FX in HEK while optimizing gamma-carboxylation Immediately after transfection, vitamin K1 (5 µg/ml) is added to the medium. The transfection levels are evaluated the day after transfection, using a control plasmid expressing GFP (Green Fluorescent Protein). The productions are carried out in "batch" mode for 7 days. At the end of production, the cells and the supernatant are separated by centrifugation. The cells are removed and the supernatant is filtered and then frozen.

Example 3

Measurement of Factor X Concentration

1—Experimental Protocol
The factor X concentration is measured by means of the commercial ELISA Zymutest Factor X (Hyphen BioMed) according to the manufacturer's recommendations. The concentrations are measured in triplicate using antigen values located in the linear zone of detection of the assay. In order to be sure that the mutations introduced do not disrupt the measurement of the concentration, the FXs are deposited in identical amount and revealed by immunoblotting with a polyclonal antibody different than the one used in the ELISA (anti-human FX polyclonal antibody (Cryopep cat No. PAHFX-S)) or by staining after SDS-PAGE (data not shown).
2—Results
2.1—Expression of Factor X Variants Transiently Expressed in CHO
The concentrations of the factor X (FX) variants present in the supernatants of the CHO-S cells transfected with the cDNAs encoding families 1 to 3 were measured by using the commercial ELISA Zymutest Factor X (FIG. 3).

As expected, the supernatants of non-transfected (control) CHO cells do not contain FX. The transfection with the vectors encoding the various FXs makes it possible to obtain levels ranging from 0.5 to 3.06 µg/ml. There is no major difference in expression of the FXs of the various families. At most, FX-IIa of family 3 is expressed 2.1× more strongly (2.64 µg/ml) than that of family 1 (1.26 µg/ml). Some constructs make it possible to obtain factor X at a higher concentration than the wild-type factor X: these are the FX-IIa (family 3) and FX-PAR1 (family 1 and 3) constructs. FX-Kal3 appears to reduce FX production.
2.2—Expression of the Factor X Variants Transiently Expressed in HEK
The concentrations of the factor X variants present in the supernatants of the HEK293S cells transfected with the cDNAs encoding families 1 to 3 were measured using the commercial ELISA Zymutest Factor X (FIG. 4). As expected, the supernatants of non-transfected (control) HEK293S cells do not contain FX. The family 1 molecules were produced at a level close to that of FX-WT (from 0.14 to 1.64 μg/ml). Only the FX-PAR1 molecule is produced at a higher level. The FX-Kal3 molecule remains the least produced molecule. Family 2 was produced in a similar manner for all the constructs, with expression values of from 1.79 to 2.54 μg/ml except for the FX-Kal3 construct produced at a lower level (0.66 μg/ml). Family 3 was produced at lower levels of from 0.2 to 1.2 μg/ml.

In conclusion, certain factor X variant constructs make it possible to produce FX at higher levels than FX-WT:
 these are, in CHO cells, the FX-IIa (family 3) and FX-PAR1 (families 1 and 3) constructs and
 in HEK cells, FX-PAR1 of family 1.

Example 4

Measurement of the Coagulant Activity of the Factor X Variants Produced in CHO-S 1—Experimental Protocol The chronometric activity of the FX variants produced by the CHO-S cells was measured using a Star automated device (Stago) in the presence of FX-deficient plasma. The FX-deficient plasma, the neoplastin and the Owren-Koller buffer come from Stago (Asnières, France).

The concentrated culture supernatant is diluted to 1/10 in Owren-Koller buffer before being added to the FX-deficient plasma. The mixture is incubated for 240 seconds at 37° C. and then the prothrombin time (PT) is initiated by adding 100 μl of neoplastin. The coagulation times (in s.) are converted into specific activity of the FX.

2—Results

The concentrated supernatants resulting from the various transfections in CHO were evaluated for their capacity to compensate for a factor X deficiency. The supernatants were incubated in an FX-deficient plasma and a PT test was carried out. The coagulation times (in s.) were converted into specific activity (SA; in seconds per μg of protein) then the percentage of specific activity compared with the wild-type FX was calculated (FIG. 5). The results are coherent between the various families. This result indicates that the differences in behavior originate mainly from the cleavage sites and not from the way in which they are cloned.

The constructs can be classified into three categories: a first category, the SA of which is similar to that of FX-WT (contains FX-control+), a second category, the SA of which is decreased compared with that of the control (contains FX-IIa, FX-PAR1, FX-PAR1M and FX-Kal3) and a third category, the activity of which in the absence of FX is greater than that of FX-WT (contains FX-FXIa1 and 2, FX-Kal1 and 2). It should be noted that the FX-Kal2 family 3 construct could not be analyzed for technical reasons (* on the graph).

These results indicate that the modifications introduced and which form family 3 (FX-FXIa1 and 2, FX-Kal1 and 2) confer, on the factor X molecules, a more effective capacity to coagulate than the wild-type factor X in the absence of endogenous factor X.

Example 5

Measurement of the Activation of the Factor X Variants Produced in CHO-S by the RVV-X Venom Fraction 1—Experimental Protocol The activation of the FX variants produced by the CHO-S cells was measured following incubation of the culture supernatants in the presence of Russell's viper venom antifactor X fraction (RVV-X). The control activated factor X, the venom fraction X (RVV-X) and the pNAPEP 1025 substrate come from Haematologic Technologies (Cryopep Montpellier, France).

The activation was studied at 37° C. in the following buffer: 25 mM HEPES, pH 7.4, 0.175 M NaCl, 5 mM $CaCl_2$ and 5 mg/ml BSA. For concentrations of 0 to 100 nM of FX, a concentration of 200 mU/ml of RVV-X was used. After incubation for 5 min, the reaction is stopped in 50 mM Tris buffer, pH 8.8, 0.475 M NaCl, 9 mM EDTA. The amount of FXa generated is monitored by measuring the rate of hydrolysis of the pNAPEP 1025 substrate (250 μM) at 405 nm.

2—Results

The supernatants of CHO expressing the family 1 variants were incubated with the RVV-X. The generation of FXa was measured following this treatment using various concentrations of FX. The presence of FXa is quantified by the rate of appearance of the product of pNAPEP 1025 in solution (in mODU/min) This generation is the reflection of the recognition and cleavage of the FXs by RVV-X and also of the capacity of the FXa generated to recognize the FX substrate. The mean of the appearance rates is calculated for the various initial concentrations of FX and this value is related to the percentage of the value of the FX-WT.

The analysis of family 1 shows in part results that are similar to the results obtained by PT, in particular for FX-control+, FX-IIa, FX-Kal1, FX-Kal2 and FX-Kal3 (FIG. 6). The FX-XIa1 and 2 molecules show an activity, but which this time is not greater than FX-WT. On the other hand, the FX-PAR1 and FX-PAR1M molecules demonstrate a significant activity greater than that observed by PT.

These results indicate that FX-PAR1M and FX-Kal2 of family 1 are more effectively activated by RVV-X than FX-WT Example 6

Measurement, in Terms of Thrombin Generation Time (TGT), of the Procoagulant Capacity of the Factor X Variants of Family 2: Activation of the Extrinsic Coagulation Pathway (TF 1 pM/PL 4 μM) in FVIII-deficient Plasma 1—Experimental Protocol
1.1—Reagents Thrombin calibrator, PPP reagent low, CK-Prest, Fluca Kit (Fluo-buffer+Fluo-substrate), PNP and FIX-deficient plasma come from Stago (Asnieres, France). The FX-deficient plasma comes from Cryopep (Montpellier, France). The FVIII-deficient plasma comes from Siemens Healthcare (Marburg, Germany). The human FX (cat No. HCX-0050), and the human FXa (cat No. HCXA-0060) come from Haematologic Technologies Inc. (Burlington, Vt., USA). The control recombinant human factor VIII comes from Baxter (Recombinate) (Maurepas, France).

1.2—Protocol

It is considered that 1 unit of FX (1 U/ml)=10 µg/ml in the plasma, corresponding to 100% FX level in the plasma.

The thrombin generation test consists in activating coagulation ex vivo either by means of a mixture of tissue factor and phospholipids (activation of the extrinsic pathway), or by means of cephalin (activation of the intrinsic pathway), and in then measuring the concentration of thrombin generated over time.

The thrombin generation tests are carried out on 80 µl of a pool of plasma optionally containing the cell supernatants or the controls, in the presence of 20 µl of PPP reagent (Stago) containing a final concentration of 1 pM of tissue factor (TF) and 4 µM of phospholipids (PL). Various plasmas can be used, normal, factor X-deficient, factor VIII-deficient or factor IX-deficient.

The reaction is initiated by adding 20 µl of Fluca-kit (substrate+$CaCl_2$) which constitutes the beginning of the measurement of the appearance of thrombin. The appearance of fluorescence is measured on a Fluoroskan Ascent fluorometer (ThermoLabsystems) at an excitation wavelength of 390 nm and at an emission length of 460 nm. The thrombinograms (curves representing the fluorescence intensity as a function of time) are then analyzed by means of the Thrombinoscope™ software which converts the fluorescence value into nM of thrombin by comparative calculation.

2—Results

The supernatants were concentrated approximately 20-fold on a Sartorius VivaSpin20-30 kDa at 2500 g for at least 1 h until the desired concentration was obtained. The Unicalibrator plasmas and also the FVIII-deficient plasmas reconstituted with 0, 0.1 or 1 U/ml are used as controls.

As expected, following the activation of coagulation with tissue factor, the FVIII-deficient plasma gives the weakest signal, corresponding to the background noise of the experiment. The Unicalibrator plasma gives a signal that is weaker than the FVIII-deficient plasma reconstituted with the FVIII concentrations (0.1 or 1 U/ml). On the other hand, the reconstitution of an FVIII-deficient plasma with FX-WT does not make it possible to generate sufficient amounts of thrombin. This reconstitution is barely greater than the deficient plasma alone (FIG. 7, table 7).

The kinetic parameters of the thrombinograms of FIG. 7 are presented in the table. Lagtime (min); ETP, total thrombin generated (nM); Peak, height of the thrombin peak (nM); ttPEAK, time of the peak maximum (min); Start Tail, velocity start time (min); Velocity, maximum rate of thrombin generation (nM/min).

All the FX variant molecules give a greater signal than FX-WT, suggesting that their capacity to generate thrombin in the absence of FVIII is significantly increased compared with FX-WT (table 7). The speeds of the FX mutants of family 2 oscillate between 2 and 4.5× that of FX-WT (FIG. 9, table 7). It should be noted that a speed of 2× is obtained with an amount of FX-Kal2 that is 30% lower (3.5 µg/ml instead of 5 µg/ml).

The mutants which make it possible to generate the largest amounts of thrombin in the absence of FVIII are, in order, FX-PAR1, FX-FXIa1, FX-IIa and FX-Kal1.

Example 7

Measurement, in Terms of the Thrombin Generation Time (TGT), of the Procoagulant Capacity of the Factor X Variants: Intrinsic Coagulation Pathway (Cephalin Alone) in FVIII-deficient Plasma 1—Experimental Protocol The reagents, the automated device and the experimental protocol are identical to those described in example 6.

The thrombin generation tests are carried out on 80 µl of a pool of normal plasma optionally containing the cell supernatants and the controls in the presence of 20 µl of cephalin (CK-Prest reconstituted with 1 ml of distilled $H_2O$) and of 20 µl of fluca-kit (substrate+$CaCl_2$). The plasmas used are a normal plasma and a factor VIII-deficient plasma.

2—Results

The supernatants used in example 6 were analyzed by TGT after activation with cephalin using the same controls.

The controls behave expectedly, the FVIII-deficient plasma does not allow any generation of IIa and a gradient of effectiveness is found when increasing the dose of FVIII (table 8).

TABLE 7

Kinetic parameters resulting from the thrombinograms obtained from the addition of FX or variants thereof of family 2 to a pool of factor VIII-deficient plasma, following activation with tissue factor (1 pM)

| Product Name | Unicalibrator | FVIII Deficient | FVIII Def + 1 U/ml rFVIII | FVIII Def + 0.1 U/ml rFVIII | FVIII Def + FX-WT (5 µg/ml) | FVIII Def + FX-control+ (5 µg/ml) | FVIII Def + FX-IIa (5 µg/ml) |
|---|---|---|---|---|---|---|---|
| Lagtime | 7.36 | 8.19 | 6.19 | 8.03 | 7.86 | 7.36 | 7.19 |
| ETP | 1271 | 314 | 1850.5 | 1415 | 1278 | 1539.5 | 1618 |
| Peak | 135.8 | 11.89 | 329.1 | 154.3 | 75.96 | 153.28 | 184.11 |
| ttPeak | 11.87 | 20.88 | 8.19 | 12.03 | 13.37 | 11.2 | 10.7 |
| StartTail | 40 | 56 | 31 | 41.5 | 70.5 | 44 | 38.5 |
| Velocity | 30.11 | 0.94 | 164.55 | 38.58 | 13.79 | 39.92 | 52.45 |

| Product Name | FVIII Def + FX-PAR1 (5 µg/ml) | FVIII Def + FX-PAR1M (5 µg/ml) | FVIII Def + FX-FXIa1 (5 µg/ml) | FVIII Def + FX-FXIa2 (5 µg/ml) | FVIII Def + FX-FXIa3 (5 µg/ml) | FVIII Def + FX-Kal1 (3.5 µg/ml) | FVIII Def + FX-Kal2 (1.65 µg/ml) |
|---|---|---|---|---|---|---|---|
| Lagtime | 6.86 | 7.36 | 6.69 | 7.69 | 7.19 | 7.36 | 7.69 |
| ETP | 1604 | 1534 | 1582 | 1467.5 | 1504 | 1408 | 1438 |
| Peak | 201.35 | 169.82 | 190.67 | 151.76 | 167.8 | 118.53 | 162.52 |
| ttPeak | 10.03 | 10.87 | 10.03 | 11.37 | 10.53 | 11.87 | 11.03 |
| StartTail | 36.5 | 41.5 | 38 | 45 | 42 | 52 | 41.5 |
| Velocity | 63.52 | 48.38 | 57.09 | 41.24 | 50.24 | 26.28 | 48.66 |

TABLE 8

Kinetic parameters resulting from the thrombinograms obtained from the addition of FX or variants thereof of family 2 to a pool of factor VIII-deficient plasma, following activation with cephalin

| Product Name | Unicalibrator | FVIII Deficient | FVIII Def + 1 U/ml rFVIII | FVIII Def + 0.1 U/ml rFVIII | FVIII Def + FX-WT (5 μg/ml) | FVIII Def + FX-control+ (5 μg/ml) | FVIII Def + FX-IIa (5 μg/ml) |
|---|---|---|---|---|---|---|---|
| Lagtime | 19.04 | 36.73 | 8.59 | 20.84 | 23.88 | 16.37 | 13.03 |
| ETP | 1149.5 | 0 | 1417.5 | 1089.5 | 589 | 1134.5 | 1284.5 |
| Peak | 271.07 | 3.48 | 292.17 | 171.4 | 35.98 | 102.19 | 235.25 |
| ttPeak | 21.04 | 70.46 | 10.53 | 24.05 | 34.4 | 24.08 | 16.04 |
| StartTail | 36 | 0 | 29.5 | 41.3 | 67.5 | 47 | 33.5 |
| Velocity | 135.54 | 0.10 | 158.79 | 48.83 | 3.42 | 13.31 | 78.16 |

| Product Name | FVIII Def + FX-PAR1 (5 μg/ml) | FVIII Def + FX-PAR1M (5 μg/ml) | FVIII Def + FX-FXIa1 (5 μg/ml) | FVIII Def + FX-FXIa2 (5 μg/ml) | FVIII Def + FX-FXIa3 (5 μg/ml) | FVIII Def + FX-KaI1 (3.5 μg/ml) | FVIII Def + FX-KaI2 (1.65 μg/ml) |
|---|---|---|---|---|---|---|---|
| Lagtime | 15.63 | 17.54 | 16.37 | 19.54 | 18.37 | 20.71 | 19.88 |
| ETP | 950.6 | 892.5 | 958 | 806 | 869 | 844.6 | 814 |
| Peak | 87.25 | 71.5 | 80.35 | 59.75 | 68.08 | 57.78 | 59.2 |
| ttPeak | 22.88 | 25.72 | 24.05 | 28.22 | 26.39 | 30.23 | 28.89 |
| StartTail | 46.5 | 51.5 | 49.5 | 57.5 | 54.5 | 61 | 58.5 |
| Velocity | 11.87 | 8.74 | 10.46 | 6.89 | 8.49 | 6.07 | 6.57 |

The kinetic parameters of the thrombinograms of FIG. 8 are presented in the table. Lagtime (min); ETP, total thrombin generated (nM); Peak, height of the thrombin peak (nM); ttPEAK, time of the peak maximum (min); Start Tail, velocity start time (min); Velocity, maximum rate of thrombin generation (nM/min).

The analysis of family 2 shows, as expected, that the wild-type FX is the least active FX molecule, showing a weak residual activity (3.4 nM/s). All the other molecules show a greater capacity to generate thrombin (table 8). The FX-Kal-1 to 3, FX-FXI-2 and FX-PAR1M molecules show an activity which is a little stronger (6.6 to 8.7 nM/s) but less than the FX-control+, FX-PAR1 and FX-FXI-1 constructs (10.5-13.3 nM/s). On the other hand, the FX-IIa molecule makes it possible to obtain a signal which is between the values obtained for 0.1 and 1 U/ml of FVIII (78.2 nM/s), very effectively correcting the FVIII deficiency. These differences in speeds show, for the mutants, a thrombin-generating effectiveness which is 1.8× greater (but for the FX-Kal2 mutant at 3.5 μg/ml) to 22.8× greater (for the FX-IIa mutant).

In conclusion, several FX mutants have the capacity to restore coagulation in the absence of FVIII following activation of the plasma with tissue factor and cephalin.

Example 8

Measurement, in Terms of Thrombin Generation Time (TGT), of the Procoagulant Capacity of the Factor X Variants of Family 2: Activation of the Extrinsic Coagulation Pathway (TF 1 pM/PL 4 μM) in FIX-deficient Plasma 1—Experimental Protocol The reagents, the automated device and the experimental protocol are identical to those described in example 6.

The thrombin generation tests are carried out on 80 μl of a pool of normal plasma optionally containing the cell supernatants and the controls in the presence of 1 pM of tissue factor (TF) and 4 μM of phospholipids (PL) and of 20 μl of fluca-kit (substrate+CaCl$_2$). The plasmas used are either normal or factor IX-deficient.

2—Results

The supernatants used in example 6 were analyzed by TGT after activation with tissue factor using, as controls, a normal plasma (Unicalibrator) or an FIX-deficient plasma reconstituted with 0, 0.1 or 1 U/ml of plasma FIX (FIG. 10, table 9).

The FIX-deficient plasma is negative (it does not enable any generation of IIa) and the reconstitution thereof with FIX allows it to generate large amounts of thrombin. However, there is no quantitative difference between the two concentrations of FIX used, thereby suggesting that they both make it possible to form a maximum amount of IIa (table 9).

TABLE 9

Kinetic parameters resulting from the thrombinograms obtained from the addition of FX or variants thereof of family 2 to a pool of factor IX-deficient plasma, following activation with tissue factor (1 pM)

| Product Name | Unicalibrator | FIX Deficient | FIX Def + FIX 1 U/ml | FIX Def + FIX 0.1 U/ml | FIX Def + FX-WT (5 μg/ml) | FIX Def + FX-control+ (5 μg/ml) | FIX Def + FX-IIa (5 μg/ml) |
|---|---|---|---|---|---|---|---|
| Lagtime | 7.33 | 4.5 | 4.83 | 5 | 6.67 | 6.67 | 6.67 |
| ETP | 1216 | 296 | 1645 | 1523.6 | 1251 | 1533 | 1540.5 |
| Peak | 97.46 | 9.74 | 292.04 | 283.36 | 59.18 | 112.48 | 138.17 |
| ttPeak | 12.83 | 19 | 7.67 | 7.83 | 14 | 12.83 | 12.5 |

TABLE 9-continued

Kinetic parameters resulting from the thrombinograms obtained from the addition of FX or variants thereof of family 2 to a pool of factor IX-deficient plasma, following activation with tissue factor (1 pM)

| | | | | | | | |
|---|---|---|---|---|---|---|---|
| StartTail | 47 | 68 | 23.6 | 24.5 | 66 | 46.5 | 38 |
| Velocity | 17.72 | 0.67 | 102.63 | 100.13 | 8.07 | 18.26 | 23.70 |

| Product Name | FIX Def + FX-PAR1 (5 µg/ml) | FIX Def + FX-PAR1M (5 µg/ml) | FIX Def + FX-FXIa1 (5 µg/ml) | FIX Def + FX-FXIa2 (5 µg/ml) | FIX Def + FX-FXIa3 (5 µg/ml) | FIX Def + FX-KaI1 (3.5 µg/ml) | FIX Def + FX-KaI2 (1.65 µg/ml) |
|---|---|---|---|---|---|---|---|
| Lagtime | 6.67 | 6.67 | 6.5 | 7 | 6.67 | 6.33 | 7 |
| ETP | 1483 | 1506 | 1580.6 | 1446 | 1467.5 | 1523.5 | 1483 |
| Peak | 160.45 | 125.64 | 125.15 | 97.1 | 123.59 | 85.83 | 103.73 |
| ttPeak | 11 | 11.83 | 11.83 | 12.67 | 11.67 | 13.33 | 12.83 |
| StartTail | 35.5 | 43 | 43.6 | 54.6 | 43 | 61.5 | 50 |
| Velocity | 37.06 | 24.35 | 23.48 | 17.13 | 24.72 | 12.26 | 17.79 |

The kinetic parameters of the thrombinograms of FIG. 10 are presented in the table. Lagtime (min); ETP, total thrombin generated (nM); Peak, height of the thrombin peak (nM); ttPEAK, time of the peak maximum (min); Start Tail, velocity start time (min); Velocity, maximum rate of thrombin generation (nM/min).

In this assay, all the mutants make it possible to generate greater amounts of IIa than FX-WT. However, the differences are less substantial than in the absence of FVIII: thus, the speed ranges from 1.50× (for FX-KaI2 at 3.5 µg/ml) to 4.60× (for FX-PAR1). In addition to this mutant, the FX-IIa, FX-PAR1M, FX-FXIa1 and FX-KaI1 molecules are the most effective (FIG. 12, table 9).

Example 9

Measurement, in Terms of Thrombin Generation Time (TGT), of the Procoagulant Capacity of the Factor X Variants of Family 2: Activation of the Intrinsic Coagulation Pathway (Cephalin) in FIX-deficient Plasma 1—Experimental Protocol The reagents, the automated device and the experimental protocol are identical to those described in example 6.

The thrombin generation tests are carried out on 80 µl of a pool of normal plasma optionally containing the cell supernatants and the controls in the presence of cephalin (CK-Prest reconstituted with 1 ml of distilled $H_2O$) and of 20 µl of fluca-kit (substrate+$CaCl_2$). The plasmas used are either normal or factor IX-deficient.

2—Results

The supernatants used in example 6 were analyzed by TGT after activation with cephalin using, as controls, a normal plasma (Unicalibrator) and an FIX-deficient plasma reconstituted with 0, 0.1 or 1 U/ml of plasma FIX (FIG. 11, table 10).

The FIX-deficient plasma is negative (it does not allow any generation of IIa) and the reconstitution thereof with FIX allows it to generate large amounts of thrombin. However, there is no quantitative difference between the two concentrations of FIX used, thereby suggesting that they form a maximum amount of IIa (table 10).

TABLE 10

Kinetic parameters resulting from the thrombinograms obtained from the addition of FX or variants thereof of family 2 to a pool of factor IX-deficient plasma, following activation with cephalin

| Product Name | Unicalibrator | FIX Deficient | FIX Def + FIX 1 U/ml | FIX Def + FIX 0.1 U/ml | FIX Def + FX-WT (5 µg/ml) | FIX Def + FX-control+ (5 µg/ml) | FIX Def + FX-IIa (5 µg/ml) |
|---|---|---|---|---|---|---|---|
| Lagtime | 29.17 | 0 | 13 | 13.33 | 36.67 | 28 | 22.17 |
| ETP | 1208 | 0 | 1539.5 | 1621.6 | 0 | 734 | 1528.5 |
| Peak | 252.9 | 0 | 378.46 | 370.94 | 12.79 | 62.02 | 240.9 |
| ttPeak | 31.67 | 0 | 14.57 | 15 | 51.83 | 36.83 | 26.83 |
| StartTail | 47 | 0 | 30 | 30.5 | 0 | 57 | 40 |
| Velocity | 101.16 | 0.00 | 226.62 | 222.12 | 0.84 | 7.02 | 51.70 |

| Product Name | FIX Def + FX-PAR1 (5 µg/ml) | FIX Def + FX-PAR1M (5 µg/ml) | FIX Def + FX-FXIa1 (5 µg/ml) | FIX Def + FX-FXIa2 (5 µg/ml) | FIX Def + FX-FXIa3 (5 µg/ml) | FIX Def + FX-KaI1 (3.5 µg/ml) | FIX Def + FX-KaI2 (1.65 µg/ml) |
|---|---|---|---|---|---|---|---|
| Lagtime | 22.17 | 25.33 | 25.6 | 29.5 | 26.67 | 29.33 | 28.5 |
| ETP | 452.5 | 407 | 370.5 | 327.5 | 385 | 319.5 | 310.5 |
| Peak | 31.86 | 25.82 | 22.34 | 17.99 | 22.39 | 17.05 | 17.53 |
| ttPeak | 32.33 | 36.17 | 37 | 42 | 38 | 41.67 | 39.83 |
| StartTail | 54.5 | 62.5 | 63 | 70 | 67.5 | 70 | 69.5 |
| Velocity | 3.14 | 2.38 | 1.94 | 1.44 | 1.98 | 1.38 | 1.55 |

The kinetic parameters of the thrombinograms of FIG. 11 are presented in the table. Lagtime (min); ETP, total thrombin generated (nM); Peak, height of the thrombin peak (nM); ttPEAK, time of the peak maximum (min); Start Tail, velocity start time (min); Velocity, maximum rate of thrombin generation (nM/min).

Following the induction of coagulation with cephalin, only three molecules make it possible to significantly generate more thrombin than FX-WT, these are FX-IIa, FX-control+ and FX-PAR1 with a speed which is 61×, 8.3× and 3.8× greater than that of FX-WT respectively (FIG. 12, table 10). However, the other mutants have speeds greater than that of FX-WT.

In conclusion, all the mutants studied make it possible to generate thrombin in the absence of FIX whatever the induction used. The FX-IIa, FX-control+ and FX-PAR1 are the most effective.

Example 10

Thrombin Activation of the Factor X Variants of Family 2 and Wild-Type Factor Xs Produced in HEK 1—Experimental Protocol The activation of the FX variants produced by the HEK cells in the presence of vitamin K epoxide reductase (VKOR) was measured following incubation of the culture supernatants in the presence of thrombin. The control activated factor X, the thrombin and the Pefachrome FXa8595 substrate comes from Haematologic Technologies (Cryopep, Montpellier, France).

The phospholipids come from Diagnostica Stago (Asnières, France).

The activation was studied at 37° C. in the following buffer: 25 mM HEPES, pH 7.4, 0.175 M NaCl, 5 mM $CaCl_2$ and 5 mg/ml BSA. For concentrations of 42.5 and 85 nM of FX, a concentration of 10 nM of thrombin and a concentration of 4 μM of phospholipids were used. After incubation for 1 hour at 37° C., the amount of FXa generated is monitored by measuring the rate of hydrolysis of the Pefachrome FXa8595 substrate (250 μM) at 405 nm.

2—Results

In order to verify that the sites intended to be cleaved by thrombin are indeed recognized by this enzyme, the concentrated supernatants of FX-WT, FX-control+ and FX-IIa were incubated in the presence of thrombin. The appearance of FXa was measured by the appearance of the substrate degradation product (FIG. 13). Plasma FXa was used as a positive control. The kinetics of appearance of the product with the mutants cannot be directly compared with those of FXa since these molecules need to be activated before releasing the activity. Moreover, since the cleavage sites for thrombin are composites, the activation of molecules is not necessarily optimal. Indeed, all the molecules conserved the original zone downstream of the cleavage site, only the upstream parts are modified. The kinetics of FXa substrate degradation by the recombinant molecules are consequently different than that by the FXa.

The results obtained confirm the data obtained by TGT with, as expected, the plasma and WT FXs being negative since they do not have a thrombin recognition site. On the other hand, FX-IIa and FX-control+ are capable of being activated by thrombin and of releasing FXa. As in the TGT measurement, FX-IIa is more effectively activated than FX-control+.

Example 11

Measurement, in Terms of Thrombin Generation Time (TGT), of the Procoagulant Capacity of the Factor X Variants of Family 1: Extrinsic Coagulation Pathway (TF 1 pM/PL 4 μM) in FVIII-deficient Plasma 1—Experimental Protocol The thrombin generation tests are carried out on 80 μl of a pool of plasma optionally containing the cell supernatants or the controls, in the presence of 20 μl of PPP reagent (Stago) containing a final concentration of 1 pM of tissue factor (TF) and 4 μM of phospholipids (PL). Various plasmas are used, normal and factor VIII-deficient.

The reaction is initiated by adding 20 μl of Fluca-kit (substrate+$CaCl_2$) which constitutes the beginning of the measurement of the appearance of thrombin. The appearance of fluorescence is measured on a Fluoroskan Ascent fluorimeter (ThermoLabsystems) at an excitation wavelength of 390 nm and at an emission length of 460 nm. The thrombinograms (curves representing the fluorescence intensity as a function of time) are then analyzed by means of the Thrombinoscope™ software which converts the fluorescence value into nM of thrombin by comparative calculation.

2—Results

The family 1 supernatants resulting from a transfection of HEK293F cells in the presence of VKOR were analyzed by TGT after activation with tissue factor using the controls already described. The controls (normal plasma, FVIII-deficient plasma reconstituted with recombinant FVIII or not reconstituted with recombinant FVIII) behave expectedly. On the other hand, FX-WT gives a signal which is moderate but greater than expected (FIGS. 14 and 16; table 11). Its mean velocity (59 nM/min) is however exceeded by those of several mutants, in particular FX-FXIa1/2, FX-Kal1/2 and FX-control+ and FX-IIa which have a velocity of at least 130% that of the control.

TABLE 11

Kinetic parameters resulting from the thrombinograms obtained from the addition of FX or variants thereof of family 1 to a pool of factor VIII-deficient plasma, following activation with tissue factor

| Group name | Unicalibrator | FVIII Deficient | FVIII Def + Recombinate 1 U/ml | FVIII Def + Recombinate 0.1 U/ml | FVIII Def + FX-WT 7.5 μg/ml | FVIII Def + FX-control+ 7.5 μg/ml | FVIII Def + FX-IIa 7.5 μg/ml |
|---|---|---|---|---|---|---|---|
| Lagtime | 8 | 9.33 | 7.17 | 9.33 | 7.83 | 7 | 7.83 |
| ETP | 1325.5 | 0 | 1795 | 1334.5 | 1545.5 | 1619 | 1852 |
| Peak | 136.55 | 12.25 | 291.84 | 125.53 | 175.6 | 230.11 | 240.61 |

TABLE 11-continued

Kinetic parameters resulting from the thrombinograms obtained from the addition of FX or variants thereof
of family 1 to a pool of factor VIII-deficient plasma, following activation with tissue factor

| ttPeak | 12.5 | 29.67 | 9.5 | 13.67 | 11.17 | 10 | 10.83 |
|---|---|---|---|---|---|---|---|
| StartTail | 40 | 0 | 33 | 46.5 | 40 | 33 | 33.5 |
| Velocity | 30.34 | 0.60 | 125.17 | 28.92 | 52.57 | 76.70 | 80.20 |

| Group name | FVIII Def + FX-PAR1 7.5 µg/ml | FVIII Def + FX-PAR1M 7.5 µg/ml | FVIII Def + FX-FXIa1 7.5 µg/ml | FVIII Def + FX-FXIa2 7.5 µg/ml | FVIII Def + FX-KaI1 7.5 µg/ml | FVIII Def + FX-KaI2 7.5 µg/ml | FVIII Def + FX-KaI3 1.65 µg/ml | FVIII Def + FX-WT 7.5 µg/ml |
|---|---|---|---|---|---|---|---|---|
| Lagtime | 8.5 | 7.5 | 5.17 | 5.83 | 6.67 | 6 | 5.67 | 7.83 |
| ETP | 1337 | 1552 | 1704 | 1678.5 | 1628 | 1542.8 | 1667 | 1565.5 |
| Peak | 112.83 | 196.08 | 310.73 | 308.24 | 252.0 | 274.07 | 289.45 | 199.2 |
| ttPeak | 13 | 10.67 | 7.17 | 7.67 | 9.17 | 8.33 | 7.83 | 10.83 |
| StartTail | 50 | 36.5 | 28.8 | 28 | 32 | 30.5 | 29 | 36.5 |
| Velocity | 25.07 | 61.85 | 155.37 | 167.52 | 100.92 | 117.63 | 134.00 | 66.40 |

The kinetic parameters of the thrombinograms of FIG. 14 are presented in the table. Lagtime (min); ETP, total thrombin generated (nM); Peak, height of the thrombin peak (nM); ttPEAK, time of the peak maximum (min); Start Tail, velocity start time (min); Velocity, maximum rate of thrombin generation (nM/min).

Example 12

Measurement, in Terms of Thrombin Generation Time (TGT), of the Procoagulant Capacity of the Factor X Variants of Family 1: Intrinsic Coagulation Pathway (Cephalin Alone) in FVIII-deficient Plasma 1—Experimental Protocol The reagents, the automated device and the experimental protocol are identical to those described in example 6.

The thrombin generation tests are carried out on 80 µl of a pool of plasma optionally containing the cell supernatants and the controls in the presence of 20 µl of cephalin (CK-Prest reconstituted with 1 ml of distilled $H_2O$) and of 20 µl of fluca-kit (substrate+$CaCl_2$). The plasmas used are a normal plasma and a factor VIII-deficient plasma.

2—Results

The family 1 supernatants resulting from a transfection of HEK293F cells in the presence of VKOR were analyzed by TGT after activaton with cephalin using the already described controls.

The controls behave expectedly, the FVIII-deficient plasma is negative (it does not allow any generation of IIa) and a gradient of effectiveness is found when increasing the dose of FVIII (FIG. 15; table 12). In this assay, the supplementation with FX (2 assays were carried out) does not make it possible to generate significant amounts of thrombin (velocities of 6.06 and 7.65 nM/min). On the other hand, the FX-IIa, FX-FXIa1 and 2 and FX-control+ mutants of family 1 make it possible to generate significantly greater amounts of thrombin of at least 3.5× that of the control (FIGS. 15 and 16; table 12).

TABLE 12

Kinetic parameters resulting from the thrombinograms obtained from the addition of FX or variants
thereof of family 1 to a pool of factor VIII-deficient plasma, following activation with cephalin

| Group name | Unicalibrator | Deficient FVIII | FVIII Def + Recombinant 1 U/ml | FVIII Def + Recombinant 0.1 U/ml | FVIII Def + FX-WT 7.5 µg/ml | FVIII Def + FX-control+ 7.5 µg/ml | FVIII Def + FX-IIa 7.5 µg/ml |
|---|---|---|---|---|---|---|---|
| Lagtime | 19.33 | 15.5 | 7.67 | 18 | 28.87 | 18.17 | 13.83 |
| ETP | 1347.5 | 0 | 1803 | 1442.5 | 938 | 1359 | 1543.5 |
| Peak | 304.16 | 0.48 | 336.45 | 278.12 | 56.51 | 167.22 | 295.77 |
| ttPeak | 21.5 | 38.33 | 9.33 | 20.17 | 38 | 23.67 | 16.17 |
| StartTail | 37 | 0 | 32 | 41.5 | 71 | 44 | 36.5 |
| Velocity | 140.17 | 0.02 | 202.70 | 128.17 | 6.06 | 30.40 | 126.40 |

| Group name | FVIII Def + FX-PAR1 7.5 µg/ml | FVIII Def + FX-PAR1M 7.5 µg/ml | FVIII Def + FX-FXIa1 7.5 µg/ml | FVIII Def + FX-FXIa2 7.5 µg/ml | FVIII Def + FX-KaI1 7.5 µg/ml | FVIII Def + FX-KaI2 7.5 µg/ml | FVIII Def + FX-KaI3 7.5 µg/ml | FVIII Def + FX-WT 7.5 µg/ml |
|---|---|---|---|---|---|---|---|---|
| Lagtime | 30.83 | 25.5 | 14 | 15.17 | 21.33 | 18 | 16 | 26.17 |
| ETP | 852 | 1052.5 | 1359.5 | 1318.5 | 1144 | 1225 | 1227 | 1035 |
| Peak | 50.44 | 76.26 | 161.43 | 145.34 | 59.5 | 108.56 | 115.43 | 67.55 |
| ttPeak | 41.17 | 33.83 | 18 | 21 | 28.5 | 24.5 | 22.33 | 35 |
| StartTail | 71 | 63 | 41.5 | 44 | 57.5 | 52 | 48 | 87 |
| Velocity | 4.88 | 9.15 | 32.29 | 24.93 | 12.48 | 16.39 | 18.24 | 7.65 |

The kinetic parameters of the thrombinograms of FIG. 15 are presented in the table. Lagtime (min); ETP, total thrombin generated (nM); Peak, height of the thrombin peak (nM); ttPEAK, time of the peak maximum (min); Start Tail, velocity start time (min); Velocity, maximum rate of thrombin generation (nM/min).

Example 13

Measurement, in Terms of Thrombin Generation Time (TGT), of the Procoagulant Capacity of the Factor X Variants of Family 1: Extrinsic Coagulation Pathway (TF 1 pM/PL 4 µM) in FIX-deficient Plasma 1—Experimental Protocol The reagents, the automated device and the experimental protocol are identical to those described in the example 6.

The thrombin generation tests are carried out on 80 µl of a pool of plasma optionally containing the cell supernatants and the controls in the presence of 20 µl of PPP reagent (Stago) containing a final concentration of 1 pM of tissue factor (TF) and 4 µM of phospholipids (PL) and of 20 µl of fluca-kit (substrate+$CaCl_2$). The plasmas used are a normal plasma and a factor IX-deficient plasma.

2—Results

The family 1 supernatants resulting from a transfection of HEK293F cells in the presence of VKOR were analyzed by TGT in FIX-deficient plasma after activation with tissue factor using the already described controls. The controls (normal plasma, FIX-deficient plasma reconstituted with plasma FIX (at 10% or 100%) not reconstituted with plasma FIX) behave expectedly. On the other hand, FX-WT gives a signal which is moderate but greater than expected (FIG. 17; table 13). Its mean velocity (23 nM/min) is however exceeded by those of all the mutants except FX-PAR1. Said mutants are, in particular, FX-FXIa1/2, FX-Kal2/3 and FX-control+ and FX-IIa, which have a velocity of at least 150% that of the control.

The kinetic parameters of the thrombinograms of FIG. 17 are presented in the table. Lagtime (min); ETP, total thrombin generated (nM); Peak, height of the thrombin peak (nM); ttPEAK, time of the peak maximum (min); Start Tail, velocity start time (min); Velocity, maximum rate of thrombin generation (nM/min).

Example 14

Measurement, in Terms of Thrombin Generation Time (TGT), of the Procoagulant Capacity of the Factor X Variants of Family 1: Intrinsic Coagulation Pathway (Cephalin) in FIX-deficient Plasma 1—Experimental Protocol The reagents, the automated device and the experimental protocol are identical to those described in example 6.

The thrombin generation tests are carried out on 80 µl of a pool of plasma optionally containing the cell supernatants and the controls in the presence of 20 µl of cephalin (CK-Prest reconstituted with 1 ml of distilled $H_2O$) and of 20 µl of fluca-kit (substrate+$CaCl_2$). The plasmas used are a normal plasma and a factor IX-deficient plasma.

2—Results

The family 1 supernatents resulting from a transfection of HEK293F cells in the presence of VKOR were analyzed by TGT after activation with cephalin using the already described controls.

The controls behave expectedly, the FIX-deficient plasma is negative (it does not allow any generation of IIa) and a gradient of effectiveness is found when increasing the dose of FIX (FIG. 18; table 14). In this assay, the supplementation with FX (2 assays were carried out) does not make it possible to generate significant amounts of thrombin (velocities of 1.24 and 1.53 nM/min). On the other hand, the FX-IIa, FX-FXIa1 and 2 and FX-control+ mutants of family 1 make it possible to generate significantly greater amounts of thrombin of at least 4.7× that of the control to 55× (FIGS. 18 and 19; table 14).

TABLE 13

Kinetic parameters resulting from the thrombinograms obtained from the addition of FX or variants thereof of family 1 to a pool of factor IX-deficient plasma, following activation with tissue factor

| Group name | Unicalibrator | FIX Deficient | FIX Def + FIX 1 U/ml | FIX Def + FIX 0.1 U/ml | FIX Def + FX-WT 7.5 µg/ml | FIX Def + FX-control+ 7.5 µg/ml | FIX Def + FX-IIa 7.5 µg/ml |
|---|---|---|---|---|---|---|---|
| Lagtime | 8.33 | 6.33 | 5.33 | 7.17 | 7.33 | 6.83 | 7.5 |
| ETP | 1345.5 | 238.5 | 1641 | 1063.5 | 1471 | 1550 | 1543 |
| Peak | 134.27 | 7.23 | 255.66 | 52.84 | 110.99 | 173.16 | 197.8 |
| ttPeak | 12.67 | 22.5 | 8.33 | 13.33 | 12.67 | 11.83 | 12.33 |
| StartTail | 41 | 70 | 26 | 46 | 48.5 | 32.5 | 31 |
| Velocity | 30.94 | 0.42 | 88.89 | 13.45 | 20.78 | 34.63 | 40.95 |

| Group name | FIX Def + FX-PAR1 7.5 µg/ml | FIX Def + FX-PAR1M 7.5 µg/ml | FIX Def + FX-FXIa1 7.5 µg/ml | FIX Def + FX-FXIa2 7.5 µg/ml | FIX Def + FX-Kal1 7.5 µg/ml | FIX Def + FX-Kal2 7.5 µg/ml | FIX Def + FIX-Kal3 1.6 µg/ml | FIX Def + FX-WT 7.5 µg/ml |
|---|---|---|---|---|---|---|---|---|
| Lagtime | 7.5 | 7.17 | 5.5 | 6.17 | 6.5 | 6.5 | 6 | 7.33 |
| ETP | 1386 | 1472.5 | 1589.5 | 1583 | 1543 | 1549 | 1594 | 1472 |
| Peak | 67.56 | 133.76 | 267.69 | 257.72 | 179.29 | 220 | 242.54 | 126.29 |
| ttPeak | 14.17 | 11.67 | 8.33 | 8.83 | 10.5 | 9.83 | 9 | 12.17 |
| StartTail | 71 | 40.5 | 27 | 27.5 | 33 | 29.5 | 28.5 | 43 |
| Velocity | 10.13 | 29.72 | 94.59 | 96.89 | 44.82 | 66.07 | 80.85 | 26.09 |

TABLE 14

Kinetic parameters resulting from the thrombinograms obtained from the addition of FX or variants thereof of family 1 to a pool of factor IX-deficient plasma, following activation with cephalin

| Group name | Unicalibrator | FIX Deficient | FIX Def + FIX 1 U/ml | Fix Def + FIX 0.1 U/ml | FIX Def + FX-WT 7.5 µg/ml | FIX Def + FX-control+ 7.5 µg/ml | FIX Def + FX-IIa 7.5 µg/ml |
|---|---|---|---|---|---|---|---|
| Lagtime | 18.33 | 42.5 | 13.67 | 31.83 | 30.5 | 22.33 | 16.33 |
| ETP | 1383.5 | 0 | 1529 | 899.5 | 316.5 | 1147 | 1448.5 |
| Peak | 311.19 | 0.49 | 369.87 | 107.53 | 16.16 | 120.28 | 279.02 |
| ttPeak | 20.33 | 57.33 | 15.33 | 36.33 | 43.5 | 29 | 20 |
| StartTail | 36.5 | 0 | 31 | 55 | 71 | 44.5 | 32.5 |
| Velocity | 155.60 | 0.03 | 222.81 | 23.90 | 1.24 | 18.03 | 76.03 |

| Group name | FIX Def + FX-PAR1 7.6 µg/ml | FIX Def + FX-PAR1M 7.6 µg/ml | FIX Def + FX-FXIa1 7.5 µg/ml | FIX Def + FX-FXIa2 7.5 µg/ml | FIX Def + FX-Kal1 7.5 µg/ml | FIX Def + FX-Kal2 7.5 µg/ml | FIX Def + FX-Kal3 1.6 µg/ml | FIX Def + FX-WT 7.5 µg/ml |
|---|---|---|---|---|---|---|---|---|
| Lagtime | 37.17 | 28.17 | 15.67 | 17 | 23 | 18.5 | 16 | 27.5 |
| ETP | 237 | 402.5 | 686 | 626.5 | 429.5 | 498.5 | 496 | 341 |
| Peak | 12.51 | 24.06 | 59.45 | 53.64 | 28.73 | 36.12 | 38.66 | 18.68 |
| ttPeak | 51.17 | 39.87 | 23.5 | 25.17 | 33 | 28.17 | 25.33 | 39.67 |
| StartTail | 71 | 68.5 | 44.5 | 45.5 | 55 | 48.5 | 51 | 70 |
| Velocity | 0.89 | 2.09 | 7.59 | 6.55 | 2.87 | 3.74 | 4.14 | 1.53 |

The kinetic parameters of the thrombinograms of FIG. 18 are presented in the table. Lagtime (min); ETP, total thrombin generated (nM); Peak, height of the thrombin peak (nM); ttPEAK, time of the peak maximum (min); Start Tail, velocity start time (min); Velocity, maximum rate of thrombin generation (nM/min).

Example 15

Measurement, in Terms of Thrombin Generation Time (TGT), of the Procoagulant Capacity of the Factor X Variants of Family 3: Extrinsic Coagulation Pathway (TF 1 pM/PL 4 µM) in FVIII-deficient Plasma 1—Experimental Protocol The thrombin generation tests are carried out on 80 µl of a pool of plasma optionally containing the cell supernatants or the controls, in the presence of 20 µl of PPP reagent (Stago) containing a final concentration of 1 pM of tissue factor (TF) and 4 µM of phospholipids (PL). Various plasmas are used, normal and factor VIII-deficient.

The reaction is initiated by adding 20 µl of Fluca-kit (substrate+$CaCl_2$) which constitutes the beginning of the measurement of the appearance of thrombin. The appearance of fluorescence is measured on a Fluoroskan Ascent fluorimeter (ThermoLabsystems) at an excitation wavelength of 390 nm and at an emission length of 460 nm. The thrombinograms (curves representing the fluorescence intensity as a function of time) are then analyzed by means of the Thrombinoscope™ software which converts the fluorescence value into nM of thrombin by comparative calculation.

2—Results

The family 3 supernatants resulting from a transfection of HEK293F cells in the presence of VKOR were analyzed by TGT after activation with tissue factor using the already described controls. The controls (normal plasma, FVIII-deficient plasma reconstituted with recombinant FVIII or not reconstituted with recombinant FVIII) behave expectedly. On the other hand, FX-WT gives a signal that is moderate but greater than expected (FIGS. 20 and 21; table 15). Its mean velocity (59 nM/min) is however exceeded by those of several mutants, in particular FX-FXIa1/2, FX-Kal1/2/3 and FX-control+ and FX-IIa, the velocities of which are above 78 nM/min (i.e. at least 130% of the control).

TABLE 15

Kinetic parameters resulting from the thrombinograms obtained from the addition of FX or variants thereof of family 3 to a pool of factor VIII-deficient plasma, following activation with tissue factor

| Group name | Unicalibration | FVIII Deficient | FVIII Def + Recombinant 1 U/ml | FVIII Def + Recombinant 0.1 U/ml | FVIII Def + FX-WT 7.5 µg/ml | FVIII Def + FX-control+ 7.5 µg/ml | FVIII Def + FX-IIa 7.5 µg/ml |
|---|---|---|---|---|---|---|---|
| Lagtime | 8 | 9.33 | 7.17 | 9.33 | 7.83 | 7.17 | 7.5 |
| ETP | 1325.5 | 0 | 1795 | 1334.5 | 1549.5 | 1641 | 1683.5 |
| Peak | 136.55 | 12.25 | 291.64 | 125.53 | 175.6 | 233.75 | 234.31 |
| ttPeak | 12.5 | 29.67 | 9.5 | 13.67 | 11.17 | 10.17 | 10.5 |
| StartTail | 40 | 0 | 33 | 46.5 | 40 | 34.5 | 34.5 |
| Velocity | 30.34 | 0.60 | 125.17 | 28.92 | 52.57 | 77.92 | 78.10 |

TABLE 15-continued

Kinetic parameters resulting from the thrombinograms obtained from the addition of FX or variants thereof of family 3 to a pool of factor VIII-deficient plasma, following activation with tissue factor

| Group name | FVIII Def + FX-PAR1 7.5 µg/ml | FVIII Def + FX-PAR1M 7.5 µg/ml | FVIII Def + FX-FXIa1 7.5 µg/ml | FVIII Def + FX-FXIa2 7.5 µg/ml | FVIII Def + FX-KaI1 7.5 µg/ml | FVIII Def + FX-KaI2 7.5 µg/ml | FVIII Def + FX-KaI3 1.65 µg/ml | FVIII Def + FX-WT 7.5 µg/ml |
|---|---|---|---|---|---|---|---|---|
| Lagtime | 6.5 | 8.5 | 5.07 | 6.33 | 8.33 | 6 | 6.33 | 7.83 |
| ETP | 1665 | 1565 | 1724 | 1724 | 1560 | 1803 | 1715.5 | 1569.5 |
| Peak | 225.48 | 189.25 | 301.86 | 251.98 | 213.57 | 303.58 | 270.6 | 199.2 |
| ttPeak | 9.5 | 11.83 | 7.67 | 8.5 | 11 | 8 | 9 | 10.83 |
| StartTail | 35 | 39.5 | 31 | 31 | 37 | 31 | 32 | 36.5 |
| Velocity | 75.16 | 56.83 | 150.93 | 129.94 | 79.93 | 151.79 | 101.35 | 66.40 |

The kinetic parameters of the thrombinograms of FIG. 20 are presented in the table. Lagtime (min); ETP, total thrombin generated (nM); Peak, height of the thrombin peak (nM); ttPEAK, time of the peak maximum (min); Start Tail, velocity start time (min); Velocity, maximum rate of thrombin generation (nM/min).

Example 14

Measurement, in Terms of Thrombin Generation Time (TGT), of the Procoagulant Capacity of the Factor X Variants of Family 3: Intrinsic Coagulation Pathway (Cephalin Alone) in FVIII-deficient Plasma 1—Experimental Protocol The reagents, the automated device and the experimental protocol are identical to those described in example 6. The thrombin generation tests are carried out on 80 µl of a pool of plasma optionally containing the cell supernatants and the controls in the presence of 20 µl of cephalin (CK-Prest reconstituted with 1 ml of distilled $H_2O$) and of 20 µl of fluca-kit (substrate+$CaCl_2$). The plasmas used are a normal plasma and a factor VIII-deficient plasma.

2—Results

The family 3 of supernatents resulting from a transfection of HEK293F cells in the presence of VKOR were analyzed by TGT after activation with cephalin using the already described controls.

The controls behave expectedly, the FVIII-deficient plasma is negative (it does not allow any generation of IIa) and a gradient of effectiveness is found when increasing the dose of FVIII (FIG. 21; table 16). The supplementation with FX (2 assays were carried out) does not make it possible to generate significant amounts of thrombin (velocities of 6.06 and 7.65 nM/min). On the other hand, the FX-IIa, FX-FXIa1 and 2 and FX-control+ mutants of family 3 make it possible to generate significant amounts of thrombin with velocities greater than 26 nM, i.e. at least 3.8× faster than FX-WT (FIG. 23; table 16).

TABLE 16

Kinetic parameters resulting from the thrombinograms obtained from the addition of FX or variants thereof of family 3 to a pool of factor VIII-deficient plasma, following activation with cephalin

| Group name | Unicalibrator | FVIII Deficient | FVIII Def + Recombinant 1 U/ml | FVIII Def + Recombinant 0.1 U/ml | FVIII Def + FX-WT 7.5 µg/ml | FVIII Def + FX-control+ 7.5 µg/ml | FVIII Def + FX-IIa 7.5 µg/ml |
|---|---|---|---|---|---|---|---|
| Lagtime | 19.33 | 15.5 | 7.67 | 18 | 28.67 | 18.57 | 14.67 |
| ETP | 1347.5 | 0 | 1803 | 1442.5 | 938 | 1451.5 | 1635.5 |
| Peak | 304.16 | 0.48 | 336.48 | 278.12 | 58.51 | 167.62 | 283.52 |
| ttPeak | 21.5 | 38.33 | 9.33 | 20.17 | 38 | 24.17 | 17 |
| StartTail | 37 | 0 | 32 | 41.8 | 71 | 46 | 38 |
| Velocity | 140.17 | 0.02 | 202.70 | 128.17 | 6.06 | 30.48 | 123.83 |

| Group name | FVIII Def + FX-PAR1 7.5 µg/ml | FVIII Def + FX-PAR1M 7.5 µg/ml | FVIII Def + FX-FXIa1 7.5 µg/ml | FVIII Def + FX-FXIa2 7.5 µg/ml | FVIII Def + FX-KaI1 7.5 µg/ml | FVIII Def + FX-KaI2 7.5 µg/ml | FVIII Def + FX-KaI3 7.5 µg/ml | FVIII Def + FX-WT 7.5 µg/ml |
|---|---|---|---|---|---|---|---|---|
| Lagtime | 19.83 | 26.17 | 14.17 | 15.17 | 24.5 | 14.5 | 17.67 | 26.17 |
| ETP | 1335.5 | 1054 | 1395.5 | 1426.5 | 1033 | 1464 | 1365.5 | 1035 |
| Peak | 113.21 | 74.25 | 160.53 | 149.07 | 69.4 | 163.57 | 119.67 | 67.55 |
| ttPeak | 27.33 | 35 | 19.5 | 20.83 | 33 | 20 | 24.67 | 35 |
| StartTail | 53.5 | 65 | 43.5 | 44.5 | 65.5 | 42.5 | 50.5 | 67 |
| Velocity | 15.09 | 8.41 | 30.14 | 26.34 | 8.15 | 29.74 | 17.10 | 7.65 |

The kinetic parameters of the thrombinograms of FIG. 23 are presented in the table. Lagtime (min); ETP, total thrombin generated (nM); Peak, height of the thrombin peak (nM); ttPEAK, time of the peak maximum (min); Start Tail, velocity start time (min); Velocity, maximum rate of thrombin generation (nM/min).

Example 15

Measurement, in Terms of Thrombin Generation Time (TGT), of the Procoagulant Capacity of the Factor X Variants of Family 3: Extrinsic Coagulation Pathway (TF 1 pM/PL 4 µM) in FIX-deficient Plasma 1—Experimental Protocol The reagents, the automated device and the experimental protocol are identical to those described in example 6.

The thrombin generation tests are carried out on 80 µl of a pool of plasma optionally containing the cell supernatants and the controls in the presence of 20 µl of PPP reagent (Stago) containing a final concentration of 1 pM of tissue factor (TF) and 4 µM of phospholipids (PL) and of 20 µl of fluca-kit (substrate+$CaCl_2$). The plasmas used are a normal plasma and a factor IX-deficient plasma.

2—Results

The family 3 supernatents resulting from a transfection of HEK293F cells in the presence of VKOR were analyzed by TGT after activation with tissue factor using the already described controls.

The controls behave expectedly, the FIX-deficient plasma is negative (it does not allow any generation of IIa) and a gradient of effectiveness is found when increasing the dose of FIX (FIG. 23; table 17). The supplementation with FX (2 assays were carried out) does not make it possible to generate significant amounts of thrombin (mean velocity of 23 nM/min). On the other hand, all the mutants of family 3, except FX-PAR1M, make it possible to generate significant amounts of thrombin with velocities greater than 33 nM, i.e. at least 140% faster than FX-WT (FIG. 23; table 17).

The kinetic parameters of the thrombinograms of FIG. 23 are presented in the table. Lagtime (min); ETP, total thrombin generated (nM); Peak, height of the thrombin peak (nM); ttPEAK, time of the peak maximum (min); Start Tail, velocity start time (min); Velocity, maximum rate of thrombin generation (nM/min).

Example 16

Measurement, in Terms of Thrombin Generation Time (TGT), of the Procoagulant Capacity of the Factor X Variants of Family 3: Intrinsic Coagulation Pathway (Cephalin) in FIX-deficient Plasma 1—Experimental Protocol The reagents, the automated device and the experimental protocol are identical to those described in example 6. The thrombin generation tests are carried out on 80 µl of a pool of normal plasma optionally containing the cell supernatants and the controls in the presence of 20 µl of cephalin (CK-Prest reconstituted with 1 ml of distilled $H_2O$) and of 20 µL of fluca-kit (substrate+$CaCl_2$). The plasmas used are a normal plasma and a factor IX-deficient plasma.

2—Results

The family 3 supernatents resulting from a transfection of HEK293F cells in the presence of VKOR were analyzed by TGT after activation with cephalin using the already described controls.

The controls behave expectedly, the FIX-deficient plasma is negative (it does not allow any generation of IIa) and a gradient of effectiveness is found when increasing the dose of FXI (FIG. 24; table 18). In this assay, the supplementation with FX (2 assays were carried out) does not make it possible to generate significant amounts of thrombin (velocities of 1.24 and 1.53 nM/min). On the other hand, the FX-IIa, FX-FXIa1 and 2, FX-Kal 2 and 3, and FX-control+ mutants of family 1 make it possible to generate significantly greater amounts of thrombin of at least 3.4× that of the control to 52× (FIGS. 24 and 25; table 18). Moreover, all the mutants, except the FX-PAR1M and FX-Kal2 mutants, are more active than FX-WT.

TABLE 17

Kinetic parameters resulting from the thrombinograms obtained from the addition of FX or variants thereof of family 3 to a pool of factor IX-deficient plasma, following activation with tissue factor

| Group name | Unicalibrator | FIX Deficient | FIX Def + FIX 1 U/ml | FIX Def + FIX 0.1 U/ml | FIX DEF + FX-WT 7.5 µg/ml | FIX Def + FX-control+ 7.5 µg/ml | FIX Def + FX-IIa 7.5 µg/ml |
|---|---|---|---|---|---|---|---|
| Lagtime | 8.33 | 5.33 | 5.33 | 7.17 | 7.33 | 7.17 | 7.17 |
| ETP | 1345.5 | 238.5 | 1641 | 1063.5 | 1471 | 1632 | 1660.5 |
| Peak | 134.27 | 7.23 | 266.66 | 82.84 | 110.99 | 185.83 | 190.32 |
| ttPeak | 12.67 | 22.5 | 8.33 | 13.33 | 12.67 | 11.67 | 12.17 |
| StartTail | 41 | 70 | 26 | 46 | 48.5 | 33.5 | 33 |
| Velocity | 30.94 | 0.42 | 58.59 | 13.45 | 20.78 | 41.30 | 38.06 |

| Group name | FIX Def + FX-PAR1 7.5 µg/ml | FIX Def + FX-PAR1M 7.5 µg/ml | FIX Def + FX-FXIa1 7.5 µg/ml | FIX Def + FX-FXIa2 7.5 µg/ml | FIX Def + FX-Kal1 7.5 µg/ml | FIX Def + FX-Kal2 7.5 µg/ml | FIX Def + FX-Kal3 1.6 µg/ml | FIX Def + FX-WT 7.5 µg/ml |
|---|---|---|---|---|---|---|---|---|
| Lagtime | 6.33 | 8 | 6 | 6.67 | 8.5 | 6 | 6.5 | 7.33 |
| ETP | 1505 | 1451 | 1599 | 1646 | 1428.5 | 1740 | 1679 | 1472 |
| Peak | 173.4 | 125.89 | 250.41 | 240.75 | 143.97 | 260.48 | 223.11 | 126.29 |
| ttPeak | 11.5 | 12.67 | 9 | 10 | 12.5 | 9 | 10.17 | 12.17 |
| StartTail | 34 | 43.5 | 28 | 30 | 41 | 28 | 30 | 43 |
| Velocity | 33.54 | 27.17 | 83.47 | 72.30 | 35.99 | 86.83 | 60.79 | 26.09 |

TABLE 18

Kinetic parameters resulting from the thrombinograms obtained from the addition of FX or variants thereof of family 3 to a pool of factor IX-deficient plasma, following activation with cephalin

| Group name | Unicalibrator | Deficient FIX | FIX Def + FIX 1 U/ml | FIX Def + FIX 0.1 U/ml | FIX Def + FX-WT 7.5 µg/ml | FIX Def + FX-control+ 7.5 µg/ml | FIX Def + FX-IIa 7.5 µg/ml |
|---|---|---|---|---|---|---|---|
| Lagtime | 18.33 | 42.5 | 13.67 | 31.83 | 30.5 | 22.5 | 17.5 |
| ETP | 1383.5 | 0 | 1529 | 899.5 | 316.5 | 1233.5 | 1485.5 |
| Peak | 311.19 | 0.49 | 369.87 | 107.63 | 16.16 | 125.06 | 255.59 |
| ttPeak | 20.33 | 57.33 | 15.33 | 36.33 | 43.5 | 29.67 | 21.17 |
| StartTail | 36.5 | 0 | 31 | 55 | 71 | 46 | 35 |
| Velocity | 155.60 | 0.03 | 222.81 | 23.90 | 1.24 | 17.44 | 72.37 |

| Group name | FIX Def + FX-PAR1 7.5 µg/ml | FIX Def + FX-PAR1M 7.5 µg/ml | FIX Def + FX-FXIa1 7.5 µg/ml | FIX Def + FX-FXIa2 7.5 µg/ml | FIX Def + FX-KaI1 7.5 µg/ml | FIX Def + FX-KaI2 7.5 µg/ml | FIX Def + FX-KaI3 1.6 µg/ml | FIX Def + FX-WT 7.5 µg/ml |
|---|---|---|---|---|---|---|---|---|
| Lagtime | 22 | 29.67 | 15 | 17.67 | 27.67 | 16.5 | 18.17 | 27.5 |
| ETP | 527 | 424.5 | 752.5 | 618 | 400 | 772.6 | 535 | 341 |
| Peak | 38.39 | 24 | 59.65 | 48.93 | 21.04 | 61.27 | 42.44 | 18.68 |
| ttPeak | 32.67 | 42 | 23.67 | 26.83 | 39.83 | 24.67 | 27.33 | 39.67 |
| StartTail | 57 | 71 | 45.5 | 46 | 70 | 48 | 49.5 | 70 |
| Velocity | 3.60 | 1.95 | 6.88 | 5.34 | 1.73 | 7.50 | 4.63 | 1.53 |

The kinetic parameters of the thrombinograms of FIG. 24 are presented in the table. Lagtime (min); ETP, total thrombin generated (nM); Peak, height of the thrombin peak (nM); ttPEAK, time of the peak maximum (min); Start Tail, velocity start time (min); Velocity, maximum rate of thrombin generation (nM/min).

The invention claimed is:

1. A protein, comprising:
   a mutated sequence of SEQ ID No. 1, said mutated sequence of SEQ ID No. 1 comprising mutation B wherein: mutation B consists of insertion of DFLAE-GLTPR (SEQ ID NO: 159) between amino acids 52 and 53 of SEQ ID No. 1.

2. The protein as claimed in claim 1, comprising SEQ ID No. 7 with mutation B.

3. The protein as claimed in claim 1, consisting of SEQ ID No. 7 with mutation B.

4. The protein as claimed in claim 2, comprising SEQ ID No. 18 or SEQ ID No. 114.

5. A protein complex comprising a protein as claimed in claim 1, and at least one protein of SEQ ID No. 2, said proteins being linked to one another by a disulfide bridge.

6. A pharmaceutical composition comprising an effective amount of the protein as claimed in claim 1.

7. A method of treating factor X deficiency, hemophilia A, or hemophilia B, comprising administering an effective amount of the protein as claimed in claim 1 to a subject in need thereof.

* * * * *